United States Patent
Sydora et al.

(10) Patent No.: US 9,120,826 B1
(45) Date of Patent: Sep. 1, 2015

(54) OLEFIN HYDROBORATION

(71) Applicant: Chevron Phillips Chemical Company LP, The Woodlands, TX (US)

(72) Inventors: Orson L. Sydora, Houston, TX (US); Mark Stradiotto, Halifax (CA); Laura Turculet, Halifax (CA); Brooke L. Small, Kingwood, TX (US); Robert C. Coffin, Zionsville, IN (US); Steven M. Bischof, Humble, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/293,833

(22) Filed: Jun. 2, 2014

(51) Int. Cl.
*C07F 5/02* (2006.01)
*C07C 1/32* (2006.01)

(52) U.S. Cl.
CPC ............... *C07F 5/025* (2013.01); *C07C 1/321* (2013.01)

(58) Field of Classification Search
CPC ........................................................ C07F 5/02
USPC .................................. 585/670; 556/7; 568/1
See application file for complete search history.

(56) References Cited

U.S. PATENT DOCUMENTS

| | | |
|---|---|---|
| 6,200,920 B1 | 3/2001 | Debras et al. |
| 6,489,428 B1 | 12/2002 | Debras et al. |
| 6,713,566 B1 | 3/2004 | Marcuccio et al. |
| 2012/0309965 A1 | 12/2012 | Sydora et al. |
| 2013/0331629 A1* | 12/2013 | Sydora et al. ............ 585/523 |
| 2014/0221645 A1* | 8/2014 | Sydora et al. ............ 544/64 |

FOREIGN PATENT DOCUMENTS

WO        0021966 A1    4/2000

OTHER PUBLICATIONS

Caballero, Ana, et al., "Ruthenium-Catalyzed Hydroboration and Dehydrogenative Borylation of Linear and Cyclic Alkenes with Pinacolborane," Organometallics, 2007, pp. 1191-1195, vol. 26, No. 5, American Chemical Society.
Cipot, Judy, et al., "Catalytic Alkene Hydroboration Mediated by Cationic and Formally Zwitterionic Rhodium(I) and Iridium(I) Derivatives of a P,N-Substituted Indene," Organometallics, 2006, pp. 5965-5968, vol. 25, No. 25, American Chemical Society.
Evans, David A., et al., "Mechanistic Study of the Rhodium(I)-Catalyzed Hydroboration Reaction," J. Am. Chem. Soc., 1992, pp. 6679-6685, vol. 114, No. 17, American Chemical Society.
Evans, David A., et al., "Rhodium(I)- and Iridium(I)-Catalyzed Hydroboration Reactions: Scope and Synthetic Applications," J. Am. Chem. Soc., 1992, pp. 6671-6679, vol. 114, No. 17, American Chemical Society.
De Klerk, Arno, et al., "Linear α-Olefins from Linear Internal Olefins by a Boron-Based Continuous Double-Bond Isomerization Process," Ind. Eng. Chem. Res., 2007, pp. 400-410, vol. 46, No. 2, American Chemical Society.
Lata, Christopher J., et al., "Dramatic Effect of Lewis Acids on the Rhodium-Catalyzed Hydroboration of Olefins," J. Am. Chem. Soc., 2010, pp. 131-137, vol. 132, No. 1, American Chemical Society.
Obligacion, Jennifer V., et al., "Bis(imino)pyridine Cobalt-Catalyzed Alkene Isomerization-Hydroboration: A Strategy for Remote Hydrofunctionalization with Terminal Selectivity," Journal of the American Chemical Society, 2013, pp. 19107-19110, vol. 135, American Chemical Society.
Obligacion, Jennifer V., et al., "Highly Selective Bis(imino)pyridine Iron-Catalyzed Alkene Hydroboration," Organic Letters, 2013, pp. 2680-2683, vol. 15, No. 11, American Chemical Society.
Pereira, Schubert, et al., "Transition Metal-Catalyzed Hydroboration of and $CCl_4$ Addition to Alkenes," J. Am. Chem. Soc., 1996, pp. 909-910, vol. 118, No. 4, American Chemical Society.
Ruddy, Adam J., et al, "(N•Phosphinoamidinate)Iron Pre-Catalysts for the Room Temperature Hydrosilylation of Carbonyl Compounds with Broad Substrate Scope at Low Loadings," Organometallics, 2013, pp. 5581-5588, vol. 32, American Chemical Society.
Yamamoto, Yasunori, et al., "Iridium-catalyzed hydroboration of alkenes with pinacolborane," Tetrahedron, 2004, pp. 10695-10700, vol. 60, Elsevier, Ltd.
McNaught, Alan D., et al., "Compendium of Chemical Terminology," International Union of Pure and Applied Chemistry, Second edition, 1997, 1 page, Wiley-Blackwell.
"Group notation revised in periodic table," Feb. 4, 1985, pp. 26-27, C&EN.
Ghebreyessus, Kesete Y., et al. "Isomerizing-Hydroboration of the Monounsaturated Fatty Acid Ester Methyl Oleate," Organometallics, 2006, pp. 3040-3044, vol. 25, No. 12, American Chemical Society.
Zhang, Lei, et al., "Iron-Catalyzed, Atom-Economical, Chemo- and Regioselective Alkene Hydroboration with Pinacolborane," Angewandte Chemie International Edition, 2013, pp. 3676-3680, vol. 52, Wiley-VCH Verlag GmbH & Co. KGaA, Weinheim.

\* cited by examiner

*Primary Examiner* — Sudhakar Katakam

(74) *Attorney, Agent, or Firm* — Conley Rose, P.C.; Rodney B. Carroll; Lynda Jolly

(57) ABSTRACT

A process comprising contacting an alkene, a hydrogen-boron bond containing compound, and a metal complex selected from the group consisting of an $N^2$-phosphinyl amidine metal complex, an $N^2$-phosphinyl formamidine complex, and an $N^2$-phosphinyl guanidine metal complex under conditions suitable to form an alkylboron compound. A process comprising contacting a linear internal alkene, a metal complex selected from the group consisting of an $N^2$-phosphinyl amidine metal complex, an $N^2$-phosphinyl formamidine complex, and an $N^2$-phosphinyl guanidine metal complex to form a terminal alkylboron compound under conditions suitable to form a terminal alkylboron compound.

22 Claims, No Drawings

OLEFIN HYDROBORATION

TECHNICAL FIELD

The present disclosure relates to the transition metal catalyzed hydroboration of olefins (e.g., alkenes). Particularly, the present disclosure relates to the use of $N^2$-phosphinyl formamidine, $N^2$-phosphinyl amidine, and $N^2$-phosphinyl guanidine, transition metal complexes as hydroboration catalysts.

BACKGROUND

Hydroboration is the addition of a borane compound to an olefin to form an organoborane. The hydroboration of olefins such as alkenes thermodynamically favors the terminal organoborane. However, hydroboration of internal olefins typically requires the utilization of expensive catalysts or harsh conditions (e.g., high temperatures) while typically suffering from poor yield and selectivity. Thus an ongoing need exists for catalysts that provide improved hydroboration of internal olefins.

SUMMARY

Disclosed herein is a process comprising contacting an alkene, a hydrogen-boron bond containing compound, and a metal complex selected from the group consisting of an $N^2$-phosphinyl amidine metal complex, an $N^2$-phosphinyl formamidine complex, and an $N^2$-phosphinyl guanidine metal complex to form an alkyl-boron compound under conditions suitable to form an alkylboron compound.

Also disclosed herein is a process comprising contacting a linear internal alkene, a metal complex selected from the group consisting of an $N^2$-phosphinyl amidine metal complex, an $N^2$-phosphinyl formamidine complex, and an $N^2$-phosphinyl guanidine metal complex to form a terminal alkylboron compound under conditions suitable to form a terminal alkylboron compound.

DETAILED DESCRIPTION

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Groups of elements of the table are indicated using the numbering scheme indicated in the version of the periodic table of elements published in *Chemical and Engineering News*, 63(5), 27, 1985. In some instances a group of elements can be indicated using a common name assigned to the group; for example alkali earth metals (or alkali metals) for Group 1 elements, alkaline earth metals (or alkaline metals) for Group 2 elements, transition metals for Group 3-12 elements, and halogens for Group 17 elements.

Regarding claim transitional terms or phrases, the transitional term "comprising", which is synonymous with "including," "containing," "having," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps and those that do not materially affect the basic and novel characteristic(s) of the claimed invention. A "consisting essentially of" claim occupies a middle ground between closed claims that are written in a "consisting of" format and fully open claims that are drafted in a "comprising" format. Absent an indication to the contrary, when describing a compound or composition "consisting essentially of" is not to be construed as "comprising," but is intended to describe the recited component that includes materials which do not significantly alter the composition or method to which the term is applied. For example, a feedstock consisting of a material A can include impurities typically present in a commercially produced or commercially available sample of the recited compound or composition. When a claim includes different features and/or feature classes (for example, a method step, feedstock features, and/or product features, among other possibilities), the transitional terms comprising, consisting essentially of, and consisting of apply only to the feature class which is utilized and it is possible to have different transitional terms or phrases utilized with different features within a claim. For example, a method can comprise several recited steps (and other non-recited steps) but utilize a catalyst system preparation consisting essentially of specific or alternatively consists of specific steps and/or utilize a catalyst system comprising recited components and other non-recited components.

While compositions and methods are described in terms of "comprising" various components or steps, the compositions and methods can also "consist essentially of" or "consist of" the various components or steps.

The terms "a," "an," and "the" are intended, unless specifically indicated otherwise, to include plural alternatives, e.g., at least one. For instance, the disclosure of "a trialkylaluminum compound" is meant to encompass one trialkylaluminum compound, or mixtures or combinations of more than one trialkylaluminum compound unless otherwise specified.

For any particular compound disclosed herein, the general structure or name presented is also intended to encompass all structural isomers, conformational isomers, and stereoisomers that can arise from a particular set of substituents, unless indicated otherwise. Thus, a general reference to a compound includes all structural isomers unless explicitly indicated otherwise; e.g., a general reference to pentane includes n-pentane, 2-methyl-butane, and 2,2-dimethylpropane while a general reference to a butyl group includes an n-butyl group, a sec-butyl group, an iso-butyl group, and a tert-butyl group. Additionally, the reference to a general structure or name encompasses all enantiomers, diastereomers, and other optical isomers whether in enantiomeric or racemic forms, as well as mixtures of stereoisomers, as the context permits or requires. For any particular formula or name that is presented, any general formula or name presented also encompasses all conformational isomers, regioisomers, and stereoisomers that can arise from a particular set of substituents.

A chemical "group" is described according to how that group is formally derived from a reference or "parent" compound, for example, by the number of hydrogen atoms formally removed from the parent compound to generate the group, even if that group is not literally synthesized in this manner. These groups can be utilized as substituents or coordinated or bonded to metal atoms. By way of example, an "alkyl group" formally can be derived by removing one hydrogen atom from an alkane, while an "alkylene group" formally can be derived by removing two hydrogen atoms from an alkane. Moreover, a more general term can be used to encompass a variety of groups that formally are derived by removing any number ("one or more") hydrogen atoms from a parent compound, which in this example can be described as an "alkane group," and which encompasses an "alkyl group," an "alkylene group," and materials have three or more hydrogens atoms, as necessary for the situation, removed from the alkane. Throughout the disclosure a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedure, unless specified otherwise or the context requires otherwise.

The term "substituted" when used to describe a group, for example, when referring to a substituted analog of a particular group, is intended to describe any non-hydrogen moiety that formally replaces a hydrogen in that group, and is intended to be non-limiting. A group or groups can also be referred to herein as "unsubstituted" or by equivalent terms such as "non-substituted," which refers to the original group in which a non-hydrogen moiety does not replace a hydrogen within that group. "Substituted" is intended to be non-limiting and include inorganic substituents or organic substituents.

A formamidine group, such as those found in a ligand of the $N^2$-phosphinyl formamidine complexes described herein, is a group having the general structure

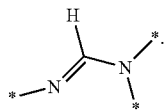

Within the formamidine group the nitrogen participating in a double bond with the central carbon atom is referred to as the $N^1$ nitrogen and the nitrogen atom participating in a single bond with the central carbon atom is referred to as the $N^2$ nitrogen. Similarly, the groups attached to the $N^1$ and $N^2$ nitrogen atoms are referred to as the $N^1$ group and $N^2$ group respectively. An $N^2$-phosphinyl formamidine group, such as those found in a ligand of the $N^2$-phosphinyl formamidine complexes described herein, has the general structure

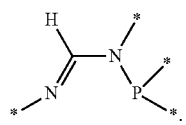

Within the $N^2$-phosphinyl formamidine group the $N^1$ and $N^2$ nitrogen atoms and $N^1$ and $N^2$ groups have the same meaning as described for the formamidine group. Consequently, an $N^2$ phosphinyl formamidine group has the phosphinyl group is attached to the $N^2$ nitrogen atom.

An amidine group, such as those found in a ligand of the $N^2$-phosphinyl amidine complexes described herein, is a group having the general structure

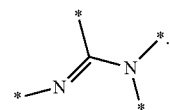

Within the amidine group the nitrogen participating in a double bond with the central carbon atom is referred to as the $N^1$ nitrogen and the nitrogen atom participating in a single bond with the central carbon atom is referred to as the $N^2$ nitrogen. Similarly, the groups attached to the $N^1$ and $N^2$ nitrogen atoms are referred to as the $N^1$ group and $N^2$ group respectively. An $N^2$-phosphinyl amidine group, such as those found in a ligand of the $N^2$-phosphinyl amidine complexes described herein, has the general structure

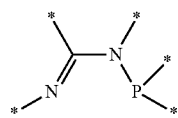

Within the $N^2$ phosphinyl amidine group the $N^1$ and $N^2$ nitrogen atoms and $N^1$ and $N^2$ groups have the same meaning as described for the amidine group. Consequently, a $N^2$-phosphinyl amidine group has the phosphinyl group is attached to the $N^2$ nitrogen atom. Within the amidine group and $N^2$-phosphinyl amidine group the carbon atom between the two nitrogen atoms is the central carbon atom and any substituent attached to it is referred to as the central carbon group. For the purpose of this disclosure and claims, a compound having a pyridine group with a 2-amine group (or its analogues—e.g., a pyrimidine ring, an imidazole ring, a compound having 2-aminopyridine group, etc . . . ) or having a 2-phosphinylamine group is not considered to constitute an amidine group or $N^2$-phosphinyl amidine group, respectively.

A guanidine group, such as those found in a ligand of the $N^2$-phosphinyl guanidine complexes described herein, is a group having the general structure

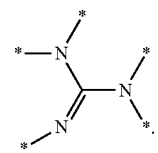

Within the guanidine core, the nitrogen participating in a double bond with the central carbon atom is referred to as the $N^1$ nitrogen and the two nitrogen atoms participating in a single bond with the central carbon atom are referred to as the $N^2$ nitrogen and the $N^3$ nitrogen. Similarly, the groups attached to the $N^1$, $N^2$ and $N^3$ nitrogen atoms are referred to as the $N^1$ group, $N^2$ group, and $N^3$ group respectively. An $N^2$-phosphinyl guanidine group, such as those found in a ligand of the $N^2$-phosphinyl guanidine complexes described herein, has the general structure

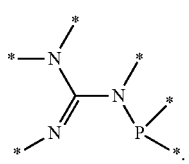

Within an $N^2$-phosphinyl guanidine group, the nitrogen participating in a double bond with the central carbon atom of the guanidine core is referred to as the $N^1$ nitrogen, the nitrogen atom participating in a single bond with the central carbon atom of the guanidine core and a bond with the phosphorus atom of the phosphinyl group is referred to as the $N^2$ nitrogen, and the remaining nitrogen atom participating in a single bond with the central carbon atom of the guanidine core is referred to as the $N^3$ nitrogen. It should be noted that a guanidine core or an $N^2$-phosphinyl guanidine group can be a portion of a larger group (or compound) which does not contain guanidine in it name. For example, while the compound 7-dimethylphosphinylimidazo[1,2-a]imidazole could be classified as a compound having an imidazo[1,2-a]imidazole core (or a compound having a phosphinylimidazo[1,2-a]imidazole group), 7-dimethylphosphinylimidazo[1,2-a]imidazole would still be classified as a compound having a guanidine core (or as a compound having an $N^2$-phosphinyl guanidine group) since it contains the defined general structure of the guanidine core (or the $N^2$-phosphinyl guanidine group).

The term "organyl group" is used herein in accordance with the definition specified by IUPAC: an organic substituent group, regardless of functional type, having one free valence at a carbon atom. Similarly, an "organylene group" refers to an organic group, regardless of functional type, derived by removing two hydrogen atoms from an organic compound, either two hydrogen atoms from one carbon atom or one hydrogen atom from each of two different carbon atoms. An "organic group" refers to a generalized group formed by removing one or more hydrogen atoms from carbon atoms of an organic compound. Thus, an "organyl group," an "organylene group," and an "organic group" can contain organic functional group(s) and/or atom(s) other than carbon and hydrogen, that is, an organic group can comprise functional groups and/or atoms in addition to carbon and hydrogen. For instance, non-limiting examples of atoms other than carbon and hydrogen include halogens, oxygen, nitrogen, phosphorus, and the like. Non-limiting examples of functional groups include ethers, aldehydes, ketones, esters, sulfides, amines, phosphines, and so forth. In one aspect, the hydrogen atom(s) removed to form the "organyl group," "organylene group," or "organic group" can be attached to a carbon atom belonging to a functional group, for example, an acyl group (—C(O)R), a formyl group (—C(O)H), a carboxy group (—C(O)OH), a hydrocarboxycarbonyl group (—C(O)OR), a cyano group (—C≡N), a carbamoyl group (—C(O)NH$_2$), a N-hydrocarbylcarbamoyl group (—C(O)NHR), or N,N'-dihydrocarbylcarbamoyl group (—C(O)NR$_2$), among other possibilities. In another aspect, the hydrogen atom(s) removed to form the "organyl group," "organylene group," or "organic group" can be attached to a carbon atom not belonging to, and remote from, a functional group, for example, —CH$_2$C(O)CH$_3$, —CH$_2$NR$_2$, and the like. An "organyl group," "organylene group," or "organic group" can be aliphatic, inclusive of being cyclic or acyclic, or can be aromatic. "Organyl groups," "organylene groups," and "organic groups" also encompass heteroatom-containing rings, heteroatom-containing ring systems, heteroaromatic rings, and heteroaromatic ring systems. "Organyl groups," "organylene groups," and "organic groups" can be linear or branched unless otherwise specified. Finally, it is noted that the "organyl group," "organylene group," or "organic group" definitions include "hydrocarbyl group," "hydrocarbylene group," "hydrocarbon group," respectively, and "alkyl group," "alkylene group," and "alkane group," respectively, as members.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl group consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional groups" definition includes the hydrocarbyl group as a member (among other groups). Similarly, an "organylene group consisting of inert functional groups" refers to an organic group formed by removing two hydrogen atoms from one or two carbon atoms of an organic compound consisting of inert functional groups and an "organic group consisting of inert functional groups" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with the metal compound of the metal complex. The term "does not complex with the metal compound" can include groups that could complex with a metal compound but in particular molecules described herein may not complex with a metal compound due to its positional relationship within a ligand. For example, while an ether group can complex with a metal compound, an ether group located at a para position of a substituted phenyl phosphinyl group can be an inert functional group because a single metal compound cannot complex with both the para ether group and the $N^2$-phosphinyl formamidine group of the same metal complex molecule. Thus, the inertness of a particular functional group is not only related to the functional group's inherent inability to complex the metal compound but can also be related to the functional group's position within the metal complex. Non-limiting examples of inert functional groups which do not substantially interfere with processes described herein can include halo (fluoro, chloro, bromo, and iodo), nitro, hydrocarboxy groups (e.g., alkoxy, and/or aroxy, among others), sulfidyl groups, and/or hydrocarbyl groups, among others.

The term "hydrocarbon" whenever used in this specification and claims refers to a compound containing only carbon and hydrogen. Other identifiers can be utilized to indicate the presence of particular groups in the hydrocarbon (e.g. halogenated hydrocarbon indicates that the presence of one or more halogen atoms replacing an equivalent number of hydrogen atoms in the hydrocarbon). The term "hydrocarbyl group" is used herein in accordance with the definition specified by IUPAC: a univalent group formed by removing a hydrogen atom from a hydrocarbon. Non-limiting examples of hydrocarbyl groups include ethyl, phenyl, tolyl, propenyl, and the like. Similarly, a "hydrocarbylene group" refers to a group formed by removing two hydrogen atoms from a hydrocarbon, either two hydrogen atoms from one carbon atom or one hydrogen atom from each of two different carbon atoms. Therefore, in accordance with the terminology used herein, a "hydrocarbon group" refers to a generalized group formed by removing one or more hydrogen atoms (as necessary for the particular group) from a hydrocarbon. A "hydrocarbyl group," "hydrocarbylene group," and "hydrocarbon group" can be acyclic or cyclic groups, and/or can be linear or branched. A "hydrocarbyl group," "hydrocarbylene group," and "hydrocarbon group" can include rings, ring systems, aromatic rings, and aromatic ring systems, which contain only carbon and hydrogen. "Hydrocarbyl groups," "hydrocarbylene groups," and "hydrocarbon groups" include, by way of example, aryl, arylene, arene, alkyl, alkylene, alkane, cycloalkyl, cycloalkylene, cycloalkane, aralkyl, aralkylene, and aralkane groups, among other groups, as members.

The term "alkane" whenever used in this specification and claims refers to a saturated hydrocarbon compound. Other identifiers can be utilized to indicate the presence of particular groups in the alkane (e.g. halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. Similarly, an "alkylene group" refers to a group formed by removing two hydrogen atoms from an alkane (either two hydrogen atoms from one carbon atom or one hydrogen atom from two different carbon atoms). An "alkane group" is a general term that refers to a group formed by removing one or more hydrogen atoms (as necessary for the particular group) from an alkane. An "alkyl group," "alkylene group," and "alkane group" can be acyclic or cyclic groups, and/or can be linear or branched unless otherwise specified. Primary, secondary, and tertiary alkyl group are derived by removal of a hydrogen atom from a primary, secondary, tertiary carbon atom, respectively, of an alkane. The n-alkyl group can be derived by removal of a hydrogen atom from a terminal carbon atom of a linear alkane. The groups $RCH_2$ ($R \neq H$), $R_2CH$ ($R \neq H$), and $R_3C$ ($R \neq H$) are primary, secondary, and tertiary alkyl groups, respectively.

A cycloalkane is a saturated cyclic hydrocarbon, with or without side chains, for example, cyclobutane. Unsaturated cyclic hydrocarbons having one or more endocyclic double or one triple bond are called cycloalkenes and cycloalkynes, respectively. Cycloalkenes and cycloalkynes having only one, only two, only three, etc. . . . endocyclic double or triple bonds, respectively, can be identified by use of the term "mono," "di," "tri: etc. . . . within the name of the cycloalkene or cycloalkyne. Cycloalkenes and cycloalkynes can further identify the position of the endocyclic double or triple bonds.

A "cycloalkyl group" is a univalent group derived by removing a hydrogen atom from a ring carbon atom of a cycloalkane. For example, a 1-methylcyclopropyl group and a 2-methylcyclopropyl group are illustrated as follows.

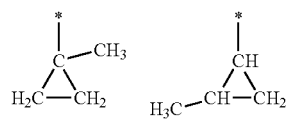

Similarly, a "cycloalkylene group" refers to a group derived by removing two hydrogen atoms from a cycloalkane, at least one of which is a ring carbon. Thus, a "cycloalkylene group" includes both a group derived from a cycloalkane in which two hydrogen atoms are formally removed from the same ring carbon, a group derived from a cycloalkane in which two hydrogen atoms are formally removed from two different ring carbons, and a group derived from a cycloalkane in which a first hydrogen atom is formally removed from a ring carbon and a second hydrogen atom is formally removed from a carbon atom that is not a ring carbon. A "cycloalkane group" refers to a generalized group formed by removing one or more hydrogen atoms (as necessary for the particular group and at least one of which is a ring carbon) from a cycloalkane. It should be noted that according to the definitions provided herein, general cycloalkane groups (including cycloalkyl groups and cycloalkylene groups) include those having zero, one, or more than one hydrocarbyl substituent groups attached to a cycloalkane ring carbon atom (e.g. a methylcyclopropyl group) and is member of the group of hydrocarbon groups. However, when referring to a cycloalkane group having a specified number of cycloalkane ring carbon atoms (e.g. cyclopentane group or cyclohexane group, among others), the base name of the cycloalkane group having a defined number of cycloalkane ring carbon atoms refers to the unsubstituted cycloalkane group (including having no hydrocarbyl groups located on cycloalkane group ring carbon atom). Consequently, a substituted cycloalkane group having a specified number of ring carbon atoms (e.g. substituted cyclopentane or substituted cyclohexane, among others) refers to the respective group having one or more substituent groups (including halogens, hydrocarbyl groups, or hydrocarboxy groups, among other substituent groups) attached to a cycloalkane group ring carbon atom. When the substituted cycloalkane group having a defined number of cycloalkane ring carbon atoms is a member of the group of hydrocarbon groups (or a member of the general group of cycloalkane groups), each substituent of the substituted cycloalkane group having a defined number of cycloalkane ring carbon atoms is limited to hydrocarbyl substituent group. One can readily discern and select general groups, specific groups, and/or individual substituted cycloalkane group(s) having a specific number of ring carbons atoms which can be utilized as member of the hydrocarbon group (or a member of the general group of cycloalkane groups).

A "cycloalkyl alkyl group" is a cycloalkyl-substituted alkyl group having a free valance at a non-cycloalkyl carbon atom (e.g. a cyclohexyl methyl group, or a 2-cyclohexyl eth-1yl group, among others). Similarly, a "cycloalkyl alkylene group" is a cycloalkyl-substituted alkylene group having two free valencies at a single non-cycloalkyl carbon atom or a free valence at two non-cycloalkyl carbon atoms while a "cycloalkyl alkane group" is a generalized is a cyclo-substituted alkane group having one or more free valencies at a non-cycloalkyl carbon atom(s). It should be noted that according the definitions provided herein, general cycloalkyl alkane groups include those having zero, one, or more than one hydrocarbyl substituent groups located on a cycloalkyl alkane cycloalkyl hydrocarbon ring or ring system carbon atom and is a member of the group of hydrocarbon groups.

However, specific cycloalkyl alkane groups specifying a particular cycloalkyl alkane group (e.g. the cyclohexyl group in a cyclohexyl methane group or a 2-cyclohexyl ethyl group, among others) refer to the specific unsubstituted aralkane groups (including no hydrocarbyl group located on the cycloalkyl alkane hydrocarbon ring or ring system carbon atom). Consequently, a substituted cycloalkyl alkane group specifying a particular cycloalkyl group refers to a respective cycloalkyl alkane group having one or more substituent groups (including halogens, hydrocarbyl groups, or hydrocarboxy groups, among others). When the substituted cycloalkyl alkane group specifying a particular cycloalkyl group is a member of the group of hydrocarbon groups (or a member of the general group of cycloalkyl alkane groups), each substituent is limited to a hydrocarbyl substituent group. One can readily discern and select substituted cycloalkyl alkane groups specifying a particular cycloalkyl group which can be utilized as a member of the group of hydrocarbon groups (or a member of the general group of cycloalkyl alkane groups).

The term "olefin" whenever used in this specification and claims refers to compounds that have at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system unless specifically stated otherwise. The term "olefin," by itself, does not indicate the presence or absence of heteroatoms and/or the presence or absence of other carbon-carbon double bonds unless explicitly indicated. Olefins having only one, only two, only three, etc. . . . carbon-carbon double bonds can be identified by use of the term "mono," "di," "tri," etc. . . . within the name of the olefin. The olefins can be further identified by the position of the carbon-carbon double bond(s).

The term "alkene" whenever used in this specification and claims refers a linear or branched, and/or acyclic or cyclic, hydrocarbon olefin that has one or more carbon-carbon double bonds. Alkenes having only one, only two, only three, etc. . . . such multiple bond can be identified by use of the term "mono," "di," "tri," etc. . . . within the name. For example, alkamonoenes, alkadienes, and alkatrienes refer to a linear or branched hydrocarbon olefins having only one carbon-carbon double bond (general formula $C_nH_{2n}$), only two carbon-carbon double bonds (general formula $C_nH_{2n-2}$), and only three carbon-carbon double bonds (general formula $C_nH_{2n-4}$), respectively. Alkenes can be further identified by the position of the carbon-carbon double bond(s). Other identifiers can be utilized to indicate the presence or absence of particular groups within an alkene. For example, a haloalkene refers to an alkene having one or more hydrogen atoms replaced with a halogen atom.

The term "alpha olefin" as used in this specification and claims refers to an olefin that has a carbon-carbon double bond between the first and second carbon atom of the longest contiguous chain of carbon atoms. The term "alpha olefin" includes linear and branched alpha olefins unless expressly stated otherwise. In the case of branched alpha olefins, a branch can be at the 2-position (a vinylidene) and/or the 3-position or higher with respect to the olefin double bond. The term "vinylidene" whenever used in this specification and claims refers to an alpha olefin having a branch at the 2-position with respect to the olefin double bond. By itself, the term "alpha olefin" does not indicate the presence or absence of heteroatoms and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon.

The term "linear alpha olefin" as used herein refers to a linear olefin having a carbon-carbon double bond between the first and second carbon atom. The term "linear alpha olefin" by itself does not indicate the presence or absence of heteroatoms and/or the presence or absence of other carbon-carbon double bonds, unless explicitly indicated. The terms "linear hydrocarbon alpha olefin" or "linear alpha olefin hydrocarbon" refers to linear alpha olefin compounds containing only hydrogen and carbon.

The term "normal alpha olefin" whenever used in this specification and claims refers to a linear hydrocarbon mono-olefin having a carbon carbon double bond between the first and second carbon atom. It is noted that "normal alpha olefin" is not synonymous with "linear alpha olefin" as the term "linear alpha olefin" can include linear olefinic compounds having a double bond between the first and second carbon atoms and having heteroatoms and/or additional double bonds.

An aliphatic compound is an acyclic or cyclic, saturated or unsaturated carbon compound, excluding aromatic compounds. Thus, an aliphatic compound is an acyclic or cyclic, saturated or unsaturated carbon compound, excluding aromatic compounds; that is, an aliphatic compound is a non-aromatic organic compound. An "aliphatic group" is a generalized group formed by removing one or more hydrogen atoms (as necessary for the particular group) from the carbon atom of an aliphatic compound. Thus, an aliphatic compound is an acyclic or cyclic, saturated or unsaturated carbon compound, excluding aromatic compounds. That is, an aliphatic compound is a non-aromatic organic compound. Aliphatic compounds and therefore aliphatic groups can contain organic functional group(s) and/or atom(s) other than carbon and hydrogen.

An aromatic compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds) and "heteroarenes," also termed "hetarenes" (heteroaromatic compounds formally derived from arenes by replacement of one or more methine (—C═) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2). While arene compounds and heteroarene compounds are mutually exclusive members of the group of aromatic compounds, a compound that has both an arene group and a heteroarene group are generally considered a heteroarene compound. Aromatic compounds, arenes, and heteroarenes can be monocyclic (e.g., benzene, toluene, furan, pyridine, methylpyridine) or polycyclic unless otherwise specified. Polycyclic aromatic compounds, arenes, and heteroarenes, include, unless otherwise specified, compounds wherein the aromatic rings can be fused (e.g., naphthalene, benzofuran, and indole), compounds where the aromatic groups can be separate and joined by a bond (e.g., biphenyl or 4-phenylpyridine), or compounds where the aromatic groups are joined by a group containing linking atoms (e.g., carbon—the methylene group in diphenylmethane; oxygen—diphenyl ether; nitrogen—triphenyl amine; among others linking groups). As disclosed herein, the term "substituted" can be used to describe an aromatic group, arene, or heteroarene wherein a non-hydrogen moiety formally replaces a hydrogen in the compound, and is intended to be non-limiting.

An "aromatic group" refers to a generalized group formed by removing one or more hydrogen atoms (as necessary for the particular group and at least one of which is an aromatic ring carbon atom) from an aromatic compound. For a univalent "aromatic group," the removed hydrogen atom must be from an aromatic ring carbon. For an "aromatic group" formed by removing more than one hydrogen atom from an aromatic compound, at least one hydrogen atom must be from an aromatic hydrocarbon ring carbon. Additionally, an "aromatic group" can have hydrogen atoms removed from the same ring of an aromatic ring or ring system (e.g., phen-1,4-ylene, pyridin-2,3-ylene, naphth-1,2-ylene, and benzofuran-2,3-ylene), hydrogen atoms removed from two different rings of a ring system (e.g., naphth-1,8-ylene and benzofuran-2,7-ylene), or hydrogen atoms removed from two isolated aromatic rings or ring systems (e.g., bis(phen-4-ylene)methane).

An arene is an aromatic hydrocarbon, with or without side chains (e.g. benzene, toluene, or xylene, among others. An "aryl group" is a group derived from the formal removal of a hydrogen atom from an aromatic ring carbon of an arene. It should be noted that the arene can contain a single aromatic hydrocarbon ring (e.g., benzene, or toluene), contain fused aromatic rings (e.g., naphthalene or anthracene), and/or contain one or more isolated aromatic rings covalently linked via a bond (e.g., biphenyl) or non-aromatic hydrocarbon group(s) (e.g., diphenylmethane). One example of an "aryl group" is ortho-tolyl (o-tolyl), the structure of which is shown here.

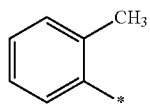 [SMILES: *c1ccccc1C]

Similarly, an "arylene group" refers to a group formed by removing two hydrogen atoms (at least one of which is from an aromatic ring carbon) from an arene. An "arene group" refers to a generalized group formed by removing one or more hydrogen atoms (as necessary for the particular group and at least one of which is an aromatic ring carbon) from an arene. However, if a group contains separate and distinct arene and heteroarene rings or ring systems (e.g. the phenyl and benzofuran moieties in 7-phenylbenzofuran) its classification depends upon the particular ring or ring system from which the hydrogen atom was removed, that is, an arene group if the removed hydrogen came from the aromatic hydrocarbon ring or ring system carbon atom (e.g. the 2 carbon atom in the phenyl group of 6-phenylbenzofuran) and a heteroarene group if the removed hydrogen carbon came from a heteroaromatic ring or ring system carbon atom (e.g. the 2 or 7 carbon atom of the benzofuran group or 6-phenylbenzofuran). It should be noted that according the definitions provided herein, general arene groups (including an aryl group and an arylene group) include those having zero, one, or more than one hydrocarbyl substituent groups located on an aromatic hydrocarbon ring or ring system carbon atom (e.g. a toluene group or a xylene group, among others) and is a member of the group of hydrocarbon groups. However, a phenyl group (or phenylene group) and/or a naphthyl group (or naphthylene group) refer to the specific unsubstituted arene groups (including no hydrocarbyl group located on an aromatic hydrocarbon ring or ring system carbon atom). Consequently, a substituted phenyl group or substituted naphthyl group refers to the respective arene group having one or more substituent groups (including halogens, hydrocarbyl groups, or hydrocarboxy groups, among others) located on an aromatic hydrocarbon ring or ring system carbon atom. When the substituted phenyl group and/or substituted naphtyl group is a member of the group of hydrocarbon groups (or a member of the general group of arene groups), each substituent is limited to a hydrocarbyl substituent group. One having ordinary skill in the art can readily discern and select general phenyl and/or naphthyl groups, specific phenyl and/or naphthyl groups, and/or individual substituted phenyl or substituted naphthyl groups which can be utilized as a member of the group of hydrocarbon groups (or a member of the general group of arene groups).

An "aralkyl group" is an aryl-substituted alkyl group having a free valance at a non-aromatic carbon atom (e.g. a benzyl group, or a 2-phenyleth-1yl group, among others). Similarly, an "aralkylene group" is an aryl-substituted alkylene group having two free valencies at a single non-aromatic carbon atom or a free valence at two non-aromatic carbon atoms while an "aralkane group" is a generalized aryl-substituted alkane group having one or more free valencies at a non-aromatic carbon atom(s). A "heteroaralkyl group" is a heteroaryl-substituted alkyl group having a free valence at a non-heteroaromatic ring or ring system carbon atom. Similarly a "heteroaralkylene group" is a heteroaryl-substituted alkylene group having two free valencies at a single non-heteroaromatic ring or ring system carbon atom or a free valence at two non-heteroaromatic ring or ring system carbon atoms while a "heteroaralkane group" is a generalized aryl-substituted alkane group having one or more free valencies at a non-heteroaromatic ring or ring system carbon atom(s). It should be noted that according the definitions provided herein, general aralkane groups include those having zero, one, or more than one hydrocarbyl substituent groups located on an aralkane aromatic hydrocarbon ring or ring system carbon atom and is a member of the group of hydrocarbon groups. However, specific aralkane groups specifying a particular aryl group (e.g. the phenyl group in a benzyl group or a 2-phenylethyl group, among others) refer to the specific unsubstituted aralkane groups (including no hydrocarbyl group located on the aralkane aromatic hydrocarbon ring or ring system carbon atom). Consequently, a substituted aralkane group specifying a particular aryl group refers to a respective aralkane group having one or more substituent groups (including halogens, hydrocarbyl groups, or hydrocarboxy groups, among others). When the substituted aralkane group specifying a particular aryl group is a member of the group of hydrocarbon groups (or a member of the general group of aralkane groups), each substituent is limited to a hydrocarbyl substituent group. One can readily discern and select substituted aralkane groups specifying a particular aryl group which can be utilized as a member of the group of hydrocarbon groups (or a member of the general group of aralkane groups).

A "halide" has its usual meaning; therefore, examples of halides include fluoride, chloride, bromide, and iodide.

Within this disclosure the normal rules of organic nomenclature will prevail. For instance, when referencing substituted compounds or groups, references to substitution patterns are taken to indicate that the indicated group(s) is (are) located at the indicated position and that all other non-indicated positions are hydrogen. For example, reference to a 4-substituted phenyl group indicates that there is a non-hydrogen substituent located at the 4 position and hydrogens located at the 2, 3, 5, and 6 positions. By way of another example, reference to a 3-substituted naphth-2-yl indicates that there is a non-hydrogen substituent located at the 3 position and hydrogens located at the 1, 4, 5, 6, 7, and 8 positions. References to compounds or groups having substitutions at positions in addition to the indicated position will be referenced using comprising or some other alternative language. For example, a reference to a phenyl group comprising a substituent at the 4 position refers to a group having a non-hydrogen atom at the 4 position and hydrogen or any non-hydrogen group at the 2, 3, 5, and 6 positions.

Unless specified otherwise, the terms contacted, combined, and "in the presence of" refer to any addition sequence, order, or concentration for contacting or combining two or more components of the oligomerization process. Combining or contacting of the metal complex, hydrogen-boron bond containing compound and alkene, according to the various methods described herein can occur in one or more contact zones under suitable contact conditions such as temperature, pressure, contact time, flow rates, etc. . . . The contact zone can be disposed in a vessel (e.g. a storage tank, tote, container, mixing vessel, reactor, etc.), a length of pipe (e.g. a tee, inlet, injection port, or header for combining component feed lines into a common line), or any other suitable apparatus for bringing the components into contact. The processes can be carried out in a batch or continuous process as is suitable for a given embodiment, with physical parameters of the contact zone being specified accordingly.

Generally, the present application is directed to processes for and/or including the hydroboration of an olefin using a metal complex. In an aspect the present application is directed to using $N^2$-phosphinyl amidine metal complexes, $N^2$-phosphinyl formamidine complexes, and $N^2$-phosphinyl guanidine metal complexes for hydroborating an alkene. In an aspect, the present application is directed to a process comprising: contacting an alkene, a hydrogen-boron bond containing compound, and a metal complex selected from the group consisting of an $N^2$-phosphinyl amidine metal complex, an $N^2$-phosphinyl formamidine complex, and an $N^2$-phosphinyl guanidine metal complex under conditions suitable to form an alkylboron compound. In another aspect, the present application is directed to a process comprising: contacting a linear internal alkene, a hydrogen-boron bond containing compound, a metal complex selected from the group consisting of an $N^2$-phosphinyl amidine metal complex, an $N^2$-phosphinyl formamidine complex, and an $N^2$-phosphinyl guanidine metal complex under conditions suitable to form a terminal alkylboron compound. The metal complexes, olefin and/or alkenes, hydrogen-boron bond containing compounds, alkylboron compounds, conditions capable of forming alkylboron compounds, conditions capable of forming terminal alkylboron compounds, and other process features are independently described herein. These independently described features can be utilized in any combination and without limitation to further describe the processes described herein. It should be noted that while these features can be disclosed under headings within this application, a heading does not limit the disclosure found therein. Additionally the various aspects and embodiments disclosed herein can be combined in any manner.

Metal Complexes

Generally, the metal complexes utilized in the processes described herein are prepared from a metal compound and an $N^2$-phosphinyl amidine, an $N^2$-phosphinyl formamidine, or an $N^2$-phosphinyl guanidine to form a metal compound complexed to an anionic form of the $N^2$-phosphinyl amidine, anionic $N^2$-phosphinyl formamidine, or anionic $N^2$-phosphinyl guanidine. While not wishing to be bound by theory, it is believed that the double bond of the $N^2$-phosphinyl amidine, the $N^2$-phosphinyl formamidine, or the $N^2$-phosphinyl guanidine can shift to the nitrogen atom bearing the phosphinyl group during the preparation of the metal complex (as shown in the structure herein). Consequently, via the naming convention described herein for the amidine, formamidine, and guanidine compounds, the phosphinyl group would be on the $N^1$ nitrogen atom amidine, formamide, and guanidine nitrogen atom of the amidine, formamide, and/or guanidine ligand of the metal complex. However, even though it is believed that the double bond has changed position (without being limited to theory) and the ligand name, according to the the naming convention described herein, should be changed, these metal complexes will be referred to herein as an $N^2$-phosphinyl amidine metal complex, an $N^2$-phosphinyl formamidine complex, and an $N^2$-phosphinyl guanidine metal complex (and the nitrogen atoms will retain the numbering convention of the amidine, formamidine, and guanidine compounds) in recognition of the starting form of the ligand utilized to form the metal complexes.

In an aspect, the metal complex can comprise, consist essentially of, or consist of a metal complex selected from the group consisting of a metal complex selected from the group consisting of an $N^2$-phosphinyl amidine metal complex, an $N^2$-phosphinyl formamidine complex, and an $N^2$-phosphinyl guanidine metal complex. In an embodiment the can comprise, consist essentially of, or consist of an $N^2$-phosphinyl amidine metal complex; alternatively, an $N^2$-phosphinyl formamidine complex; or alternatively, an $N^2$-phosphinyl guanidine metal complex. Further aspects and/or embodiments of the $N^2$-phosphinyl amidine metal complexes, an $N^2$-phosphinyl formamidine complexes, and an $N^2$-phosphinyl guanidine metal complexes, are described herein and can be utilized, without limitation, to further described the metal complexes utilized in the process described herein.

Metal Complexes

In an aspect, the $N^2$-phosphinyl formamidine metal complex which can be utilized in an aspect and/or embodiment disclosed herein can have Structure NPFMC1.

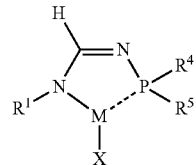

Structure NPFMC1

$R^1$, $R^4$, $R^5$, M and/or X within the $N^2$-phosphinyl formamidine metal complex Structure NPFMC1 are independently described herein and can be utilized without limitation to further describe the $N^2$-phosphinyl formamidine metal complex having Structure NPFMC1. In other embodiments, the $N^2$ phosphinyl formamidine metal complex can have any specific structure disclosed herein.

In an aspect, the $N^2$-phosphinyl amidine metal complex can have Structure NPAMC1.

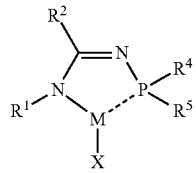

Structure NPAMC1

$R^1$, $R^2$, $R^4$, $R^5$, M and/or X within the $N^2$-phosphinyl formamidine metal complex Structure NPAMC1 are independently described herein and can be utilized without limitation to further describe the $N^2$-phosphinyl amidine metal complex having Structure NPAMC1. In other embodiments, the $N^2$-phosphinyl amidine metal complex can have any specific structure disclosed herein.

In an aspect, the $N^2$-phosphinyl guanidine metal complex can have Structure GuMC1, GuMC2, or GuMC3: alternatively, Structure GuMC1; alternatively, Structure GuMC2; or alternatively, Structure GuMC3.

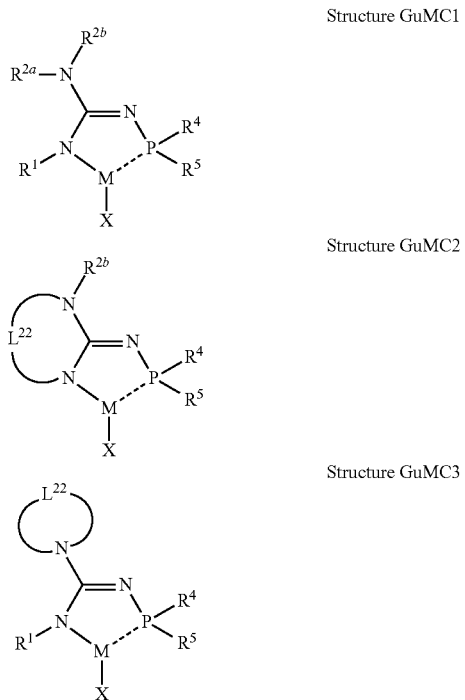

Structure GuMC1

Structure GuMC2

Structure GuMC3

$R^1$, $R^{2a}$, $R^{2b}$, $R^4$, $R^5$, $L^{12}$, $L^{22}$, M and/or X within $N^2$-phosphinyl guanidine metal complex Structures GuMC1, GuMC2, or GuMC3 are independently described herein and can be utilized without limitation to further describe the $N^2$-phosphinyl guanidine metal complexes having Structures GuMC1, GuMC2, or GuMC3. In other embodiments, the $N^2$-phosphinyl guanidine metal complex can have any specific structure disclosed herein.

It should be noted that within this application and claims the $N^2$-phosphinyl formamidine metal complexes having Structure NPFMC1, the $N^2$-phosphinyl amidine metal complexes having Structure NPAMC1, and/or the $N^2$-phosphinyl guanidine metal complexes having Structures GuMC1, GuMC2, or GuMC3 can include neutral ligands which are not shown in the structures. Further, any other general or specific $N^2$-phosphinyl formamidine metal complex, $N^2$-phosphinyl amidine metal complex, and/or $N^2$-phosphinyl guanidine metal complex provided in this application and claims may include neutral ligands which are not shown in their structures.

Generally, $R^1$ for the $N^2$-phosphinyl formamidine metal complexes, the $N^2$-phosphinyl amidine metal complexes, and/or the $N^2$-phosphinyl guanidine metal complexes can be an organyl group; alternatively, an organyl group consisting essentially of inert functional groups; or alternatively, a hydrocarbyl jfgroup. In an embodiment, the $R^1$ organyl group for the $N^2$-phosphinyl formamidine metal complexes, the $N^2$-phosphinyl amidine metal complexes, and/or the $N^2$-phosphinyl guanidine metal complexes can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, $R^1$ organyl group consisting essentially of inert functional groups for the $N^2$-phosphinyl formamidine metal complexes, the $N^2$-phosphinyl amidine metal complexes, and/or the $N^2$-phosphinyl guanidine metal complexes can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, the $R^1$ hydrocarbyl group for the $N^2$-phosphinyl formamidine metal complexes, the $N^2$-phosphinyl amidine metal complexes, and/or the $N^2$-phosphinyl guanidine metal complexes can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In yet other embodiments, the $R^1$ group for the $N^2$-phosphinyl formamidine metal complexes, the $N^2$-phosphinyl amidine metal complexes, and/or the $N^2$-phosphinyl guanidine metal complexes can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group.

In an aspect, $R^1$ for the $N^2$-phosphinyl formamidine metal complexes, the $N^2$-phosphinyl amidine metal complexes, and/or the $N^2$-phosphinyl guanidine metal complexes can be a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, or a $C_6$ to $C_{30}$ substituted aryl group; alternatively, a $C_4$ to $C_{30}$ cycloalkyl group or a $C_4$ to $C_{30}$ substituted cycloalkyl group; alternatively, a $C_6$ to $C_{30}$ aryl group or a $C_6$ to $C_{30}$ substituted aryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_6$ to $C_{30}$ aryl group; or alternatively, a $C_6$ to $C_{30}$ substituted aryl group. In an embodiment, $R^1$ for the $N^2$-phosphinyl formamidine metal complexes, the $N^2$-phosphinyl amidine metal complexes, and/or the $N^2$-phosphinyl guanidine metal complexes can be a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; alternatively, a $C_4$ to $C_{20}$ cycloalkyl group or a $C_4$ to $C_{20}$ substituted cycloalkyl group; alternatively, a $C_6$ to $C_{20}$ aryl group or a $C_6$ to $C_{20}$ substituted aryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_6$ to $C_{20}$ aryl group; or alternatively, a $C_6$ to $C_{20}$ substituted aryl group. In other embodiments, $R^1$ for the $N^2$-phosphinyl formamidine metal complexes, the $N^2$-phosphinyl amidine metal complexes, and/or the $N^2$-phosphinyl guanidine metal complexes can be a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, or a $C_6$ to $C_{15}$ substituted aryl group; alternatively, a $C_4$ to $C_{15}$ cycloalkyl group or a $C_4$ to $C_{15}$ substituted cycloalkyl group; alternatively, a $C_6$ to $C_{15}$ aryl group or a $C_6$ to $C_{15}$ substituted aryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_6$ to $C_{15}$ aryl group; or alternatively, a $C_6$ to $C_{15}$ substituted aryl group. In further embodiments, $R^1$ for the $N^2$-phosphinyl formamidine metal complexes, the $N^2$-phosphinyl amidine metal complexes, and/or the $N^2$-phosphinyl guanidine metal complexes can be a $C_1$ to $C_5$ alkyl group. Substituents (general and specific) are independently disclosed herein and can be utilized without limitation to further describe substituted groups which can be utilized as $R^1$ for the $N^2$-phosphinyl formamidine metal complexes, the $N^2$-phosphinyl amidine metal complexes, and/or the $N^2$-phosphinyl guanidine metal complexes.

In an embodiment, $R^1$ for the $N^2$-phosphinyl formamidine metal complexes, the $N^2$-phosphinyl amidine metal complexes, and/or the $N^2$-phosphinyl guanidine metal complexes can be a methyl group, an ethyl group, a propyl group, a butyl group, a pentyl group, a hexyl group, a heptyl group, an octyl group, a nonyl group, or a decyl group. In some embodiments, $R^1$ for the $N^2$-phosphinyl formamidine metal complexes, the $N^2$-phosphinyl amidine metal complexes, and/or the $N^2$-phosphinyl guanidine metal complexes can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, the alkyl groups which can be utilized as $R^1$ for the $N^2$-phosphinyl formamidine metal complexes, the $N^2$-phosphinyl amidine metal complexes, and/or the $N^2$-phosphinyl guanidine metal complexes can be substituted. Each substituent of a substituted alkyl group independently can be a halogen or a hydrocarboxy group; alternatively, a halogen; or alternatively, a hydrocarboxy group. Halogens and hydrocarboxy groups (general and specific) that can be utilized as substituents are independently disclosed herein and can be utilized without limitation to further describe the substituted alkyl group which can be utilized as $R^1$ for the $N^2$-phosphinyl formamidine metal complexes, the $N^2$-phosphinyl amidine metal complexes, and/or the $N^2$-phosphinyl guanidine metal complexes.

In an embodiment, $R^1$ for the $N^2$-phosphinyl formamidine metal complexes, the $N^2$-phosphinyl amidine metal complexes, and/or the $N^2$-phosphinyl guanidine metal complexes can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^1$ for the $N^2$-phosphinyl formamidine metal complexes, the $N^2$-phosphinyl amidine metal complexes, and/or the $N^2$-phosphinyl guanidine metal complexes can be a cyclopentyl group, a substituted cyclopentyl group, a cyclohexyl group, or a substituted cyclohexyl group. In other embodiments, $R^1$ for the $N^2$-phosphinyl formamidine metal complexes, the $N^2$-phosphinyl amidine metal complexes, and/or the $N^2$-phosphinyl guanidine metal complexes can be a cyclopentyl group or a substituted cyclopentyl group; or alternatively, a cyclohexyl group or a substituted cyclohexyl group. In further embodiments, $R^1$ for the $N^2$-phosphinyl formamidine metal complexes, the $N^2$-phosphinyl amidine metal complexes, and/or the $N^2$-phosphinyl guanidine metal complexes can be a cyclopentyl group; alternatively, a substituted cyclopentyl group; a cyclohexyl group; or alternatively, a substituted cyclohexyl group. Substituents (general and specific) are independently disclosed herein and can be utilized without limitation to further describe the substituted cycloalkyl group which can be utilized as $R^1$ for the $N^2$-phos-phinyl formamidine metal complexes, the $N^2$-phosphinyl amidine metal complexes, and/or the $N^2$-phosphinyl guanidine metal complexes.

In an aspect, $R^1$ for the $N^2$-phosphinyl formamidine metal complexes, the $N^2$-phosphinyl amidine metal complexes, and/or the $N^2$-phosphinyl guanidine metal complexes can have Structure G1:

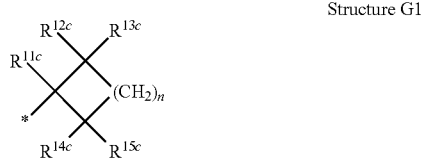

Structure G1 wherein the undesignated valency is attached to the $N^1$ nitrogen atom of the $N^2$-phosphinyl formamidine metal complex, the $N^2$-phosphinyl amidine metal complex, and/or the $N^2$-phosphinyl guanidine metal complex. Generally, $R^{11c}$, $R^{12c}$, $R^{13c}$, $R^{14c}$, and $R^{15c}$ can independently be hydrogen or a non-hydrogen substituent, and n can be an integer from 1 to 5. In an embodiment wherein $R^1$ for the $N^2$-phosphinyl formamidine metal complexes, the $N^2$-phosphinyl amidine metal complexes, and/or the $N^2$-phosphinyl guanidine metal complexes has Structure G1, $R^{11c}$, $R^{13c}$, $R^{14c}$, and $R^{15c}$ can be hydrogen and $R^{12c}$ can be any non-hydrogen substituent disclosed herein; or alternatively, $R^{11c}$, $R^{13c}$, and $R^{15c}$ can be hydrogen and $R^{12c}$ and $R^{14c}$ independently can be any non-hydrogen substituent disclosed herein. In an embodiment, n for Structure G1 can be an integer from 1 to 4; or alternatively, from 2 to 4. In other embodiments, n for Structure G1 can be 2 or 3; alternatively, 2; or alternatively 3. Substituents (general and specific) are independently disclosed herein and can be utilized without limitation to further describe a non-hydrogen substituent which can be utilized without limitation as $R^{11c}$, $R^{12c}$, $R^{13c}$, $R^{14c}$, and/or $R^{15c}$ for the $R^1$ having Structure G1 for the $N^2$-phosphinyl formamidine metal complexes, the $N^2$-phosphinyl amidine metal complexes, and/or the $N^2$-phosphinyl guanidine metal complexes group.

In an embodiment wherein $R^1$ for the $N^2$-phosphinyl formamidine metal complexes, the $N^2$-phosphinyl amidine metal complexes, and/or the $N^2$-phosphinyl guanidine metal complexes has Structure G1, $R^{11c}$, $R^{13c}$, $R^{14c}$, and $R^{15c}$ can be hydrogen and $R^{12c}$ can be any non-hydrogen substituent indicated herein; or alternatively, $R^{11c}$, $R^{13c}$, and $R^{15c}$ can be hydrogen and $R^{12c}$ and $R^{14c}$ can be any non-hydrogen substituent indicated herein. In some embodiments, wherein $R^1$ for the $N^2$-phosphinyl formamidine metal complexes, the $N^2$-phosphinyl amidine metal complexes, and/or the $N^2$-phosphinyl guanidine metal complexes has Structure G1, $R^{11c}$, $R^{13c}$, $R^{14c}$, and $R^{15c}$ can be hydrogen and $R^{12c}$ can be any alkyl group, alkoxy group, or halogen indicated herein; or alternatively, $R^{11c}$, $R^{13c}$, and $R^{15c}$ can be hydrogen and $R^{12c}$ and $R^{14c}$ can be any alkyl group, alkoxy group, or halogen indicated herein. In other embodiments, wherein $R^1$ for the $N^2$-phosphinyl formamidine metal complexes, the $N^2$-phosphinyl amidine metal complexes, and/or the $N^2$-phosphinyl guanidine metal complexes has Structure G1, $R^{11c}$, $R^{13c}$, $R^{14c}$, and $R^{15c}$ can be hydrogen and $R^{12c}$ can be any alkyl group substituent indicated herein; or alternatively, $R^{11c}$, $R^{13c}$, and $R^{15c}$ can be hydrogen and $R^{12c}$ and $R^{14c}$ can be any alkyl group substituent indicated herein. In another embodiment wherein $R^1$ for the $N^2$-phosphinyl formamidine metal complexes, the $N^2$-phosphinyl amidine metal complexes, and/or the $N^2$-phosphinyl guanidine metal complexes has Structure G1, $R^{11c}$, $R^{12c}$, $R^{13c}$, $R^{14c}$, and $R^{15c}$ can be hydrogen. In an embodiment, $R^{11c}$, $R^{12c}$, $R^{13c}$, $R^{14c}$, and $R^{15c}$ independently can be hydrogen, or an alkyl group; alternatively, $R^{11c}$, $R^{12c}$, and $R^{14c}$ can be hydrogen and $R^{13c}$ and $R^{15c}$ can be are alkyl groups; or alternatively, $R^{11c}$ can be hydrogen and $R^{12c}$, $R^{13c}$, $R^{14c}$, and $R^{15c}$ can be alkyl groups. Specific substituent halogens, hydrocarbyl groups, hydrocarboxy groups, alkyl group, and alkoxy groups are independently disclosed herein and can be utilized without limitation to further describe the $R^1$ group having Structure G1 for the $N^2$-phosphinyl formamidine metal complexes, the $N^2$-phosphinyl amidine metal complexes, and/or the $N^2$-phosphinyl guanidine metal complexes.

In an aspect, $R^1$ for the $N^2$-phosphinyl formamidine metal complexes, the $N^2$-phosphinyl amidine metal complexes, and/or the $N^2$-phosphinyl guanidine metal complexes can be a phenyl group, a substituted phenyl group; phenyl group; or alternatively, a substituted phenyl group. In an embodiment, the $R^1$ substituted phenyl group can be a 2-substituted phenyl group, a 3-substituted phenyl group, a 4-substituted phenyl group, a 2,4 disubstituted phenyl group, a 2,6-disubstituted phenyl group, 3,5-disubstituted phenyl group, or a 2,4,6-trisubstituted phenyl group. In other embodiments, the $R^1$ substituted phenyl group for the $N^2$-phosphinyl formamidine metal complexes, the $N^2$-phosphinyl amidine metal complexes, and/or the $N^2$-phosphinyl guanidine metal complexes can be a 2-substituted phenyl group, a 4-substituted phenyl group, a 2,4-disubstituted phenyl group, a 2,6-di-substituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2 substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-di-substituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3 substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents (general and specific) are independently disclosed herein and can be utilized without limitation to further describe any substituted phenyl group which can be utilized as $R^1$ for the $N^2$-phosphinyl formamidine metal complexes, the $N^2$-phosphinyl amidine metal complexes, and/or the $N^2$-phosphinyl guanidine metal complexes.

In an aspect, the $R^1$ for the $N^2$-phosphinyl formamidine metal complexes, the $N^2$-phosphinyl amidine metal complexes, and/or the $N^2$-phosphinyl guanidine metal complexes can have Structure G2:

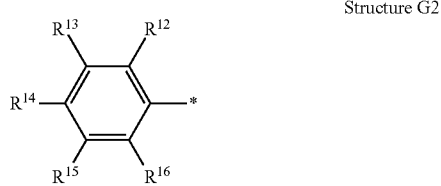

Structure G2 wherein the undesignated valency is attached to the $N^1$ nitrogen atom of the $N^2$-phosphinyl formamidine metal complex, the $N^2$-phosphinyl amidine metal complex, and/or the $N^2$-phosphinyl guanidine metal complex. Generally, $R^{12}$, $R^{13}$, $R^{14}$, $R^{15}$, and $R^{16}$ independently can be hydrogen or a non-hydrogen substituent. In an embodiment wherein $R^1$ for the $N^2$-phosphinyl formamidine metal complexes, the $N^2$-phosphinyl amidine metal complexes, and/or the $N^2$-phosphinyl guanidine metal complexes has Structure G2, $R^{12}$, $R^{13}$, $R^{14}$, $R^{15}$, and $R^{16}$ can be hydrogen, $R^{13}$, $R^{14}$, $R^{15}$, and $R^{16}$ can be hydrogen and $R^{12}$ can be a non-hydrogen substituent, $R^{12}$, $R^{14}$, $R^{15}$, and $R^{16}$ can be hydrogen and $R^{13}$ can be a non-hydrogen substituent, $R^{12}$, $R^{13}$, $R^{15}$, and $R^{16}$ can be hydrogen and $R^{14}$ can be a non-hydrogen substituent, $R^{13}$, $R^{15}$, and $R^{16}$ can be hydrogen and $R^{12}$ and $R^{14}$ can be non-hydrogen substituents, $R^{13}$, $R^{14}$, and $R^{15}$ can be hydrogen and $R^{12}$ and $R^{16}$ can be non-hydrogen substituents, $R^{12}$, $R^{14}$, and $R^{16}$ can be hydrogen and $R^{13}$ and $R^{15}$ can be non-hydrogen substituents, or $R^{13}$ and $R^{15}$ can be hydrogen and $R^{12}$, $R^{14}$, and $R^{16}$ can be non-hydrogen substituents. In some embodiments wherein $R^1$ for the $N^2$-phosphinyl formamidine metal complexes, the $N^2$-phosphinyl amidine metal complexes, and/or the $N^2$-phosphinyl guanidine metal complexes has Structure G2, $R^{13}$, $R^{14}$, $R^{15}$, and $R^{16}$ can be hydrogen and $R^{12}$ can be a non-hydrogen substituent, $R^{12}$, $R^{13}$, $R^{15}$, and $R^{16}$ can be hydrogen and $R^{14}$ can be a non-hydrogen substituent, $R^{13}$, $R^{15}$, and $R^{16}$ can be hydrogen and $R^{12}$ and $R^{14}$ can be non-hydrogen substituents, $R^{13}$, $R^{14}$, and $R^{15}$ can be hydrogen and $R^{12}$ and $R^{16}$ can be non-hydrogen substituents, or $R^{13}$ and $R^{15}$ can be hydrogen and $R^{12}$, $R^{14}$, and $R^{16}$ can be non-hydrogen substituents; alternatively, $R^{13}$, $R^{14}$, $R^{15}$, and $R^{16}$ can be hydrogen and $R^{12}$ can be a non-hydrogen substituent, $R^{12}$, $R^{13}$, $R^{15}$, and $R^{16}$ can be hydrogen and $R^{14}$ can be a non-hydrogen substituent, $R^{13}$, $R^{15}$, and $R^{16}$ can be hydrogen and $R^{12}$ and $R^{14}$ can be non-hydrogen substituents, or $R^{13}$, $R^{14}$, and $R^{15}$ can be hydrogen and $R^{12}$ and $R^{16}$ can be non-hydrogen substituents; alternatively, $R^{12}$, $R^{14}$, $R^{15}$, and $R^{16}$ can be hydrogen and $R^{13}$ can be a non-hydrogen substituent, or $R^{12}$, $R^{14}$, and $R^{16}$ can be hydrogen and $R^{13}$ and $R^{15}$ can be non-hydrogen substituents; alternatively, $R^{13}$, $R^{14}$, $R^{15}$, and $R^{16}$ can be hydrogen and $R^{12}$ can be a non-hydrogen substituent, or $R^{12}$, $R^{13}$, $R^{15}$, and $R^{16}$ can be hydrogen and $R^{14}$ can be a non-hydrogen substituent; alternatively, $R^{13}$, $R^{15}$, and $R^{16}$ can be hydrogen and $R^{12}$ and $R^{14}$ can be non-hydrogen substituents, $R^{13}$, $R^{14}$, and $R^{15}$ can be hydrogen and $R^{12}$ and $R^{16}$ can be non-hydrogen substituents, or $R^{13}$ and $R^{15}$ can be hydrogen and $R^{12}$, $R^{14}$, and $R^{16}$ can be non-hydrogen substituents; or alternatively, $R^{13}$, $R^{15}$, and $R^{16}$ can be hydrogen and $R^{12}$ and $R^{14}$ can be non-hydrogen substituents, or $R^{13}$, $R^{14}$, and $R^{15}$ can be hydrogen and $R^{12}$ and $R^{16}$ can be non-hydrogen substituents. In other embodiments wherein $R^1$ for the $N^2$-phosphinyl formamidine metal complexes, the $N^2$-phosphinyl amidine metal complexes, and/or the $N^2$-phosphinyl guanidine metal complexes has Structure G2, $R^{12}$, $R^{13}$, $R^{14}$, $R^{15}$, and $R^{16}$ can be hydrogen; alternatively, $R^{13}$, $R^{14}$, $R^{15}$, and $R^{16}$ can be hydrogen and $R^{12}$ can be a non-hydrogen substituent; alternatively, $R^{12}$, $R^{14}$, $R^{15}$, and $R^{16}$ can be hydrogen and $R^{13}$ can be a non-hydrogen substituent; alternatively, $R^{12}$, $R^{13}$, $R^{15}$, and $R^{16}$ can be hydrogen and $R^{14}$ can be a non-hydrogen substituent; alternatively, $R^{13}$, $R^{15}$ and $R^{16}$ can be hydrogen and $R^{12}$ and $R^{14}$ can be non-hydrogen substituents; alternatively, $R^{13}$, $R^{14}$, and $R^{15}$ can be hydrogen and $R^{12}$ and $R^{16}$ can be non-hydrogen substituents; alternatively, $R^{12}$, $R^{14}$, and $R^{16}$ can be hydrogen and $R^{13}$ and $R^{15}$ can be non-hydrogen substituents; or alternatively, $R^{13}$ and $R^{15}$ can be hydrogen and $R^{12}$, $R^{14}$, and $R^{16}$ can be non-hydrogen substituents. Substituents (general and specific) are independently disclosed herein and can be utilized without limitation as $R^{12}$, $R^{13}$, $R^{14}$, $R^{15}$, and $R^{16}$ for the $R^1$ group having Structure G2 for the $N^2$-phosphinyl formamidine metal complexes, the $N^2$-phosphinyl amidine metal complexes, and/or the $N^2$-phosphinyl guanidine metal complexes.

In an embodiment, when the $N^1$ nitrogen atom of the $N^2$-phosphinyl formamidine metal complex, $N^2$-phosphinyl amidine metal complex, and/or $N^2$-phosphinyl guanidine metal complex is attached to a carbon atom of a cycloalkane or arene ring or ring system, the cyclic $R^1$ group for the $N^2$-phosphinyl formamidine metal complexes, the $N^2$-phosphinyl amidine metal complexes, and/or the $N^2$-phosphinyl guanidine metal complexes can comprise at least one substituent located on a carbon atom adjacent to the carbon atom attached to $N^1$ nitrogen atom of the $N^2$-phosphinyl formamidine metal complex, $N^2$-phosphinyl amidine metal complex, and/or $N^2$-phosphinyl guanidine metal complex. In some embodiments, when the $N^1$ nitrogen atom of the $N^2$-phosphinyl formamidine metal complex, $N^2$-phosphinyl amidine metal complex, and/or $N^2$-phosphinyl guanidine metal complex is attached to a carbon atom of a cycloalkane or arene ring or ring system, the cyclic $R^1$ group for the $N^2$-phosphinyl formamidine metal complexes, the $N^2$-phosphinyl amidine metal complexes, and/or the $N^2$-phosphinyl guanidine metal complexes can comprise at least one substituent located on each carbon atom adjacent to the carbon atom attached to $N^1$ nitrogen atom of the $N^2$-phosphinyl formamidine metal complex, $N^2$-phosphinyl amidine metal complex, and/or $N^2$-phosphinyl guanidine metal complex. In another embodiment, when the $N^1$ nitrogen atom of the $N^2$-phosphinyl formamidine metal complex, $N^2$-phosphinyl amidine metal complex, and/or $N^2$-phosphinyl guanidine metal complex is attached to a carbon atom of a cycloalkane or arene ring or ring system, the cyclic $R^1$ group for the $N^2$-phosphinyl formamidine metal complexes, the $N^2$-phosphinyl amidine metal complexes, and/or the $N^2$-phosphinyl guanidine metal complexes can consist of one substituent located on each carbon atom adjacent to the carbon atom attached to $N^1$ nitrogen atom of the $N^2$-phosphinyl formamidine metal complex, $N^2$-phosphinyl amidine metal complex, and/or $N^2$-phosphinyl guanidine metal complex. In other embodiments, when the $N^1$ nitrogen atom of the $N^2$-phosphinyl formamidine metal complex, $N^2$-phosphinyl amidine metal complex, and/or $N^2$-phosphinyl guanidine metal complex is attached to a carbon atom of a cycloalkane or arene ring or ring system, the cyclic $R^1$ group for the $N^2$-phosphinyl formamidine metal complexes, the $N^2$-phosphinyl amidine metal complexes, and/or the $N^2$-phosphinyl guanidine metal complexes can comprise only one substituent located on a carbon atom adjacent to the carbon atom attached to $N^1$ nitrogen atom of the $N^2$-phosphinyl formamidine metal complex, $N^2$-phosphinyl amidine metal complex, and/or $N^2$-phosphinyl guanidine metal complex. In another embodiment, when the $N^1$ nitrogen atom of the $N^2$-phosphinyl formamidine metal complex, $N^2$-phosphinyl amidine metal complex, and/or $N^2$-phosphinyl guanidine metal complex is attached to a carbon atom of a cycloalkane or arene ring or ring system, the cyclic $R^1$ group for the $N^2$-phosphinyl formamidine metal complexes, the $N^2$-phosphinyl amidine metal complexes, and/or the $N^2$-phosphinyl guanidine metal complexes can comprise only one substituent located on each carbon atom adjacent to the carbon atom attached to $N^1$ nitrogen atom of the $N^2$-phosphinyl formamidine metal complex, $N^2$-phosphinyl amidine metal complex, and/or $N^2$-phosphinyl guanidine metal complex. In yet another embodiment, when the $N^1$ nitrogen atom of the $N^2$-phosphinyl formamidine group is attached to a carbon atom of a cycloalkane or arene ring or ring system, the cyclic $R^1$ group for the $N^2$-phosphinyl formamidine metal complexes, the $N^2$-phosphinyl amidine metal complexes, and/or the $N^2$-phosphinyl guanidine metal complexes can consist of only one substituent located on each carbon atom adjacent to the carbon atom attached to $N^1$ nitrogen atom of the $N^2$-phosphinyl formamidine metal complex, $N^2$-phosphinyl amidine metal complex, and/or $N^2$-phosphinyl guanidine metal complex.

In a non-limiting embodiment, $R^1$ for the $N^2$-phosphinyl formamidine metal complexes, the $N^2$-phosphinyl amidine metal complexes, and/or the $N^2$-phosphinyl guanidine metal complexes can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6-dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In other non-limiting embodiments, $R^1$ for the $N^2$-phosphinyl formamidine metal complexes, the $N^2$-phosphinyl amidine metal complexes, and/or the $N^2$-phosphinyl guanidine metal complexes can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl group substituents (general and specific) are independently described herein and can be utilized, without limitation, to further describe the alkylphenyl, dialkylphenyl, trialkylphenyl, alkylcyclohexyl, dialkylcyclohexyl, alkylcyclopentyl, or dialkylcyclopentyl groups that can be utilized $R^1$ for the $N^2$-phosphinyl formamidine metal complexes, the $N^2$-phosphinyl amidine metal complexes, and/or the $N^2$-phosphinyl guanidine metal complexes. Generally, the alkyl substituents of a dialkyl or trialkyl phenyl, cyclohexyl, or cyclopentyl group can be the same; or alternatively, the alkyl substituents of a dialkyl or trialkyl phenyl, cyclohexyl, or cyclopentyl group can be different.

In another non-limiting embodiment, $R^1$ for the $N^2$-phosphinyl formamidine metal complexes, the $N^2$-phosphinyl amidine metal complexes, and/or the $N^2$-phosphinyl guanidine metal complexes can be a phenyl group, a 2-alkoxyphenyl group, a 3-alkoxyphenyl group, a 4-alkoxyphenyl group, or a 3,5-dialkoxyphenyl group; alternatively, a 2-alkoxyphenyl group or a 4-alkoxyphenyl group; alternatively, a 3-alkoxyphenyl group or a 3,5-dialkoxyphenyl group; alternatively, a 2-alkoxyphenyl group; alternatively, a 3-alkoxyphenyl group; alternatively, a 4-alkoxyphenyl group; alternatively, a 3,5-dialkoxyphenyl group. Alkoxy group substituents (general and specific) are independently described herein and can be utilized, without limitation, to further describe the alkoxyphenyl or dialkoxyphenyl groups that can be utilized $R^1$ for the $N^2$-phosphinyl formamidine metal complexes, the $N^2$-phosphinyl amidine metal complexes, and/or the $N^2$-phosphinyl guanidine metal complexes. Generally, the alkoxy substituents of a dialkoxyphenyl group can be the same; or alternatively, the alkoxy substituents of a dialkoxyphenyl group can be different.

In other non-limiting embodiments, $R^1$ for the $N^2$-phosphinyl formamidine metal complexes, the $N^2$-phosphinyl amidine metal complexes, and/or the $N^2$-phosphinyl guanidine metal complexes can be a phenyl group, a 2-halophenyl group, a 3-halo-phenyl group, a 4-halophenyl group, a 2,6-dihalophenyl group, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenyl group; or alternatively, a 3,5-dihalophenyl group. Halides are independently described herein and can be utilized, without limitation, to further describe the halophenyl or dihalophenyl groups that can be utilized as $R^1$ for the $N^2$-phosphinyl formamidine metal complexes, the $N^2$-phosphinyl amidine metal complexes, and/or the $N^2$-phosphinyl guanidine metal complexes. Generally, the halides of a dihalophenyl group can be the same; or alternatively, the halides of a dihalophenyl group can be different.

In a non-limiting embodiment, $R^1$ for the $N^2$-phosphinyl formamidine metal complexes, the $N^2$-phosphinyl amidine metal complexes, and/or the $N^2$-phosphinyl guanidine metal complexes can be a 2-methylphenyl group, a 2-ethylphenyl group, a 2-n-propylphenyl group, a 2-isopropylphenyl group, a 2-tert-butylphenyl group, a 3-methylphenyl group, a 2,6-dimethylphenyl group, a 2,6-diethylphenyl group, a 2,6-di-n-propylphenyl group, a 2,6-diisopropyl-phenyl group, a 2,6-di-tert-butylphenyl group, a 2-isopropyl-6-methylphenyl group, a 3,5-dimethyl group, or a 2,4,6-trimethylphenyl group; alternatively, a 2-methylphenyl group, a 2-ethylphenyl group, a 2-n-propylphenyl group, a 2-isopropylphenyl group, or a 2-tert-butylphenyl group; alternatively, a 2,6-dimethylphenyl group, a 2,6-diethylphenyl group, a 2,6-di-n-propylphenyl group, a 2,6-diisopropyl-phenyl group, a 2,6-di-tert-butylphenyl group, or a 2-isopropyl-6-methylphenyl group; alternatively, a 2-methylphenyl group; alternatively, a 2-ethylphenyl group; alternatively, a 2-n-propylphenyl group; alternatively, a 2-isopropylphenyl group; alternatively, a 2-tert-butylphenyl group; alternatively, a 3-methylphenyl group; alternatively, a 2,6-dimethylphenyl group; alternatively, a 2,6-diethylphenyl group; alternatively, a 2,6-di-n-propylphenyl group; alternatively, a 2,6-diisopropylphenyl group; alternatively, a 2,6-di-tert-butylphenyl group; alternatively, a 2-isopropyl-6-methylphenyl group; alternatively, a 3,5-dimethylphenyl group; or alternatively, a 2,4,6-trimethylphenyl group. In another non-limiting embodiment, $R^1$ for the $N^2$-phosphinyl formamidine metal complexes, the $N^2$-phosphinyl amidine metal complexes, and/or the $N^2$-phosphinyl guanidine metal complexes can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; alternatively, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group; alternatively, a 2-ethylcyclohexyl group; alternatively, a 2-isopropylcyclohexyl group; alternatively, a 2-tert-butylcyclohexyl group; alternatively, a 2,6-dimethylcyclohexyl group; alternatively, a 2,6-diethylcyclohexyl group; alternatively, a 2,6-diisopropylcyclohexyl group; or alternatively, a 2,6-di-tert-butylcyclohexyl group.

In a non-limiting embodiment, $R^1$ for the $N^2$-phosphinyl formamidine metal complexes, the $N^2$-phosphinyl amidine metal complexes, and/or the $N^2$-phosphinyl guanidine metal complexes can be a 3-methoxyphenyl group, a 3-ethoxyphenyl group, a 3-isopropoxyphenyl group, a 3-tert-butoxyphenyl group, a 4-methoxyphenyl group, a 4-ethoxyphenyl group, a 4-isopropoxyphenyl group, a 4-tert-butoxyphenyl group, a 3,5-dimethoxyphenyl group, a 3,5-diethoxyphenyl group, a 3,5-diisopropoxyphenyl group, or a 3,5-di-tert-butoxyphenyl group; alternatively, a 3-methoxyphenyl group, a 3-ethoxyphenyl group, a 3-isopropoxyphenyl group, or a 3-tert-butoxyphenyl group; alternatively, a 4-methoxyphenyl group, a 4-ethoxyphenyl group, a 4-isopropoxyphenyl group, or a 4-tert-butoxyphenyl group; or alternatively, a 3,5-dimethoxyphenyl group, a 3,5-diethoxyphenyl group, a 3,5-diisopropoxyphenyl group, or a 3,5-di-tert-butoxyphenyl group. In other non-limiting embodiments, $R^1$ for the $N^2$-phosphinyl formamidine metal complexes, the $N^2$-phosphinyl amidine metal complexes, and/or the $N^2$-phosphinyl guanidine metal complexes can be a 3-methoxyphenyl group; alternatively, a 3-ethoxyphenyl group; alternatively, a 3-isopropoxyphenyl group; alternatively, a 3-tert-butoxyphenyl group; alternatively, a 4-methoxyphenyl group; alternatively, a 4-ethoxyphenyl group; alternatively, a 4-isopropoxyphenyl group; alternatively, a 4-tert-butoxyphenyl group; alternatively, a 3,5-dimethoxyphenyl group; alternatively, a 3,5-diethoxyphenyl group; alternatively, a 3,5-diisopropoxyphenyl group; or alternatively, a 3,5-di-tert-butoxyphenyl group.

Generally, $R^2$ for the $N^2$-phosphinyl amidine metal complexes can be an organyl group; alternatively, an organyl group consisting essentially of inert functional groups; or alternatively, a hydrocarbyl group. In an embodiment, $R^2$ for the $N^2$-phosphinyl amidine metal complexes can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, $R^2$ for the $N^2$-phosphinyl amidine metal complexes can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, $R^2$ for the $N^2$-phosphinyl amidine metal complexes can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In yet other embodiments, $R^2$ for the $N^2$-phosphinyl amidine metal complexes can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group.

In an aspect, $R^2$ for the $N^2$-phosphinyl amidine metal complexes can be a $C_1$ to $C_{30}$ alkyl group, a $C_4$ to $C_{30}$ cycloalkyl group, a $C_4$ to $C_{30}$ substituted cycloalkyl group, a $C_5$ to $C_{30}$ cycloalkyl alkyl group, a $C_5$ to $C_{30}$ substituted cycloalkyl alkyl group, a $C_6$ to $C_{30}$ aryl group, a $C_6$ to $C_{30}$ substituted aryl group, a $C_7$ to $C_{30}$ aralkyl group, or a $C_7$ to $C_{30}$ substituted aralkyl group; alternatively, a $C_4$ to $C_{30}$ cycloalkyl group or a $C_4$ to $C_{30}$ substituted cycloalkyl group; alternatively, a $C_5$ to $C_{30}$ cycloalkyl alkyl group or a $C_5$ to $C_{30}$ substituted cycloalkyl alkyl group; alternatively, a $C_6$ to $C_{30}$ aryl group or a $C_6$ to $C_{30}$ substituted aryl group; alternatively, a $C_7$ to $C_{30}$ aralkyl group or a $C_7$ to $C_{30}$ substituted aralkyl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_5$ to $C_{30}$ cycloalkyl alkyl group; alternatively, a $C_5$ to $C_{30}$ substituted cycloalkyl alkyl group; alternatively, a $C_6$ to $C_{30}$ aryl group; alternatively, a $C_6$ to $C_{30}$ substituted aryl group; alternatively, a $C_7$ to $C_{30}$ aralkyl group; or alternatively, a $C_7$ to $C_{30}$ substituted aralkyl group. In an embodiment, $R^2$ for the $N^2$-phosphinyl amidine metal complexes can be a $C_1$ to $C_{15}$ alkyl group, a $C_4$ to $C_{20}$ cycloalkyl group, a $C_4$ to $C_{20}$ substituted cycloalkyl group, a $C_5$ to $C_{20}$ cycloalkyl alkyl group, a $C_5$ to $C_{20}$ substituted cycloalkyl alkyl group, a $C_6$ to $C_{20}$ aryl group, or a $C_6$ to $C_{20}$ substituted aryl group, a $C_7$ to $C_{20}$ aralkyl group, or a $C_7$ to $C_{20}$ substituted aralkyl group; alternatively, a $C_4$ to $C_{20}$ cycloalkyl group or a $C_4$ to $C_{20}$ substituted cycloalkyl group; alternatively, a $C_5$ to $C_{20}$ cycloalkyl alkyl group or a $C_5$ to $C_{20}$ substituted cycloalkyl alkyl group; alternatively, a $C_6$ to $C_{20}$ aryl group or a $C_6$ to $C_{20}$ substituted aryl group; alternatively, a $C_7$ to $C_{20}$ aralkyl group or a $C_7$ to $C_{20}$ substituted aralkyl group alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_5$ to $C_{20}$ cycloalkyl alkyl group; alternatively, a $C_5$ to $C_{20}$ substituted cycloalkyl alkyl group; alternatively, a $C_6$ to $C_{20}$ aryl group; alternatively, a $C_6$ to $C_{20}$ substituted aryl group; alternatively, a $C_7$ to $C_{20}$ aralkyl group; or alternatively, a $C_7$ to $C_{20}$ substituted aralkyl group. In other embodiments, $R^2$ for the $N^2$-phosphinyl amidine metal complexes can be a $C_1$ to $C_{10}$ alkyl group, a $C_4$ to $C_{15}$ cycloalkyl group, a $C_4$ to $C_{15}$ substituted cycloalkyl group, a $C_5$ to $C_{15}$ cycloalkyl alkyl group, a $C_5$ to $C_{15}$ substituted cycloalkyl alkyl group, a $C_6$ to $C_{15}$ aryl group, a $C_6$ to $C_{15}$ substituted aryl group, a $C_7$ to $C_{15}$ aralkyl group, or a $C_7$ to $C_{15}$ substituted aralkyl group; alternatively, a $C_4$ to $C_{15}$ cycloalkyl group or a $C_4$ to $C_{15}$ substituted cycloalkyl group; alternatively, a $C_5$ to $C_{15}$ cycloalkyl alkyl group or a $C_5$ to $C_{15}$ substituted cycloalkyl alkyl group; alternatively, a $C_6$ to $C_{15}$ aryl group or a $C_6$ to $C_{15}$ substituted aryl group; alternatively, a $C_7$ to $C_{15}$ aralkyl group or a $C_7$ to $C_{15}$ substituted aralkyl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_5$ to $C_{15}$ cycloalkyl alkyl group; alternatively, a $C_5$ to $C_{15}$ substituted cycloalkyl alkyl group; alternatively, a $C_6$ to $C_{15}$ aryl group; alternatively, a $C_6$ to $C_{15}$ substituted aryl group; alternatively, a $C_7$ to $C_{15}$ aralkyl group; or alternatively, a $C_7$ to $C_{15}$ substituted aralkyl group. In further embodiments, $R^2$ for the $N^2$-phosphinyl amidine metal complexes can be a $C_1$ to $C_5$ alkyl group. Substituents (general and specific) are independently disclosed herein and can be utilized without limitation to further describe substituted groups which can be utilized as $R^2$ for the $N^2$-phosphinyl amidine metal complexes.

In an embodiment, $R^2$ for the $N^2$-phosphinyl amidine metal complexes can be a methyl group, an ethyl group, a propyl group, a butyl group, a pentyl group, a hexyl group, a heptyl group, an octyl group, a nonyl group, or a decyl group. In some embodiments, $R^2$ for the $N^2$-phosphinyl amidine metal complexes can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, the alkyl groups which can be utilized as $R^2$ for the $N^2$-phosphinyl amidine metal complexes can be substituted. Each substituent of a substituted alkyl group independently can be a halogen or a hydrocarboxy group; alternatively, a halogen; or alternatively, a hydrocarboxy group. Halogens and hydrocarboxy groups (general and specific) that can be utilized as substituents are independently disclosed herein and can be utilized without limitation to further describe the substituted alkyl group which can be utilized as $R^2$ for the $N^2$-phosphinyl amidine metal complexes.

In an embodiment, $R^2$ for the $N^2$-phosphinyl amidine metal complexes can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^2$ for the $N^2$-phosphinyl amidine metal complexes can be a cyclopentyl group, a substituted cyclopentyl group, a cyclohexyl group, or a substituted cyclohexyl group. In other embodiments, $R^2$ for the $N^2$-phosphinyl amidine metal complexes can be a cyclopentyl group or a substituted cyclopentyl group; or alternatively, a cyclohexyl group or a substituted cyclohexyl group. In further embodiments, $R^2$ for the $N^2$-phosphinyl amidine metal complexes can be a cyclopentyl group; alternatively, a substituted cyclopentyl group; alternatively, a cyclohexyl group; or alternatively, a substituted cyclohexyl group. Substituents (general and specific) are independently disclosed herein and can be utilized without limitation to further describe the substituted cycloalkyl group which can be utilized as $R^2$ for the $N^2$-phosphinyl amidine metal complexes.

In an aspect, $R^2$ for the $N^2$-phosphinyl amidine metal complexes can have Structure G3:

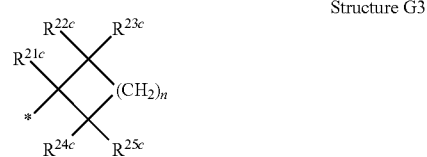

Structure G3 wherein the undesignated valency is attached to the $N^1$ nitrogen atom of the $N^2$-phosphinyl amidine metal complex. Generally, $R^{21c}$, $R^{22c}$, $R^{23c}$, $R^{24c}$, and $R^{25c}$ can independently be hydrogen or a non-hydrogen substituent, and n can be an integer from 1 to 5. In an embodiment wherein $R^2$ for the $N^2$-phosphinyl amidine metal complexes has Structure G3, $R^{21c}$, $R^{23c}$, $R^{24c}$, and $R^{25c}$ can be hydrogen and $R^{22c}$ can be any non-hydrogen substituent disclosed herein; or alternatively, $R^{21c}$, $R^{23c}$, and $R^{25c}$ can be hydrogen and $R^{22c}$ and $R^{24c}$ independently can be any non-hydrogen substituent disclosed herein. In an embodiment, n for Structure G3 can be an integer from 1 to 4; or alternatively, from 2 to 4. In other embodiments, n for Structure G3 can be 2 or 3; alternatively, 2; or alternatively 3. Substituents (general and specific) are independently disclosed herein and can be utilized without limitation to further describe a non-hydrogen substituent which can be utilized without limitation as $R^{21c}$, $R^{22c}$, $R^{23c}$, $R^{24c}$, and/or $R^{25c}$ for the $R^2$ group for the $N^2$-phosphinyl amidine metal complexes having Structure G3.

In an aspect, $R^2$ for the $N^2$-phosphinyl amidine metal complexes can be a phenyl group, a substituted phenyl group; alternatively, a phenyl group; or alternatively, a substituted phenyl group. In an embodiment, the $R^2$ substituted phenyl group can be a 2-substituted phenyl group, a 3-substituted phenyl group, a 4-substituted phenyl group, a 2,4 disubstituted phenyl group, a 2,6-disubstituted phenyl group, 3,5-disubstituted phenyl group, or a 2,4,6-trisubstituted phenyl group. In other embodiments, the $R^2$ substituted phenyl group for the $N^2$-phosphinyl amidine metal complexes can be a 2-substituted phenyl group, a 4-substituted phenyl group, a 2,4-disubstituted phenyl group, a 2,6-di-substituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2 substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-di-substituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3 substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents (general and specific) are independently disclosed herein and can be utilized without limitation to further describe any substituted phenyl group which can be utilized as $R^2$ for the $N^2$-phosphinyl amidine metal complexes.

In an aspect, the $R^2$ for the $N^2$-phosphinyl amidine metal complexes can have Structure G4:

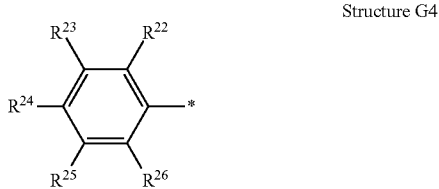

Structure G4 wherein the undesignated valency is attached to the $N^1$ nitrogen atom of the $N^2$-phosphinyl amidine metal complex. Generally, $R^{22}$, $R^{23}$, $R^{24}$, $R^{25}$, and $R^{26}$ independently can be hydrogen or a non-hydrogen substituent. In an embodiment wherein $R^2$ for the $N^2$-phosphinyl amidine metal complexes has Structure G4, $R^{22}$, $R^{23}$, $R^{24}$, $R^{25}$, and $R^{26}$ can be hydrogen, $R^{23}$, $R^{24}$, $R^{25}$, and $R^{26}$ can be hydrogen and $R^{22}$ can be a non-hydrogen substituent, $R^{22}$, $R^{24}$, $R^{25}$, and $R^{26}$ can be hydrogen and $R^{23}$ can be a non-hydrogen substituent, $R^{22}$, $R^{23}$, $R^{25}$, and $R^{26}$ can be hydrogen and $R^{24}$ can be a non-hydrogen substituent, $R^{23}$, $R^{25}$, and $R^{26}$ can be hydrogen and $R^{22}$ and $R^{24}$ can be non-hydrogen substituents, $R^{23}$, $R^{24}$, and $R^{25}$ can be hydrogen and $R^{22}$ and $R^{26}$ can be non-hydrogen substituents, $R^{22}$, $R^{24}$, and $R^{26}$ can be hydrogen and $R^{23}$ and $R^{25}$ can be non-hydrogen substituents, or $R^{23}$ and $R^{25}$ can be hydrogen and $R^{22}$, $R^{24}$, and $R^{26}$ can be non-hydrogen substituents. In some embodiments wherein $R^2$ for the $N^2$-phosphinyl amidine metal complexes has Structure G4, $R^{23}$, $R^{24}$, $R^{25}$, and $R^{26}$ can be hydrogen and $R^{22}$ can be a non-hydrogen substituent, $R^{22}$, $R^{23}$, $R^{25}$, and $R^{26}$ can be hydrogen and $R^{24}$ can be a non-hydrogen substituent, $R^{23}$, $R^{25}$, and $R^{26}$ can be hydrogen and $R^{22}$ and $R^{24}$ can be non-hydrogen substituents, $R^{23}$, $R^{24}$, and $R^{25}$ can be hydrogen and $R^{22}$ and $R^{26}$ can be non-hydrogen substituents, or $R^{23}$ and $R^{25}$ can be hydrogen and $R^{22}$, $R^{24}$, and $R^{26}$ can be non-hydrogen substituents; alternatively, $R^{23}$, $R^{24}$, $R^{25}$, and $R^{26}$ can be hydrogen and $R^{22}$ can be a non-hydrogen substituent, $R^{22}$, $R^{23}$, $R^{25}$, and $R^{26}$ can be hydrogen and $R^{24}$ can be a non-hydrogen substituent, $R^{23}$, $R^{25}$, and $R^{26}$ can be hydrogen and $R^{22}$ and $R^{24}$ can be non-hydrogen substituents, or $R^{23}$, $R^{24}$, and $R^{25}$ can be hydrogen and $R^{22}$ and $R^{26}$ can be non-hydrogen substituents; alternatively, $R^{22}$, $R^{24}$, $R^{25}$, and $R^{26}$ can be hydrogen and $R^{23}$ can be a non-hydrogen substituent, or $R^{22}$, $R^{24}$, and $R^{26}$ can be hydrogen and $R^{23}$ and $R^{25}$ can be non-hydrogen substituents; alternatively, $R^{23}$, $R^{24}$, $R^{25}$, and $R^{26}$ can be hydrogen and $R^{22}$ can be a non-hydrogen substituent, or $R^{22}$, $R^{23}$, $R^{25}$, and $R^{26}$ can be hydrogen and $R^{24}$ can be a non-hydrogen substituent; alternatively, $R^{23}$, $R^{25}$, and $R^{26}$ can be hydrogen and $R^{22}$ and $R^{24}$ can be non-hydrogen substituents, $R^{23}$, $R^{24}$, and $R^{25}$ can be hydrogen and $R^{22}$ and $R^{26}$ can be non-hydrogen substituents, or $R^{23}$ and $R^{25}$ can be hydrogen and $R^{22}$, $R^{24}$, and $R^{26}$ can be non-hydrogen substituents; or alternatively, $R^{23}$, $R^{25}$, and $R^{26}$ can be hydrogen and $R^{22}$ and $R^{24}$ can be non-hydrogen substituents, or $R^{23}$, $R^{24}$, and $R^{25}$ can be hydrogen and $R^{22}$ and $R^{26}$ can be non-hydrogen substituents. In other embodiments wherein $R^2$ for the $N^2$-phosphinyl amidine metal complexes has Structure G4, $R^{22}$, $R^{23}$, $R^{24}$, $R^{25}$, and $R^{26}$ can be hydrogen; alternatively, $R^{23}$, $R^{24}$, $R^{25}$, and $R^{26}$ can be hydrogen and $R^{22}$ can be a non-hydrogen substituent; alternatively, $R^{22}$, $R^{24}$, $R^{25}$, and $R^{26}$ can be hydrogen and $R^{23}$ can be a non-hydrogen substituent; alternatively, $R^{22}$, $R^{23}$, $R^{25}$, and $R^{26}$ can be hydrogen and $R^{24}$ can be a non-hydrogen substituent; alternatively, $R^{23}$, $R^{25}$, and $R^{26}$ can be hydrogen and $R^{22}$ and $R^{24}$ can be non-hydrogen substituents; alternatively, $R^{23}$, $R^{24}$, and $R^{25}$ can be hydrogen and $R^{22}$ and $R^{26}$ can be non-hydrogen substituents; alternatively, $R^{22}$, $R^{24}$, and $R^{26}$ can be hydrogen and $R^{23}$ and $R^{25}$ and can be non-hydrogen substituents; or alternatively, $R^{23}$ and $R^{25}$ can be hydrogen and $R^{22}$, $R^{24}$, and $R^{26}$ can be non-hydrogen substituents. Substituents (general and specific) are independently disclosed herein and can be utilized without limitation as $R^{22}$, $R^{23}$, $R^{24}$, $R^{25}$, and $R^{26}$ for the $R^2$ group having Structure G4 for the $N^2$-phosphinyl amidine metal complexes.

In a non-limiting embodiment, $R^2$ for the $N^2$-phosphinyl amidine metal complexes can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6-dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In other non-limiting embodiments, $R^2$ for the $N^2$-phosphinyl amidine metal complexes can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, a cyclopentyl group; alternatively, a 2-alkylcyclopentyl group; or alternatively, a 2,5-dialkylcyclopentyl group. Alkyl group substituents (general and specific) are independently described herein and can be utilized, without limitation, to further describe the alkylphenyl, dialkylphenyl, trialkylphenyl, alkylcyclohexyl, dialkylcyclohexyl, alkylcyclopentyl, or dialkylcyclopentyl groups that can be utilized $R^2$ for the $N^2$-phosphinyl amidine metal complexes. Generally, the alkyl substituents of a dialkyl or trialkyl phenyl, cyclohexyl, or cyclopentyl group can be the same; or alternatively, the alkyl substituents of a dialkyl or trialkyl phenyl, cyclohexyl, or cyclopentyl group can be different.

In another non-limiting embodiment, $R^2$ for the $N^2$-phosphinyl amidine metal complexes can be a phenyl group, a 2-alkoxyphenyl group, a 3-alkoxyphenyl group, a 4-alkoxyphenyl group, or a 3,5-dialkoxyphenyl group; alternatively, a 2-alkoxyphenyl group or a 4-alkoxyphenyl group; alternatively, a 3-alkoxyphenyl group or a 3,5-dialkoxyphenyl group; alternatively, a 2-alkoxyphenyl group; alternatively, a 3-alkoxyphenyl group; alternatively, a 4-alkoxyphenyl group; alternatively, a 3,5-dialkoxyphenyl group. Alkoxy group substituents (general and specific) are independently described herein and can be utilized, without limitation, to further describe the alkoxyphenyl or dialkoxyphenyl groups that can be utilized $R^2$ for the $N^2$-phosphinyl amidine metal complexes. Generally, the alkoxy substituents of a dialkoxyphenyl group can be the same; or alternatively, the alkoxy substituents of a dialkoxyphenyl group can be different.

In other non-limiting embodiments, $R^2$ for the $N^2$-phosphinyl amidine metal complexes can be a phenyl group, a 2-halophenyl group, a 3-halo-phenyl group, a 4-halophenyl group, a 2,6-dihalophenyl group, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenyl group; or alternatively, a 3,5-dihalophenyl group. Halides are independently described herein and can be utilized, without limitation, to further describe the halophenyl or dihalophenyl groups that can be utilized as $R^2$ for the $N^2$-phosphinyl amidine metal complexes. Generally, the halides of a dihalophenyl group can be the same; or alternatively, the halides of a dihalophenyl group can be different.

In a non-limiting embodiment, $R^2$ for the $N^2$-phosphinyl amidine metal complexes can be a 2-methylphenyl group, a 2-ethylphenyl group, a 2-n-propylphenyl group, a 2-isopropylphenyl group, a 2-tert-butylphenyl group, a 3-methylphenyl group, a 2,6-dimethylphenyl group, a 2,6-diethylphenyl group, a 2,6-di-n-propylphenyl group, a 2,6-diisopropyl-phenyl group, a 2,6-di-tert-butylphenyl group, a 2-isopropyl-6-methylphenyl group, a 3,5-dimethyl group, or a 2,4,6-trimethylphenyl group; alternatively, a 2-methylphenyl group, a 2-ethylphenyl group, a 2-n-propylphenyl group, a 2-isopropylphenyl group, or a 2-tert-butylphenyl group; alternatively, a 2,6-dimethylphenyl group, a 2,6-diethylphenyl group, a 2,6-di-n-propylphenyl group, a 2,6-diisopropyl-phenyl group, a 2,6-di-tert-butylphenyl group, or a 2-isopropyl-6-methylphenyl group; alternatively, a 2-methylphenyl group; alternatively, a 2-ethylphenyl group; alternatively, a 2-n-propylphenyl group; alternatively, a 2-isopropylphenyl group; alternatively, a 2-tert-butylphenyl group; alternatively, a 3-methylphenyl group; alternatively, a 2,6-dimethylphenyl group; alternatively, a 2,6-diethylphenyl group; alternatively, a 2,6-di-n-propylphenyl group, a 2,6-diisopropylphenyl group; alternatively, a 2,6-di-tert-butylphenyl group; alternatively, a 2-isopropyl-6-methylphenyl group; alternatively, a 3,5-dimethylphenyl group; or alternatively, a 2,4,6-trimethylphenyl group. In another non-limiting embodiment, $R^2$ for the $N^2$-phosphinyl amidine metal complexes can be a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; alternatively, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group; alternatively, a 2-ethylcyclohexyl group; alternatively, a 2-isopropylcyclohexyl group; alternatively, a 2-tert-butylcyclohexyl group; alternatively, a 2,6-dimethylcyclohexyl group; alternatively, a 2,6-diethylcyclohexyl group; alternatively, a 2,6-diisopropylcyclohexyl group; or alternatively, a 2,6-di-tert-butylcyclohexyl group.

In a non-limiting embodiment, $R^2$ for the $N^2$-phosphinyl amidine metal complexes can be a 3-methoxyphenyl group, a 3-ethoxyphenyl group, a 3-isopropoxyphenyl group, a 3-tert-butoxyphenyl group, a 4-methoxyphenyl group, a 4-ethoxyphenyl group, a 4-isopropoxyphenyl group, a 4-tert-butoxyphenyl group, a 3,5-dimethoxyphenyl group, a 3,5-diethoxyphenyl group, a 3,5-diisopropoxyphenyl group, or a 3,5-di-tert-butoxyphenyl group; alternatively, a 3-methoxyphenyl group, a 3-ethoxyphenyl group, a 3-isopropoxyphenyl group, or a 3-tert-butoxyphenyl group; alternatively, a 4-methoxyphenyl group, a 4-ethoxyphenyl group, a 4-isopropoxyphenyl group, or a 4-tert-butoxyphenyl group; or alternatively, a 3,5-dimethoxyphenyl group, a 3,5-diethoxyphenyl group, a 3,5-diisopropoxyphenyl group, or a 3,5-di-tert-butoxyphenyl group. In other non-limiting embodiments, $R^2$ for the $N^2$-phosphinyl amidine metal complexes can be a 3-methoxyphenyl group; alternatively, a 3-ethoxyphenyl group; alternatively, a 3-isopropoxyphenyl group; alternatively, a 3-tert-butoxyphenyl group; alternatively, a 4-methoxyphenyl group; alternatively, a 4-ethoxyphenyl group; alternatively, a 4-isopropoxyphenyl group; alternatively, a 4-tert-butoxyphenyl group; alternatively, a 3,5-dimethoxyphenyl group; alternatively, a 3,5-diethoxyphenyl group; alternatively, a 3,5-diisopropoxyphenyl group; or alternatively, a 3,5-di-tert-butoxyphenyl group.

In an aspect, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be hydrogen or an organyl group; alternatively, hydrogen; or alternatively, an organyl group. In another aspect, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be hydrogen or an organyl group consisting essentially of inert functional groups; alternatively, hydrogen; or alternatively, an organyl group consisting essentially of inert functional groups. In an aspect, $R^{2a}$ and/or $R^{2b}$ for the N2-phosphinyl guanidine metal complexes having Structure GuMC1 and/or $R^{2b}$ for the $N^2$-phosphinyl guanidine metal complex having Structure GuMC2 independently can be hydrogen or a hydrocarbyl group; alternatively, hydrogen; or alternatively, a hydrocarbyl group. In an embodiment, $R^{2a}$ and $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In some embodiments, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In other embodiments, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group. In yet other embodiments, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a $C_3$ to $C_{30}$ aromatic group; alternatively, a $C_3$ to $C_{20}$ aromatic group; alternatively, a $C_3$ to $C_{15}$ aromatic group; or alternatively, a $C_3$ to $C_{10}$ aromatic group.

In an aspect, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, or a $C_6$ to $C_{30}$ substituted aryl group; alternatively, a $C_4$ to $C_{30}$ cycloalkyl group or a $C_4$ to $C_{30}$ substituted cycloalkyl group; alternatively, a $C_6$ to $C_{30}$ aryl group or a $C_6$ to $C_{30}$ substituted aryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_6$ to $C_{30}$ aryl group; or alternatively, a $C_6$ to $C_{30}$ substituted aryl group. In an embodiment, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; alternatively, a $C_4$ to $C_{20}$ cycloalkyl group or a $C_4$ to $C_{20}$ substituted cycloalkyl group; alternatively, a $C_6$ to $C_{20}$ aryl group or a $C_6$ to $C_{20}$ substituted aryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_6$ to $C_{20}$ aryl group; or alternatively, a $C_6$ to $C_{20}$ substituted aryl group. In other embodiments, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, or a $C_6$ to $C_{15}$ substituted aryl group; alternatively, a $C_4$ to $C_{15}$ cycloalkyl group or a $C_4$ to $C_{15}$ substituted cycloalkyl group; alternatively, a $C_6$ to $C_{15}$ aryl group or a $C_6$ to $C_{15}$ substituted aryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_6$ to $C_{15}$ aryl group; or alternatively, a $C_6$ to $C_{15}$ substituted aryl group. In further embodiments, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a $C_1$ to $C_5$ alkyl group. Substituents (general and specific) are independently disclosed herein and can be utilized without limitation to further describe substituted groups which can be utilized as $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2.

In an embodiment, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a methyl group, an ethyl group, a propyl group, a butyl group, a pentyl group, a hexyl group, a heptyl group, an octyl group, a nonyl group, or a decyl group. In some embodiments, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group; alternatively, an ethyl group; alternatively, an n-propyl group; alternatively, an iso-propyl group; alternatively, a tert-butyl group; or alternatively, a neopentyl group. In some embodiments, the alkyl groups which can be utilized as $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 can be substituted. Each substituent of a substituted alkyl group independently can be a halogen or a hydrocarboxy group; alternatively, a halogen; or alternatively, a hydrocarboxy group. Halogens and hydrocarboxy groups (general and specific) that can be utilized as substituents are independently disclosed herein and can be utilized without limitation to further describe the substituted alkyl group which can be utilized as $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2.

In an embodiment $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a cyclopentyl group, a substituted cyclopentyl group, a cyclohexyl group, or a substituted cyclohexyl group. In other embodiments, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a cyclopentyl group or a substituted cyclopentyl group; or alternatively, a cyclohexyl group or a substituted cyclohexyl group. In further embodiments, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a cyclopentyl group; alternatively, a substituted cyclopentyl group; a cyclohexyl group; or alternatively, a substituted cyclohexyl group. Substituents (general and specific) are independently disclosed herein and can be utilized without limitation to further describe the substituted cycloalkyl group which can be utilized as $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2.

In an aspect, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can have Structure G11 and Structure G12, respectively. In an aspect, $R^{2b}$ for the $N^2$-phosphinyl guanidine metal complex having Structure GuMC2 can have Structure G12.

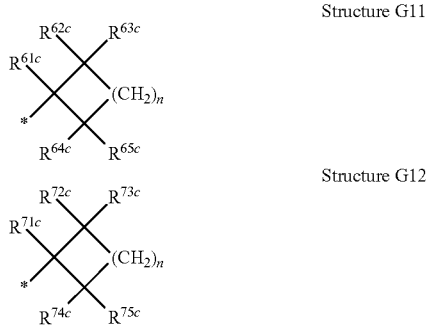

Structure G11

Structure G12 within Structure G11 and Structure G12, the undesignated valency of Structure G11 and Structure G12 is attached to the $N^3$ nitrogen atom of the $N^2$-phosphinyl guanidine metal complex. Generally, $R^{61c}$, $R^{62c}$ $R^{63c}$, $R^{64c}$, and $R^{65c}$ of Structure G11 and $R^{71c}$, $R^{72c}$, $R^{73c}$, $R^{74c}$, and $R^{75c}$ of Structure G12 independently can be hydrogen or a non-hydrogen substituent, and each n independently can be an integer from 1 to 5. In an embodiment wherein $R^2$ has Structure G11, $R^{61c}$, $R^{63c}$, $R^{64c}$, and $R^{65c}$ can be hydrogen and $R^{62c}$ can be any non-hydrogen substituent disclosed herein; or alternatively, $R^{61c}$, $R^{63c}$, and $R^{65c}$ can be hydrogen and $R^{62c}$ and $R^{64c}$ independently can be any non-hydrogen substituent disclosed herein. In an embodiment wherein $R^{2b}$ has Structure G12, $R^{71c}$, $R^{73c}$, $R^{74c}$, and $R^{75c}$ can be hydrogen and $R^{72c}$ can be any non-hydrogen substituent disclosed herein; or alternatively, $R^{71c}$, $R^{73c}$, and $R^{75c}$ can be hydrogen and $R^{72c}$ and $R^{74c}$ independently can be any non-hydrogen substituent disclosed herein. In an embodiment, n for Structure G11 and or Structure G12 independently can be an integer from 1 to 4; or alternatively, from 2 to 4. In other embodiments, n for Structure G11 and or Structure G12 independently can be 2 or 3; alternatively, 2; or alternatively 3. Substituents (general and specific) are independently disclosed herein and can be utilized without limitation as $R^{61c}$, $R^{62c}$, $R^{63c}$, $R^{64c}$, and $R^{65c}$ for the $R^{2a}$ group having Structure G11 for the $N^2$-phosphinyl guanidine metal complexes having Structure GuMC1 and/or $R^{71c}$, $R^{72c}$, $R^{73c}$, $R^{74c}$, and $R^{75c}$ for the $R^{2b}$ group having Structure G12 for the $N^2$-phosphinyl guanidine metal complexes having Structure GuMC1 and/or $R^{2b}$ for the $N^2$-phosphinyl guanidine metal complex having Structure GuMC2.

In an embodiment, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a phenyl group or a substituted phenyl group. In some embodiments, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a phenyl group; or alternatively, a substituted phenyl group. In an embodiment, the $R^{2a}$ and/or $R^{2b}$ substituted phenyl group for the $N^2$-phosphinyl guanidine metal complexes having Structure GuMC1 and/or $R^{2b}$ for the $N^2$-phosphinyl guanidine metal complex having Structure GuMC2 independently can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other embodiments, the $R^{2a}$ and/or $R^{2b}$ substituted phenyl group for the $N^2$-phosphinyl guanidine metal complexes having Structure GuMC1 and/or $R^{2b}$ for the $N^2$-phosphinyl guanidine metal complex having Structure GuMC2 independently can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-disubstituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents (general and specific) are independently disclosed herein and can be utilized without limitation to further describe any substituted phenyl group which can be utilized as $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2.

In an aspect, $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2 independently can have Structure G13 and Structure G14, respectively. In an aspect, $R^{2b}$ for the $N^2$-phosphinyl guanidine metal complex having Structure GuMC2 can have Structure G14.

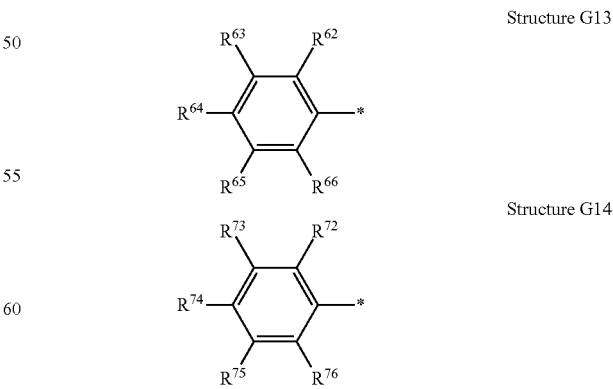

Structure G13

Structure G14

Within Structure G13 and Structure G14, the undesignated valency of Structure G13 and Structure G14 is attached to the $N^3$ nitrogen atom of the $N^2$-phosphinyl guanidine metal complexes having Structure GuMC1 and/or $R^{2b}$ for the $N^2$-phosphinyl guanidine metal complex having Structure GuMC2. Generally, $R^{62}$, $R^{63}$, $R^{64}$, $R^{65}$, and $R^{66}$ of Structure G13 and $R^{72}$, $R^{73}$, $R^{74}$, $R^{75}$, and $R^{76}$ of Structure G14 independently can be hydrogen or a non-hydrogen substituent. In an embodiment wherein $R^2$, for the $N^2$-phosphinyl guanidine metal complexes having Structure GuMC1 has Structure G13, $R^{62}$, $R^{63}$, $R^{64}$, $R^{65}$, and $R^{66}$ can be hydrogen, $R^{63}$, $R^{64}$, $R^{65}$, and $R^{66}$ can be hydrogen and $R^{62}$ can be a non-hydrogen substituent, $R^{62}$, $R^{64}$, $R^{65}$ and $R^{66}$ can be hydrogen and $R^{63}$ can be a non-hydrogen substituent, $R^{62}$, $R^{63}$, $R^{65}$, and $R^{66}$ can be hydrogen and $R^{64}$ can be a non-hydrogen substituent, $R^{63}$, $R^{65}$, and $R^{66}$ can be hydrogen and $R^{62}$ and $R^{64}$ can be non-hydrogen substituents, $R^{63}$, $R^{64}$ and $R^{65}$ can be hydrogen and $R^{62}$ and $R^{66}$ can be non-hydrogen substituents, $R^{62}$, $R^{64}$, and $R^{66}$ can be hydrogen and $R^{63}$ and $R^{65}$ can be non-hydrogen substituents, or $R^{63}$ and $R^{65}$ can be hydrogen and $R^{62}$, $R^{64}$, and $R^{66}$ can be non-hydrogen substituents. In some embodiments wherein $R^{2a}$ for the $N^2$-phosphinyl guanidine metal complexes having Structure GuMC1 has Structure G13, $R^{63}$, $R^{64}$, $R^{65}$, and $R^{66}$ can be hydrogen and $R^{62}$ can be a non-hydrogen substituent, $R^{62}$, $R^{63}$, $R^{65}$, and $R^{66}$ can be hydrogen and $R^{64}$ can be a non-hydrogen substituent, $R^{63}$, $R^{65}$ and $R^{66}$ can be hydrogen and $R^{62}$ and $R^{64}$ can be non-hydrogen substituents, $R^{63}$, $R^{64}$, and $R^{65}$ can be hydrogen and $R^{62}$ and $R^{66}$ can be non-hydrogen substituents, or $R^{63}$ and $R^{65}$ can be hydrogen and $R^{62}$, $R^{64}$ and $R^{66}$ can be non-hydrogen substituents; alternatively, $R^{63}$, $R^{64}$, $R^{65}$, and $R^{66}$ can be hydrogen and $R^{62}$ can be a non-hydrogen substituent, $R^{62}$, $R^{63}$, $R^{65}$, and $R^{66}$ can be hydrogen and $R^{64}$ can be a non-hydrogen substituent, $R^{63}$, $R^{65}$ and $R^{66}$ can be hydrogen and $R^{62}$ and $R^{64}$ can be non-hydrogen substituents, or $R^{63}$, $R^{64}$, and $R^{65}$ can be hydrogen and $R^{62}$ and $R^{66}$ can be non-hydrogen substituents; alternatively, $R^{62}$, $R^{64}$, $R^{65}$, and $R^{66}$ can be hydrogen and $R^{63}$ can be a non-hydrogen substituent, or $R^{62}$, $R^{64}$, and $R^{66}$ can be hydrogen and $R^{63}$ and $R^{65}$ can be non-hydrogen substituents; alternatively, $R^{63}$, $R^{64}$, $R^{65}$, and $R^{66}$ can be hydrogen and $R^{62}$ can be a non-hydrogen substituent, or $R^{62}$, $R^{63}$, $R^{65}$, and $R^{66}$ can be hydrogen and $R^{64}$ can be a non-hydrogen substituent; alternatively, $R^{63}$, $R^{65}$, and $R^{66}$ can be hydrogen and $R^{62}$ and $R^{64}$ can be non-hydrogen substituents, $R^{63}$, $R^{64}$, and $R^{65}$ can be hydrogen and $R^{62}$ and $R^{66}$ can be non-hydrogen substituents, or $R^{63}$ and $R^{65}$ can be hydrogen and $R^{62}$, $R^{64}$, and $R^{66}$ can be non-hydrogen substituents; or alternatively, $R^{63}$, $R^{65}$, and $R^{66}$ can be hydrogen and $R^{62}$ and $R^{64}$ can be non-hydrogen substituents, or $R^{63}$, $R^{64}$, and $R^{65}$ can be hydrogen and $R^{62}$ and $R^{66}$ can be non-hydrogen substituents. In other embodiments wherein $R^{2a}$ for the $N^2$-phosphinyl guanidine metal complexes having Structure GuMC1 has Structure G13, $R^{62}$, $R^{63}$, $R^{64}$, $R^{65}$, and $R^{66}$ can be hydrogen; alternatively, $R^{63}$, $R^{64}$, $R^{65}$, and $R^{66}$ can be hydrogen and $R^{62}$ can be a non-hydrogen substituent; alternatively, $R^{62}$, $R^{64}$, $R^{65}$, and $R^{66}$ can be hydrogen and $R^{63}$ can be a non-hydrogen substituent; alternatively, $R^{62}$, $R^{63}$, $R^{65}$, and $R^{66}$ can be hydrogen and $R^{64}$ can be a non-hydrogen substituent; alternatively, $R^{63}$, $R^{65}$ and $R^{66}$ can be hydrogen and $R^{62}$ and $R^{64}$ can be non-hydrogen substituents; alternatively, $R^{63}$, $R^{64}$, and $R^{65}$ can be hydrogen and $R^{62}$ and $R^{66}$ can be non-hydrogen substituents; alternatively, $R^{62}$, $R^{64}$, and $R^{66}$ can be hydrogen and $R^{63}$ and $R^{65}$ and can be non-hydrogen substituents; or alternatively, $R^{63}$ and $R^{65}$ can be hydrogen and $R^{62}$, $R^{64}$, and $R^{66}$ can be non-hydrogen substituents. In an embodiment wherein $R^{2b}$ for the $N^2$-phosphinyl guanidine metal complexes having Structure GuMC1 and/or $R^{2b}$ for the $N^2$-phosphinyl guanidine metal complex having Structure GuMC2 has Structure G14, $R^{72}$, $R^{73}$, $R^{74}$, $R^{75}$, and $R^{76}$ can be hydrogen, $R^{73}$, $R^{74}$, $R^{75}$, and $R^{76}$ can be hydrogen and $R^{72}$ can be a non-hydrogen substituent, $R^{72}$, $R^{74}$, $R^{75}$, and $R^{76}$ can be hydrogen and $R^{73}$ can be a non-hydrogen substituent, $R^{72}$, $R^{73}$, $R^{75}$, and $R^{76}$ can be hydrogen and $R^{74}$ can be a non-hydrogen substituent, $R^{73}$, $R^{75}$, and $R^{76}$ can be hydrogen and $R^{72}$ and $R^{74}$ can be non-hydrogen substituents, $R^{73}$, $R^{74}$, and $R^{75}$ can be hydrogen and $R^{72}$ and $R^{76}$ can be non-hydrogen substituents, $R^{72}$, $R^{74}$, and $R^{76}$ can be hydrogen and $R^{73}$ and $R^{75}$ can be non-hydrogen substituents, or $R^{73}$ and $R^{75}$ can be hydrogen and $R^{72}$, $R^{74}$, and $R^{76}$ can be non-hydrogen substituents. In some embodiments wherein $R^{2b}$ for the $N^2$-phosphinyl guanidine metal complexes having Structure GuMC1 and/or $R^{2b}$ for the $N^2$-phosphinyl guanidine metal complex having Structure GuMC2 has Structure G14, $R^{73}$, $R^{74}$, $R^{75}$, and $R^{76}$ can be hydrogen and $R^{72}$ can be a non-hydrogen substituent, $R^{72}$, $R^{73}$, $R^{75}$, and $R^{76}$ can be hydrogen and $R^{74}$ can be a non-hydrogen substituent, $R^{73}$, $R^{75}$, and $R^{76}$ can be hydrogen and $R^{72}$ and $R^{74}$ can be non-hydrogen substituents, $R^{73}$, $R^{74}$, and $R^{75}$ can be hydrogen and $R^{72}$ and $R^{76}$ can be non-hydrogen substituents, or $R^{73}$ and $R^{75}$ can be hydrogen and $R^{72}$, $R^{74}$, and $R^{76}$ can be non-hydrogen substituents; alternatively, $R^{73}$, $R^{74}$, $R^{75}$, and $R^{76}$ can be hydrogen and $R^{72}$ can be a non-hydrogen substituent, $R^{72}$, $R^{73}$, $R^{75}$, and $R^{76}$ can be hydrogen and $R^{74}$ can be a non-hydrogen substituent, $R^{73}$, $R^{75}$, and $R^{76}$ can be hydrogen and $R^{72}$ and $R^{74}$ can be non-hydrogen substituents, or $R^{73}$, $R^{74}$, and $R^{75}$ can be hydrogen and $R^{72}$ and $R^{76}$ can be non-hydrogen substituents; alternatively, $R^{72}$, $R^{74}$, $R^{75}$, and $R^{76}$ can be hydrogen and $R^{73}$ can be a non-hydrogen substituent, or $R^{72}$, $R^{74}$, and $R^{76}$ can be hydrogen and $R^{73}$ and $R^{75}$ can be non-hydrogen substituents; alternatively, $R^{73}$, $R^{74}$, $R^{75}$, and $R^{76}$ can be hydrogen and $R^{72}$ can be a non-hydrogen substituent, or $R^{72}$, $R^{73}$, $R^{75}$, and $R^{76}$ can be hydrogen and $R^{74}$ can be a non-hydrogen substituent; alternatively, $R^{73}$, $R^{75}$, and $R^{76}$ can be hydrogen and $R^{72}$ and $R^{74}$ can be non-hydrogen substituents, $R^{73}$, $R^{74}$, and $R^{75}$ can be hydrogen and $R^{72}$ and $R^{76}$ can be non-hydrogen substituents, or $R^{73}$ and $R^{75}$ can be hydrogen and $R^{72}$, $R^{74}$, and $R^{76}$ can be non-hydrogen substituents; or alternatively, $R^{73}$, $R^{75}$, and $R^{76}$ can be hydrogen and $R^{72}$ and $R^{74}$ can be non-hydrogen substituents, or $R^{73}$, $R^{74}$, and $R^{75}$ can be hydrogen and $R^{72}$ and $R^{76}$ can be non-hydrogen substituents. In other embodiments wherein $R^{2b}$ for the $N^2$-phosphinyl guanidine metal complexes having Structure GuMC1 and/or $R^{2b}$ for the $N^2$-phosphinyl guanidine metal complex having Structure GuMC2 has Structure G14, $R^{72}$, $R^{73}$, $R^{74}$, $R^{75}$, and $R^{76}$ can be hydrogen; alternatively, $R^{73}$, $R^{74}$, $R^{75}$, and $R^{76}$ can be hydrogen and $R^{72}$ can be a non-hydrogen substituent; alternatively, $R^{72}$, $R^{74}$, $R^{75}$, and $R^{76}$ can be hydrogen and $R^{73}$ can be a non-hydrogen substituent; alternatively, $R^{72}$, $R^{73}$, $R^{75}$, and $R^{76}$ can be hydrogen and $R^{74}$ can be a non-hydrogen substituent; alternatively, $R^{73}$, $R^{75}$, and $R^{76}$ can be hydrogen and $R^{72}$ and $R^{74}$ can be non-hydrogen substituents; alternatively, $R^{73}$, $R^{74}$, and $R^{75}$ can be hydrogen and $R^{72}$ and $R^{76}$ can be non-hydrogen substituents; alternatively, $R^{72}$, $R^{74}$, and $R^{76}$ can be hydrogen and $R^{73}$ and $R^{75}$ and can be non-hydrogen substituents; or alternatively, $R^{73}$ and $R^{75}$ can be hydrogen and $R^{72}$, $R^{74}$, and $R^{76}$ can be non-hydrogen substituents. Substituents (general and specific) are independently disclosed herein and can be utilized without limitation as $R^{62}$, $R^{63}$, $R^{64}$, $R^{65}$, and/or $R^{66}$ for the $R^{2a}$ group having Structure G13 and/or $R^{72}$, $R^{73}$, $R^{74}$, $R^{75}$, and/or $R^{76}$ for the $R^{2b}$ group having Structure G14 for the $N^2$-phosphinyl guanidine metal complexes having Structure GuMC1 and/or $R^{2b}$ for the $N^2$-phosphinyl guanidine metal complex having Structure GuMC2.

In a non-limiting embodiment, $R^{2a}$ and $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a phenyl group, a 2-alkyl-phenyl group, a 3-alkylphenyl group, a 4-alkylphenyl group, a 2,4-dialkylphenyl group, a 2,6-dialkyl-phenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkyl-phenyl group; alternatively, a 2-alkylphenyl group or a 4-alkylphenyl group; alternatively, a 2,4-dialkyl-phenyl group, a 2,6-dialkylphenyl group, or a 2,4,6-trialkylphenyl group; alternatively, a 2,4-dialkyl-phenyl group or a 2,6-dialkylphenyl group; alternatively, a 2,6-dialkylphenyl group, or a 2,4,6-trialkyl-phenyl group; alternatively, a 3-alkylphenyl group or a 3,5-dialkylphenyl group; alternatively, a 2-alkyl-phenyl group or a 2,6-dialkylphenyl group; alternatively, a 2-alkylphenyl group; alternatively, a 3-alkyl-phenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In another non-limiting embodiment, $R^{2a}$ and $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a phenyl group, a 2-alkoxyphenyl group, a 3-alkoxyphenyl group, a 4-alkoxyphenyl group, or 3,5-dialkoxyphenyl group; alternatively, a 2-alkoxyphenyl group or a 4-alkoxyphenyl group; alternatively, a 3-alkoxyphenyl group or 3,5-dialkoxyphenyl group; alternatively, a 2-alkoxyphenyl group; alternatively, 3-alkoxyphenyl group; alternatively, a 4-alkoxyphenyl group; alternatively, 3,5-dialkoxyphenyl group. In other non-limiting embodiments, $R^{2a}$ and $R^{2b}$ independently can be a phenyl group, a 2-halophenyl group, a 3-halophenyl group, a 4-halophenyl group, a 2,6-dihalophenyl group, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenyl group; or alternatively, a 3,5-dihalophenyl group. Halides, alkyl group substituents (general and specific), and alkoxy group substituents (general and specific) are independently described herein and can be utilized, without limitation, to further describe the alkylphenyl, dialkylphenyl, trialkylphenyl, alkoxyphenyl, dialkoxyphenyl, halophenyl, or dihalophenyl groups that can be utilized as $R^{2a}$ and/or $R^{2b}$ for the $N^2$-phosphinyl guanidine metal complexes having Structure GuMC1 and/or $R^{2b}$ for the $N^2$-phosphinyl guanidine metal complex having Structure GuMC2. Generally, the halides, alkyl substituents, or alkoxy substituents of a dialkyl, trialkyl phenyl, dialkoxyphenyl, or dihalophenyl groups can be the same; or alternatively the halo, alkyl substituents, or alkoxy substituents of alkylphenyl, dialkylphenyl, trialkylphenyl, dialkoxyphenyl, or dihalophenyl groups can be different.

In a non-limiting embodiment, $R^{2a}$ and $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a 2-methylphenyl group, a 2-ethylphenyl group, a 2-isopropylphenyl group, a 2-tert-butylphenyl group, a 4-methylphenyl group, a 4-ethylphenyl group, a 4-isopropylphenyl group, or a 4-tert-butylphenyl group; alternatively, a 2-methyl-phenyl group, a 2-ethylphenyl group, a 2-isopropylphenyl group, or a 2-tert-butylphenyl group; alternatively, a 4-methylphenyl group, a 4-ethylphenyl group, a 4-isopropylphenyl group, or a 4-tert-butylphenyl group; alternatively, a 2-methylphenyl group; alternatively, a 2-ethylphenyl group; alternatively, a 2-isopropylphenyl group; alternatively, a 2-tert-butylphenyl group; alternatively, a 4-methylphenyl group; alternatively, a 4-ethylphenyl group; alternatively, a 4-isopropylphenyl group; or alternatively, a 4-tert-butylphenyl group. In another non-limiting embodiment, $R^{2a}$ and $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be a 2-methoxyphenyl group, a 2-ethoxyphenyl group, a 2-isopropoxyphenyl group, a 2-tert-butoxyphenyl group, a 4-methoxyphenyl group, a 4-ethoxyphenyl group, a 4-isopropoxyphenyl group, or a 4-tert-butoxyphenyl group; alternatively, a 2-methoxyphenyl group, a 2-ethoxyphenyl group, a 2-isopropoxyphenyl group, or a 2-tert-butoxyphenyl group; alternatively, a 4-methoxyphenyl group, a 4-ethoxyphenyl group, a 4-isopropoxyphenyl group, or a 4-tert-butoxyphenyl group; alternatively, a 2-methoxyphenyl group; alternatively, a 2-ethoxyphenyl group; alternatively, a 2-isopropoxyphenyl group; alternatively, a 2-tert-butoxyphenyl group; alternatively, a 4-methoxyphenyl group; alternatively, a 4-ethoxyphenyl group; alternatively, a 4-isopropoxyphenyl group; or alternatively, a 4-tert-butoxyphenyl group. In other non-limiting embodiments, $R^{2a}$ and $R^{2b}$ for the $N^2$-phosphinyl guanidine metal complexes having Structure GuMC1 and/or $R^{2b}$ for the $N^2$-phosphinyl guanidine metal complex having Structure GuMC2 independently can be independently can be a 2-fluorophenyl group, a 2-chlorophenyl group, a 3-fluorophenyl group, a 3-chlorophenyl group, a 4-fluorophenyl group, a 4-chlorophenyl group, a 3,5-difluorophenyl group, or a 3,5-dichlorophenyl group; alternatively, a 2-fluorophenyl group or a 2-chlorophenyl group; alternatively, a 3-fluorophenyl group or a 3-chloro-phenyl group; alternatively, a 4-fluorophenyl group or a 4-chlorophenyl group; alternatively, a 3,5-difluorophenyl group or a 3,5-dichlorophenyl group; alternatively, a 3-fluorophenyl group, a 3-chlorophenyl group, a 3,5-difluorophenyl group or a 3,5-dichlorophenyl group; alternatively, a 3-fluorophenyl group or a 3,5-difluorophenyl group; alternatively, a 2-fluorophenyl group; alternatively, a 2-chlorophenyl group; alternatively, a 3-fluorophenyl group; alternatively, a 3-chlorophenyl group; alternatively, a 4-fluorophenyl group; alternatively, a 4-chlorophenyl; alternatively, a 3,5-difluorophenyl group; or alternatively, a 3,5-dichlorophenyl group.

In an aspect, $R^1$ and $R^{2a}$ of the $N^2$-phosphinyl guanidine metal complexes having Structure GuMC1 can be joined to form a group, $L^{12}$, wherein $L^{12}$, the $N^1$ nitrogen atom, and the $N^3$ nitrogen atom can form a ring or a ring system (e.g., $N^2$-phosphinyl guanidine metal complex Structure GuMC2). In an embodiment, $L^{12}$ of the $N^2$-phosphinyl guanidine metal complex having Structure GuMC2 can be an organylene group; alternatively, an organylene group consisting of inert functional groups; or alternatively, a hydrocarbylene group. The organylene group which can be utilized as $L^{12}$ of the $N^2$-phosphinyl guanidine metal complex having Structure GuMC2 can be a $C_2$ to $C_{20}$ organylene group; alternatively, a $C_2$ to $C_{15}$ organylene group; alternatively, a $C_2$ to $C_{10}$ organylene group; or alternatively, a $C_2$ to $C_5$ organylene group. The organylene group consisting of inert functional groups which can be utilized as $L^{12}$ of the $N^2$-phosphinyl guanidine metal complex having Structure GuMC2 can be a $C_2$ to $C_{20}$ organylene group consisting of inert functional groups; alternatively, a $C_2$ to $C_{15}$ organylene group consisting of inert functional groups; alternatively, a $C_2$ to $C_{10}$ organylene group consisting of inert functional groups; or alternatively, a $C_2$ to $C_5$ organylene group consisting of inert functional groups. The hydrocarbylene group which can be utilized as $L^{12}$ of the $N^2$-phosphinyl guanidine metal complex having Structure GuMC2 can be a $C_2$ to $C_{20}$ hydrocarbylene group; alternatively, a $C_2$ to $C_{15}$ hydrocarbylene group; alternatively, a $C_2$ to $C_{10}$ hydrocarbylene group; or alternatively, a $C_2$ to $C_5$ hydrocarbylene group.

In an embodiment, $L^{12}$ of the $N^2$-phosphinyl guanidine metal complex having Structure GuMC2 can have any structure provided in Table 1. In some embodiments, $L^{12}$ of the $N^2$-phosphinyl guanidine metal complexes having Structure GuMC2 can have Structure 1L, Structure 2L, Structure 3L, Structure 4L or Structure 5L. In some embodiments, $L^{12}$ of the $N^2$-phosphinyl guanidine metal complex having Structure GuMC2 can have Structure 2L or Structure 3L; alternatively, Structure 4L or Structure 5L. In other embodiments, $L^{12}$ of the $N^2$-phosphinyl guanidine metal complexes having Structure GuMC2 can have Structure 1L; alternatively, Structure 2L; alternatively, Structure 3L; alternatively, Structure 4L; or alternatively, Structure 5L. In some embodiments, $L^{12}$ of the $N^2$-phosphinyl guanidine metal complex having Structure GuMC2 can have Structure 6L. It should be noted that when $L^{12}$ has Structure 6L the corresponding $R^{2b}$ is null because of the double bond link (depicted as real but can be delocalized through aromatic resonance) with the $N^3$ nitrogen atom of the $N^2$-phosphinyl guanidine metal complex.

TABLE 1

Potential Structure for Linking Groups $L^{12}$ and/or $L^{23}$.

| | |
|---|---|
| —$(CR^{L1}R^{L2})_m$— | Structure 1L |
| —$CR^{L3}R^{L4}$—$CR^{L5}R^{L6}$— | Structure 2L |
| —$CR^{L3}R^{L4}$—$CR^{L7}R^{L8}$—$CR^{L5}R^{L6}$— | Structure 3L |
| —$CR^{11L}$=$CR^{12L}$— | Structure 4L |
| 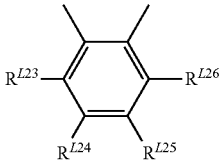 | Structure 5L |
| =$CR^{27}$—$CR^{28}$=$CR^{29}$— | Structure 6L |

Within the structures of Table 1, the undesignated valencies represent the points at which $L^{12}$ of the $N^2$-phosphinyl guanidine metal complex having Structure GuMC2, when present, attach to the respective nitrogen atoms of the $N^2$-phosphinyl guanidine metal complex. Generally, m can be an integer ranging from 2 to 5. In further embodiments, m can be 2 or 3; alternatively, m can be 2; or alternatively, m can be 3. $R^{L1}$ and $R^{L2}$ of the linking group having Structure 1L, $R^{L3}$, $R^{L4}$, $R^{L5}$, and $R^{L6}$ of the linking group having Structure 2L, $R^{L3}$, $R^{L4}$, $R^{L5}$, $R^{L6}$, $R^{L7}$, and $R^{L8}$, of the linking group having Structure 3L, $R^{L11}$ and $R^{L12}$ of the linking group having Structure 4L, $R^{L22}$, $R^{L23}$, $R^{L24}$, $R^{L25}$, and $R^{L26}$ of the linking group having Structure 5L, $R^{L27}$, $R^{L28}$, and $R^{L29}$ of the linking group having Structure 6L independently can be a hydrogen or a non-hydrogen substituent group (any general or specific described herein); or alternatively, hydrogen. Non-hydrogen substituent group (general and specific) are independently disclosed herein and can be utilized without limitation to further describe the linking group having Structure 1L, Structure 2L, Structure 3L, Structure 4L, and/or Structure 5L. In an embodiment, $L^{12}$ of the $N^2$-phosphinyl guanidine metal complex having Structure GuMC2 can be an eth-1,2-ylene group (—$CH_2CH_2$—), an ethen-1,2-ylene group (—CH=CH—), a prop-1,3-ylene group (—$CH_2CH_2CH_2$—), a 1-methylethen-1,2-ylene group (—C(CH$_3$)=CH—), a but-1,3-ylene group (—$CH_2CH_2CH(CH_3)$—), a 3-methylbut-1,3-ylene group (—$CH_2CH_2C(CH_3)_2$—), or a phen-1,2-ylene group. In some non-limiting embodiments, $L^{12}$ of the $N^2$-phosphinyl guanidine metal complex having Structure GuMC2 be an eth-1,2-ylene group (—$CH_2CH_2$—), a prop-1,3-ylene group (—$CH_2CH_2CH_2$—), a 1-methylethen-1,2-ylene group (—C(CH$_3$)=CH—), a but-1,3-ylene group (—$CH_2CH_2CH(CH_3)$—), or a 3-methylbut-1,3-ylene group (—$CH_2CH_2C(CH_3)_2$—); alternatively, an eth-1,2-ylene group (—$CH_2CH_2$—), an ethen-1,2-ylene group (—CH=CH—), a prop-1,3-ylene group (—$CH_2CH_2CH_2$—), or a phen-1,2-ylene group; alternatively, an eth-1,2-ylene group (—$CH_2CH_2$—) or a prop-1,3-ylene group (—$CH_2CH_2CH_2$—); alternatively, an ethen-1,2-ylene group (—CH=CH—) or a phen-1,2-ylene group. In other embodiments, $L^{12}$ of the $N^2$-phosphinyl guanidine metal complex having Structure GuMC2 can be an eth-1,2-ylene group (—$CH_2CH_2$—); alternatively, an ethen-1,2-ylene group (—CH=CH—); alternatively, a prop-1,3-ylene group (—$CH_2CH_2CH_2$—); alternatively, a 1-methylethen-1,2-ylene group (—C(CH$_3$)=CH—); alternatively, a but-,3-lene group (—$CH_2CH_2CH(CH_3)$—); alternatively, a 3-methylbut-1,3-ylene group (—$CH_2CH_2C(CH_3)_2$—); or alternatively, a phen-1,2-ylene group. In some embodiments, $L^{12}$ of the $N^2$-phosphinyl guanidine metal complex having Structure GuMC2 can be a —CH=CH—CH= group. In an embodiment, $L^{12}$ of the $N^2$-phosphinyl guanidine metal complex having Structure GuMC2 can have a structure that can comprise at least one substituent located on the carbon atom attached to the $N^1$ nitrogen atom of the $N^2$-phosphinyl guanidine metal complex; alternatively, can comprise only one substituent located on the carbon atom attached to the $N^1$ nitrogen atom of the $N^2$-phosphinyl guanidine metal complex; or alternatively, can comprise two substituents located on the carbon atom attached to the $N^1$ nitrogen atom of the $N^2$-phosphinyl guanidine metal complex. In another embodiment, $L^{12}$ of the $N^2$-phosphinyl guanidine metal complex having Structure GuMC2 can have a structure that can consist of one substituent located on the carbon atom attached to $N^1$ nitrogen atom of the $N^2$-phosphinyl guanidine metal complex; or alternatively, can consist of two substituents located on the carbon atom attached to N nitrogen atom of the $N^2$-phosphinyl guanidine metal complex.

In an embodiment, $R^{2a}$ and $R^{2b}$ of the $N^2$-phosphinyl guanidine metal complexes having Structure GuMC1 can be joined to form a group, $L^{22}$, wherein $R^{2a}$, $R^{2b}$, and the $N^3$ nitrogen (or $L^{22}$ and the $N^3$ nitrogen) forms a ring or ring system ($N^2$-phosphinyl guanidine metal complex Structure GuMC3). In an embodiment, $L^{22}$ of the $N^2$-phosphinyl guanidine metal complexes having Structure GuMC3 can be an organylene group; alternatively, an organylene group consisting of inert functional groups; or alternatively, a hydrocarbylene group. The organylene group which can be utilized as $L^{22}$ of the $N^2$-phosphinyl guanidine metal complexes having Structure GuMC3 can be a $C_3$ to $C_{20}$ organylene group; alternatively, a $C_3$ to $C_{15}$ organylene group; or alternatively, a $C_3$ to $C_{10}$ organylene group. The organylene group consisting of inert functional groups which can be utilized as $L^{22}$ of the $N^2$-phosphinyl guanidine metal complexes having Structure GuMC3 can be a $C_3$ to $C_{20}$ organylene group consisting of inert functional groups; alternatively, a $C_3$ to $C_{15}$ organylene group consisting of inert functional groups; or alternatively, a $C_3$ to $C_{10}$ organylene group consisting of inert functional groups. The hydrocarbylene group which can be utilized as $L^{22}$ of the $N^2$-phosphinyl guanidine metal complexes having Structure GuMC3 can be a $C_4$ to $C_{20}$ hydrocarbylene group; alternatively, a $C_4$ to $C_{15}$ hydrocarbylene group; or alternatively, a $C_4$ to $C_{10}$ hydrocarbylene group.

In an embodiment, $L^{22}$ of the $N^2$-phosphinyl guanidine metal complexes having Structure GuMC3 can have any structure provided in Table 2. In some embodiments, $L^{22}$ of the $N^2$-phosphinyl guanidine metal complexes having Structure GuMC3 can have Structure 11L, Structure 12L, Structure 13L, Structure 14L, Structure 15L; or Structure 16L. In other embodiments, the linking group can have Structure 11L; alternatively, Structure 12L; alternatively, Structure 13L; alternatively, Structure 14L; or alternatively, Structure 15L.

TABLE 2

| Potential Structure for Linking Groups $L^{22}$. | |
|---|---|
| —$(CR^{L31}R^{L32})_n$— | Structure 11L |
| —$CR^{L41}R^{L42}$—$CR^{L45}R^{L46}CR^{L47}R^{L48}CR^{L43}R^{L44}$— | Structure 12L |
| —$CR^{L41}R^{L42}$—$CR^{L45}R^{L46}$—$CR^{L49}R^{L50}$—$CR^{L47}R^{L48}$— $CR^{L43}R^{L44}$— | Structure 13L |
| —$CR^{L41}R^{L42}$—$CR^{L45}R^{L46}$—O—$CR^{L47}R^{L48}$— $CR^{L43}R^{L44}$— | Structure 14L |
| —$CR^{L51}$=$CR^{L53}$—$CR^{L54}$=$CR^{L52}$— | Structure 15L |

Within the structures of Table 2, the undesignated valencies represent the points at which $L^{22}$ of the $N^2$-phosphinyl guanidine metal complexes having Structure GuMC3, when present, attaches to the $N^3$ nitrogen atom of the $N^2$-phosphinyl guanidinemetal complex. Generally, n can be an integer ranging from 4 to 7. In further embodiments, n can be 4 or 5; alternatively, n can be 4; or alternatively, n can be 5. $R^{L31}$ and $R^{L32}$ of the linking group having Structure 11L, $R^{L41}$, $R^{L42}$, $R^{L43}$, $R^{L44}$, $R^{L45}$, $R^{L46}$, $R^{L47}$, and $R^{L48}$ of the linking group having Structure 12L, $R^{L41}$, $R^{L42}$, $R^{L43}$, $R^{L44}$, $R^{L45}$, $R^{L46}$, $R^{L47}$, $R^{L48}$, $R^{L49}$, and $R^{L50}$ of the linking group having Structure 13L, $R^{L41}$, $R^{L42}$, $R^{L43}$, $R^{L44}$, $R^{L45}$, $R^{L46}$, $R^{L47}$, and $R^{L48}$ of the linking group having Structure 14L, $R^{L41}$, $R^{L42}$, $R^{L43}$, $R^{L44}$, $R^{L45}$, $R^{L46}$, $R^{L47}$, and $R^{L48}$ of the linking group having Structure 15L, and $R^{L51}$, $R^{L52}$, $R^{L53}$, and $R^{L54}$ of the linking group having Structure 16L independently can be a hydrogen or a non-hydrogen substituent group (any general or specific described herein); alternatively, hydrogen. Non-hydrogen substituent groups (general and specific) are independently disclosed herein and can be utilized without limitation to further describe the linking group having Structure 11L, Structure 12L, Structure 13L, Structure 14L, and/or Structure 15L. In an embodiment, $L^{22}$ can be a but-1,4-ylene group, a pent-1,4-ylene group, a pent-1,5-ylene group, a hex-2,5-ylene group, a hex-1,5-ylene group, a hept-2,5-ylene group, a buta-1,3-dien-1,4-ylene group, or a bis(eth-2-yl)ether group; alternatively, a but-1,4-ylene group, a pent-1,5-ylene group, or a bis(eth-2-yl)ether group; alternatively, a but-1,4-ylene group; alternatively, a pent-1,5-ylene group; alternatively, a buta-1,3-dien-1,4-ylene group; or alternatively, a bis(eth-2-yl)ether group.

In an embodiment, the $N^2$-phosphinyl guanidine metal complex Structure GuMC6, GuMC7, GuMC8, GuMC9, GuMC10, GuMC11, GuMC12, GuMC13, or GuMC14; alternatively, Structure GuMC6 or GuMC7; alternatively, GuMC8, GuMC9, or GuMC10, GuMC11; alternatively, Structure GuMC12 GuMC13, or GuMC14; alternatively, Structure GuMC6; alternatively, Structure GuMC7; alternatively, Structure GuMC8; alternatively, Structure GuMC9; alternatively, Structure GuMC10; alternatively, Structure GuMC11; alternatively, Structure GuMC12; alternatively, Structure GuMC13; or alternatively, Structure GuMC14.

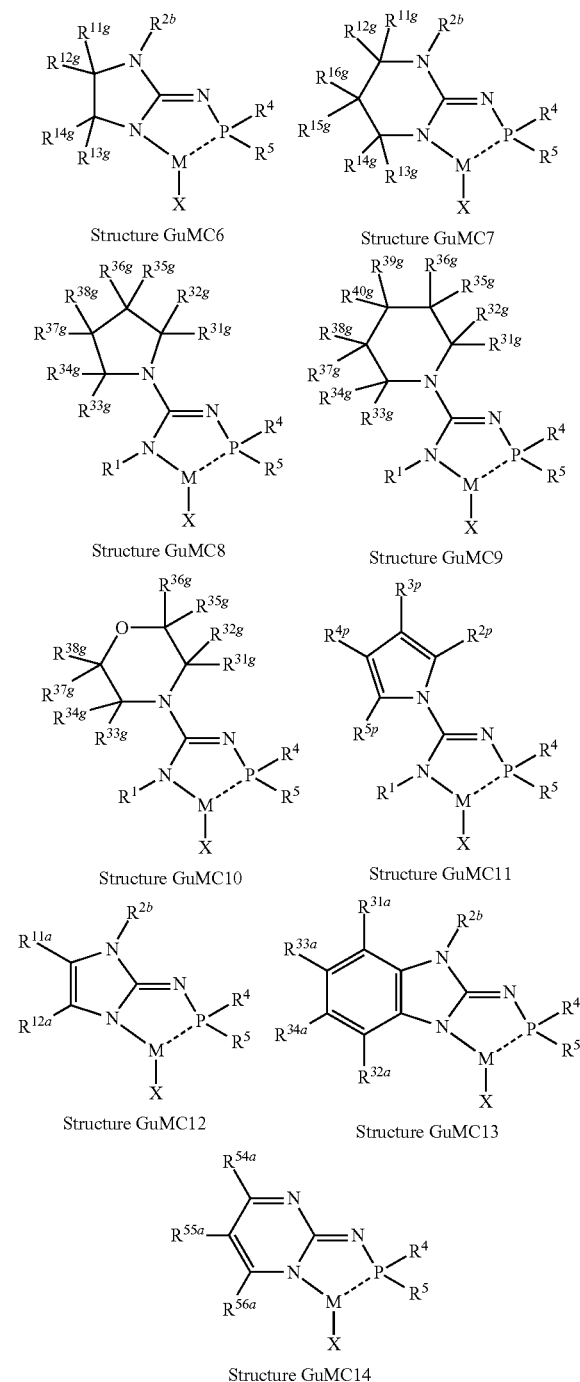

Structure GuMC6

Structure GuMC7

Structure GuMC8

Structure GuMC9

Structure GuMC10

Structure GuMC11

Structure GuMC12

Structure GuMC13

Structure GuMC14

Within the $N^2$-phosphinyl guanidine metal complexes having Structures GuMC6 to GuMC14, $R^1$, $R^{2a}$, $R^{2b}$, $R^4$, and $R^5$ have been previously described for the $N^2$-phosphinyl Guanidine compound Structures GuMC1-GuMC3. Any aspect or embodiment of these $R^1$, $R^{2a}$, $R^{2b}$, $R^4$, and $R^5$ descriptions (general or specific) can be utilized, without limitation, to further describe any of the ligand Structures GuMC6-GuMC14 in which $R^1$, $R^{2a}$, $R^{2b}$, $R^4$, and/or $R^5$ appears. Within the $N^2$-phosphinyl guanidine complexes having Structures GuMC6-GuMC14, $R^{11g}$-$R^{14g}$ of Structure GuMC6, $R^{11g}$-$R^{16g}$ of Structure GuMC7, $R^{31g}$-$R^{38g}$ of Structure GuMC8, $R^{31g}$-$R^{40g}$ of Structure GuMC9, $R^{2p}$-$R^{5p}$ of Structure GuMC11, $R^{11a}$-$R^{12a}$ of Structure GuMC12, $R^{31a}$-$R^{34a}$ of Structure GuMC13, and/or $R^{54a}$-$R^{56a}$ of Structure GuMC14 independently can be hydrogen or any substituent group (general or specific) described herein; or alternatively, hydrogen.

In an aspect, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be an organyl group; alternatively, an organyl group consisting essentially of inert functional groups; or alternatively, a hydrocarbyl group. In an embodiment, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_5$ organyl group. In an embodiment, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a $C_1$ to $C_{30}$ organyl group consisting essentially of inert functional groups; alternatively, a $C_1$ to $C_{20}$ organyl group consisting essentially of inert functional groups; alternatively, a $C_1$ to $C_{15}$ organyl group consisting essentially of inert functional groups; alternatively, a $C_1$ to $C_{10}$ organyl group consisting essentially of inert functional groups; or alternatively, a $C_1$ to $C_5$ organyl group consisting essentially of inert functional groups. In an embodiment, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_5$ hydrocarbyl group In yet other embodiments, $R^4$ and $R^5$ for the $N^2$-phosphinyl formamidine metal complexes, the $N^2$-phosphinyl amidine metal complexes, and/or the $N^2$-phosphinyl guanidine metal complexes can be independently selected from a $C_6$ to $C_{30}$ aromatic group; alternatively, a $C_6$ to $C_{20}$ aromatic group; alternatively, a $C_6$ to $C_{15}$ aromatic group; or alternatively, a $C_6$ to $C_{10}$ aromatic group. In an aspect, $R^4$ and $R^5$ can be joined to form a ring (regardless of particular type of group—organyl, organyl consisting of inert functional groups, hydrocarbyl, or any species within) containing the phosphorus atom of the $N^2$-phosphinyl formamidine metal complex, the $N^2$-phosphinyl amidine metal complex, and/or the $N^2$-phosphinyl guanidine metal complex.

In another aspect, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a $C_1$ to $C_{30}$ alkyl group, a $C_4$ to $C_{30}$ cycloalkyl group, a $C_4$ to $C_{30}$ substituted cycloalkyl group, a $C_6$ to $C_{30}$ aryl group, or a $C_6$ to $C_{30}$ substituted aryl group; alternatively, a $C_4$ to $C_{30}$ cycloalkyl group or a $C_4$ to $C_{30}$ substituted cycloalkyl group; alternatively, a $C_6$ to $C_{30}$ aryl group or a $C_6$ to $C_{30}$ substituted aryl group; alternatively, a $C_1$ to $C_{30}$ alkyl group; alternatively, a $C_4$ to $C_{30}$ cycloalkyl group; alternatively, a $C_4$ to $C_{30}$ substituted cycloalkyl group; alternatively, a $C_6$ to $C_{30}$ aryl group; or alternatively, a $C_6$ to $C_{30}$ substituted aryl group. In an embodiment, $R^4$ and $R^5$ for the $N^2$-phosphinyl formamidine metal complexes, the $N^2$-phosphinyl amidine metal complexes, and/or the $N^2$-phosphinyl guanidine metal complexes independently can be a $C_1$ to $C_{15}$ alkyl group, a $C_4$ to $C_{20}$ cycloalkyl group, a $C_4$ to $C_{20}$ substituted cycloalkyl group, a $C_6$ to $C_{20}$ aryl group, or a $C_6$ to $C_{20}$ substituted aryl group; alternatively, a $C_4$ to $C_{20}$ cycloalkyl group or a $C_4$ to $C_{20}$ substituted cycloalkyl group; alternatively, a $C_6$ to $C_{20}$ aryl group or a $C_6$ to $C_{20}$ substituted aryl group; alternatively, a $C_1$ to $C_{15}$ alkyl group; alternatively, a $C_4$ to $C_{20}$ cycloalkyl group; alternatively, a $C_4$ to $C_{20}$ substituted cycloalkyl group; alternatively, a $C_6$ to $C_{20}$ aryl group; or alternatively, a $C_6$ to $C_{20}$ substituted aryl group. In other embodiments, $R^4$ and $R^5$ independently can be a $C_1$ to $C_{10}$ alkyl group, a $C_4$ to $C_{15}$ cycloalkyl group, a $C_4$ to $C_{15}$ substituted cycloalkyl group, a $C_6$ to $C_{15}$ aryl group, or a $C_6$ to $C_{15}$ substituted aryl group; alternatively, a $C_4$ to $C_{15}$ cycloalkyl group or a $C_4$ to $C_{15}$ substituted cycloalkyl group; alternatively, a $C_6$ to $C_{15}$ aryl group or a $C_6$ to $C_{15}$ substituted aryl group; alternatively, a $C_1$ to $C_{10}$ alkyl group; alternatively, a $C_4$ to $C_{15}$ cycloalkyl group; alternatively, a $C_4$ to $C_{15}$ substituted cycloalkyl group; alternatively, a $C_6$ to $C_{15}$ aryl group; or alternatively, a $C_6$ to $C_{15}$ substituted aryl group. In further embodiments, $R^4$ and $R^5$ for the $N^2$-phosphinyl formamidine metal complexes, the $N^2$-phosphinyl amidine metal complexes, and/or the $N^2$-phosphinyl guanidine metal complexes independently can be a $C_1$ to $C_5$ alkyl group. Substituents (general and specific) are independently disclosed herein and can be utilized without limitation to further describe substituted groups which can be utilized as $R^4$ and/or $R^5$ for the $N^2$-phosphinyl formamidine metal complexes, the $N^2$-phosphinyl amidine metal complexes, and/or the $N^2$-phosphinyl guanidine metal complexes.

In a further aspect, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a methyl group, an ethyl group, a propyl group, a butyl group, a pentyl group, a hexyl group, a heptyl group, an octyl group, a nonyl group, or a decyl group. In some embodiments, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a methyl group, an ethyl group, an n-propyl group, an iso-propyl group, an n-butyl group, an iso-butyl group, a sec-butyl group, a tert-butyl group, an n-pentyl group, an iso-pentyl group, a sec-pentyl group, or a neopentyl group; alternatively, a methyl group, an ethyl group, an iso-propyl group, a tert-butyl group, or a neopentyl group; alternatively, a methyl group, an ethyl group, an n-propyl group, an n-butyl group, an n-pentyl group, or an n-hexyl group; alternatively, a methyl group; alternatively, an ethyl group; alternatively, an n-propyl group; alternatively, an iso-propyl group; alternatively, an n-butyl group; alternatively, a tert-butyl group; alternatively, an n-pentyl group; alternatively, a neopentyl group; or alternatively, an n-hexyl group. In some embodiments, the alkyl groups which can be utilized as $R^4$ and/or $R^5$ for the $N^2$-phosphinyl formamidine metal complexes, the $N^2$-phosphinyl amidine metal complexes, and/or the $N^2$-phosphinyl guanidine metal complexes can be substituted. Each substituent of a substituted alkyl group independently can be a halogen or a hydrocarboxy group; alternatively, a halogen; or alternatively, a hydrocarboxy group. Halogens, and hydrocarboxy groups (general and specific) are independently disclosed herein and can be utilized without limitation to further describe the substituted alkyl group which can be utilized as $R^4$ and/or $R^5$ for the $N^2$-phosphinyl formamidine metal complexes, the $N^2$-phosphinyl amidine metal complexes, and/or the $N^2$-phosphinyl guanidine metal complexes.

In a further aspect, $R^4$ and $R^5$ for the $N^2$-phosphinyl formamidine metal complexes, the $N^2$-phosphinyl amidine metal complexes, and/or the $N^2$-phosphinyl guanidine metal complexes independently can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In some embodiments, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a cyclopentyl group, a substituted cyclopentyl group, a cyclohexyl group, or a substituted cyclohexyl group. In other embodiments, $R^4$ and/or $R^5$ for the $N^2$-phosphinyl formamidine metal complexes, the $N^2$-phosphinyl amidine metal complexes, and/or the $N^2$-phosphinyl guanidine metal complexes can be a cyclopentyl group or a substituted cyclopentyl group; or alternatively, a cyclohexyl group or a substituted cyclohexyl group. In further embodiments, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a cyclopentyl group; alternatively, a substituted cyclopentyl group; a cyclohexyl group; or alternatively, a substituted cyclohexyl group. Substituents (general and specific) are independently disclosed herein and can be utilized without limitation to further describe the substituted cycloalkyl group which can be utilized as $R^4$ and/or $R^5$ for the $N^2$-phosphinyl formamidine metal complexes, the $N^2$-phosphinyl amidine metal complexes, and/or the $N^2$-phosphinyl guanidine metal complexes.

In an aspect, $R^4$ for the $N^2$-phosphinyl formamidine metal complexes, the $N^2$-phosphinyl amidine metal complexes, and/or the $N^2$-phosphinyl guanidine metal complexes can have Structure G7:

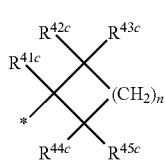

Structure G7 wherein, the undesignated valency is attached to the phosphorus atom of the $N^2$-phosphinyl formamidine metal complexes, the $N^2$-phosphinyl amidine metal complexes, and/or the $N^2$-phosphinyl guanidine metal complexes. Generally, $R^{41c}$, $R^{42c}$, $R^{43c}$, $R^{44c}$, and $R^{45c}$ independently can be hydrogen or a non-hydrogen substituent, and n can be an integer from 1 to 5. In an embodiment wherein $R^4$ has Structure G7 for the $N^2$-phosphinyl formamidine metal complexes, the $N^2$-phosphinyl amidine metal complexes, and/or the $N^2$-phosphinyl guanidine metal complexes, $R^{41c}$, $R^{43c}$, $R^{44c}$, and $R^{45c}$ can be hydrogen and $R^{32c}$ can be any non-hydrogen substituent disclosed herein; or alternatively, $R^{41c}$, $R^{43c}$, and $R^{45c}$ can be hydrogen and $R^{42c}$ and $R^{44c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively 3. Substituents (general and specific) are independently disclosed herein and can be utilized without limitation to further describe a non-hydrogen substituent which can be utilized without limitation as $R^{41c}$, $R^{42c}$, $R^{43c}$, $R^{44c}$, and/or $R^{45c}$ for the $R^4$ group having Structure G7 for the $N^2$-phosphinyl formamidine metal complexes, the $N^2$-phosphinyl amidine metal complexes, and/or the $N^2$-phosphinyl guanidine metal complexes.

In an aspect, $R^5$ for the $N^2$-phosphinyl formamidine metal complexes, the $N^2$-phosphinyl amidine metal complexes, and/or the $N^2$-phosphinyl guanidine metal complexes can have Structure G8:

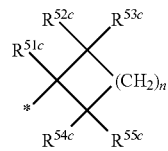

Structure G8 wherein, the undesignated valency is attached to the phosphorus atom of the $N^2$-phosphinyl formamidine metal complexes, the $N^2$-phosphinyl amidine metal complexes, and/or the $N^2$-phosphinyl guanidine metal complexes. Generally, $R^{51c}$, $R^{52c}$, $R^{53c}$, $R^{54c}$, and $R^{55c}$ independently can be hydrogen or a non-hydrogen substituent, and n can be an integer from 1 to 5. In an embodiment wherein $R^5$ has Structure G8 for the $N^2$-phosphinyl formamidine metal complexes, the $N^2$-phosphinyl amidine metal complexes, and/or the $N^2$-phosphinyl guanidine metal complexes, $R^{51c}$, $R^{53c}$, $R^{54c}$, and $R^{55c}$ can be hydrogen and $R^{32c}$ can be any non-hydrogen substituent disclosed herein; or alternatively, $R^{51c}$, $R^{53c}$, and $R^{55c}$ can be hydrogen and $R^{52c}$ and $R^{54c}$ independently can be any non-hydrogen substituent disclosed herein. In an embodiment, n can be an integer from 1 to 4; or alternatively, from 2 to 4. In other embodiments, n can be 2 or 3; alternatively, 2; or alternatively 3. Substituents (general and specific) are independently disclosed herein and can be utilized without limitation to further describe a non-hydrogen substituent which can be utilized without limitation as $R^{51c}$, $R^{52c}$, $R^{53c}$, $R^{54c}$, and/or $R^{55c}$ for the $R^5$ group having Structure G8 for the $N^2$-phosphinyl formamidine metal complexes, the $N^2$-phosphinyl amidine metal complexes, and/or the $N^2$-phosphinyl guanidine metal complexes.

In an aspect, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a phenyl group or a substituted phenyl group; alternatively, a phenyl group; or alternatively, a substituted phenyl group. Substituents (general and specific) are independently disclosed herein and can be utilized without limitation to further describe any substituted phenyl group which can be utilized as $R^4$ and/or $R^5$ for the $N^2$-phosphinyl formamidine metal complexes, the $N^2$-phosphinyl amidine metal complexes, and/or the $N^2$-phosphinyl guanidine metal complexes.

In an embodiment, the $R^4$ and/or $R^5$ substituted phenyl group for the $N^2$-phosphinyl formamidine metal complexes, the $N^2$-phosphinyl amidine metal complexes, and/or the $N^2$-phosphinyl guanidine metal complexes can be a 2-substituted phenyl group, a 3-substituted phenyl group, a 4-substituted phenyl group, a 2,4-disubstituted phenyl group, a 2,6-disubstituted phenyl group, a 3,5-disubstituted phenyl group, or a 2,4,6-trisubstituted phenyl group. In other embodiments, the $R^4$ and/or $R^5$ substituted phenyl group for the $N^2$-phosphinyl formamidine metal complexes, the $N^2$-phosphinyl amidine metal complexes, and/or the $N^2$-phosphinyl guanidine metal complexes can be a 2-substituted phenyl group, a 4-substituted phenyl group, a 2,4-disubstituted phenyl group, a 2,6-disubstituted phenyl group, or a 2,4,6-trisubstituted phenyl group; alternatively, a 2-substituted phenyl group, a 4-substituted phenyl group, a 2,4-disubstituted phenyl group, or a 2,6-disubstituted phenyl group; alternatively, a 3-substituted phenyl group or a 3,5-disubstituted phenyl group; alternatively, a 2-substituted phenyl group or a 4-substituted phenyl group; alternatively, a 2,4-disubstituted phenyl group, a 2,6-disubstituted phenyl group, or a 2,4,6-trisubstituted phenyl group; alternatively, a 2,6-disubstituted phenyl group or a 2,4,6-trisubstituted phenyl group; alternatively, a 2,4-disubstituted phenyl group or a 2,6-disubstituted phenyl group; alternatively, a 2-substituted phenyl group; alternatively, a 3-substituted phenyl group; alternatively, a 4-substituted phenyl group; alternatively, a 2,4-disubstituted phenyl group; alternatively, a 2,6-disubstituted phenyl group; alternatively, a 3,5-disubstituted phenyl group; or alternatively, a 2,4,6-trisubstituted phenyl group. Substituents (general and specific) are independently disclosed herein and can be utilized without limitation to further describe any substituted phenyl group which can be utilized as $R^4$ and/or $R^5$ for the $N^2$-phosphinyl formamidine metal complexes, the $N^2$-phosphinyl amidine metal complexes, and/or the $N^2$-phosphinyl guanidine metal complexes.

In an aspect, $R^4$ for the $N^2$-phosphinyl formamidine metal complexes, the $N^2$-phosphinyl amidine metal complexes, and/or the $N^2$-phosphinyl guanidine metal complexes have Structure G9:

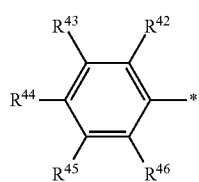

Structure G9 wherein the undesignated valency is attached to the phosphorus atom of the $N^2$-phosphinyl formamidine metal complex, the $N^2$-phosphinyl amidine metal complex, and/or the $N^2$-phosphinyl guanidine metal complex. Generally, $R^{42}$, $R^{43}$, $R^{44}$, $R^{45}$, and $R^{46}$ can independently be a hydrogen or a non-hydrogen substituent. In an embodiment wherein $R^4$ has Structure G9 for the $N^2$-phosphinyl formamidine metal complexes, the $N^2$-phosphinyl amidine metal complexes, and/or the $N^2$-phosphinyl guanidine metal complexes, $R^{42}$, $R^{43}$, $R^{44}$, $R^{45}$, and $R^{46}$ can be hydrogen, $R^{43}$, $R^{44}$, $R^{45}$, and $R^{46}$ can be hydrogen and $R^{42}$ can be a non-hydrogen substituent, $R^{42}$, $R^{44}$, $R^{45}$, and $R^{46}$ can be hydrogen and $R^{43}$ can be a non-hydrogen substituent, $R^{42}$, $R^{43}$, $R^{45}$, and $R^{46}$ can be hydrogen and $R^{44}$ can be a non-hydrogen substituent, $R^{43}$, $R^{45}$, and $R^{46}$ can be hydrogen and $R^{42}$ and $R^{44}$ can be non-hydrogen substituents, $R^{43}$, $R^{44}$, and $R^{45}$ can be hydrogen and $R^{42}$ and $R^{46}$ can be non-hydrogen substituents, $R^{42}$, $R^{44}$, and $R^{46}$ can be hydrogen and $R^{43}$ and $R^{45}$ can be non-hydrogen substituents, or $R^{43}$ and $R^{45}$ can be hydrogen and $R^{42}$, $R^{44}$, and $R^{46}$ can be non-hydrogen substituents. In some embodiments wherein $R^4$ has Structure G9 for the $N^2$-phosphinyl formamidine metal complexes, the $N^2$-phosphinyl amidine metal complexes, and/or the $N^2$-phosphinyl guanidine metal complexes, $R^{43}$, $R^{44}$, $R^{45}$, and $R^{46}$ can be hydrogen and $R^{42}$ can be a non-hydrogen substituent, $R^{42}$, $R^{43}$, $R^{45}$, and $R^{46}$ can be hydrogen and $R^{44}$ can be a non-hydrogen substituent, $R^{43}$, $R^{45}$, and $R^{46}$ can be hydrogen and $R^{42}$ and $R^{44}$ can be non-hydrogen substituents, $R^{43}$, $R^{44}$, and $R^{45}$ can be hydrogen and $R^{42}$ and $R^{46}$ can be non-hydrogen substituents, or $R^{43}$ and $R^{45}$ can be hydrogen and $R^{42}$, $R^{44}$, and $R^{46}$ can be non-hydrogen substituents; alternatively, $R^{43}$, $R^{44}$, $R^{45}$, and $R^{46}$ can be hydrogen and $R^{42}$ can be a non-hydrogen substituent, $R^{42}$, $R^{43}$, $R^{45}$, and $R^{46}$ can be hydrogen and $R^{44}$ can be a non-hydrogen substituent, $R^{43}$, $R^{45}$, and $R^{46}$ can be hydrogen and $R^{42}$ and $R^{44}$ can be non-hydrogen substituents, or $R^{43}$, $R^{44}$, and $R^{45}$ can be hydrogen and $R^{42}$ and $R^{46}$ can be non-hydrogen substituents; alternatively, $R^{42}$, $R^{44}$, $R^{45}$, and $R^{46}$ can be hydrogen and $R^{43}$ can be a non-hydrogen substituent, or $R^{42}$, $R^{43}$, $R^{45}$, and $R^{46}$ can be hydrogen and $R^{44}$ can be a non-hydrogen substituent; alternatively, $R^{43}$, $R^{45}$, and $R^{46}$ can be hydrogen and $R^{42}$ and $R^{44}$ can be non-hydrogen substituents, $R^{43}$, $R^{44}$, and $R^{45}$ can be hydrogen and $R^{42}$ and $R^{46}$ can be non-hydrogen substituents, or $R^{43}$ and $R^{45}$ can be hydrogen and $R^{42}$, $R^{44}$, and $R^{46}$ can be non-hydrogen substituents; or alternatively, $R^{43}$, $R^{45}$, and $R^{46}$ can be hydrogen and $R^{42}$ and $R^{44}$ can be non-hydrogen substituents, or $R^{43}$, $R^{44}$, and $R^{45}$ can be hydrogen and $R^{42}$ and $R^{46}$ can be non-hydrogen substituents. In other embodiments wherein $R^4$ has Structure G9 for the $N^2$-phosphinyl formamidine metal complexes, the $N^2$-phosphinyl amidine metal complexes, and/or the $N^2$-phosphinyl guanidine metal complexes, $R^{42}$, $R^{43}$, $R^{44}$, $R^{45}$, and $R^{46}$ can be hydrogen; alternatively, $R^{43}$, $R^{44}$, $R^{45}$, and $R^{46}$ can be hydrogen and $R^{42}$ can be a non-hydrogen substituent; alternatively, $R^{42}$, $R^{44}$, $R^{45}$, and $R^{46}$ can be hydrogen and $R^{43}$ can be a non-hydrogen substituent; alternatively, $R^{42}$, $R^{43}$, $R^{45}$, and $R^{46}$ can be hydrogen and $R^{44}$ can be a non-hydrogen substituent; alternatively, $R^{43}$, $R^{45}$, and $R^{46}$ can be hydrogen and $R^{42}$ and $R^{44}$ can be non-hydrogen substituents; alternatively, $R^{43}$, $R^{44}$, and $R^{45}$ can be hydrogen and $R^{42}$ and $R^{46}$ can be non-hydrogen substituents; alternatively, $R^{42}$, $R^{44}$, and $R^{46}$ can be hydrogen and $R^{43}$ and $R^{45}$ and can be non-hydrogen substituents; or alternatively, $R^{43}$ and $R^{45}$ can be hydrogen and $R^{42}$, $R^{44}$, and $R^{46}$ can be non-hydrogen substituents. Substituents (general and specific) are independently disclosed herein and can be utilized without limitation as $R^{42}$, $R^{43}$, $R^4$, $R^{45}$, and $R^{46}$ for the $R^4$ group having Structure G9 for the $N^2$-phosphinyl formamidine metal complexes, the $N^2$-phosphinyl amidine metal complexes, and/or the $N^2$-phosphinyl guanidine metal complexes.

In an aspect, $R^5$ for the $N^2$-phosphinyl formamidine metal complexes, the $N^2$-phosphinyl amidine metal complexes, and/or the $N^2$-phosphinyl guanidine metal complexes can have Structure G10:

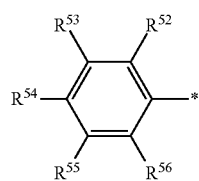

Structure G10 wherein the undesignated valency is attached to the phosphorus atom of the $N^2$-phosphinyl formamidine metal complex, the $N^2$-phosphinyl amidine metal complex, and/or the $N^2$-phosphinyl guanidine metal complex. Generally, $R^{52}$, $R^{53}$, $R^{54}$, $R^{55}$, and $R^{56}$ independently can be hydrogen or a non-hydrogen substituent. In an embodiment wherein $R^5$ has Structure G10 for the $N^2$-phosphinyl formamidine metal complexes, the $N^2$-phosphinyl amidine metal complexes, and/or the $N^2$-phosphinyl guanidine metal complexes, $R^{52}$, $R^{53}$, $R^{54}$, $R^{55}$, and $R^{56}$ can be hydrogen, $R^{53}$, $R^{54}$, $R^{55}$, and $R^{56}$ can be hydrogen and $R^{52}$ can be a non-hydrogen substituent, $R^{52}$, $R^{54}$, $R^{55}$, and $R^{56}$ can be hydrogen and $R^{53}$ can be a non-hydrogen substituent, $R^{52}$, $R^{53}$, $R^{55}$, and $R^{56}$ can be hydrogen and $R^{54}$ can be a non-hydrogen substituent, $R^{53}$, $R^{55}$, and $R^{56}$ can be hydrogen and $R^{52}$ and $R^{54}$ can be non-hydrogen substituents, $R^{53}$, $R^{54}$, and $R^{55}$ can be hydrogen and $R^{52}$ and $R^{56}$ can be non-hydrogen substituents, $R^{52}$, $R^{54}$, and $R^{56}$ can be hydrogen and $R^{53}$ and $R^{55}$ can be non-hydrogen substituents, or $R^{53}$ and $R^{55}$ can be hydrogen and $R^{52}$, $R^{54}$, and $R^{56}$ can be non-hydrogen substituents. In some embodiments wherein $R^5$ has Structure G10 for the $N^2$-phosphinyl formamidine metal complexes, the $N^2$-phosphinyl amidine metal complexes, and/or the $N^2$-phosphinyl guanidine metal complexes, $R^{53}$, $R^{54}$, $R^{55}$, and $R^{56}$ can be hydrogen and $R^{52}$ can be a non-hydrogen substituent, $R^{52}$, $R^{53}$, $R^{55}$, and $R^{56}$ can be hydrogen and $R^{54}$ can be a non-hydrogen substituent, $R^{53}$, $R^{55}$, and $R^{56}$ can be hydrogen and $R^{52}$ and $R^{54}$ can be non-hydrogen substituents, $R^{53}$, $R^{54}$, and $R^{55}$ can be hydrogen and $R^{52}$ and $R^{56}$ can be non-hydrogen substituents, or $R^{53}$ and $R^{55}$ can be hydrogen and $R^{52}$, $R^{54}$, and $R^{56}$ can be non-hydrogen substituents; alternatively, $R^{53}$, $R^{54}$, $R^{55}$, and $R^{56}$ can be hydrogen and $R^{52}$ can be a non-hydrogen substituent, $R^{52}$, $R^{53}$, $R^{55}$, and $R^{56}$ can be hydrogen and $R^{54}$ can be a non-hydrogen substituent, $R^{53}$, $R^{55}$, and $R^{56}$ can be hydrogen and $R^{52}$ and $R^{54}$ can be non-hydrogen substituents, or $R^{53}$, $R^{54}$, and $R^{55}$ can be hydrogen and $R^{52}$ and $R^{56}$ can be non-hydrogen substituents; alternatively, $R^{52}$, $R^{54}$, $R^{55}$, and $R^{56}$ can be hydrogen and $R^{53}$ can be a non-hydrogen substituent, or $R^{52}$, $R^{54}$, and $R^{56}$ can be hydrogen and $R^{53}$ and $R^{55}$ can be non-hydrogen substituents; alternatively, $R^{53}$, $R^{54}$, $R^{55}$, and $R^{56}$ can be hydrogen and $R^{52}$ can be a non-hydrogen substituent, or $R^{52}$, $R^{53}$, $R^{55}$, and $R^{56}$ can be hydrogen and $R^{54}$ can be a non-hydrogen substituent; alternatively, $R^{53}$, $R^{55}$, and $R^{56}$ can be hydrogen and $R^{52}$ and $R^{54}$ can be non-hydrogen substituents, $R^{53}$, $R^{54}$, and $R^{55}$ can be hydrogen and $R^{52}$ and $R^{56}$ can be non-hydrogen substituents, or $R^{53}$ and $R^{55}$ can be hydrogen and $R^{52}$, $R^{54}$, and $R^{56}$ can be non-hydrogen substituents; or alternatively, $R^{53}$, $R^{55}$, and $R^{56}$ can be hydrogen and $R^{52}$ and $R^{54}$ can be non-hydrogen substituents, or $R^{53}$, $R^{54}$, and $R^{55}$ can be hydrogen and $R^{52}$ and $R^{56}$ can be non-hydrogen substituents. In other embodiments wherein $R^5$ has Structure G10 for the $N^2$-phosphinyl formamidine metal complexes, the $N^2$-phosphinyl amidine metal complexes, and/or the $N^2$-phosphinyl guanidine metal complexes, $R^{52}$, $R^{53}$, $R^{54}$, $R^{55}$, and $R^{56}$ can be hydrogen; alternatively, $R^{53}$, $R^{54}$, $R^{55}$, and $R^{56}$ can be hydrogen and $R^{52}$ can be a non-hydrogen substituent; alternatively, $R^{52}$, $R^{54}$, $R^{55}$, and $R^{56}$ can be hydrogen and $R^{53}$ can be a non-hydrogen substituent; alternatively, $R^{52}$, $R^{53}$, $R^{55}$, and $R^{56}$ can be hydrogen and $R^{54}$ can be a non-hydrogen substituent; alternatively, $R^{53}$, $R^{55}$ and $R^{56}$ can be hydrogen and $R^{52}$ and $R^{54}$ can be non-hydrogen substituents; alternatively, $R^{53}$, $R^{54}$, and $R^{55}$ can be hydrogen and $R^{52}$ and $R^{56}$ can be non-hydrogen substituents; alternatively, $R^{52}$, $R^{54}$, and $R^{56}$ can be hydrogen and $R^{53}$ and $R^{55}$ and can be non-hydrogen substituents; or alternatively, $R^{53}$ and $R^{55}$ can be hydrogen and $R^{52}$, $R^{54}$, and $R^{56}$ can be non-hydrogen substituents. Substituents (general and specific) are independently disclosed herein and can be utilized without limitation as $R^{52}$, $R^{53}$, $R^{54}$, $R^{55}$, and $R^{56}$ for the $R^5$ group having Structure G10 for the $N^2$-phosphinyl formamidine metal complexes, the $N^2$-phosphinyl amidine metal complexes, and/or the $N^2$-phosphinyl guanidine metal complexes.

In an aspect, $R^4$ and $R^5$ for the $N^2$-phosphinyl formamidine metal complexes, the $N^2$-phosphinyl amidine metal complexes, and/or the $N^2$-phosphinyl guanidine metal complexes can be joined to form a cyclic group including the phosphorus atom. In an embodiment when $R^4$ and $R^5$ for the $N^2$-phosphinyl formamidine metal complexes, the $N^2$-phosphinyl amidine metal complexes, and/or the $N^2$-phosphinyl guanidine metal complexes are joined to form a cyclic group including the phosphorus atom of the $N^2$-phosphinyl formamidine metal complex, the $N^2$-phosphinyl amidine metal complex, and/or the $N^2$-phosphinyl guanidine metal complex, the phosphinyl group can be a phosphol-1-yl group, a substituted phosphol-1-yl group, a 2,3-dihydrophosphol-1-yl group, a substituted 2,3-dihydrophosphol-1-yl group, a 3,5-dihydrophosphol-1-yl group, a substituted 3,5-dihydrophosphol-1-yl group, a phospholan-1-yl group, a substituted phospholan-1-yl group, a 1,2-dihydrophosphinin-1-yl group, a substituted, 1,2-dihydro-phosphinin-1-yl group, a 1,4-dihydrophosphinin-1-yl group, a substituted 1,4-dihydrophosphinin-1-yl group, a 1,2,3,4-tetrahydrophosphinin-1-yl group, a substituted 1,2,3,4-tetrahydrophosphinin-1-yl group, a 1,2,3,6-tetrahydrophosphinin-1-yl group, a substituted 1,2,3,6-tetrahydrophosphinin-1-yl group, a phosphinan-1-yl group, or a substituted phosphinan-1-yl group. In some embodiments, when $R^4$ and $R^5$ for the $N^2$-phosphinyl formamidine metal complexes, the $N^2$-phosphinyl amidine metal complexes, and/or the $N^2$-phosphinyl guanidine metal complexes are joined to form a cyclic group including the phosphorus atom of the $N^2$-phosphinyl formamidine metal complex, the $N^2$-phosphinyl amidine metal complex, and/or the $N^2$-phosphinyl guanidine metal complex, the phosphinyl group can be a phosphol-1-yl group or a substituted phosphol-1-yl group; alternatively, a 2,3-dihydrophosphol-1-yl group or a substituted 2,3-dihydrophosphol-1-yl group; alternatively, a 3,5-dihydrophosphol-1-yl group or a substituted 3,5-dihydrophosphol-1-yl group; alternatively, a phospholan-1-yl group or a substituted phospholan-1-yl group; alternatively, a 1,2-dihydro-phosphinin-1-yl group or a substituted, 1,2-dihydrophosphinin-1-yl group; alternatively, a 1,4-dihydro-phosphinin-1-yl group or a substituted 1,4-dihydrophosphinin-1-yl group; alternatively, a 1,2,3,4-tetra-hydrophosphinin-1-yl group or a substituted 1,2,3,4-tetrahydrophosphinin-1-yl group; alternatively, a 1,2,3,6-tetrahydrophosphinin-1-yl group or a substituted 1,2,3,6-tetrahydrophosphinin-1-yl group; or alternatively, a phosphinan-1-yl group or a substituted phosphinan-1-yl group. In some embodiments, when $R^4$ and $R^5$ for the $N^2$-phosphinyl formamidine metal complexes, the $N^2$-phosphinyl amidine metal complexes, and/or the $N^2$-phosphinyl guanidine metal complexes are joined to form a cyclic group including the phosphorus atom of the $N^2$-phosphinyl formamidine metal complex, the $N^2$-phosphinyl amidine metal complex, and/or the $N^2$-phosphinyl guanidine metal complex, the phosphinyl group can be a phosphol-1-yl group, a 2,3-dihydrophosphol-1-yl group, a 3,5-dihydrophosphol-1-yl group, a phospholan-1-yl group, a 1,2-dihydrophosphinin-1-yl group, a 1,4-dihydrophosphinin-1-yl group, a 1,2,3,4-tetrahydrophosphinin-1-yl group, a 1,2,3,6-tetrahydrophosphinin-1-yl group, or a phosphinan-1-yl group. In other embodiments, when $R^4$ and $R^5$ for the $N^2$-phosphinyl formamidine metal complexes, the $N^2$-phosphinyl amidine metal complexes, and/or the $N^2$-phosphinyl guanidine metal complexes are joined to form a cyclic group including the phosphorus atom of the $N^2$-phosphinyl formamidine metal complex, the $N^2$-phosphinyl amidine metal complex, and/or the $N^2$-phosphinyl guanidine metal complex, the phosphinyl group can be a substituted phosphol-1-yl group, a substituted 2,3-dihydrophosphol-1-yl group, a substituted 3,5-dihydrophosphol-1-yl group, a substituted phospholan-1-yl group, a substituted, 1,2-dihydrophosphinin-1-yl group, a substituted 1,4-dihydrophosphinin-1-yl group, a substituted 1,2,3,4-tetrahydrophosphinin-1-yl group, a substituted 1,2,3,6-tetrahydrophosphinin-1-yl group, or a substituted phosphinan-1-yl group. In yet other embodiments, when $R^4$ and $R^5$ for the $N^2$-phosphinyl formamidine metal complexes, the $N^2$-phosphinyl amidine metal complexes, and/or the $N^2$-phosphinyl guanidine metal complexes are joined to form a cyclic group including the phosphorus atom of the $N^2$-phosphinyl formamidine metal complex, the $N^2$-phosphinyl amidine metal complex, and/or the $N^2$-phosphinyl guanidine metal complex, the phosphinyl group can be a phospholan-1-yl group, a substituted phospholan-1-yl group, a phosphinan-1-yl group, or a substituted phosphinan-1-yl group; alternatively, a phospholan-1-yl group or a phosphinan-1-yl group; or alternatively, a substituted phospholan-1-yl group or a substituted phosphinan-1-yl group. In further embodiments, when $R^4$ and $R^5$ for the $N^2$-phosphinyl formamidine metal complexes, the $N^2$-phosphinyl amidine metal complexes, and/or the $N^2$-phosphinyl guanidine metal complexes are joined to form a cyclic group including the phosphorus atom of the $N^2$-phosphinyl formamidine metal complex, the $N^2$-phosphinyl amidine metal complex, and/or the $N^2$-phosphinyl guanidine metal complex, the phosphinyl group can be a phosphol-1-yl group; alternatively, a substituted phosphol-1-yl group; alternatively, a 2,3-dihydrophosphol-1-yl group; alternatively, a substituted 2,3-dihydrophosphol-1-yl group; alternatively, a 3,5-dihydrophosphol-1-yl group; alternatively, a substituted 3,5-dihydrophosphol-1-yl group; alternatively, a phospholan-1-yl group; alternatively, a substituted phospholan-1-yl group; alternatively, a 1,2-dihydrophosphinin-1-yl group; alternatively, a substituted, 1,2-dihydrophosphinin-1-yl group; alternatively, a 1,4-dihydrophosphinin-1-yl group; alternatively, a substituted 1,4-dihydrophosphinin-1-yl group; alternatively, a 1,2,3,4-tetrahydrophosphinin-1-yl group; alternatively, a substituted 1,2,3,4-tetrahydrophosphinin-1-yl group; alternatively, a 1,2,3,6-tetrahydrophosphinin-1-yl group; alternatively, a substituted 1,2,3,6-tetrahydrophosphinin-1-yl group; alternatively, a phosphinan-1-yl group; or alternatively, a substituted phosphinan-1-yl group. Substituents (general and specific) are independently disclosed herein and can be utilized without limitation to further describe substituted groups where $R^4$ and $R^5$ for the $N^2$-phosphinyl formamidine metal complexes, the $N^2$-phosphinyl amidine metal complexes, and/or the $N^2$-phosphinyl guanidine metal complexes are joined to form a cyclic group including the phosphorus atom.

In an embodiment, when $R^4$ and $R^5$ for the $N^2$-phosphinyl formamidine metal complexes, the $N^2$-phosphinyl amidine metal complexes, and/or the $N^2$-phosphinyl guanidine metal complexes are joined to form a cyclic group including the phosphorus atom of the $N^2$-phosphinyl formamidine metal complex, the $N^2$-phosphinyl amidine metal complex, and/or the $N^2$-phosphinyl guanidine metal complex, the cyclic group including the phosphorus atom can comprise at least one substituent on a carbon atom adjacent to the phosphorus atom attached to the $N^2$ nitrogen atom of the $N^2$-phosphinyl formamidine metal complex, the $N^2$-phosphinyl amidine metal complex, and/or the $N^2$-phosphinyl guanidine metal complex. In some embodiments, when $R^4$ and $R^5$ for the $N^2$-phosphinyl formamidine metal complexes, the $N^2$-phosphinyl amidine metal complexes, and/or the $N^2$-phosphinyl guanidine metal complexes are joined to form a cyclic group including the phosphorus atom of the $N^2$-phosphinyl formamidine metal complex, the $N^2$-phosphinyl amidine metal complex, and/or the $N^2$-phosphinyl guanidine metal complex, the cyclic group including the phosphorus atom can comprise at least one substituent on each carbon atom adjacent to the phosphorus atom attached to the $N^2$ nitrogen atom of the $N^2$-phosphinyl formamidine metal complex, the $N^2$-phosphinyl amidine metal complex, and/or the $N^2$-phosphinyl guanidine metal complex. In other embodiments, when $R^4$ and $R^5$ for the $N^2$-phosphinyl formamidine metal complexes, the $N^2$-phosphinyl amidine metal complexes, and/or the $N^2$-phosphinyl guanidine metal complexes are joined to form a cyclic group including the phosphorus atom of the $N^2$-phosphinyl formamidine metal complex, the $N^2$-phosphinyl amidine metal complex, and/or the $N^2$-phosphinyl guanidine metal complex, the cyclic group including the phosphorus atom can comprise, or consist of, only one substituent on a carbon atom adjacent to the phosphorus atom attached to the $N^2$ nitrogen atom of the $N^2$-phosphinyl formamidine metal complex, the $N^2$-phosphinyl amidine metal complex, and/or the $N^2$-phosphinyl guanidine metal complex. In yet other embodiments, when $R^4$ and $R^5$ for the $N^2$-phosphinyl formamidine metal complexes, the $N^2$-phosphinyl amidine metal complexes, and/or the $N^2$-phosphinyl guanidine metal complexes are joined to form a cyclic group including the phosphorus atom of the $N^2$-phosphinyl formamidine metal complex, the $N^2$-phosphinyl amidine metal complex, and/or the $N^2$-phosphinyl guanidine metal complex, the cyclic group including the phosphorus atom can comprise, or consist of, only one substituent on each carbon atom adjacent to the phosphorus atom attached to the $N^2$ nitrogen atom of the $N^2$-phosphinyl formamidine metal complex, the $N^2$-phosphinyl amidine metal complex, and/or the $N^2$-phosphinyl guanidine metal complex. Substituents (general and specific) are independently disclosed herein and can be utilized without limitation to further describe substituted group(s) where $R^4$ and $R^5$ for the $N^2$-phosphinyl formamidine metal complexes, the $N^2$-phosphinyl amidine metal complexes, and/or the $N^2$-phosphinyl guanidine metal complexes are joined to form a cyclic group including the phosphorus atom.

In an embodiment, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a phenyl group, a 2-alkylphenyl group, a 3-alkylphenyl group, a 4-alkylphenyl group, a 2,4-dialkylphenyl group, a 2,6-dialkylphenyl group, a 3,5-dialkylphenyl group, or a 2,4,6-trialkylphenyl group; alternatively, a 2-alkylphenyl group, a 4-alkylphenyl group, a 2,4-dialkylphenyl group, a 2,6-dialkylphenyl group, or a 2,4,6-trialkylphenyl group; alternatively, a 2-alkylphenyl group or a 4-alkylphenyl group; alternatively, a 2,4-dialkylphenyl group, a 2,6-dialkylphenyl group, or a 2,4,6-trialkylphenyl group; alternatively, a 2,4-dialkylphenyl group or a 2,6-dialkylphenyl group; alternatively, a 2,6-dialkylphenyl group, or a 2,4,6-trialkylphenyl group; alternatively, a 3-alkylphenyl group or a 3,5-dialkylphenyl group; alternatively, a 2-alkylphenyl group or a 2,6-dialkylphenyl group; alternatively, a 2-alkylphenyl group; alternatively, a 3-alkylphenyl group; alternatively, a 4-alkylphenyl group; alternatively, a 2,4-dialkylphenyl group; alternatively, a 2,6-dialkylphenyl group; alternatively, a 3,5-dialkylphenyl group; or alternatively, a 2,4,6-trialkylphenyl group. In other non-limiting embodiments, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a cyclohexyl group, a 2-alkylcyclohexyl group, or a 2,6-dialkylcyclohexyl group; alternatively, a cyclopentyl group, a 2-alkylcyclopentyl group, or a 2,5-dialkylcyclopentyl group; alternatively, a cyclohexyl group; alternatively, a 2-alkylcyclohexyl group; alternatively, a 2,6-dialkylcyclohexyl group; alternatively, cyclopentyl group; alternatively, a 2-alkylcyclopentyl group; or alternatively, a 2,5-dialkylcyclopentyl group. Alkyl group substituents (general and specific) are independently described herein and can be utilized, without limitation, to further describe the alkylphenyl, dialkylphenyl, trialkylphenyl, alkylcyclohexyl, dialkylcyclohexyl, alkylcyclopentyl, or dialkylcyclopentyl groups that can be utilized as $R^4$ and/or $R^5$ for the $N^2$-phosphinyl formamidine metal complexes, the $N^2$-phosphinyl amidine metal complexes, and/or the $N^2$-phosphinyl guanidine metal complexes. Generally, the alkyl substituents of a dialkyl or trialkyl phenyl, cyclohexyl, or cyclopentyl group can be the same; or alternatively the alkyl substituents of a dialkyl or trialkyl phenyl, cyclohexyl, or cyclopentyl group can be different.

In another non-limiting embodiment, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a phenyl group, a 2-alkoxyphenyl group, a 3-alkoxyphenyl group, a 4-alkoxyphenyl group, or a 3,5-dialkoxyphenyl group; alternatively, a 2-alkoxyphenyl group or a 4-alkoxyphenyl group; alternatively, a 3-alkoxyphenyl group or a 3,5-dialkoxyphenyl group; alternatively, a 2-alkoxyphenyl group, alternatively, a 3-alkoxyphenyl group; alternatively, a 4-alkoxyphenyl group; alternatively, a 3,5-dialkoxyphenyl group. Alkoxy group substituents (general and specific) are independently described herein and can be utilized, without limitation, to further describe the alkoxyphenyl or dialkoxyphenyl groups that can be utilized as $R^4$ and/or $R^5$ for the $N^2$-phosphinyl formamidine metal complexes, the $N^2$-phosphinyl amidine metal complexes, and/or the $N^2$-phosphinyl guanidine metal complexes. Generally, the alkoxy substituents of a dialkoxyphenyl groups can be the same; or alternatively the alkoxy substituents of a dialkoxyphenyl group can be different.

In other non-limiting embodiments, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a phenyl group, a 2-halophenyl group, a 3-halophenyl group, a 4-halophenyl group, a 2,6-dihalophenylgroup, or a 3,5-dialkylphenyl group; alternatively, a 2-halophenyl group, a 4-halophenyl group, or a 2,6-dihalophenyl group; alternatively, a 2-halophenyl group or a 4-halophenyl group; alternatively, a 3-halophenyl group or a 3,5-dihalophenyl group; alternatively, a 2-halophenyl group; alternatively, a 3-halophenyl group; alternatively, a 4-halophenyl group; alternatively, a 2,6-dihalophenylgroup; or alternatively, a 3,5-dihalophenyl group. Halides are independently described herein and can be utilized, without limitation, to further describe the halophenyl or dihalophenyl groups that can be utilized $R^4$ and/or $R^5$ for the $N^2$-phosphinyl formamidine metal complexes, the $N^2$-phosphinyl amidine metal complexes, and/or the $N^2$-phosphinyl guanidine metal complexes. Generally, the halides of a dihalophenyl group can be the same; or alternatively the halides of a dihalophenyl group can be different.

In a non-limiting embodiment, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a 2-methylphenyl group, a 2-ethylphenyl group, a 2-isopropylphenyl group, a 2-tert-butylphenyl group, a 3-methylphenyl group, a 2,6-dimethylphenyl group, a 2,6-diethylphenyl group, a 2,6-diisopropylphenyl group, a 2,6-di-tert-butylphenyl group, a 3,5-dimethyl group, or a 2,4,6-trimethylphenyl group; alternatively, a 2-methylphenyl group, a 2-ethylphenyl group, a 2-isopropylphenyl group, or a 2-tert-butylphenyl group; alternatively, a 2,6-dimethylphenyl group, a 2,6-diethylphenyl group, a 2,6-diisopropylphenyl group, or a 2,6-di-tert-butylphenyl group; alternatively, 2-methylphenyl group; alternatively, a 2-ethylphenyl group; alternatively, a 2-isopropylphenyl group; alternatively, a 2-tert-butylphenyl group; alternatively, a 3-methylphenyl group; alternatively, a 2,6-dimethylphenyl group; alternatively, a 2,6-diethylphenyl group; alternatively, a 2,6-diisopropylphenyl group; alternatively, a 2,6-di-tert-butylphenyl group; alternatively, a 3,5-dimethyl group; or alternatively, a 2,4,6-trimethylphenyl group. In another non-limiting embodiment, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a cyclohexyl group, a 2-methylcyclohexyl group, a 2-ethylcyclohexyl group, a 2-isopropylcyclohexyl group, a 2-tert-butylcyclohexyl group, a 2,6-dimethylcyclohexyl group, a 2,6-diethylcyclohexyl group, a 2,6-diisopropylcyclohexyl group, or a 2,6-di-tert-butylcyclohexyl group; alternatively, a 2-methylcyclohexyl group, a 2-ethylcyclohexyl group, a 2-isopropylcyclohexyl group, or a 2-tert-butylcyclohexyl group; alternatively, a 2,6-dimethylcyclohexyl group, a 2,6-diethylcyclohexyl group, a 2,6-diisopropylcyclohexyl group, or a 2,6-di-tert-butylcyclohexyl group; alternatively, a cyclohexyl group; alternatively, a 2-methylcyclohexyl group; alternatively, a 2-ethylcyclohexyl group; alternatively, a 2-isopropylcyclohexyl group; alternatively, a 2-tert-butylcyclohexyl group; alternatively, a 2,6-dimethylcyclohexyl group; alternatively, a 2,6-diethylcyclohexyl group; alternatively, a 2,6-diisopropylcyclohexyl group; or alternatively, a 2,6-di-tert-butylcyclohexyl group.

In a non-limiting embodiment, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a 2-methoxyphenyl group, a 2-ethoxyphenyl group, a 2-isopropoxyphenyl group, a 2-tert-butoxyphenyl group, a 3-methoxyphenyl group, a 3-ethoxyphenyl group, a 3-isopropoxyphenyl group, a 3-tert-butoxyphenyl group, a 4-methoxyphenyl group, a 4-ethoxyphenyl group, a 4-isopropoxyphenyl group, a 4-tert-butoxyphenyl group, a 2,4-dimethoxyphenyl group, a 2,4-diethoxyphenyl group, a 2,4-diisopropoxyphenyl group, a 2,4-di-tert-butoxyphenyl group, a 3,5-dimethoxyphenyl group, a 3,5-diethoxyphenyl group, a 3,5-diisopropoxyphenyl group, a 3,5-di-tert-butoxyphenyl group, a 2,6-dimethoxyphenyl group, a 2,6-diethoxyphenyl group, a 2,6-diisopropoxyphenyl group, a 2,6-di-tert-butoxyphenyl group, or a 2,4,6-trimethoxyphenyl group; alternatively, a 2-methoxyphenyl group, a 2-ethoxyphenyl group, a 2-isopropoxyphenyl group, or a 2-tert-butoxyphenyl group; alternatively, a 3-methoxyphenyl group, a 3-ethoxyphenyl group, a 3-isopropoxyphenyl group, or a 3-tert-butoxyphenyl group; alternatively, a 4-methoxyphenyl group, a 4-ethoxyphenyl group, a 4-isopropoxyphenyl group, or a 4-tert-butoxyphenyl group; alternatively, a 2,4-dimethoxyphenyl group, a 2,4-diethoxyphenyl group, a 2,4-diisopropoxyphenyl group, or a 2,4-di-tert-butoxyphenyl group, alternatively, a 3,5-dimethoxyphenyl group, a 3,5-diethoxyphenyl group, a 3,5-diisopropoxyphenyl group, or a 3,5-di-tert-butoxyphenyl group; or alternatively, a 2,6-dimethoxyphenyl group, a 2,6-diethoxyphenyl group, a 2,6-diisopropoxyphenyl group, or a 2,6-di-tert-butoxyphenyl group. In other non-limiting embodiments, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a 2-methoxyphenyl group; alternatively, a 2-ethoxyphenyl group; alternatively, a 2-isopropoxyphenyl group; alternatively, a 2-tert-butoxyphenyl group; alternatively, a 3-methoxyphenyl group; alternatively, a 3-ethoxyphenyl group; alternatively, a 3-isopropoxyphenyl group; alternatively, a 3-tert-butoxyphenyl group; alternatively, a 4-methoxyphenyl group; alternatively, a 4-ethoxyphenyl group; alternatively, a 4-isopropoxyphenyl group; alternatively, a 4-tert-butoxyphenyl group; alternatively, a 2,4-dimethoxyphenyl group; alternatively, a 2,4-diethoxyphenyl group; alternatively, a 2,4-diisopropoxyphenyl group; alternatively, a 2,4-di-tert-butoxyphenyl group; alternatively, a 3,5-dimethoxyphenyl group; alternatively, a 3,5- diethoxyphenyl group; alternatively, a 3,5-diisopropoxyphenyl group; alternatively, a 3,5-di-tert-butoxyphenyl group; alternatively, a 2,6-dimethoxyphenyl group; alternatively, a 2,6-diethoxyphenyl group; alternatively, a 2,6-diisopropoxyphenyl group; alternatively, a 2,6-di-tert-butoxyphenyl group; or alternatively, a 2,4,6-trimethoxyphenyl group.

In another non-limiting embodiment, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a 2-fluorophenyl group, a 2-chlorophenyl group, a 3-fluorophenyl group, a 3-chlorophenyl group, a 4-fluorophenyl group, a 4-chlorophenyl group, a 3,5-difluorophenyl group, or a 3,5-dichlorophenyl group; alternatively, a 2-fluorophenyl group or a 2-chlorophenyl group; alternatively, a 3-fluorophenyl group or a 3-chloro-phenyl group; alternatively, a 4-fluorophenyl group or a 4-chlorophenyl group; alternatively, a 3,5-difluorophenyl group or a 3,5-dichlorophenyl group; alternatively, a 3-fluorophenyl group, a 3-chlorophenyl group, a 3,5-difluorophenyl group or a 3,5-dichlorophenyl group; or alternatively, a 3-fluorophenyl group or a 3,5-difluorophenyl group. In another non-limiting embodiment, $R^4$ and/or $R^5$ for the $N^2$-phosphinyl formamidine metal complexes, the $N^2$-phosphinyl amidine metal complexes, and/or the $N^2$-phosphinyl guanidine metal complexes independently can be a 2-fluorophenyl group; alternatively, a 2-chlorophenyl group; alternatively, a 3-fluorophenyl group; alternatively, a 3-chlorophenyl group; alternatively, a 4-fluorophenyl group; alternatively, a 4-chlorophenyl group; alternatively, a 3,5-difluorophenyl group; or alternatively, a 3,5-dichlorophenyl group.

Generally, the $R^4$ and/or $R^5$ groups of the phosphinyl group for the $N^2$-phosphinyl formamidine metal complexes, the $N^2$-phosphinyl amidine metal complexes, and/or the $N^2$-phosphinyl guanidine metal complexes independently can be any $R^4$ or $R^5$ group for the $N^2$-phosphinyl formamidine metal complexes, the $N^2$-phosphinyl amidine metal complexes, and/or the $N^2$-phosphinyl guanidine metal complexes described herein and utilized in any combination to further describe the phosphinyl group of any $N^2$-phosphinyl formamidine metal complexes described herein. In an embodiment, $R^4$ and $R^5$ for the $N^2$-phosphinyl formamidine metal complexes, the $N^2$-phosphinyl amidine metal complexes, and/or the $N^2$-phosphinyl guanidine metal complexes can be the same. In other embodiments $R^4$ and $R^5$ for the $N^2$-phosphinyl formamidine metal complexes, the $N^2$-phosphinyl amidine metal complexes, and/or the $N^2$-phosphinyl guanidine metal complexes can be different.

In an aspect, the phosphinyl group of the $N^2$-phosphinyl formamidine metal complexes, the $N^2$-phosphinyl amidine metal complexes, and/or the $N^2$-phosphinyl guanidine metal complexes can be a diphenylphosphinyl group or a dialkylphosphinyl group; alternatively, a diphenylphosphinyl group; or alternatively, a dialkylphosphinyl group. In another aspect, the phosphinyl group of the $N^2$-phosphinyl formamidine metal complexes, the $N^2$-phosphinyl amidine metal complexes, and/or the $N^2$-phosphinyl guanidine metal complexes can be a bis(dihalo substituted phenyl)phosphinyl group, a bis(dialkyl substituted phenyl)phosphinyl group, a bis(dialkoxy substituted phenyl)phosphinyl group, a bis(trialkylphenyl)phosphinyl group, or a bis(trialkoxyphenyl) phosphinyl group; alternatively, a bis(dihalo substituted phenyl)phosphinyl group; alternatively, a bis(dialkyl substituted phenyl)phosphinyl group; alternatively, a bis(dialkoxy substituted phenyl)phosphinyl group; alternatively, a bis(trialkylphenyl)phosphinyl group; or alternatively, a bis(trialkoxyphenyl)phosphinyl group. Halogens, alkyl group substituents (general and specific), and alkoxy group substituents (general and specific) are independently described herein (e.g., as substituents for substituted $R^1$ groups) and can be utilized, without limitation to further describe the phosphinyl group which can be utilized in the $N^2$-phosphinyl formamidine metal complexes, the $N^2$-phosphinyl amidine metal complexes, and/or the $N^2$-phosphinyl guanidine metal complexes.

In a non-limiting aspect, the phosphinyl group of the $N^2$-phosphinyl formamidine metal complexes, the $N^2$-phosphinyl amidine metal complexes, and/or the $N^2$-phosphinyl guanidine metal complexes can be a dimethylphosphinyl group, a diethylphosphinyl group, a diisopropylphosphinyl group, a di-tert-butylphosphinyl group, or a di-neo-pentylphosphinyl group; alternatively, a dimethylphosphinyl group; alternatively, a diethyl phosphinyl group; alternatively, a diisopropylphosphinyl group; alternatively, a di-tert-butylphosphinyl group; or alternatively, a di-neo-pentylphosphinyl group. In some non-limiting embodiments, the phosphinyl group of the $N^2$-phosphinyl formamidine metal complexes, the $N^2$-phosphinyl amidine metal complexes, and/or the $N^2$-phosphinyl guanidine metal complexes can be a dicyclopentyl phosphinyl group, a dicyclohexyl phosphinyl group; alternatively, a dicyclopentylphosphinyl group; or alternatively, a dicyclohexylphosphinyl group.

In yet another non-limiting aspect, the phosphinyl group of the $N^2$-phosphinyl formamidine metal complexes, the $N^2$-phosphinyl amidine metal complexes, and/or the $N^2$-phosphinyl guanidine metal complexes can be a bis(2-fluorophenyl)phosphinyl group, a bis(2-chlorophenyl)phosphinyl group, a bis(3-fluorophenyl)phosphinyl group, a bis(3-chlorophenyl)phosphinyl group, a bis(4-fluorophenyl)phosphinyl group, or a bis(4-chlorophenyl)phosphinyl group. In some non-limiting embodiments, the phosphinyl group of the $N^2$-phosphinyl formamidine metal complexes, the $N^2$-phosphinyl amidine metal complexes, and/or the $N^2$-phosphinyl guanidine metal complexes can be a bis(2-fluorophenyl)phosphinyl group, a bis(3-fluorophenyl)phosphinyl group, or a bis(4-fluorophenyl)phosphinyl group; or alternatively, a bis(2-chlorophenyl)phosphinyl group, a bis(3-chlorophenyl)phosphinyl group, or a bis(4-chlorophenyl) phosphinyl group. In other non-limiting embodiments, the phosphinyl group of the $N^2$-phosphinyl formamidine metal complexes, the $N^2$-phosphinyl amidine metal complexes, and/or the $N^2$-phosphinyl guanidine metal complexes can be a bis(2-fluorophenyl)phosphinyl group; alternatively, a bis(2-chlorophenyl)phosphinyl group; alternatively, a bis(3-fluorophenyl)phosphinyl group; alternatively, a bis(3-chlorophenyl)phosphinyl group; alternatively, a bis(4-fluorophenyl) phosphinyl group; or alternatively, a bis(4-chlorophenyl) phosphinyl group.

In yet another non-limiting aspect, the phosphinyl group of the $N^2$-phosphinyl formamidine metal complexes, the $N^2$-phosphinyl amidine metal complexes, and/or the $N^2$-phosphinyl guanidine metal complexes can be a diphenylphosphinyl group, a bis(2-methylphenyl)phosphinyl group, a bis(2-ethylphenyl)phosphinyl group, a bis(2-isopropylphenyl)phosphinyl group, a bis(2-tert-butylphenyl)phosphinyl group, a bis(3-methylphenyl)phosphinyl group, a bis(3-ethylphenyl)phosphinyl group, bis(3-isopropylphenyl)phosphinyl group, a bis(3-tert-butylphenyl)phosphinyl group, a diphenylphosphinyl group, a bis(4-methylphenyl)phosphinyl group, a bis(4-ethylphenyl)phosphinyl group, a bis(4-isopropylphenyl)phosphinyl group, or a bis(4-tert-butylphenyl)phosphinyl group. In a non-limiting embodiment, the phosphinyl group of the $N^2$-phosphinyl formamidine metal complexes, the $N^2$-phosphinyl amidine metal complexes, and/or the $N^2$-phosphinyl guanidine metal complexes can be a bis(2-methylphenyl)phosphinyl group, a bis(2-ethylphenyl)phosphinyl group, a bis(2-isopropylphenyl)phosphinyl group, or a bis(2-tert-butylphenyl)phosphinyl group; alternatively, a diphenylphosphinyl group, a bis(3-methylphenyl)phosphinyl group, a bis(3-ethylphenyl)phosphinyl group, a bis(3-isopropylphenyl)phosphinyl group, or a bis(3-tert-butylphenyl)phosphinyl group; or alternatively, a diphenylphosphinyl group, a bis(4-methylphenyl)phosphinyl group, a bis(4-ethylphenyl)phosphinyl group, a bis(4-isopropylphenyl)phosphinyl group, or a bis(4-tert-butylphenyl)phosphinyl group. In other non-limiting embodiments, the phosphinyl group of the $N^2$-phosphinyl formamidine metal complexes, the $N^2$-phosphinyl amidine metal complexes, and/or the $N^2$-phosphinyl guanidine metal complexes can be a diphenylphosphinyl group; alternatively, a bis(2-methylphenyl)phosphinyl group; alternatively, a bis(2-ethylphenyl)phosphinyl group; alternatively, a bis(2-isopropylphenyl)phosphinyl group; alternatively, a bis(2-tert-butylphenyl)phosphinyl group; alternatively, a bis(3-methylphenyl)phosphinyl group; alternatively, a bis(3-ethylphenyl)phosphinyl group; alternatively, a bis(3-isopropylphenyl)phosphinyl group; alternatively, a bis(3-tert-butylphenyl)phosphinyl group; alternatively, a diphenylphosphinyl group; alternatively, a bis(4-methylphenyl)phosphinyl group; alternatively, a bis(4-ethylphenyl)phosphinyl group; alternatively, a bis(4-isopropylphenyl)phosphinyl group; or alternatively, a bis(4-tert-butylphenyl)phosphinyl group.

In yet another non-limiting aspect, the phosphinyl group of the $N^2$-phosphinyl formamidine metal complexes, the $N^2$-phosphinyl amidine metal complexes, and/or the $N^2$-phosphinyl guanidine metal complexes can be a diphenylphosphinyl group, a bis(2-methoxyphenyl)phosphinyl group, a bis(2-ethoxyphenyl)phosphinyl group, a bis(2-isopropoxyphenyl)phosphinyl group, a bis(2-tert-butoxyphenyl)phosphinyl group, a bis(3-methoxyphenyl)phosphinyl group, a bis(3-ethoxyphenyl)phosphinyl group, a bis(3-isopropoxyphenyl)phosphinyl group, a bis(3-tert-butoxyphenyl)phosphinyl group, a diphenoxyphosphinyl group, a bis(4-methoxyphenyl)phosphinyl group, a bis(4-ethoxyphenyl)phosphinyl group, bis(4-isopropoxyphenyl)phosphinyl group, or a bis(4-tert-butoxyphenyl)phosphinyl group. In a non-limiting embodiment, the phosphinyl group of the $N^2$-phosphinyl formamidine metal complexes, the $N^2$-phosphinyl amidine metal complexes, and/or the $N^2$-phosphinyl guanidine metal complexes can be a bis(2-methoxyphenyl)phosphinyl group, a bis(2-ethoxyphenyl)phosphinyl group, a bis(2-isopropoxyphenyl)phosphinyl group, or a bis(2-tert-butoxyphenyl)phosphinyl group; alternatively, a diphenoxyphosphinyl group, a bis(3-methoxyphenyl)phosphinyl group, a bis(3-ethoxyphenyl)phosphinyl group, a bis(3-isopropoxyphenyl)phosphinyl group, or a bis(3-tert-butoxyphenyl)phosphinyl group; or alternatively, a diphenoxyphosphinyl group, a bis(4-methoxyphenyl)phosphinyl group, a bis(4-ethoxyphenyl)phosphinyl group, a bis(4-isopropoxyphenyl)phosphinyl group, or a bis(4-tert-butoxyphenyl)phosphinyl group. In other non-limiting embodiments, the phosphinyl group of the $N^2$-phosphinyl formamidine metal complexes, the $N^2$-phosphinyl amidine metal complexes, and/or the $N^2$-phosphinyl guanidine metal complexes can be a diphenylphosphinyl group; alternatively, a bis(2-methoxyphenyl) phosphinyl group; alternatively, a bis(2-ethoxyphenyl)phosphinyl group; alternatively, a bis(2-isopropoxyphenyl) phosphinyl group; alternatively, a bis(2-tert-butoxyphenyl) phosphinyl group; alternatively, a bis(3-methoxyphenyl) phosphinyl group; alternatively, a bis(3-ethoxyphenyl) phosphinyl group; alternatively, a bis(3-isopropoxyphenyl) phosphinyl group; alternatively, a bis(3-tert-butoxyphenyl) phosphinyl group; alternatively, a diphenoxyphosphinyl group; alternatively, a bis(4-methoxyphenyl)phosphinyl group; alternatively, a bis(4-ethoxyphenyl)phosphinyl group; alternatively, a bis(4-isopropoxyphenyl)phosphinyl group; or alternatively, a bis(4-tert-butoxyphenyl)phosphinyl group.

Generally, the metal of the $N^2$-phosphinyl formamidine metal complexes, the $N^2$-phosphinyl amidine metal complexes, and/or the $N^2$-phosphinyl guanidine metal complexes can be any metal atom. In an embodiment, the metal of the $N^2$-phosphinyl formamidine metal complexes, the $N^2$-phosphinyl amidine metal complexes, and/or the $N^2$-phosphinyl guanidine metal complexes can be a transition metal. In some embodiments, the metal of the $N^2$-phosphinyl formamidine metal complexes, the $N^2$-phosphinyl amidine metal complexes, and/or the $N^2$-phosphinyl guanidine metal complexes can be a Group 7, Group 8, Group 9, or Group 10 metal; alternatively, a Group 8 or Group 9 metal; alternatively, a Group 7 metal; alternatively, a Group 8 metal; alternatively, a Group 9 metal; or alternatively, a Group 10 metal. In other embodiments, the metal of the $N^2$-phosphinyl formamidine metal complexes, the $N^2$-phosphinyl amidine metal complexes, and/or the $N^2$-phosphinyl guanidine metal complexes can be Mn, Tc, Re, Fe, Ru, Os, Co, Rh, Ir, Ni, Pd, or Pt; alternatively, Mn, Re, Fe, Ru, Co, Rh, Ir, Ni, Pd, or Pt; alternatively, Mn, Fe, Co, or Ni; alternatively, Fe or Ru; alternatively, Co, Rh, or Ir; alternatively, Fe or Co; alternatively, Fe; alternatively, Ru; alternatively, Co; alternatively, Rh; or alternatively Ir.

Generally, the metal of the $N^2$-phosphinyl formamidine metal complexes, the $N^2$-phosphinyl amidine metal complexes, and/or the $N^2$-phosphinyl guanidine metal complexes can have any positive oxidation state available to the metal atom. In an embodiment, metal of the $N^2$-phosphinyl formamidine metal complexes, the $N^2$-phosphinyl amidine metal complexes, and/or the $N^2$-phosphinyl guanidine metal complexes can have an oxidation state of from +2 to +6; alternatively, from +2 to +4; or alternatively, from +2 or +3. In some embodiments, the metal of the $N^2$-phosphinyl formamidine metal complexes, the $N^2$-phosphinyl amidine metal complexes, and/or the $N^2$-phosphinyl guanidine metal complexes can have an oxidation state of +1; alternatively, +2; alternatively, +3; or alternatively, +4.

In an aspect, X of the $N^2$-phosphinyl formamidine metal complexes, the $N^2$-phosphinyl amidine metal complexes, and/or the $N^2$-phosphinyl guanidine metal complexes can be a strongly basic heteroanionic ligand. In an embodiment, the strongly basic heteroanionic ligand can be a ligand having an anionic charge located on a heteroatom wherein the conjugate acid has a Bordwell pKa in DMSO greater than 20. In an embodiment, X of the $N^2$-phosphinyl formamidine metal complexes, the $N^2$-phosphinyl amidine metal complexes, and/or the $N^2$-phosphinyl guanidine metal complexes can be a hydrocarboxide, a hydrocarbylazanide (anion of an amine also commonly referred to as an amide), a trihydrocarbylsilylazanide, or a hydrocarylphosphinide (anion of a phosphine); alternatively, a hydrocarboxide, a hydrocarbylazanides, or a trihydrocarbylsilylazanide; alternatively, a hydrocarboxide; alternatively, a hydrocarbylazanides; alternatively, trihydrocarbylsilylazanide; or alternatively, a hydrocarylphosphinide.

In an aspect, the hydrocarboxide which can be utilized as X of the $N^2$-phosphinyl formamidine metal complexes, the $N^2$-phosphinyl amidine metal complexes, and/or the $N^2$-phosphinyl guanidine metal complexes can be a $C_1$ to $C_{20}$ hydrocarboxide; alternatively, a $C_1$ to $C_{15}$ hydrocarboxide; alternatively, a $C_1$ to $C_{10}$ hydrocarboxide; or alternatively, a $C_1$ to $C_5$ hydrocarboxide. In some embodiments the hydrocarboxide which can be utilized as X of the $N^2$-phosphinyl formamidine metal complexes, the $N^2$-phosphinyl amidine metal complexes, and/or the $N^2$-phosphinyl guanidine metal complexes can be an alkoxide, aryloxide, or aralkoxide; alternatively, an alkoxide; or alternatively, an aryloxide. In an embodiment, the alkoxide which can be utilized as X of the $N^2$-phosphinyl formamidine metal complexes, the $N^2$-phosphinyl amidine metal complexes, and/or the $N^2$-phosphinyl guanidine metal complexes can be a $C_1$ to $C_{20}$ alkoxide; alternatively, a $C_1$ to $C_{15}$ alkoxide; alternatively, a $C_1$ to $C_{10}$ alkoxide; or alternatively, a $C_1$ to $C_5$ alkoxide. In an embodiment, the aryloxide which can be utilized as X of the $N^2$-phosphinyl formamidine metal complexes, the $N^2$-phosphinyl amidine metal complexes, and/or the $N^2$-phosphinyl guanidine metal complexes can be a $C_6$ to $C_{20}$ aryloxide; alternatively, a $C_6$ to $C_{15}$ aryloxide; or alternatively, a $C_6$ to $C_{10}$ aryloxide. In an embodiment, the aralkoxide which can be utilized as X of the $N^2$-phosphinyl formamidine metal complexes, the $N^2$-phosphinyl amidine metal complexes, and/or the $N^2$-phosphinyl guanidine metal complexes can be a $C_7$ to $C_{20}$ aralkoxide; alternatively, a $C_7$ to $C_{15}$ aralkoxide; or alternatively, a $C_7$ to $C_{10}$ aralkoxide. Hydrocarbyl groups (general and specific hydrocarbyl groups, alkyl groups, aryl group, and/or aralkylgroups) are described herein as potential substituent groups. These groups can be utilized without limitation to further describe the hydrocarboxides which can be utilized as X of the $N^2$-phosphinyl formamidine metal complexes, the $N^2$-phosphinyl amidine metal complexes, and/or the $N^2$-phosphinyl guanidine metal complexes In some embodiments, the alkoxide which can be utilized as X of the $N^2$-phosphinyl formamidine metal complexes, the $N^2$-phosphinyl amidine metal complexes, and/or the $N^2$-phosphinyl guanidine metal complexes can be methoxide, ethoxide, a propoxide, a butoxide, or a pentoxide; alternatively, methoxide, ethoxide, isopropoxide, tert-butoxide, or neopentoxide; alternatively, methoxide; alternatively, ethoxide; alternatively, iso-propoxide; alternatively, tert-butoxide; or alternatively, neopentoxide. In an embodiment, the aryloxide which can be utilized as X of the $N^2$-phosphinyl formamidine metal complexes, the $N^2$-phosphinyl amidine metal complexes, and/or the $N^2$-phosphinyl guanidine metal complexes can be phenoxide. In an embodiment, the aralkoxide which can be utilized as X of the $N^2$-phosphinyl formamidine metal complexes, the $N^2$-phosphinyl amidine metal complexes, and/or the $N^2$-phosphinyl guanidine metal complexes can be benzoxide.

In an aspect, the hydrocarbylazanide which can be utilized as X of the $N^2$-phosphinyl formamidine metal complexes, the $N^2$-phosphinyl amidine metal complexes, and/or the $N^2$-phosphinyl guanidine metal complexes can be a monohydrocarbylazanide or a dihydrocarbylazanide; alternatively, a monohydrocarbylazanide; or alternatively, a dihydrocarbylazanide. In an embodiment, the monohydrocarbylazanide which can be utilized as X of the $N^2$-phosphinyl formamidine metal complexes, the $N^2$-phosphinyl amidine metal complexes, and/or the $N^2$-phosphinyl guanidine metal complexes can be a $C_1$ to $C_{20}$ monohydrocarbylazanide; alternatively, a $C_1$ to $C_{15}$ monohydrocarbylazanide; alternatively, a $C_1$ to $C_{10}$ monohydrocarbylazanide; or alternatively, a $C_1$ to $C_5$ monohydrocarbylazanide. In an embodiment, the dihydrocarbylazanide which can be utilized as X of the $N^2$-phosphinyl formamidine metal complexes, the $N^2$-phosphinyl amidine metal complexes, and/or the $N^2$-phosphinyl guanidine metal complexes can be a $C_2$ to $C_{40}$ dihydrocarbylazanide; alternatively, a $C_2$ to $C_{30}$ dihydrocarbylazanide; alternatively, a $C_2$ to $C_{20}$ dihydrocarbylazanide; or alternatively, a $C_2$ to $C_{10}$ dihydrocarbylazanide. In some embodiments the hydrocarbylazanide (mono or di) which can be utilized as X of the $N^2$-phosphinyl formamidine metal complexes, the $N^2$-phosphinyl amidine metal complexes, and/or the $N^2$-phosphinyl guanidine metal complexes can be an alkylazanide (mono or di), arylazanide (mono or di), or aralkylazanide (mono or di); alternatively, an alkylazanide (mono or di); or alternatively, an arylazanide (mono or di). In an embodiment, the monoalkylazanide which can be utilized as X of the $N^2$-phosphinyl formamidine metal complexes, the $N^2$-phosphinyl amidine metal complexes, and/or the $N^2$-phosphinyl guanidine metal complexes can be a $C_1$ to $C_{20}$ monoalkylazanide; alternatively, a $C_1$ to $C_{15}$ monoalkylazanide; alternatively, a $C_1$ to $C_{10}$ monoalkylazanide; or alternatively, a $C_1$ to $C_5$ monoalkylazanide. In an embodiment, the dialkylazanide which can be utilized as X of the $N^2$-phosphinyl formamidine metal complexes, the $N^2$-phosphinyl amidine metal complexes, and/or the $N^2$-phosphinyl guanidine metal complexes can be a $C_1$ to $C_{40}$ dialkylazanide; alternatively, a $C_1$ to $C_{30}$ dialkylazanide; alternatively, a $C_1$ to $C_{20}$ dialkylazanide; or alternatively, a $C_1$ to $C_{10}$ dialkylazanide. In an embodiment, the monoarylazanide which can be utilized as X of the $N^2$-phosphinyl formamidine metal complexes, the $N^2$-phosphinyl amidine metal complexes, and/or the $N^2$-phosphinyl guanidine metal complexes can be a $C_6$ to $C_{20}$ monoarylazanide; alternatively, a $C_6$ to $C_{15}$ monoarylazanide; or alternatively, a $C_6$ to $C_{10}$ monoarylazanide. In an embodiment, the diarylazanide which can be utilized as X of the $N^2$-phosphinyl formamidine metal complexes, and/or the $N^2$-phosphinyl guanidine metal complexes can be a $C_{12}$ to $C_{40}$ diarylazanide; alternatively, a $C_{12}$ to $C_{30}$ diarylazanide; or alternatively, a $C_{12}$ to $C_{20}$ diarylazanide. In an embodiment, the monoaralkylazanide which can be utilized as X of the $N^2$-phosphinyl formamidine metal complexes, the $N^2$-phosphinyl amidine metal complexes, and/or the $N^2$-phosphinyl guanidine metal complexes can be a $C_7$ to $C_{20}$ monoaralkylazanide; alternatively, a $C_7$ to $C_{15}$ monoaralkylazanide; or alternatively, a $C_7$ to $C_{10}$ monoaralkylazanide. In an embodiment, the diaralkylazanide which can be utilized as X of the $N^2$-phosphinyl formamidine metal complexes, the $N^2$-phosphinyl amidine metal complexes, and/or the $N^2$-phosphinyl guanidine metal complexes can be a $C_7$ to $C_{20}$ diaralkylazanide; alternatively, a $C_7$ to $C_{15}$ diaralkylazanide; or alternatively, a $C_7$ to $C_{10}$ diaralkylazanide. In some embodiments, the hydrocarbyl groups (general hydrocarbyl groups, alkyl groups, aryl group, and/or aralkylgroups) for the hydrocarbylazanide which can be utilized as X of the $N^2$-phosphinyl formamidine metal complexes, the $N^2$-phosphinyl amidine metal complexes, and/or the $N^2$-phosphinyl guanidine metal complexes can be the same; or alternatively, they can be different. Hydrocarbyl groups (general and specific hydrocarbyl groups, alkyl groups, aryl group, and/or aralkylgroups) are described herein as potential substituent groups. These groups can be utilized without limitation to further describe the azanides (mono or di) which can be utilized as X of the $N^2$-phosphinyl formamidine metal complexes, the $N^2$-phosphinyl amidine metal complexes, and/or the $N^2$-phosphinyl guanidine metal complexes.

In an embodiment, the hydrocarbylazanide which can be utilized as X of the $N^2$-phosphinyl formamidine metal complexes, the $N^2$-phosphinyl amidine metal complexes, and/or the $N^2$-phosphinyl guanidine metal complexes can be methylazanide, dimethylazanide, ethylazanide, diethylazanide, a propylazanide, a dipropylazanide, a butylazanide, a dibutylazanide, a pentylazanide, a dipentylazanide, phenylazanide, diphenylazanide, a tolylazanide, a ditolylazanide, a xylylazanide, a dixylylazanide, a benzylazanide, or a dibenzylazanide; or alternatively, methylazanide, ethylazanide, a propylazanide, a butylazanide, a pentylazanide, a phenylazanide, a tolylazanide, a xylylazanide, or a benzylazanide; alternatively, dimethylazanide, diethylazanide, a dipropylazanide, a dibutylazanide, a dipentylazanide, diphenylazanide, a ditolylazanide, a dixylylazanide, or a dibenzylazanide. In some embodiments, the hydrocarbylazanide which can be utilized as X of the $N^2$-phosphinyl formamidine metal complexes, the $N^2$-phosphinyl amidine metal complexes, and/or the $N^2$-phosphinyl guanidine metal complexes can be methylazanide, dimethylazanide, ethylazanide, diethylazanide, isopropylazanide, diisopropylazanide, tert-butylazanide, di-tert-butylazanide, a neopentylazanide, or a dineopentylazanide; alternatively, methylazanide, ethylazanide, isopropylazanide, a tert-butylazanide, or neopentylazanide; alternatively, dimethylazanide, diethylazanide, diisopropylazanide, di-tert-butylazanide, or dineopentylazanide; alternatively, phenylazanide, a tolylazanide, or a xylylazanide; alternatively, diphenylazanide, a ditolylazanide, a dixylylazanide, or a dibenzylazanide; alternatively, methylazanide; alternatively, dimethylazanide; alternatively, ethylazanide; alternatively, diethylazanide; alternatively, isopropylazanide; alternatively, diisopropylazanide; alternatively, tert-butylazanide; alternatively, di-tert-butylazanide; alternatively, a neopentylazanide; alternatively a dineopentylazanide; alternatively, phenylazanide; alternatively, diphenylazanide; alternatively, a tolylazanide; alternatively, a ditolylazanide; alternatively, a xylylazanide; alternatively, a dixylylazanide; alternatively, a benzylazanide; or alternatively, a dibenzylazanide.

In an aspect, the trihydrocarbylsilylazanide which can be utilized as X of the $N^2$-phosphinyl formamidine metal complexes, the $N^2$-phosphinyl amidine metal complexes, and/or the $N^2$-phosphinyl guanidine metal complexes can be a mono(trihydrocarbylsilyl)azanide or a bis(trihydrocarbylsilyl)azanide; alternatively, a mono(trihydrocarbylsilyl)azanide; or alternatively, a bis(trihydrocarbylsilyl)azanide. In an embodiment, the mono(trihydrocarbylsilyl)azanide which can be utilized as X of the $N^2$-phosphinyl formamidine metal complexes, the $N^2$-phosphinyl amidine metal complexes, and/or the $N^2$-phosphinyl guanidine metal complexes can be a $C_3$ to $C_{30}$ mono(trihydrocarbylsilyl)azanide; alternatively, a $C_3$ to $C_{24}$ mono(trihydrocarbylsilyl)azanide; alternatively, a $C_3$ to $C_{15}$ mono(trihydrocarbylsilyl)azanide; or alternatively, a $C_3$ to $C_{10}$ mono(trihydrocarbylsilyl)azanide. In an embodiment, the bis(trihydrocarbylsilyl)azanide which can be utilized as X of the $N^2$-phosphinyl formamidine metal complexes, the $N^2$-phosphinyl amidine metal complexes, and/or the $N^2$-phosphinyl guanidine metal complexes can be a $C_6$ to $C_{60}$ bis(trihydrocarbylsilyl)azanide; alternatively, a $C_6$ to $C_{48}$ bis(trihydrocarbylsilyl)azanide; alternatively, a $C_6$ to $C_{30}$ bis(trihydrocarbylsilyl)azanide; or alternatively, a $C_6$ to $C_{20}$ bis(trihydrocarbylsilyl)azanide. Generally, each hydrocarbyl group of the mono(trihydrocarbylsilyl)azanide or a (bis-trihydrocarbylsilyl)azanide which can be utilized as the X of the $N^2$-phosphinyl formamidine metal complexes, the $N^2$-phosphinyl amidine metal complexes, and/or the $N^2$-phosphinyl guanidine metal complexes independently can be an alkyl group, an aryl group, or an aralkyl group; alternatively, an alkyl group; alternatively, an aryl group; or alternatively, an aralkyl group. In an embodiment, each alkyl group of the mono(trihydrocarbylsilyl)azanide or a bis(trihydrocarbylsilyl)azanide which can be utilized as the X of the $N^2$-phosphinyl formamidine metal complexes, the $N^2$-phosphinyl amidine metal complexes, and/or the $N^2$-phosphinyl guanidine metal complexes independently can be a $C_1$ to $C_{15}$ alky group; alternatively, a $C_1$ to $C_{10}$ alkyl group; or alternatively, a $C_1$ to $C_5$ alkyl group. In an embodiment, each aryl group of the mono(trihydrocarbylsilyl)azanide or bis(trihydrocarbylsilyl)azanide which can be utilized as the X of the $N^2$-phosphinyl formamidine metal complexes, the $N^2$-phosphinyl amidine metal complexes, and/or the $N^2$-phosphinyl guanidine metal complexes independently can be a $C_6$ to $C_{15}$ aryl group; or alternatively, a $C_6$ to $C_{10}$ aryl group. In an embodiment, each aralkyl group of the mono(trihydrocarbylsilyl)azanide or bis(trihydrocarbylsilyl)azanide which can be utilized as the X of the $N^2$-phosphinyl formamidine metal complexes, the $N^2$-phosphinyl amidine metal complexes, and/or the $N^2$-phosphinyl guanidine metal complexes independently can be a $C_7$ to $C_{15}$ aryl group; or alternatively, a $C_7$ to $C_{10}$ aryl group. In some embodiments, the hydrocarbyl groups (general hydrocarbyl groups, alkyl groups, aryl group, and/or aralkylgroups) for the mono(trihydrocarbylsilyl)azanide or bis(trihydrocarbylsilyl)azanide which can be utilized as X of the $N^2$-phosphinyl formamidine metal complexes, the $N^2$-phosphinyl amidine metal complexes, and/or the $N^2$-phosphinyl guanidine metal complexes can be the same; or alternatively, they can be different. Hydrocarbyl groups (general and specific hydrocarbyl groups, alkyl groups, aryl group, and/or aralkylgroups) are described herein as potential substituent groups. These groups can be utilized without limitation to further describe the hydrocarbyl groups which can be utilized in the trihydrocarbylsilylazanides used as X of the $N^2$-phosphinyl formamidine metal complexes, the $N^2$-phosphinyl amidine metal complexes, and/or the $N^2$-phosphinyl guanidine metal complexes.

In an embodiment, each alkyl group used in a mono(trihydrocarbylsilyl)azanide or a bis(trihydrocarbylsilyl)azanide for the X of the $N^2$-phosphinyl formamidine metal complexes, the $N^2$-phosphinyl amidine metal complexes, and/or the $N^2$-phosphinyl guanidine metal complexes independently can be a methyl group, an ethyl group, a propyl group, a butyl group, or a pentyl group; alternatively, a methyl group; alternatively, an ethyl group; alternatively, a propyl group; alternatively, a butyl group; or alternatively, a pentyl group. In an embodiment, each aryl group used in a mono(trihydrocarbylsilyl)azanide or a bis(trihydrocarbylsilyl)azanide for the X of the $N^2$-phosphinyl formamidine metal complexes, the $N^2$-phosphinyl amidine metal complexes, and/or the $N^2$-phosphinyl guanidine metal complexes independently can be a phenyl group, a tolyl group, or a xylyl; alternatively, a phenyl group; alternatively, a tolyl group; or alternatively, a xylyl group. In an embodiment, each aralkyl group used in a mono(trihydrocarbylsilyl)azanide or a bis(trihydrocarbylsilyl)azanide for the X of the $N^2$-phosphinyl formamidine metal complexes, the $N^2$-phosphinyl amidine metal complexes, and/or the $N^2$-phosphinyl guanidine metal complexes independently can be a benzyl group. In an embodiment, the trihydrocarbylsilylazanide which can be utilized as X of the $N^2$-phosphinyl formamidine metal complexes, the $N^2$-phosphinyl amidine metal complexes, and/or the $N^2$-phosphinyl guanidine metal complexes can be trimethylsilylazanide, bis (trimethylsilyl)azanide, triethylsilylazanide, bis(triethylsilyl)azanide, a tripropylsilylazanide, a bis(tripropylsilyl)azanide, a tributylsilylazanide, a bis(tributylsilyl)azanide, triphenylsilylazanide, or bis(triphenylsilyl)azanide; alternatively, trimethylsilylazanide, triethylsilylazanide, a tripropylsilylazanide, or a tributylsilylazanide; alternatively, bis(trimethylsilyl)azanide, bis(triethylsilyl)azanide, a bis(tripropylsilyl)azanide, or a bis(tributylsilyl)azanide; alternatively, trimethylsilylazanide; alternatively, bis(trimethylsilyl)azanide; alternatively, triethylsilylazanide; alternatively, bis(triethylsilyl)azanide; alternatively, a tripropylsilylazanide; alternatively, a bis(tripropylsilyl)azanide; alternatively, a tributylsilylazanide; alternatively, a bis(tributylsilyl)azanide; alternatively, triphenylsilylazanide; or alternatively, bis(triphenylsilyl) azanide.

In an aspect, the hydrocarbylphosphinide which can be utilized as X of the $N^2$-phosphinyl formamidine metal complexes, the $N^2$-phosphinyl amidine metal complexes, and/or the $N^2$-phosphinyl guanidine metal complexes can be a monohydrocarbylphosphinide or a dihydrocarbylphosphinide; alternatively, a monohydrocarbylphosphinide; or alternatively, a dihydrocarbylphosphinide. In an embodiment, the monohydrocarbylphosphinide which can be utilized as X of the $N^2$-phosphinyl formamidine metal complexes, the $N^2$-phosphinyl amidine metal complexes, and/or the $N^2$-phosphinyl guanidine metal complexes can be a $C_1$ to $C_{20}$ monohydrocarbylphosphinide; alternatively, a $C_1$ to $C_{15}$ monohydrocarbylphosphinide; alternatively, a $C_1$ to $C_{10}$ monohydrocarbylphosphinide; or alternatively, a $C_1$ to $C_5$ monohydrocarbylphosphinide. In an embodiment, the dihydrocarbylphosphinide which can be utilized as X of the $N^2$-phosphinyl formamidine metal complexes, the $N^2$-phosphinyl amidine metal complexes, and/or the $N^2$-phosphinyl guanidine metal complexes can be a $C_2$ to $C_{40}$ dihydrocarbylphosphinide; alternatively, a $C_2$ to $C_{30}$ dihydrocarbylphosphinide; alternatively, a $C_2$ to $C_{20}$ dihydrocarbylphosphinide; or alternatively, a $C_2$ to $C_{10}$ dihydrocarbylphosphinide. In some embodiments the hydrocarbylphosphinide (mono or di) which can be utilized as X of the $N^2$-phosphinyl formamidine metal complexes, the $N^2$-phosphinyl amidine metal complexes, and/or the $N^2$-phosphinyl guanidine metal complexes can be an alkylphosphinide (mono or di), arylphosphinide (mono or di), or aralkylphosphinide (mono or di); alternatively, an alkylphosphinide (mono or di); or alternatively, an arylphosphinide (mono or di). In an embodiment, the monoalkylphosphinide which can be utilized as X of the $N^2$-phosphinyl formamidine metal complexes, the $N^2$-phosphinyl amidine metal complexes, and/or the $N^2$-phosphinyl guanidine metal complexes can be a $C_1$ to $C_{20}$ monoalkylphosphinide; alternatively, a $C_1$ to $C_{15}$ monoalkylphosphinide; alternatively, a $C_1$ to $C_{10}$ monoalkylphosphinide; or alternatively, a $C_1$ to $C_5$ monoalkylphosphinide. In an embodiment, the dialkylphosphinide which can be utilized as X of the $N^2$-phosphinyl formamidine metal complexes, the $N^2$-phosphinyl amidine metal complexes, and/or the $N^2$-phosphinyl guanidine metal complexes can be a $C_1$ to $C_{40}$ dialkylphosphinide; alternatively, a $C_1$ to $C_{30}$ dialkylphosphinide; alternatively, a $C_1$ to $C_{20}$ dialkylphosphinide; or alternatively, a $C_1$ to $C_{10}$ dialkylphosphinide. In an embodiment, the monoarylphosphinide which can be utilized as X of the $N^2$-phosphinyl formamidine metal complexes, the $N^2$-phosphinyl amidine metal complexes, and/or the $N^2$-phosphinyl guanidine metal complexes can be a $C_6$ to $C_{20}$ monoarylphosphinide; alternatively, a $C_6$ to $C_{15}$ monoarylphosphinide; or alternatively, a $C_6$ to $C_{10}$ monoarylphosphinide. In an embodiment, the diarylphosphinide which can be utilized as X of the $N^2$-phosphinyl formamidine metal complexes, the $N^2$-phosphinyl amidine metal complexes, and/or the $N^2$-phosphinyl guanidine metal complexes can be a $C_{12}$ to $C_{40}$ diarylphosphinide; alternatively, a $C_{12}$ to $C_{30}$ diarylphosphinide; or alternatively, a $C_{12}$ to $C_{20}$ diarylphosphinide. In an embodiment, the monoaralkylphosphinide which can be utilized as X of the $N^2$-phosphinyl formamidine metal complexes, the $N^2$-phosphinyl amidine metal complexes, and/or the $N^2$-phosphinyl guanidine metal complexes can be a $C_7$ to $C_{20}$ monoaralkylphosphinide; alternatively, a $C_7$ to $C_{15}$ monoaralkylphosphinide; or alternatively, a $C_7$ to $C_{10}$ monoaralkylphosphinide. In an embodiment, the diaralkylphosphinide which can be utilized as X of the $N^2$-phosphinyl formamidine metal complexes, the $N^2$-phosphinyl amidine metal complexes, and/or the $N^2$-phosphinyl guanidine metal complexes can be a $C_7$ to $C_{20}$ diaralkylphosphinide; alternatively, a $C_7$ to $C_{15}$ diaralkylphosphinide; or alternatively, a $C_7$ to $C_{10}$ diaralkylphosphinide. In some embodiments, the hydrocarbyl groups (general hydrocarbyl groups, alkyl groups, aryl group, and/or aralkylgroups) for the hydrocarbylphosphinide which can be utilized as X of the $N^2$-phosphinyl formamidine metal complexes, the $N^2$-phosphinyl amidine metal complexes, and/or the $N^2$-phosphinyl guanidine metal complexes can be the same; or alternatively, they can be different. Hydrocarbyl groups (general and specific hydrocarbyl groups, alkyl groups, aryl group, and/or aralkylgroups) are described herein as potential substituent groups. These groups can be utilized without limitation to further describe the hydrocarbyl which can be utilized in the hydrocarbylphosphinides (mono or di) used as X of the $N^2$-phosphinyl formamidine metal complexes, the $N^2$-phosphinyl amidine metal complexes, and/or the $N^2$-phosphinyl guanidine metal complexes.

In an embodiment, the hydrocarbylphosphinide which can be utilized as X of the $N^2$-phosphinyl formamidine metal complexes, the $N^2$-phosphinyl amidine metal complexes, and/or the $N^2$-phosphinyl guanidine metal complexes can be methylphosphinide, dimethylphosphinide, ethylphosphinide, diethylphosphinide, a propylphosphinide, a dipropylphosphinide, a butylphosphinide, a dibutylphosphinide, a pentylphosphinide, a dipentylphosphinide, phenylphosphinide, diphenylphosphinide, a tolylphosphinide, a ditolylphosphinide, a xylylphosphinide, a dixylylphosphinide, a benzylphosphinide, or a dibenzylphosphinide; or alternatively, methylphosphinide, ethylphosphinide, a propylphosphinide, a butylphosphinide, a pentylphosphinide, a phenylphosphinide, a tolylphosphinide, a xylylphosphinide, or a benzylphosphinide; alternatively, dimethylphosphinide, diethylphosphinide, a dipropylphosphinide, a dibutylphosphinide, a dipentylphosphinide, diphenylphosphinide, a ditolylphosphinide, a dixylylphosphinide, or a dibenzylphosphinide. In some embodiments, the hydrocarbylphosphinide which can be utilized as X of the $N^2$-phosphinyl formamidine metal complexes, the $N^2$-phosphinyl amidine metal complexes, and/or the $N^2$-phosphinyl guanidine metal complexes can be methylphosphinide, dimethylphosphinide, ethylphosphinide, diethylphosphinide, isopropylphosphinide, diisopropylphosphinide, tert-butylphosphinide, di-tert-butylphosphinide, a neopentylphosphinide, or a dineopentylphosphinide; alternatively, methylphosphinide, ethylphosphinide, isopropylphosphinide, a tert-butylphosphinide, or neopentylphosphinide; alternatively, dimethylphosphinide, diethylphosphinide, diisopropylphosphinide, di-tert-butylphosphinide, or dineopentylphosphinide; alternatively, phenylphosphinide, a tolylphosphinide, or a xylylphosphinide; alternatively, diphenylphosphinide, a ditolylphosphinide, a dixylylphosphinide, or a dibenzylphosphinide; alternatively, methylphosphinide; alternatively, dimethylphosphinide; alternatively, ethylphosphinide; alternatively, diethylphosphinide; alternatively, isopropylphosphinide; alternatively, diisopropylphosphinide; alternatively, tert-butylphosphinide; alternatively, di-tert-butylphosphinide; alternatively, a neopentylphosphinide; alternatively a dineopentylphosphinide; alternatively, phenylphosphinide; alternatively, diphenylphosphinide; alternatively, a tolylphosphinide; alternatively, a ditolylphosphinide; alternatively, a xylylphosphinide; alternatively, a dixylylphosphinide; alternatively, a benzylphosphinide; or alternatively, a dibenzylphosphinide.

Olefins

A wide range of olefins can be utilized in the process for the hydroboration of an olefin using a metal complex of the types disclosed herein. In some embodiments, the olefin can be an alkene. For example, the processes described herein can be applicable to olefins as small as propylene and as large as waxes having 70 or 75 carbon atoms per molecule. In any aspect and/or in any embodiment described herein, the olefin can comprise, or consist essentially of, or can be, a $C_2$ to $C_{60}$ olefin; alternatively, a $C_4$ to $C_{50}$ olefin; alternatively, a $C_6$ to $C_{30}$ olefin; alternatively, a $C_6$ to $C_{20}$ olefin; or alternatively, a $C_6$ to $C_{14}$ olefin; or alternatively, a $C_2$ to $C_{60}$ alkene; alternatively, a $C_4$ to $C_{50}$ alkene; alternatively, a $C_6$ to $C_{30}$ alkene; alternatively, a $C_6$ to $C_{20}$ alkene; or alternatively, a $C_6$ to $C_{14}$ alkene. In an embodiment, the olefin or alkene can comprise, consist essentially of, or consists of, $C_6$ olefin or alkene, a $C_8$ olefin or alkene, a $C_{10}$ olefin or alkene, a $C_{12}$ olefin or alkene, a $C_{14}$ olefin or alkene, a $C_{16}$ olefin or alkene, a $C_{18}$ olefin or alkene, or any combination thereof; alternatively, a $C_6$ olefin or alkene, a $C_8$ olefin or alkene, a $C_{10}$ olefin or alkene, a $C_{12}$ olefin or alkene, a $C_{14}$ olefin or alkene, or any combination thereof; alternatively, a $C_6$ olefin or alkene; alternatively, a $C_8$ olefin or alkene; alternatively, a $C_{10}$ olefin or alkene; alternatively, a $C_{12}$ olefin or alkene; alternatively, a $C_{14}$ olefin or alkene; alternatively, a $C_{16}$ olefin or alkene; or alternatively, a $C_{18}$ olefin or alkene.

In an embodiment, the olefin or alkene, regardless of carbon number, can be a terminal olefin or alkene, an internal olefin or alkene, or a combination thereof; alternatively, a terminal olefin or alkene; or alternatively, an internal olefin or alkene. In some embodiments, the alkene (regardless of carbon number, and whether terminal and/or internal) can be a linear olefin or alkene, a branched olefin or alkene, or a combination thereof; alternatively, a linear olefin or alkene; or alternatively, a branched olefin or alkene. In other embodiments, the olefin or alkene (regardless of carbon number and whether terminal or internal, and/or linear or branched) can be an acyclic olefin or alkene, a cyclic olefin or alkene, or any combination thereof; alternatively, an acyclic olefin or alkene; or alternatively, a cyclic olefin or alkene. In a particular embodiment, the olefin or alkene (regardless of carbon number) can comprise, consist essentially of, or can be, a linear terminal alkene, a linear internal alkene, or any combination thereof; alternatively, a linear terminal alkene; or alternatively, a linear internal alkene.

In an embodiment, the olefin or alkenes can comprise, consist essentially of or be an alkene having any carbon number described herein. In some embodiments, the alkene can comprise, consist essentially of, or be, a butene, a pentene, a hexene, a heptene, an octene, a nonene, a decene, an undecene, a dodecene, a tridecene, a tetradecene, a pentadecene, a hexadecene, a heptadecene, an octadecene, or a combination thereof; or alternatively, a hexene, an octene, a decene, a dodecene, a tetradecene, a hexadecene, an octadecene, or a combination thereof. In some embodiments, the alkene can comprise, consist essentially of, or be 1-hexene, 1-octene, 1-decene, 1-dodecene, 1-tetradecene, 1-hexadecene, 1-octadecene, or a combination thereof; alternatively, 1-hexene, 1-octene, 1-decene, 1-dodecene, or a combination thereof; alternatively, 1-hexene; alternatively, 1-octene; alternatively, 1-decene; or alternatively, 1-dodecene. In other embodiments, the alkene can comprise, consist essentially of, or be, internal hexene(s), internal octene(s), internal decene(s), internal dodecene(s), internal tetradecene(s), internal hexadecene(s), internal octadecene(s), or a combination thereof; alternatively, internal hexene(s), internal octene(s), internal decene(s), internal dodecene(s), or a combination thereof; alternatively, internal hexene(s); alternatively, internal octene(s); alternatively, internal decene(s); or alternatively, internal dodecene(s). In yet other embodiments, the alkene can comprise, consist essentially of, or be, linear internal hexene(s), linear internal octene(s), linear internal decene(s), linear internal dodecene(s), linear internal tetradecene(s), linear internal hexadecene(s), linear internal octadecene(s), or a combination thereof; alternatively, linear internal hexene(s), linear internal octene(s), linear internal decene(s), linear internal dodecene(s), or a combination thereof; alternatively, linear internal hexene(s); alternatively, linear internal octene(s); alternatively, linear internal decene(s); or alternatively, linear internal dodecene(s). In some embodiments, any internal olefin describe herein can comprise, consist essentially of, of consist of, a cis-olefin (or alkene), a trans-olefin (or alkene), or any combination thereof; alternatively, a cis-olefin (or alkene); or alternatively, a trans-olefin (or alkene).

Hydrogen-Boron Bond Containing Compound

Generally, the hydrogen-boron bond containing compound can be any compound having a hydrogen-boron bond. In an aspect, the hydrogen-boron bond containing compound can comprise, consist essentially of, or be, borane, diborane, a borane-amine complex, a borane-phosphine complex, a borane-phosphite complex, a borane-ether complex, a borane-sulfide complex, a hydrogen borinic acid ester, a hydrogen boronic acid ester, a hydrogen monoaminoborane, a hydrogen diaminoborane, a hydrogen azaborolidine, a hydrogen diazaborlidine, or any combination thereof. In some embodiments, the hydrogen-boron bond containing compound can comprise, consist essentially of, or be, borane, diborane, a borane-amine complex, a borane-phosphine complex, a borane-ether complex, a borane-sulfide complex, a hydrogen borinic acid ester, a hydrogen boronic acid ester, a hydrogen monoaminoborane, a hydrogen diaminoborane, or any combination thereof; alternatively, borane, diborane, a borane-amine complex, a borane-phosphine complex, a borane-ether complex, a borane-sulfide complex, a hydrogen borinic acid ester, a hydrogen boronic acid ester, or any combination thereof; alternatively, borane, diborane, a borane-amine complex, a borane-phosphine complex, a borane-ether complex, a borane-sulfide complex, or any combination thereof; alternatively, borane, diborane, or any combination thereof; alternatively, a borane-amine complex, a borane-phosphine complex, a borane-phosphite complex, a borane-ether complex, a borane-sulfide complex, or any combination thereof; a hydrogen borinic acid ester, a hydrogen boronic acid ester, a hydrogen monoaminoborane, a hydrogen diaminoborane, or any combination thereof; alternatively, a hydrogen borinic acid ester, a hydrogen boronic acid ester, or any combination thereof; or alternatively, a hydrogen monoaminoborane, a hydrogen diaminoborane, or any combination thereof. In other embodiments, the hydrogen-boron bond containing compound can comprise, consist essentially of, or be, borane; alternatively, diborane; alternatively, a borane-amine complex; alternatively, a borane-phosphine complex; alternatively, a borane-phosphite complex; alternatively, a borane-ether complex; alternatively, a borane-sulfide complex; alternatively, a hydrogen borinic acid ester; alternatively, a hydrogen boronic acid ester; alternatively, a hydrogen monoaminoborane; or alternatively, a hydrogen diaminoborane. In other embodiments, the hydrogen-boron bond containing compound can comprise, consist essentially of, or be, a hydrogen borinic thio acid ester or a hydrogen boronic thio acid ester; alternatively, a hydrogen borinic thio acid ester; or alternatively, a hydrogen boronic thio acid ester. In yet other embodiments, the hydrogen-boron bond containing compound can comprise, consist essentially of, or be, a borohydride compound salt. In some embodiments, the hydrogen-boron bond containing compound can comprise, consist essentially of, or be, a hydrogen borohalide, a hydroborohalide amine complex, a hydroborohalide phosphine complex, a hydroborohalide amine complex, ether complex, a hydroborohalide sulfide complex, or any combination thereof; alternatively, a hydroborohalide amine complex, a hydroborohalide phosphine complex, a hydroborohalide amine complex, an ether complex, a hydroborohalide sulfide complex, or any combination thereof; alternatively, a hydrogen borohalide; alternatively, a hydroborohalide amine complex; alternatively, a hydroborohalide phosphine complex; alternatively, a hydroborohalide amine complex; alternatively, an ether complex; or alternatively, a hydroborohalide sulfide complex.

In an embodiment, the borohydride compound salt can be represented by the formula $A^m[BH_4]^{-1}{}_n$, $A^m[BH_3R^{b1}]^{-1}{}_n$, $A^m[BH_2(R^{b1})_2]^{-1}{}_n$, or $A^m[BH(R^{b1})_3]^{-1}{}_n$; alternatively, $A^m[BH_4]^{-1}{}_n$; alternatively, $A^m[BH_3R^{b1}]^{-1}{}_n$; alternatively, $A^m[BH_2(R^{b1})_2]^{-1}{}_n$; or alternatively, $A^m[BH(R^{b1})_3]^{-1}{}_n$. Generally, A, $R^{b1}$ (when present), m, and n of the borohydride compound salt having the formula $A^m[BH_4]^{-1}{}_n$, $A^m[BH_3R^{b1}]^{-1}{}_n$, $A^m[BH_2(R^{b1})_2]^{-1}{}_n$, or $A^m[BH(R^{b1})_3]^{-1}{}_n$ are independent elements of the borohydride compound salt. These elements of the borohydride compound salt having the formula $A^m[BH_4]^{-1}{}_n$, $A^m[BH_3R^{b1}]^{-1}{}_n$, $A^m[BH_2(R^{b1})_2]^{-1}{}_n$, or $A^m[BH(R^{b1})_3]^{-1}{}_n$ are independently described herein and these independently described elements can be combined in any fashion to further describe borohydride compound salts contemplated by the present disclosure. Generally, A of the borohydride compound salts having the formula $A^m[BH_4]^{-1}{}_n$, $A^m[BH_3R^{b1}]^{-1}{}_n$, $A^m[BH_2(R^{b1})_2]^{-1}{}_n$, or $A^m[BH(R^{b1})_3]^{-1}{}_n$ can be any suitable cation having a charge, m, of +1 to +6; alternatively, +1 to +4; alternatively, +1 to +3, alternatively, +1 to +2; alternatively, +1; alternatively, +2, or alternatively, +3. In an embodiment of the borohydride compound salts having the formula $A^m[BH_3R^{b1}]^{-1}{}_n$, $A^m[BH_2(R^{b1})_2]^{-1}{}_n$, or $A^m[BH(R^{b1})_3]^{-1}{}_n$, the sum of m and n can be zero.

In an embodiment of the borohydride compound salts having the formula $A^m[BH_4]^{-}{}_n$, $A^m[BH_3R^{b1}]^{-1}{}_n$, $A^m[BH_2(R^{b1})_2]^{-1}{}_n$, or $A^m[BH(R^{b1})_3]^{-1}{}_n$, A can be a Group 1A element. In some embodiments, A can be lithium, sodium, or potassium; alternatively, lithium; alternatively sodium; or alternatively, potassium. In other borohydride compound salt embodiments, A can be beryllium, uranium, or aluminum; alternatively beryllium; alternatively, uranium; or alternatively, aluminum. In an aspect A can be a polyatomic cation. In yet other borohydride compound salt embodiments, A can be ammonium, phosphonium, fluoronium, tropylium, or guanidinium; alternatively, ammonium; alternatively, phosphonium; alternatively, fluoronium; alternatively, tropylium; or alternatively, guanidinum.

Generally, one or more, or each $R^{b1}$ of the borohydride compound salts having the $A^m[BH_3R^{b1}]^{-1}{}_n$, $A^m[BH_2(R^{b1})_2]^{-1}{}_n$, or $A^m[BH(R^{b1})_3]^{-1}{}_n$ independently can be an organyl group or organocarboxy group; alternatively, an organyl group; alternatively, a organocarboxy group; alternatively, a hydrocarbyl group or a hydrocarboxy group; alternatively, a hydrocarbyl group; or alternatively, a hydrocarboxy group. In an embodiment, each $R^{b1}$ of the borohydride compound salt independently can be a $C_1$ to $C_{30}$ organyl group; alternatively, a $C_1$ to $C_{20}$ organyl group; alternatively, a $C_1$ to $C_{15}$ organyl group; alternatively, a $C_1$ to $C_{10}$ organyl group; or alternatively, a $C_1$ to $C_6$ organyl group. In an embodiment, each $R^{b1}$ organocarboxy group of the borohydride compound salt independently can be a $C_1$ to $C_{30}$ organocarboxy group; alternatively, a $C_1$ to $C_{20}$ organocarboxy group; alternatively, a $C_1$ to $C_{15}$ organocarboxy group; alternatively, a $C_1$ to $C_{10}$ organocarboxy group; or alternatively, a $C_1$ to $C_6$ organocarboxy group. In an embodiment, each $R^{b1}$ hydrocarbyl group of the borohydride compound salt independently can be a $C_1$ to $C_{30}$ hydrocarbyl group; alternatively, a $C_1$ to $C_{20}$ hydrocarbyl group; alternatively, a $C_1$ to $C_{15}$ hydrocarbyl group; alternatively, a $C_1$ to $C_{10}$ hydrocarbyl group; or alternatively, a $C_1$ to $C_6$ hydrocarbyl group. In other embodiments each $R^{b1}$ hydrocarboxy group of the borohydride compound salt independently can be a $C_1$ to $C_{30}$ hydrocarboxy group; alternatively, a $C_1$ to $C_{20}$ hydrocarboxy group; alternatively, a $C_1$ to $C_{15}$ hydrocarboxy group; alternatively, a $C_1$ to $C_{10}$ hydrocarboxy group; or alternatively, a $C_1$ to $C_6$ hydrocarboxy group. In some embodiments, the $R^{b1}$ groups of $A^m[BH_2(R^{b1})_2]^{-1}{}_n$ can be the same; or alternatively, the $R^{b1}$ groups of $A^m[BH_2(R^{b1})_2]^{-1}{}_n$ can be different. In some embodiments of the borohydride compound salt having the formula $A^m[BH(R^{b1})_3]^{-1}{}_n$, all of the $R^{b1}$ groups of $A^m[BH(R^{b1})_3]_n$ can be the same; alternatively, two of the $R^{b1}$ groups of $A^m[BH(R^{b1})_3]^{-1}{}_n$ can be the same; or alternatively, all three of the $R^{b1}$ groups of $A^m[BH(R^{b1})_3]^{-1}{}_n$ can be different. In some embodiments of the borohydride compound salts having the formula $A^m[BH_2(R^{b1})_2]^{-1}{}_n$ the two $R^{b1}$ groups can be linked to form a ring or ring system (including bicyclic ring systems) containing the boron atom; in this instance, the joined $R^{b1}$ groups can be designated $R^{j1}$. In some embodiments of the borohydride compound salts having the $A^m[BH(R^{b1})_3]^{-1}{}_n$, two (or alternatively three) of the $R^{b1}$ groups can be linked to form a ring or ring system (including bicyclic, tricyclic ring systems) containing the boron atom; in these instance two joined $R^{b1}$ groups can be designated $R^j$, while three joined $R^{b1}$ groups can be designated $R^{j2}$.

In an embodiment, the hydrogen-boron bond containing compound can be represented by the formula $H_2BR^{b4}$ or $HB(R^{b4})_2$; alternatively, $H_2BR^{b4}$; or alternatively, $HB(R^{b4})_2$. Generally, one or more, or each $R^{b4}$ of the hydrogen-boron bond containing compound represented by the formula $H_2BR^{b4}$ or $HB(R^{b4})_2$; alternatively, $H_2BR^{b4}$; or alternatively $HB(R^{b4})_2$ independently can be an organyl group; or alternatively, a hydrocarbyl group. In an embodiment, one or more, or each organyl group $R^{b5}$ of the hydrogen-boron bond containing compound can be represented by the formula $H_2BR^{b4}$ or $HB(R^{b4})_2$; alternatively, $H_2BR^{b4}$; or alternatively $HB(R^{b4})_2$ independently can be a $C_1$ to $C_{15}$ organyl group; alternatively, a $C_1$ to $C_{10}$ organyl group; or alternatively, a $C_1$ to $C_6$ organyl group. In an embodiment, one or more, or each $R^{b4}$ hydrocarbyl group of the hydrogen-boron bond containing compound can be represented by the formula $H_2BR^{b4}$ or $HB(R^{b4})_2$; alternatively, $H_2BR^{b4}$; or alternatively $HB(R^{b4})_2$ independently can be a $C_1$ to $C_{15}$ hydrocarbyl group; alternatively, a $C_1$ to $C_{10}$ hydrocarbyl group; or alternatively, a $C_1$ to $C_6$ hydrocarbyl group. In some embodiments, the $R^{b4}$ groups of $HB(R^{b4})_2$ can be the same; or alternatively, the $R^{b4}$ groups of $HB(R^{b4})_2$ can be different. In an embodiment, the hydrogen-boron bond containing compound represented by the formula $H_2BR^{b4}$ can be a $C_1$ to $C_{15}$ hydrogen-boron bond containing compound having the formula $H_2BR^{b4}$; alternatively, $C_1$ to $C_{10}$ hydrogen-boron bond containing compound having the formula $H_2BR^{b4}$; or alternatively, $C_1$ to $C_6$ hydrogen-boron bond containing compound having the formula $H_2BR^{b4}$. In an embodiment, the hydrogen-boron bond containing compound represented by the formula $HB(R^{b4})_2$ can be a $C_2$ to $C_{30}$ hydrogen-boron bond containing compound having the formula $HB(R^{b4})_2$; alternatively, a $C_2$ to $C_{20}$ hydrogen-boron bond containing compound having the formula $HB(R^{b4})_2$; or alternatively, a $C_2$ to $C_{12}$ hydrogen-boron bond containing compound having the formula $HB(R^{b4})_2$. In some embodiments where the hydrogen-boron bond containing compound has the formula $HB(R^{b4})_2$, the two $R^{b4}$ groups can be the same; or alternatively, the two $R^{b4}$ groups can be different. In some embodiments where the hydrogen-boron bond containing compound has the formula $HB(R^{b4})_2$, the two $R^{b4}$ groups of $HB(R^{b4})_2$ can be joined to form a ring or ring system containing the boron atom. In this instance, the two linked $R^{b4}$ groups can be designated $R^{j3}$.

In an embodiment, the hydroborohalide can be represented by the formula $H_2BX$ or $HBX_2$; alternatively, $H_2BX$; or alternatively, $HBX_2$. In some embodiments, the hydroborohalide can be represented by the formula $HB(R^{b4})X$. Generally, each X of the hydroborohalide having the formula $H_2BX$, $HBX_2$, and/or $HB(R^{b4})X$ independently can be any halide. In some embodiments, each X of the hydroborohalide having the formula $H_2BX$ or $HBX_2$ independently can be fluoride, chloride, bromide, iodide; alternatively, chloride or bromide; alternatively, chloride; alternatively, bromide; or alternatively, iodide. Generally, the $R^{b4}$ group of the hydroborohalide having the formula $HB(R^{b4})X$ can be any appropriate $R^{b4}$ described herein (e.g., any $R^{b4}$ group described herein for the hydrogen-boron bond containing compound having the formula $H_2BR^{b4}$ and/or $HB(R^{b4})_2$).

In an aspect, the hydrogen-boron bond containing compound can be a neutral ligand complexed hydrogen-boron bond containing compound. In an embodiment, the neutral ligand of the neutral ligand complexed hydrogen-boron bond containing compound can be an amine, a phosphine, an ether, a sulfide, or any combination thereof; alternatively, an amine; alternatively, a phosphine; alternatively, an ether; or alternatively, a sulfide. These neutral ligand complexed hydrogen-boron bond containing compound can be designated by the formula NL-BH where NL can represent any neutral ligand or neutral structure provide herein and BH can represent a hydrogen-boron bond containing compound described herein or any hydrogen-boron bond containing compound having the formula $BH_3$, $H_2BR^{b4}$, $HB(R^{b4})_2$, $H_2BX$, and/or $HBX_2$ (e.g., a hydrogen-boron bond containing compound having the formula $BH_3$, $H_2BR^{b4}$, $HB(R^{b4})_2$, $H_2BX$, or $HBX_2$; alternatively, $H_2BR^{b4}$ or $HB(R^{b4})_2$; alternatively, $H_2BX$ or $HBX_2$; alternatively, $BH_3$; alternatively, $H_2BR^{b4}$; alternatively, $HB(R^{b4})_2$; alternatively, $H_2BX$; or alternatively, $HBX_2$. $BH_3$, $H_2BR^{b4}$, $HB(R^{b4})_2$, $H_2BX$, or $HBX_2$; alternatively, $H_2BR^{b4}$ or $HB(R^{b4})_2$; alternatively, $H_2BX$ or $HBX_2$; alternatively, $BH_3$; alternatively, $H_2BR^{b4}$; alternatively, $HB(R^{b4})_2$; alternatively, $H_2BX$; or alternatively, $HBX_2$). The neutral ligand complexed hydrogen-boron bond containing compound can be further represented by replacing NL with any general or specific neutral ligand provided herein or any general or specific ligand formula provided herein and/or replacing BH with any hydrogen-boron bond containing compound provided herein or general or specific hydrogen-boron bond containing compound formula provided herein. For example, one general amine-hydroborohalide complex can be designated as amine-$BH_3$, a tertiary amine-borane complex can be represented as $[(R^{b5})_3N]BH_3$, and a trimethylamine-borane complex can be represented by the formula $[(CH_3)_3N]BH_3$. As a second example, one general sulfide-hydroborohalide complex can be designated as a sulfide-$BH_2X$, a less general sulfide-hydroborohalide complex can be represented as $[(R^{b8})_2S]BH_2X$, and a dimethysulfide-monochloride borane complex can be represented by the formula $[(CH_3)_2S]BH_2Cl$. Other, general and specific neutral ligand complexed hydrogen-boron bond containing compounds designation can be readily envisioned and used.

In an embodiment, a hydrogen-boron bond containing compound-amine complex can be represented by the formula $[(R^{b5})_qNH_{3-q}]BH_3$. In an embodiment, a hydrogen-boron bond containing compound-amine complex can be represented by the formula $[(R^{b5})_qNH_{3-q}]BH_2R^{b4}$ or $[(R^{b5})_qNH_{3-q}]BH(R^{b4})_2$; alternatively, $[(R^{b5})_qNH_{3-q}]BH_2R^{b4}$; or alternatively, $[(R^{b5})_qNH_{3-q}]BH(R^{b4})_2$. In the formulas $[(R^{b5})_qNH_{3-q}]BH_2R^{b4}$ and $[(R^{b5})_qNH_{3-q}]BH(R^{b4})_2$, q can be an integer ranging from 0 to 3; alternatively, 0, alternatively 1; alternatively, 2; or alternatively, 3. In an embodiment, a borane-amine complex can be represented by the formula $[(R^{b5})_qNH_{3-q}]HB(R^{b4})X$. Generally, in the formulas $[(R^{b5})_qNH_{3-q}]BH_2R^{b4}$ $[(R^{b5})_qNH_{3-q}]BH(R^{b4})_2$, and/or $[(R^{b5})_qNH_{3-q}]HB(R^{b4})X$, $R^{b4}$ can be any group described herein for the hydrogen-boron bond containing compound represented by the formulas $H_2BR^{b4}$ and/or $HB(R^{b4})_2$. Further, the $H_2BR^{b4}$, $HB(R^{b4})_2$, or $HB(R^{b4})X$ portion of the borane-amine complex can be any compound having the formula $H_2BR^{b4}$, $HB(R^{b4})_2$, $HB(R^{b4})X$ described and/or provided herein. In an embodiment, a hydroborohalide-amine complex can be represented by the formula $[(R^{b5})_rNH_{3-r}]BH_2X$ or $[(R^{b5})_rNH_{3-r}]BHX_2$; alternatively, $[(R^{b5})_rNH_{3-r}]BH_2X$; alternatively, $[(R^{b5})_rNH_{3-r}]BHX_2$; or alternatively, $[(R^{b5})_qNH_{3-q}]HB(R^{b4})X$. In the formulas $[(R^{b5})_rNH_{3-r}]BH_2X$ or $[(R^{b5})_rNH_{3-r}]BHX_2$, r can be an integer ranging from 0 to 3; alternatively, 0, alternatively 1; alternatively, 2; or alternatively, 3. Additionally, in the formulas $[(R^{b5})_rNH_{3-r}]BH_2X$, $[(R^{b5})_rNH_{3-r}]BHX_2$, and $[(R^{b5})_qNH_{3-q}]HB(R^{b4})X$, X can be any halide described herein for the hydroborohalide compound represented by the formulas $BH_2X$ and/or $BHX_2$, or $BH_2X$ and/or $BHX_2$ can be any compound having the formula $BH_2X$ or $BHX_2$ described and/or provided herein. In an embodiment, the amine of amine complexes can be $NH_3$ (i.e., $[(R^{b5})_qNH_{3-q}]$ or $[(R^{b5})_rNH_{3-r}]$ where q and r are 0). In an embodiment where the amine has the formula $R^{b5}NH_2$ (i.e., $[(R^{b5})_qNH_{3-q}]$ or $[(R^{b5})_rNH_{3-r}]$ where q and r are 1), the amine of the amine complexes can be a $C_1$ to $C_{15}$ amine; alternatively, a $C_1$ to $C_{10}$ amine; or alternatively, a $C_1$ to $C_6$ amine. In an embodiment where the amine has the formula $(R^{b5})_2NH$ (i.e., $[(R^{b5})_qNH_{3-q}]$ or $[(R^{b5})_rNH_{3-r}]$ where q and r are 2), the amine of the amine complexes can be a $C_2$ to $C_{30}$ amine; alternatively, a $C_2$ to $C_{20}$ amine; or alternatively, a $C_2$ to $C_{12}$ amine. In an embodiment where the amine has the formula $(R^{b5})_3N$ (i.e., $[(R^{b5})_qNH_{3-q}]$ or $[(R^{b5})_rNH_{3-r}]$ where q and r are 3), the amine of the amine complexes can be a $C_3$ to $C_{45}$ amine; alternatively, a $C_3$ to $C_{30}$ amine; or alternatively, a $C_3$ to $C_{18}$ amine. Generally, each $R^{b5}$ of the amine complexes independently can be an organyl group; or alternatively, a hydrocarbyl group. In an embodiment, each $R^{b5}$ organyl group of the amine complexes independently can be a $C_1$ to $C_{15}$ organyl group; alternatively, a $C_1$ to $C_{10}$ organyl group; or alternatively, a $C_1$ to $C_6$ organyl group. In an embodiment, each $R^{b5}$ hydrocarbyl group of the amine complexes independently can be a $C_1$ to $C_{15}$ hydrocarbyl group; alternatively, a $C_1$ to $C_{10}$ hydrocarbyl group; or alternatively, a $C_1$ to $C_6$ hydrocarbyl group. In some amine complex embodiments where the amine has the formula $(R^{b5})_2NH$ (i.e., $[(R^{b5})_qNH_{3-q}]$ or $[(R^{b5})_rNH_{3-r}]$ where q and r are 2, the two $R^{b5}$ groups can be the same; or alternatively, the two $R^{b5}$ groups can be different. In some amine complex embodiments where the amine has the formula $(R^{b5})_3N$ (i.e., $[(R^{b5})_qNH_{3-q}]$ or $[(R^{b5})_rNH_{3-r}]$ where q and r are 3, all of the $R^{b5}$ groups can be the same; alternatively, two of the $R^{b5}$ groups can be the same and the third $R^{b5}$ different; or alternatively, all three of the $R^{b5}$ groups can be different. In some amine complex embodiments where the amine has the formula $(R^{b5})_2NH$ (i.e., $[(R^{b5})_qNH_{3-q}]$ or $[(R^{b5})_rNH_{3-r}]$ where q and r are 2), the two $R^{b5}$ groups can be linked to form a ring or ring system (including bicyclic ring systems) containing the amine nitrogen atom; in this instance the two linked $R^{b5}$ groups can be designated $R^{j2}$. In some amine complex embodiments where the amine has the formula $(R^{b5})_3N$ (i.e., $[(R^{b5})_qNH_{3-q}]$ or $[(R^{b5})_rNH_{3-r}]$ where q and r are 3), two or three $R^{b5}$ groups can be linked to form a ring or ring system (including bicyclic, tricyclic ring systems) containing the amine nitrogen atom; in these instances two linked $R^{b5}$ groups can be designated $R^{j4}$ while three linked $R^{b5}$ groups can be designated $R^{j5}$. In an embodiment, three joined $R^{b5}$ groups can be joined to form a pyridine compound.

In an embodiment, a hydrogen-boron bond containing compound-phosphine complex can be represented by the formula $[(R^{b6})_qPH_{3-q}]BH_3$. In an embodiment, a hydrogen-boron bond containing compound-phosphine complex can be represented by the formula $[(R^{b6})_qPH_{3-q}]BH_2R^{b4}$ or $[(R^{b6})_qPH_{3-q}]BH(R^{b4})_2$; alternatively, $[(R^{b6})_qPH_{3-q}]BH_2R^{b4}$; or alternatively, $[(R^{b6})_qPH_{3-q}]BH(R^{b4})_2$. In the formulas $[(R^{b6})_qPH_{3-q}]BH_2R^{b4}$ and $[(R^{b6})_qPH_{3-q}]BH(R^{b4})_2$, q can be an integer ranging from 0 to 3; alternatively, 0, alternatively 1; alternatively, 2; or alternatively, 3. In an embodiment, a borane-phosphine complex can be represented by the formula $[(R^{b6})_qPH_{3-q}]HB(R^{b4})X$. Generally, in the formulas $[(R^{b6})_qPH_{3-q}]BH_2R^{b4}$, $[(R^{b6})_qPH_{3-q}]BH(R^{b4})_2$, and/or $[(R^{b6})_qPH_{3-q}]HB(R^{b4})X$, $R^{b4}$ can be any group described herein for the hydrogen-boron bond containing compound represented by the formulas $H_2BR^{b4}$ and/or $HB(R^{b4})_2$. Further, the $H_2BR^{b4}$, $HB(R^{b4})_2$, or $HB(R^{b4})X$ portion of the borane-phosphine complex can be any compound having the formula $H_2BR^{b4}$, $HB(R^{b4})_2$, or $HB(R^{b4})X$ described and/or provided herein. In an embodiment, a hydroborohalide-phosphine complex can be represented by the formula $[(R^{b6})_rPH_{3-r}]BH_2X$ or $[(R^{b6})_rPH_{3-r}]BHX_2$; alternatively, $[(R^{b6})_rPH_{3-r}]BH_2X$; alternatively, $[(R^{b6})_rPH_{3-r}]BHX_2$; or alternatively, $[(R^{b6})_qPH_{3-q}]HB(R^{b4})X$. In the formulas $[(R^{b6})_rPH_{3-r}]BH_2X$ or $[(R^{b6})_rPH_{3-r}]BHX_2$, r can be an integer ranging from 0 to 3; alternatively, 0, alternatively 1; alternatively, 2; or alternatively, 3. Additionally, in the formulas $[(R^{b6})_rPH_{3-r}]BH_2X$, $[(R^{b6})_rPH_{3-r}]BHX_2$, and $[(R^{b6})_qPH_{3-q}]HB(R^{b4})X$, X can be any halide described herein for the hydroborohalide compound represented by the formulas $BH_2X$ and/or $BHX_2$, or $BH_2X$ and/or $BHX_2$ can be any compound having the formula $BH_2X$ or $BHX_2$ described and/or provided herein. In an embodiment, the phosphine of the phosphine complexes can be $PH_3$ (i.e., $[(R^{b6})_qPH_{3-q}]$ or $[(R^{b6})_rPH_{3-r}]$ where q and r are 0). In an embodiment where the phosphine has the formula $R^{b6}PH_2$ (i.e., $[(R^{b6})_qPH_{3-q}]$ or $[(R^{b6})_rPH_{3-r}]$ where q and r are 1), the phosphine of the phosphine complexes can be a $C_1$ to $C_{15}$ phosphine; alternatively, a $C_1$ to $C_{10}$ phosphine; or alternatively, a $C_1$ to $C_6$ phosphine. In an embodiment where the phosphine has the formula $(R^{b6})_2PH$ (i.e., $[(R^{b6})_qPH_{3-q}]$ or $[(R^{b6})_rPH_{3-r}]$ where q and r are 2), the phosphine of the phosphine complexes can be a $C_2$ to $C_{30}$ phosphine; alternatively, a $C_2$ to $C_{20}$ phosphine; or alternatively, a $C_2$ to $C_{12}$ phosphine. In an embodiment where the phosphine has the formula $(R^{b6})_3P$ (i.e., $[(R^{b6})_qPH_{3-q}]$ or $[(R^{b6})_rPH_{3-r}]$ where q and r are 3), the phosphine of the phosphine complexes can be a $C_3$ to $C_{45}$ phosphine; alternatively, a $C_3$ to $C_{30}$ phosphine; or alternatively, a $C_3$ to $C_{18}$ phosphine. Generally, each $R^{b6}$ of the phosphine complexes independently can be an organyl group; or alternatively, a hydrocarbyl group. In an embodiment, each $R^{b6}$ organyl group of the phosphine complexes independently can be a $C_1$ to $C_{15}$ organyl group; alternatively, a $C_1$ to $C_{10}$ organyl group; or alternatively, a $C_1$ to $C_6$ organyl group. In an embodiment, each $R^{b6}$ hydrocarbyl group of the phosphine complexes independently can be a $C_1$ to $C_{15}$ hydrocarbyl group; alternatively, a $C_1$ to $C_{10}$ hydrocarbyl group; or alternatively, a $C_1$ to $C_6$ hydrocarbyl group. In some phosphine complex embodiments where the phosphine has the formula $(R^{b6})_2PH$ (i.e., $[(R^{b6})_qPH_{3-q}]$ or $[(R^{b6})_rPH_{3-r}]$ where q and r are 2), the two $R^{b6}$ groups can be the same; or alternatively, the two $R^{b6}$ groups can be different. In some phosphine complex embodiments where the phosphine has the formula $(R^{b6})_3P$ (i.e., $[(R^{b6})_qPH_{3-q}]$ or $[(R^{b6})_rPH_{3-r}]$ where q and r are 3), all of the $R^{b6}$ groups can be the same; alternatively, two of the $R^{b6}$ groups can be the same and the third $R^{b6}$ group different; or alternatively, all three of the $R^{b6}$ groups of can be different. In some phosphine complex embodiments where the phosphine has the formula $(R^{b6})_2PH$ (i.e., $[(R^{b6})_qPH_{3-q}]$ or $[(R^{b6})_rPH_{3-r}]$ where q and r are 2), the two $R^{b6}$ groups can be linked to form a ring or ring system (including bicyclic ring systems) containing the phosphine phosphorous atom; in this instance the two linked $R^{b6}$ groups can be designated $R^{j4}$. In some phosphine complex embodiments where the phosphine has the formula $(R^{b6})_3P$ (i.e., $[(R^{b6})_qPH_{3-q}]$ or $[(R^{b6})_rPH_{3-r}]$ where q and r are 3), two or three $R^{b6}$ groups can be linked to form a ring or ring system (including bicyclic, tricyclic ring systems) containing the phosphine phosphorous atom; in these instances the two linked $R^{b6}$ groups can be designated $R^{j6}$ while three linked $R^{b6}$ groups can be designated $R^{j7}$.

In an aspect, the hydrogen-boron bond containing compound can be a hydrogen-boron bond containing compound-trihalophosphine complex. In an embodiment, a borane-trihalophosphine complex can be represented by the formula $[(X^1)_3P]BH_3$. In an embodiment, a hydrogen-boron bond containing compound-trihalophosphine complex can be represented by the formula $[(X^1)_3P]BH_2R^{b4}$ or $[(X^1)_3P]BH(R^{b4})_2$; alternatively, $[(X^1)_3P]BH_2R^{b4}$; or alternatively, $[(X^1)_3P]BH(R^{b4})_2$. In the formulas $[(X^1)_3P]BH_2R^{b4}$ and $[(X^1)_3P]BH(R^{b4})_2$, $R^{b4}$ can be any group described herein for the hydrogen-boron bond containing compound represented by the formulas $H_2BR^{b4}$ and/or $HB(R^{b4})_2$, or $H_2BR^{b4}$ and/or $HB(R^{b4})_2$ can be any compound having the formula $H_2BR^{b4}$ or $HB(R^{b4})_2$ described and/or provided herein. In an embodiment, a hydroborohalide-trihalophosphine complex can be represented by the formula $[(X^1)_3P]BH_2X$ or $[(X^1)_3P]BHX_2$; alternatively, $[(X^1)_3P]BH_2X$; or alternatively, $[(X^1)_3P]BHX_2$. In the formulas $[(X^1)_3P]BH_2X$ or $[(X^1)_3P]BHX_2$, X can be any halide described herein for the hydroborohalide compound represented by the formulas $BH_2X$ and/or $BHX_2$, or $BH_2X$ and/or $BHX_2$ can be any compound having the formula $BH_2X$ or $BHX_2$ described and/or provided herein. In an embodiment, each $X^1$ of the hydrogen-boron bond containing compound-trihalophosphine complexes independently can be any halo group. In some embodiments, each $X^1$ of the hydrogen-boron bond containing compound-trihalophosphine complexes independently can be fluoro, chloro, bromo, or iodo; or alternatively, fluoro.

In an embodiment, a hydrogen-boron bond containing compound-phosphite complex can be represented by the formula $[(R^{b7}O)_3P]BH_3$. In an embodiment, a hydrogen-boron bond containing compound-phosphite complex can be represented by the formula $[(R^{b7}O)_3P]BH_2R^{b4}$ or $[(R^{b7}O)_3P]BH(R^{b4})_2$; alternatively, $[(R^{b7}O)_3P]BH_2R^{b4}$; or alternatively, $[(R^{b7}O)_3P]BH(R^{b4})_2$. In the formulas $[(R^{b7}O)_3P]BH_2R^{b4}$ and $[(R^{b7}O)_3P]BH(R^{b4})_2$, $R^{b4}$ can be any group described herein for the hydrogen-boron bond containing compound represented by the formulas $H_2BR^{b4}$ and/or $HB(R^{b4})_2$, or $H_2BR^{b4}$ and/or $HB(R^{b4})_2$ can be any compound having the formula $H_2BR^{b4}$ or $HB(R^{b4})_2$ described and/or provided herein. In an embodiment, a hydroborohalide-phosphite complex can be represented by the formula $[(R^{b7}O)_3P]BH_2X$ or $[(R^{b7}O)_3P]BHX_2$; alternatively, $[(R^{b7}O)_3P]BH_2X$; or alternatively, $[(R^{b7}O)_3P]BHX_2$. In the formulas $[(R^{b7}O)_3P]BH_2X$ or $[(R^{b7}O)_3P]BHX_2$, X can be any halide described herein for the hydroborohalide compound represented by the formulas $BH_2X$ and/or $BHX_2$, or $BH_2X$ and/or $BHX_2$ can be any compound having the formula $BH_2X$ or $BHX_2$ described and/or provided herein. In an embodiment, the phosphite of the phosphite complexes can be a $C_3$ to $C_{45}$ phosphite; alternatively, a $C_3$ to $C_{30}$ phosphite; or alternatively, a $C_3$ to $C_{18}$ phosphite. Generally, each $R^{b7}$ of the phosphite complexes independently can be an organyl group; or alternatively, a hydrocarbyl group. In an embodiment, each $R^{b7}$ organyl group of the phosphite complexes independently can be a $C_1$ to $C_{15}$ organyl group; alternatively, a $C_1$ to $C_{10}$ organyl group; or alternatively, a $C_1$ to $C_6$ organyl group. In an embodiment, each $R^{b7}$ hydrocarbyl group of the phosphite complexes independently can be a $C_1$ to $C_{15}$ hydrocarbyl group; alternatively, a $C_1$ to $C_{10}$ hydrocarbyl group; or alternatively, a $C_1$ to $C_6$ hydrocarbyl group. In some phosphite complex embodiments all of the $R^{b7}$ groups can be the same; alternatively, two of the $R^{b7}$ groups can be the same and the third different; or alternatively, all three of the $R^{b7}$ groups of can be different. In some phosphite complex embodiments, two $R^{b7}$ groups can be linked to form a ring or ring system (including bicyclic, tricyclic ring systems) containing the phosphite phosphorous atom; in this instance the two linked $R^{b6}$ groups can be designated $R^{j8}$.

In an embodiment, a hydrogen-boron bond containing compound-ether complex can be represented by the formula $[(R^{b8})_2O]BH_3$. In an embodiment, a hydrogen-boron bond containing compound-ether complex can be represented by the formula $[(R^{b8})_2O]BH_2R^{b4}$ or $[(R^{b8})_2O]BH(R^{b4})_2$; alternatively, $[(R^{b8})_2O]BH_2R^{b4}$; or alternatively, $[(R^{b8})_2O]BH(R^{b4})_2$. In an embodiment, a borane-ether complex can be represented by the formula $[(R^{b8})_2O]HB(R^{b4})X$. Generally, in the formulas $[(R^{b8})_2O]BH_2R^{b4}$, $[(R^{b8})_2O]BH(R^{b4})_2$, and/or $[(R^{b8})_2O]HB(R^{b4})X$, $R^{b4}$ can be any group described herein for the hydrogen-boron bond containing compound represented by the formulas $H_2BR^{b4}$ and/or $HB(R^{b4})_2$. Further, $H_2BR^{b4}$, $HB(R^{b4})_2$, or $[(R^{b8})_2O]HB(R^{b4})X$ portion of the borane-ether complex can be any compound having the formula $H_2BR^{b4}$, $HB(R^{b4})_2$, or $[(R^{b8})_2O]HB(R^{b4})X$ described and/or provided herein. In an embodiment, a hydroborohalide-ether complex can be represented by the formula $[(R^{b8})_2O]BH_2X$ or $[(R^{b8})_2O]BHX_2$; alternatively, $[(R^{b8})_2O]BH_2X$; alternatively, $[(R^{b8})_2O]BHX_2$; or alternatively, $[(R^{b8})_2O]HB(R^{b4})X$. In the formulas $[(R^{b8})_2O]BH_2X$, $[(R^{b8})_2O]BHX_2$, or $[(R^{b8})_2O]HB(R^{b4})X$, X can be any halide described herein for the hydroborohalide compound represented by the formulas $BH_2X$ and/or $BHX_2$, or $BH_2X$ and/or $BHX_2$ can be any compound having the formula $BH_2X$ or $BHX_2$ described and/or provided herein. In an embodiment, the ether of the ether complexes can be a $C_2$ to $C_{30}$ ether; alternatively, a $C_2$ to $C_{20}$ ether; or alternatively, a $C_2$ to $C_{12}$ ether. Generally, each $R^{b8}$ of the ether complexes independently can be an organyl group; or alternatively, a hydrocarbyl group. In an embodiment, each $R^{b8}$ organyl group of the ether complexes independently can be a $C_1$ to $C_{15}$ organyl group; alternatively, a $C_1$ to $C_{10}$ organyl group; or alternatively, a $C_1$ to $C_6$ organyl group. In an embodiment, each $R^{b8}$ hydrocarbyl group of the ether complexes independently can be a $C_1$ to $C_{15}$ hydrocarbyl group; alternatively, a $C_1$ to $C_{10}$ hydrocarbyl group; or alternatively, a $C_1$ to $C_6$ hydrocarbyl group. In some ether complex embodiments, the two $R^{b8}$ groups can be the same; or alternatively, the two $R^{b8}$ groups can be different. In some ether complex embodiments, the two $R^{b8}$ groups can be linked to form a ring or ring system (including bicyclic ring systems) containing the ether oxygen atom; in this instance the two linked $R^{b8}$ groups can be designated $R^{j10}$.

In an embodiment, a hydrogen-boron bond containing compound-sulfide complex can be represented by the formula $[(R^{b9})_2S]BH_3$. In an embodiment, a hydrogen-boron bond containing compound-sulfide complex can be represented by the formula $[(R^{b9})_2S]BH_2R^{b4}$ or $[(R^{b9})_2S]BH(R^{b4})_2$; alternatively, $[(R^{b9})_2S]BH_2R^{b4}$; or alternatively, $[(R^{b9})_2S]BH(R^{b4})_2$. In an embodiment, a borane-amine complex can be represented by the formula $[(R^{b9})_2S]HB(R^{b4})X$. Generally, in the formulas $[(R^{b9})_2S]BH_2R^{b4}$, $[(R^{b9})_2S]BH(R^{b4})_2$, or $[(R^{b9})_2S]HB(R^{b4})X$, $R^{b4}$ can be any group described herein for the hydrogen-boron bond containing compound represented by the formulas $H_2BR^{b4}$ and/or $HB(R^{b4})_2$. Further, the $H_2BR^{b4}$, $HB(R^{b4})_2$, $HB(R^{b4})X$ portion of the borane-sulfide complex can be any compound having the formula $H_2BR^{b4}$, $HB(R^{b4})_2$, $HB(R^{b4})X$ described and/or provided herein. In an embodiment, a hydroborohalide-sulfide complex can be represented by the formula $[(R^{b9})_2S]BH_2X$ or $[(R^{b9})_2S]BHX_2$; alternatively, $[(R^{b9})_2S]BH_2X$; alternatively, $[(R^{b9})_2S]BHX_2$; or alternatively, $[(R^{b9})_2S]HB(R^{b4})X$. In the formulas $[(R^{b9})_2S]BH_2X$, $[(R^{b9})_2S]BHX_2$, or $[(R^{b9})_2S]HB(R^{b4})X$, X can be any halide described herein for the hydroborohalide compound represented by the formulas $BH_2X$ and/or $BHX_2$, or $BH_2X$ and/or $BHX_2$ can be any compound having the formula $BH_2X$ or $BHX_2$ described and/or provided herein. In an embodiment, the sulfide of the sulfide complexes can be a $C_2$ to $C_{30}$ sulfide; alternatively, a $C_2$ to $C_{20}$ sulfide; or alternatively, a $C_2$ to $C_{12}$ sulfide. Generally, each $R^{b9}$ of the sulfide complexes independently can be an organyl group; or alternatively, a hydrocarbyl group. In an embodiment, each $R^{b9}$ organyl group of the sulfide complexes independently can be a $C_1$ to $C_{15}$ organyl group; alternatively, a $C_1$ to $C_{10}$ organyl group; or alternatively, a $C_1$ to $C_6$ organyl group. In an embodiment, each $R^{b9}$ hydrocarbyl group of the sulfide complexes independently can be a $C_1$ to $C_{15}$ hydrocarbyl group; alternatively, a $C_1$ to $C_{10}$ hydrocarbyl group; or alternatively, a $C_1$ to $C_6$ hydrocarbyl group. In some sulfide complex embodiments, the two $R^{b9}$ groups can be the same; or alternatively, the two $R^{b9}$ groups can be different. In some sulfide complex embodiments, the two $R^{b9}$ groups can be linked to form a ring or ring system (including bicyclic ring systems) containing the sulfide sulfur atom; in this instance the two linked $R^{b9}$ groups can be designated $R^{j11}$.

In an embodiment, the hydrogen borinic acid ester can be represented by the formula $H_2BOR^{b10}$. In an embodiment, hydrogen borinic acid ester can be a $C_1$ to $C_{15}$ hydrogen borinic acid ester; alternatively, a $C_1$ to $C_{10}$ hydrogen borinic acid ester; or alternatively, a $C_1$ to $C_6$ hydrogen borinic acid ester. In an embodiment, the hydrogen boronic acid ester can be represented by the formula $HB(OR^{b11})_2$. In an embodiment, the hydrogen boronic acid ester can be a $C_2$ to $C_{30}$ hydrogen boronic acid ester; alternatively, a $C_2$ to $C_{20}$ hydrogen boronic acid ester; or alternatively, a $C_1$ to $C_{12}$ hydrogen boronic acid ester. Generally, the $R^{b10}$ of the hydrogen borinic acid ester or each $R^{b11}$ of the hydrogen boronic acid ester independently can be an organyl group; or alternatively, a hydrocarbyl group. In an embodiment, the $R^{b10}$ organyl group of the hydrogen borinic acid ester or each $R^{b11}$ organyl group of the hydrogen boronic acid ester independently can be a $C_1$ to $C_{15}$ organyl group; alternatively, a $C_1$ to $C_{10}$ organyl group; or alternatively, a $C_1$ to $C_6$ organyl group. In an embodiment, the $R^{b10}$ hydrocarbyl group of the hydrogen borinic acid ester or each $R^{b11}$ hydrocarbyl group of the hydrogen boronic acid ester independently can be a $C_1$ to $C_{15}$ hydrocarbyl group; alternatively, a $C_1$ to $C_{10}$ hydrocarbyl group; or alternatively, a $C_1$ to $C_6$ hydrocarbyl group. In some embodiments, the $R^{b11}$ groups of $HB(OR^{b11})_2$ can be the same; or alternatively, the $R^{b11}$ groups of $HB(OR^{b11})_2$ can be different. In some embodiments, the two $R^{b11}$ groups of HB(OR$^{b11}$)$_2$ can be joined to form a ring or ring system containing the two oxygen atoms and the boron atom of the hydrogen boronic acid ester; in this instance the two linked R$^{b11}$ groups can be designated R$^{j12}$. In some embodiments, any hydrogen borinic acid ester described herein can be complexed to any neutral ligand described herein to form a hydrogen borinic acid ester-neutral ligand complex.

In an embodiment, the hydrogen borinic thio acid ester can be represented by the formula H$_2$BSR$^{b12}$. In an embodiment, the hydrogen borinic thio acid ester can be a C$_1$ to C$_{15}$ hydrogen borinic acid ester; alternatively, a C$_1$ to C$_{10}$ hydrogen borinic thio acid ester; or alternatively, a C$_1$ to C$_6$ hydrogen borinic acid ester. In an embodiment, the hydrogen boronic thio acid ester can be represented by the formula HB(SR$^{b13}$)$_2$. In an embodiment, the hydrogen boronic thio acid ester can be a C$_2$ to C$_{30}$ hydrogen boronic thio acid ester; alternatively, a C$_2$ to C$_{20}$ hydrogen boronic thio acid ester; or alternatively, a C$_1$ to C$_{12}$ hydrogen boronic thio acid ester. Generally, the R$^{b12}$ of the hydrogen borinic thio acid ester or each R$^{b13}$ of the hydrogen boronic thio acid ester independently can be an organyl group; or alternatively, a hydrocarbyl group. In an embodiment, the R$^{b12}$ organyl group of the hydrogen borinic thio acid ester or each R$^{b13}$ organyl group of the hydrogen boronic thio acid ester independently can be a C$_1$ to C$_{15}$ organyl group; alternatively, a C$_1$ to C$_{10}$ organyl group; or alternatively, a C$_1$ to C$_6$ organyl group. In an embodiment, the R$^{b12}$ hydrocarbyl group of the hydrogen borinic thio acid ester or each R$^{b13}$ hydrocarbyl group of the hydrogen boronic thio acid ester independently can be a C$_1$ to C$_{15}$ hydrocarbyl group; alternatively, a C$_1$ to C$_{10}$ hydrocarbyl group; or alternatively, a C$_1$ to C$_6$ hydrocarbyl group. In some embodiments, the R$^{b13}$ groups of HB(OR$^{b13}$)$_2$ can be the same; or alternatively, the R$^{b13}$ groups of HB(OR$^{b13}$)$_2$ can be different. In some embodiments, the two R$^{b13}$ groups of HB(OR$^{b13}$)$_2$ can be joined to form a ring or ring system containing the two sulfur atoms and the boron atom of the hydrogen boronic thio acid ester; in this instance the two linked R$^{b13}$ groups can be designated R$^{j13}$. In some embodiments, any hydrogen borinic thio acid ester described herein can be complexed to any neutral ligand described herein to form a hydrogen borinic thio acid ester-neutral ligand complex.

In an embodiment, the hydrogen monoaminoborane can be represented by the formula H$_2$BNHR$^{b14}$ or H$_2$BN(R$^{b14}$)$_2$; alternatively, H$_2$BNHR$^{b14}$; or alternatively, H$_2$BN(R$^{b14}$)$_2$. In an embodiment, the hydrogen monoaminoborane having the formula H$_2$BNHR$^{b14}$ can be a C$_1$ to C$_{15}$ hydrogen monoaminoborane; alternatively, a C$_1$ to C$_{10}$ hydrogen monoaminoborane; or alternatively, a C$_1$ to C$_6$ hydrogen monoaminoborane. In an embodiment, the hydrogen monoaminoborane having the formula H$_2$BN(R$^{b14}$)$_2$ can be a C$_2$ to C$_{30}$ hydrogen monoaminoborane; alternatively, a C$_2$ to C$_{20}$ hydrogen monoaminoborane; or alternatively, a C$_2$ to C$_{12}$ hydrogen monoaminoborane. In an embodiment, the hydrogen diaminoborane can be represented by the formula HB(NHR$^{b15}$)$_2$ or HB(N(R$^{b15}$)$_2$)$_2$; alternatively, HB(NHR$^{b15}$)$_2$; or alternatively, HB(N(R$^{b15}$)$_2$)$_2$. In an embodiment, the hydrogen diaminoborane having the formula HB(NHR$^{b15}$)$_2$ can be a C$_2$ to C$_{30}$ hydrogen diaminoborane; alternatively, a C$_2$ to C$_{20}$ hydrogen diaminoborane; or alternatively, a C$_2$ to C$_{12}$ hydrogen diaminoborane. In an embodiment, the hydrogen diaminoborane having the formula HB(N(R$^{b15}$)$_2$)$_2$ can be a C$_4$ to C$_{60}$ hydrogen diaminoborane; alternatively, a C$_4$ to C$_{40}$ hydrogen diaminoborane; or alternatively, a C$_4$ to C$_{24}$ hydrogen diaminoborane. Generally, each R$^{b14}$ of the hydrogen monoaminoborane or each R$^{b15}$ of the hydrogen diaminoborane independently can be an organyl group; or alternatively, a hydrocarbyl group. In an embodiment, each R$^{b14}$ of the hydrogen monoaminoborane or each R$^{b15}$ of the hydrogen diaminoborane independently can be a C$_1$ to C$_{15}$ organyl group; alternatively, a C$_1$ to C$_{10}$ organyl group; or alternatively, a C$_1$ to C$_6$ organyl group. In an embodiment, each R$^{b14}$ of the hydrogen monoaminoborane or each R$^{b15}$ of the hydrogen diaminoborane independently can be a C$_1$ to C$_{15}$ hydrocarbyl group; alternatively, a C$_1$ to C$_{10}$ hydrocarbyl group; or alternatively, a C$_1$ to C$_6$ hydrocarbyl group. In an embodiment, the two R$^{b14}$ groups of the hydrogen monoaminoborane having the formula H$_2$BN(R$^{b14}$)$_2$ can be the same; or alternatively, two R$^{b14}$ groups of the hydrogen monoaminoborane having the formula H$_2$BN(R$^{b14}$)$_2$ can be different. In some embodiment, the two R$^{b14}$ groups of the hydrogen monoaminoborane having the formula H$_2$BN(R$^{b14}$)$_2$ can be joined to form a ring or ring system containing the nitrogen atoms of the amino group; in this instance the two linked R$^{b14}$ groups can be designated R$^{j14}$. In an embodiment, the two R$^{b15}$ groups of the hydrogen monoaminoborane having the formula HB(N(R$^{b15}$)$_2$)$_2$ can be the same; or alternatively, two R$^{b15}$ groups of the hydrogen monoaminoborane having the formula HB(N(R$^{b15}$)$_2$)$_2$ can be different. In some embodiments, the R$^{b15}$ groups connected to the same nitrogen atom in a hydrogen diamino borane having the formula HB(N(R$^{b15}$)$_2$)$_2$ can be joined to form a ring or ring system containing the nitrogen atom of the amino group; in this instance the two linked R$^{b15}$ groups can be designated R$^{j14}$. In other embodiments, one R$^{b15}$ group from each of the amino group of the hydrogen diamino borane having the formula HB(NHR$^{b15}$)$_2$ or HB(N(R$^{b15}$)$_2$)$_2$ can be joined to form ring or ring system containing the two nitrogen atoms and the boron atom of the hydrogen diaminoborane; in this instance the two linked R$^{b15}$ groups can be designated R$^{j15}$.

In an embodiment, each R$^{b1}$ of a hydrogen-boron bond containing salt described herein, each R$^{b4}$ of a hydrogen-boron bond containing compound having the formula H$_2$BR$^{b4}$ or HB(R$^{b4}$)$_2$ (and any neutral ligand complex thereof) described herein, each R$^{b5}$ of a borane-amine complex described herein, each R$^{b6}$ of a borane-phosphine complex described herein, each R$^{b7}$ of a borane-phosphite complex described herein, each R$^{b8}$ of a borane-ether complex described herein, each R$^{b9}$ of a borane-sulfide complex described herein, the R$^{b10}$ of a hydrogen borinic acid ester described herein, each R$^{b11}$ of a hydrogen boronic acid ester described herein, the R$^{b12}$ of a hydrogen borinic thio acid ester described herein, each R$^{b13}$ of a hydrogen boronic thio acid ester described herein, each R$^{b14}$ of a hydrogen monoaminoborane described herein, each R$^{b15}$ of a hydrogen diaminoborane described herein, independently can be a C$_1$ to C$_{15}$ alkyl group, a C$_4$ to C$_{15}$ cycloalkyl group, a C$_4$ to C$_{15}$ substituted cycloalkyl group, a C$_6$ to C$_{15}$ aryl group, or a C$_7$ to C$_{15}$ substituted aryl group; alternatively, a C$_4$ to C$_{15}$ cycloalkyl group or a C$_4$ to C$_{15}$ substituted cycloalkyl group; alternatively, a C$_6$ to C$_{15}$ aryl group or a C$_7$ to C$_{15}$ substituted aryl group; alternatively, a C$_1$ to C$_{15}$ alkyl group; alternatively, a C$_4$ to C$_{15}$ cycloalkyl group; alternatively, a C$_4$ to C$_{15}$ substituted cycloalkyl group; alternatively, a C$_6$ to C$_{15}$ aryl group; or alternatively, a C$_7$ to C$_{15}$ substituted aryl group. In other embodiments, each R$^{b1}$ of a hydrogen-boron bond containing salt described herein, each R$^{b4}$ of a hydrogen-boron bond containing compound having the formula H$_2$BR$^{b4}$ or HB(R$^{b4}$)$_2$ (and any neutral ligand complex thereof) described herein, each R$^{b5}$ of a borane-amine complex described herein, each R$^{b6}$ of a borane-phosphine complex described herein, each R$^{b7}$ of a borane-phosphite complex described herein, each R$^{b8}$ of a borane-ether complex described herein, each R$^{b9}$ of a borane-sulfide complex described herein, the R$^{b10}$ of a hydrogen borinic acid ester described herein, each R$^{b11}$ of a hydrogen boronic acid ester described herein, the $R^{b12}$ of a hydrogen borinic thio acid ester described herein, each $R^{b13}$ of a hydrogen boronic thio acid ester described herein, each $R^{b14}$ of a hydrogen monoaminoborane described herein, each $R^{b15}$ of a hydrogen diaminoborane described herein, independently can be $C_1$ to $C_{10}$ alkyl group, a $C_4$ to $C_{10}$ cycloalkyl group, a $C_4$ to $C_{10}$ substituted cycloalkyl group, a $C_6$ to $C_{10}$ aryl group, or a $C_7$ to $C_{10}$ substituted aryl group; alternatively, a $C_4$ to $C_{10}$ cycloalkyl group or a $C_4$ to $C_{10}$ substituted cycloalkyl group; alternatively, a $C_6$ to $C_{10}$ aryl group or a $C_7$ to $C_{10}$ substituted aryl group; alternatively, a $C_1$ to $C_{10}$ alkyl group; alternatively, a $C_4$ to $C_{10}$ cycloalkyl group; alternatively, a $C_4$ to $C_{10}$ substituted cycloalkyl group; alternatively, a $C_6$ to $C_{10}$ aryl group; alternatively, a $C_7$ to $C_{10}$ substituted aryl group; alternatively, a $C_1$ to $C_6$ alkyl group. In the substituted cycloalkyl group and the substituted aryl group embodiments, the substituent(s) can be alkyl groups. Substituents groups (general and specific including alkyl group substituents) are independently disclosed herein and can be utilized without limitation to further describe substituted cycloalkyl groups and/or the substituted aryl groups which can be utilized as a $R^{b1}$ of a hydrogen-boron bond containing salt described herein, a $R^{b4}$ of a hydrogen-boron bond containing compound having the formula $H_2BR^{b4}$ or $HB(R^{b4})_2$ (and any neutral ligand complex thereof) described herein, a $R^{b5}$ of a borane-amine complex described herein, a $R^{b6}$ of a borane-phosphine complex described herein, a $R^{b7}$ of a borane-phosphite complex described herein, a $R^{b8}$ of a borane-ether complex described herein, a $R^{b9}$ of a borane-sulfide complex described herein, a $R^{b10}$ a hydrogen borinic acid ester described herein, a $R^{b11}$ of a hydrogen boronic acid ester described herein, a $R^{b12}$ of a hydrogen borinic thio acid ester described herein, a $R^{b13}$ of a hydrogen boronic thio acid ester described herein, each $R^{b14}$ a hydrogen monoaminoborane described herein, a $R^{b15}$ of a hydrogen diaminoborane described herein.

In an embodiment, each $R^{b1}$ of a hydrogen-boron bond containing salt described herein, each $R^{b4}$ of a hydrogen-boron bond containing compound having the formula $H_2BR^{b4}$ or $HB(R^{b4})_2$ (and any neutral ligand complex thereof) described herein, each $R^{b5}$ of a borane-amine complex described herein, each $R^{b6}$ of a borane-phosphine complex described herein, each $R^{b7}$ of a borane-phosphite complex described herein, each $R^{b8}$ of a borane-ether complex described herein, each $R^{b9}$ of a borane-sulfide complex described herein, the $R^{b10}$ of a hydrogen borinic acid ester described herein, each $R^{b11}$ of a hydrogen boronic acid ester described herein, the $R^{b12}$ of a hydrogen borinic thio acid ester described herein, each $R^{b13}$ of a hydrogen boronic thio acid ester described herein, each $R^{b14}$ of a hydrogen monoaminoborane described herein, each $R^{b15}$ of a hydrogen diaminoborane described herein, independently can be a methyl group, an ethyl group, a propyl group, a butyl group, a pentyl group, or a hexyl group; or alternatively, a methyl group; alternatively, an ethyl group, alternatively, a propyl group; alternatively, a butyl group; alternatively, a pentyl group; or alternatively, a hexyl group. In other embodiments, each $R^{b1}$ of a hydrogen-boron bond containing salt described herein, each $R^{b4}$ of a hydrogen-boron bond containing compound having the formula $H_2BR^{b4}$ or $HB(R^{b4})_2$ (and any neutral ligand complex thereof) described herein, each $R^{b5}$ of a borane-amine complex described herein, each $R^{b6}$ of a borane-phosphine complex described herein, each $R^{b7}$ of a borane-phosphite complex described herein, each $R^{b8}$ of a borane-ether complex described herein, each $R^{b9}$ of a borane-sulfide complex described herein, the $R^{b10}$ of a hydrogen borinic acid ester described herein, each $R^{b11}$ of a hydrogen boronic acid ester described herein, the $R^{b12}$ of a hydrogen borinic thio acid ester described herein, each $R^{b13}$ of a hydrogen boronic thio acid ester described herein, each $R^{b14}$ of a hydrogen monoaminoborane described herein, each $R^{b15}$ of a hydrogen diaminoborane described herein, independently can be a methyl group, an ethyl group, a prop-1-yl group, a but-1-yl group, an but-2-yl group, a 2-methyprop-2-yl group, a pent-1-yl group, a 2-methylbut-1-yl group, a 3-methylbut-2-yl group, a neopentyl group, or a 2,3-dimethylbutyl group; alternatively, a prop-1-yl group; alternatively, a but-1-yl group; alternatively, an but-2-yl group; alternatively, a 2-methyprop-2-yl group; alternatively, a pent-1-yl group; alternatively, a 2-methylbut-1-yl group; alternatively, a 3-methylbut-2-yl group; alternatively, a neopentyl group; or alternatively, a 2,3-dimethylbutyl group.

In an embodiment, each $R^{b1}$ of a hydrogen-boron bond containing salt described herein, each $R^{b4}$ of a hydrogen-boron bond containing compound having the formula $H_2BR^{b4}$ or $HB(R^{b4})_2$ (and any neutral ligand complex thereof) described herein, each $R^{b5}$ of a borane-amine complex described herein, each $R^{b6}$ of a borane-phosphine complex described herein, each $R^{b7}$ of a borane-phosphite complex described herein, each $R^{b8}$ of a borane-ether complex described herein, each $R^{b9}$ of a borane-sulfide complex described herein, the $R^{b10}$ of a hydrogen borinic acid ester described herein, each $R^{b11}$ of a hydrogen boronic acid ester described herein, the $R^{b12}$ of a hydrogen borinic thio acid ester described herein, each $R^{b13}$ of a hydrogen boronic thio acid ester described herein, each $R^{b14}$ of a hydrogen monoaminoborane described herein, each $R^{b15}$ of a hydrogen diaminoborane described herein, independently can be a cyclobutyl group, a cyclopentyl group, a 2-substituted cyclopentyl group, a cyclohexyl group, a 2-substituted cyclohexyl group, a cycloheptyl group, a norborn-2-yl group, a cyclooctyl group, a bicyclo(3.3.0)octan-1-yl group, an adamant-1-yl group, an adamant-2-yl group, or a 2,6,6-trimethylbicyclo (3.1.1)heptan-3-yl group; alternatively, a cyclopentyl group, a 2-substituted cyclopentyl group, a cyclohexyl group, or a 2-substituted cyclohexyl group; alternatively, a cyclopentyl group; alternatively, a 2-substituted cyclopentyl group; alternatively, a cyclohexyl group; or alternatively, a 2-substituted cyclohexyl group. In some embodiments, each $R^{b1}$ of a hydrogen-boron bond containing salt described herein, each $R^{b4}$ of a hydrogen-boron bond containing compound having the formula $H_2BR^{b4}$ or $HB(R^{b4})_2$ (and any neutral ligand complex thereof) described herein, each $R^{b5}$ of a borane-amine complex described herein, each $R^{b6}$ of a borane-phosphine complex described herein, each $R^{b7}$ Of a borane-phosphite complex described herein, each $R^{b8}$ of a borane-ether complex described herein, each $R^{b9}$ of a borane-sulfide complex described herein, the $R^{b10}$ of a hydrogen borinic acid ester described herein, each $R^{b11}$ of a hydrogen boronic acid ester described herein, the $R^{b12}$ of a hydrogen borinic thio acid ester described herein, each $R^{b13}$ of a hydrogen boronic thio acid ester described herein, each $R^{b14}$ of a hydrogen monoaminoborane described herein, each $R^{b15}$ of a hydrogen diaminoborane described herein, independently can be, a cyclobutyl group, a cyclopentyl group, a 2-methylcyclopentyl group, a cyclohexyl group, a 2-methylcyclohexyl group, a cycloheptyl group, a norborn-2-yl group, a cyclooctyl group, a bicyclo(3.3.0)octan-1-yl group, an adamant-1-yl group, an adamant-2-yl group, or a 2,6,6-trimethylbicyclo(3.1.1)heptan-3-yl group; alternatively, a cyclopentyl group, a 2-methylcyclopentyl group, a cyclohexyl group, or a 2-methylcyclohexyl group; alternatively, a cyclobutyl group; alternatively, a cyclopentyl group; alternatively, a 2-methylcyclopentyl group; alternatively, a cyclohexyl group; alternatively, a 2-methylcyclohexyl group; alternatively, a cycloheptyl group; alternatively, a norborn-2-yl group; alternatively, a cyclooctyl group; alternatively, a bicyclo(3.3.0)octan-1-yl group; alternatively, an adamant-1-yl group; alternatively, an adamant-2-yl group; or alternatively, a 2,6,6-trimethylbicyclo(3.1.1)heptan-3-yl group.

In an embodiment, each $R^{b1}$ of a hydrogen-boron bond containing salt described herein, each $R^{b4}$ of a hydrogen-boron bond containing compound having the formula $H_2BR^{b4}$ or $HB(R^{b4})_2$ (and any neutral ligand complex thereof) described herein, each $R^{b5}$ of a borane-amine complex described herein, each $R^{b6}$ of a borane-phosphine complex described herein, each $R^{b7}$ of a borane-phosphite complex described herein, each $R^{b8}$ of a borane-ether complex described herein, each $R^{b9}$ of a borane-sulfide complex described herein, the $R^{b10}$ of a hydrogen borinic acid ester described herein, each $R^{b11}$ of a hydrogen boronic acid ester described herein, the $R^{b12}$ of a hydrogen borinic thio acid ester described herein, each $R^{b13}$ of a hydrogen boronic thio acid ester described herein, each $R^{b14}$ of a hydrogen monoaminoborane described herein, each $R^{b15}$ of a hydrogen diaminoborane described herein, independently can be a phenyl group or a substituted phenyl group; alternatively, a phenyl group or a methylphenyl group; alternatively, a phenyl group, a 2-methylphenyl group, or a 4-methylphenyl group; alternatively, a phenyl group; alternatively, a substituted phenyl group; alternatively, a methylphenyl group; alternatively, a 2-methylphenyl group; or alternatively, a 4-methylphenyl group.

In an embodiment, each $R^{b1}$ of a hydrogen-boron bond containing salt described herein independently can be an alkoxy group, a cycloalkoxy group, or an aroxy group; alternatively, an alkoxy group; alternatively, an cycloalkoxy group; or alternatively, an aroxy group. In some embodiments, each $R^{b1}$ of a hydrogen-boron bond containing salt described herein independently can be an $C_1$ to $C_{15}$ alkoxy group, a $C_4$ to $C_{15}$ cycloalkoxy group, a $C_4$ to $C_{15}$ substituted cycloalkoxy group, a $C_6$ to $C_{15}$ aroxy group, or a $C_7$ to $C_{15}$ substituted aroxy group; alternatively, a $C_4$ to $C_{15}$ cycloalkoxy group or a $C_4$ to $C_{15}$ substituted cycloalkoxy group; alternatively, a $C_6$ to $C_{15}$ aroxy group or a $C_7$ to $C_{15}$ substituted aroxy group; alternatively, a $C_1$ to $C_{15}$ alkoxy group; alternatively, a $C_4$ to $C_{15}$ cycloalkoxy group; alternatively, a $C_4$ to $C_{15}$ substituted cycloalkoxy group; alternatively, a $C_6$ to $C_{15}$ aroxy group; or alternatively, a $C_7$ to $C_{15}$ substituted aroxyl group. In an embodiment, each $R^{b1}$ of a hydrogen-boron bond containing salt described herein independently can be $C_1$ to $C_{10}$ alkoxy group, a $C_4$ to $C_{10}$ cycloalkoxy group, a $C_4$ to $C_{10}$ substituted cycloalkoxy group, a $C_6$ to $C_{10}$ aroxy group, or a $C_7$ to $C_{10}$ substituted aroxy group; alternatively, a $C_4$ to $C_{10}$ cycloalkoxy group or a $C_4$ to $C_{10}$ substituted cycloalkoxy group; alternatively, a $C_6$ to $C_{10}$ aroxy group or a $C_7$ to $C_{10}$ substituted aroxy group; alternatively, a $C_1$ to $C_{10}$ alkoxy group; alternatively, a $C_4$ to $C_{10}$ cycloalkoxy group; alternatively, a $C_4$ to $C_{10}$ substituted cycloalkoxy group; alternatively, a $C_6$ to $C_{10}$ aroxy group; alternatively, a $C_7$ to $C_{10}$ substituted aroxy group; or alternatively, $C_1$ to $C_6$ alkoxy group. In the substituted cycloalkyl group and the substituted aryl group embodiments, the substituent(s) can be alkyl groups. Substituents groups (general and specific including alkyl group substituents) are independently disclosed herein and can be utilized without limitation to further describe substituted cycloalkyl groups and/or the substituted aryl groups which can be utilized as an $R^{b1}$ of a hydrogen-boron bond containing salt described herein.

In an embodiment, each $R^{b1}$ of a hydrogen-boron bond containing salt described herein independently can be a methoxy group, an ethoxy group, a propoxy group, a butoxy group, or a pentoxy group; alternatively, a propoxy group; alternatively, a butoxy group; or alternatively, a pentoxy group. In an embodiment, each $R^{b1}$ of a hydrogen-boron bond containing salt described herein independently can be a methoxy group, an ethoxy group, an n-propoxy group, an isopropoxy group, an n-butoxy group, an isobutoxy group, a tert-butoxy group, an n-pentoxy group, or a neo-pentoxy group; alternatively, a methoxy group; alternatively, an ethoxy group; alternatively, an n-propoxy group; alternatively, an isopropoxy group; alternatively, an n-butoxy group; alternatively, an isobutoxy group; alternatively, a tert-butoxy group; alternatively, an n-pentoxy group; or alternatively, a neo-pentoxy group.

In an embodiment, each $R^{b1}$ of a hydrogen-boron bond containing salt described herein independently can be a cyclobutoxy group, a cyclopentoxy group, a substituted cyclopentoxy group, a cyclohexoxy group, a substituted cyclohexoxy group, a cycloheptoxy group, or a cyclooctoxy group; alternatively, a cyclopentoxy group, a substituted cyclopentoxy group, a cyclohexoxy group, or a substituted cyclohexoxy group; alternatively, a substituted cyclopentoxy group; or alternatively, a substituted cyclohexoxy group. In some embodiments, each $R^{b1}$ of a hydrogen-boron bond containing salt described herein independently can be a cyclobutoxy group, a cyclopentoxy group, a cyclohexoxy group, a cycloheptoxy group, or a cyclooctoxy group; alternatively, a cyclopentoxy group, or a cyclohexoxy group; alternatively, a cyclobutoxy group; alternatively, a cyclopentoxy group; alternatively, a cyclohexoxy group; alternatively, a cycloheptoxy group; or alternatively, cyclooctoxy group. In an embodiment, each $R^{b1}$ of a hydrogen-boron bond containing salt described herein independently can be a phenoxy group or a substituted phenoxy group; alternatively, a phenoxy group or a methylphenoxy group; alternatively, a phenoxy group, a 2-methylphenoxy group, or a 4-methylphenoxy group; alternatively, a phenoxy group; alternatively, a substituted phenoxy group; alternatively, a methylphenoxy group; alternatively, a 2-methylphenoxy group; or alternatively, a 4-methylphenoxy group As described herein two $R^{b1}$ groups can be joined as a $R^{j1}$ group (to form a ring or ring system containing the boron atom of the hydrogen-boron bond containing salt), two $R^{b4}$ groups can be joined as a $R^{j3}$ group (to form a ring or ring system containing the boron atom of a hydrogen-boron bond containing compound), two $R^{b5}$ groups can be joined as a $R^{j4}$ group (to form a cyclic amine neutral ligand), two $R^{b6}$ groups can be joined as a $R^6$ group (to form a cyclic phosphine neutral ligand), two $R^{b8}$ groups can be joined as a $R^{j10}$ group (to form a cyclic ether neutral ligand), two $R^{b9}$ groups can be joined as a $R^{j11}$ group (to form a cyclic sulfide neutral ligand), two $R^{b14}$ groups can be joined as a $R^{14}$ group (to form a cyclic amino group), or two $R^{b15}$ groups can be joined as a $R^{j14}$ (to form a cyclic amino group). In an embodiment, the $R^{j1}$ group, the $R^{j3}$ group, the $R^{j4}$ group, the $R^{j6}$ group, the $R^{j10}$ group, the $R^{j11}$ group, the $R^{14}$ group, or the $R^{j14}$ group can be a $C_4$ to $C_{20}$ hydrocarbylene group, alternatively, a $C_4$ to $C_{15}$ hydrocarbylene group, or alternatively, a $C_4$ to $C_{10}$ hydrocarbylene group. In other embodiments, the $R^{j1}$ group, the $R^{j3}$ group, the $R^{j4}$ group, the $R^{j6}$ group, the $R^{j10}$ group, the $R^{j11}$ group, the $R^{j14}$ group, or the $R^{j14}$ group can be represented by $-(CR^{d1}R^{d2})_4-$, $-CR^{d1}R^{d2}(CH_2)_2CR^{d1}R^{d2}-$, $-(CR^{d1}R^{d2})_5-$, $-CR^{d1}R^{d2}(CH_2)_3CR^{d1}R^{d2}-$, or $-CR^{d3}=CR^{d4}CR^{d5}=CR^{d6}-$; alternatively, $-(CR^{d1}R^{d2})_4-$; alternatively, $-CR^{d1}R^{d2}(CH_2)_2CR^{d1}R^{d2}-$; alternatively, $-(CR^{d1}R^{d2})_5-$; alternatively, $-CR^{d1}R^{d2}(CH_2)_3CR^{d1}R^{d2}-$; or alternatively, $-CR^{d3}=CR^{d4}CR^{d5}=CR^{d6}-$. In these $R^{j1}$ groups, $R^{j3}$ groups, $R^{j4}$ groups, $R^{j6}$ groups, $R^{j10}$ groups, $R^{j11}$ groups, $R^{j14}$ groups, and/or $R^{j14}$ groups, each $R^{d1}$, $R^{d2}$, $R^{d3}$, $R^{d4}$, $R^{d5}$, or $R^{d6}$ independently can be a hydrocarbyl group substituent; or alternatively an alkyl group substituent. Hydrocarbyl substituents (general and specific including alkyl group substituents) are independently disclosed herein and can be utilized without limitation to further describe $R^{d1}$, $R^{d2}$, $R^{d3}$, $R^{d4}$, $R^{d5}$, or $R^{d6}$ of the $R^{j1}$ group, $R^{j3}$ group, $R^{j4}$ group, $R^{j6}$ group, $R^{j10}$ group, $R^{j11}$ group, $R^{j14}$ group, and/or $R^{j14}$ group. In other embodiments, the $R^{j1}$ group, the $R^{j3}$ group, the $R^{j4}$ group, the $R^{j6}$ group, the $R^{j10}$ group, the $R^{j11}$ group, the $R^{j14}$ group, or the $R^{j14}$ group can be represented by —$(CH_2)_4$—, —$(CH_2)_5$—, —CH=CHCH=CH—; alternatively, —$(CH_2)_4$—; alternatively, —$(CH_2)_5$—; or alternatively, or —CH=CHCH=CH—. In some embodiments, the two $R^{b1}$ groups joined as a $R^{j1}$ group (to form a ring or ring system containing the boron atom of the hydrogen-boron bond containing salt), the two $R^{b4}$ groups joined as a $R^{j3}$ group (to form a ring or ring system containing the boron atom of a hydrogen-boron bond containing compound) can be a cycloocta-1,5-diyl group.

As described herein two $R^{b1}$ groups can be joined as a $R^{j1}$ group (to form a cyclic boronic acid ester of the containing the boron atom and two oxygen atoms of the boronic acid ester of a hydrogen-boron bond containing salt), two $R^{b7}$ groups can be joined as a $R^{j8}$ group (to form a cyclic phosphite neutral ligand), two $R^{b11}$ groups can be joined as a $R^{j12}$ group (to form a cyclic boronic acid ester of the containing the boron atom and two oxygen atoms of the boronic acid ester), two $R^{b13}$ groups can be joined as a $R^{j13}$ group (to form a cyclic boronic thio acid ester of the containing the boron atom and two sulfur atoms of the boronic thio acid ester), or two $R^{b15}$ groups can be joined as $R^{j15}$ group (to form a cyclic hydrogen diamino borane containing the boron atom and two nitrogen atoms of the hydrogen diamino borane). In some embodiments, the $R^{j1}$ group, the $R^{j8}$ group, the $R^{j12}$ group, the $R^{j13}$ group, or the $R^{j15}$ group can be a $C_2$ to $C_{20}$ hydrocarbylene group, alternatively, a $C_2$ to $C_{15}$ hydrocarbylene group, or alternatively, a $C_2$ to $C_{10}$ hydrocarbylene group. In other embodiments, the $R^{j1}$ group, the $R^{j8}$ group, the $R^{j12}$ group, the $R^{j13}$ group, or the $R^{j15}$ group can be represented by —$(CR^{e1}R^{32})_2$—, —$(CR^{e1}R^{e2})_3$—, —$CR^{e1}R^{e2}(CH_2)CR^{e1}R^{e2}$—, or —$CR^{e3}=CR^{e4}$—; alternatively, —$(CR^{e1}R^{32})_2$—; alternatively, —$(CR^{e1}R^{e2})_3$—; alternatively, —$CR^{e1}R^{e2}(CH_2)CR^{e1}R^{e2}$—; or alternatively, —$CR^{e3}=CR^{e4}$—. In these $R^{j1}$ groups, $R^{j8}$ groups, $R^{j12}$ groups, $R^{j13}$ groups, and/or $R^{j15}$ groups, each $R^{e1}$, $R^{e2}$, $R^{e3}$, or $R^{e4}$ independently can be a hydrocarbyl group substituent; or alternatively an alkyl group substituent. Hydrocarbyl substituents (general and specific including alkyl group substituents) are independently disclosed herein and can be utilized without limitation to further describe $R^{e1}$, $R^{e2}$, $R^{e3}$, or $R^{e4}$ of the $R^{j1}$ group, $R^{j8}$ group, $R^{j12}$ group, $R^{j13}$ group, and/or $R^{j15}$ group. In other embodiments, the $R^{j1}$ group, the $R^{j8}$ group, the $R^{j12}$ group, the $R^{j13}$ group, or the $R^{j15}$ group can be represented by —$(CH_2)_2$—, —$(CH_2)_3$—, —CH=CH—; alternatively, —$(CH_2)_2$; alternatively, —$(CH_2)_3$—; or alternatively, or —CH=CH—.

As described herein three $R^{b1}$ groups can be joined as an $R^{j2}$ group (to form a ring or ring system containing the boron atom), three $R^{b5}$ groups can be joined as an $R^{j5}$ group (to form a cyclic amine neutral ligand), or three $R^{b6}$ groups can be joined as an $R^{j7}$ group (to form a cyclic phosphine neutral ligand). In an embodiment, the $R^{j2}$ group, the $R^{j5}$ group, the $R^{j7}$ group, or the $R^{j9}$ group can be a $C_8$ to $C_{20}$ hydrocarbon group, or alternatively, a $C_8$ to $C_{15}$ hydrocarbon group. In other embodiments, the $R^{j2}$ group, the $R^{j5}$ group, or the $R^{j7}$ group can be represented by —$CR^{g1}((CR^{g2}R^{g3})_2CR^{g4g5}$—$)_2$, —$CR^{g1}((CH_2)_2CR^{g4g5}$—$)_2$, —$CR^{g1}(CR^{g2}R^{g3})_2CR^{g4g5}$—$)(CR^{g2}R^{g3})_3CR^{g4g5}$—), —$CR^{g1}(CH_2)_2CR^{g4g5}$—$)(CH_2)_3CR^{g4g5}$—), or —$CR^{g1}((CH)_3CR^{g4g5}$—$)_2$; alternatively, —$CR^{g1}((CR^{g2}R^{g3})_2CR^{g4g5}$—$)_2$; alternatively, —$CR^{g1}((CH_2)_2CR^{g4g5}$—$)_2$; alternatively, —$CR^{g1}(CR^{g2}R^{g3})_2CR^{g4g5}$—$)(CR^{g2}R^{g3})_3CR^{g4g5}$—); alternatively, —$CR^{g1}(CH_2)_2CR^{g4g5}$—$)(CH_2)_3CR^{g4g5}$—); or alternatively, —$CR^{g1}((CH)_3CR^{g4g5}$—$)_2$. In other embodiments, the $R^{j5}$ group can be represented by =$CR^{g6}$=$CR^{g7}$ $CR^{g8}$=$CR^{g9}$—. In these $R^{j2}$ groups, $R^{j5}$ groups, and/or $R^{j7}$ groups, each $R^{g1}$, $R^{g2}$, $R^{g3}$, $R^{g4}$, $R^{g5}$, $R^{g6}$, $R^{g7}$, $R^{g8}$, $R^{g9}$ independently can be a hydrocarbyl group substituent; or alternatively an alkyl group substituent. Hydrocarbyl substituents (general and specific including alkyl group substituents) are independently disclosed herein and can be utilized without limitation to further describe $R^{g1}$, $R^{g2}$, $R^{g3}$, $R^{g4}$, $R^{g5}$, $R^{g6}$, $R^{g7}$, $R^{g8}$, $R^{g9}$ of the $R^{j2}$ group, $R^{j5}$ group, and/or $R^{j7}$ group. In other embodiments, the $R^{j2}$ group, the $R^{j5}$ group, or the $R^{j7}$ group can be represented by —$CH((CH_2)_2CH$—$)_2$, —$CH(CH_2)_2CH$—$)(CH_2)_3CH$—), or —$CH((CH)_3CH$—$)_2$; alternatively, —$CH((CH_2)_2CH$—$)_2$; alternatively, —$CH(CH_2)_2CH$—$)(CH_2)_3CH$—); or alternatively, —$CH((CH)_3CH$—$)_2$. In other embodiments, the $R^{j5}$ group can be represented by =CH=CHCN=CH—.

In an embodiment, the borohydride compound portion of the borohydride compound salt, which can be utilized as the hydrogen-boron bond containing compound in the processes described herein, can be borohydride (i.e., $BH_4^-$), cyanoborohydride (i.e., $(CN)BH_3^-$), trimethylboron hydride, triethylboron hydride, tripropylboron hydride, tri-n-butylboron hydride, tricyclopentylboron hydride, tri(2-methylcyclopentyl)boron hydride, tricyclohexylboron hydride, tri(2-methylcyclohexyl)boron hydride, triphenylboron hydride, 9-borabicyco[3.3.1]nonane hydride (9-BBN hydride), methyl 9-borabicyco[3.3.1]nonane hydride, ethyl 9-borabicyco[3.3.1]nonane hydride, propyl 9-borabicyco[3.3.1]nonane hydride, isopropyl 9-borabicyco[3.3.1]nonane hydride, n-butyl 9-borabicyco[3.3.1]nonane hydride, tert-butyl 9-borabicyco[3.3.1]nonane hydride, 2,3-but-2-yl 9-borabicyco[3.3.1]nonane hydride, cyclobutyl 9-borabicyco[3.3.1]nonane hydride, cyclopentyl 9-borabicyco[3.3.1]nonane hydride, 2-methylcyclopentyl 9-borabicyco[3.3.1]nonane hydride, cyclohexyl 9-borabicyco[3.3.1]nonane hydride, 2-methylcyclohexyl 9-borabicyco[3.3.1]nonane hydride, 2-norbornyl 9-borabicyco[3.3.1]nonane hydride, phenyl 9-borabicyco[3.3.1]nonane hydride, or benzyl 9-borabicyco[3.3.1]nonane hydride; alternatively, trimethylboron hydride, triethylboron hydride, tripropylboron hydride, tri-n-butylboron hydride, tricyclopentylboron hydride, tri(2-methylcyclopentyl)boron hydride, tricyclohexylboron hydride, tri(2-methylcyclohexyl)boron hydride, or triphenylboron hydride; or alternatively, 9-borabicyco[3.3.1]nonane hydride (9-BBN hydride), methyl 9-borabicyco[3.3.1]nonane hydride, ethyl 9-borabicyco[3.3.1]nonane hydride, propyl 9-borabicyco[3.3.1]nonane hydride, isopropyl 9-borabicyco[3.3.1]nonane hydride, n-butyl 9-borabicyco[3.3.1]nonane hydride, tert-butyl 9-borabicyco[3.3.1]nonane hydride, 2,3-but-2-yl 9-borabicyco[3.3.1]nonane hydride, cyclobutyl 9-borabicyco[3.3.1]nonane hydride, cyclopentyl 9-borabicyco[3.3.1]nonane hydride, 2-methylcyclopentyl 9-borabicyco[3.3.1]nonane hydride, cyclohexyl 9-borabicyco[3.3.1]nonane hydride, 2-methylcyclohexyl 9-borabicyco[3.3.1]nonane hydride, 2-norbornyl 9-borabicyco[3.3.1]nonane hydride, phenyl 9-borabicyco[3.3.1]nonane hydride, or benzyl 9-borabicyco[3.3.1]nonane hydride. In some embodiments, the borohydride compound portion of the borohydride compound salt, which can be utilized as the hydrogen-boron bond containing compound in the processes described herein, can be borohydride (i.e., BH$_4$); alternatively, cyanoborohydride (i.e., (CN)BH$_3$—); alternatively, trimethylboron hydride; alternatively, triethylboron hydride; alternatively, tripropylboron hydride; alternatively, tri-n-butylboron hydride; alternatively, tricyclopentylboron hydride; alternatively, tri(2-methylcyclopentyl)boron hydride; alternatively, tricyclohexylboron hydride; alternatively, tri(2-methylcyclohexyl)boron hydride; alternatively, triphenylboron hydride; alternatively, 9-borabicyco[3.3.1]nonane hydride; alternatively, methyl 9-borabicyco[3.3.1]nonane hydride; alternatively, ethyl 9-borabicyco[3.3.1]nonane hydride; alternatively, propyl 9-borabicyco[3.3.1]nonane hydride; alternatively, isopropyl 9-borabicyco[3.3.1]nonane hydride; alternatively, n-butyl 9-borabicyco[3.3.1]nonane hydride; alternatively, tert-butyl 9-borabicyco[3.3.1]nonane hydride; alternatively, 2,3-but-2-yl 9-borabicyco[3.3.1]nonane hydride; alternatively, cyclobutyl 9-borabicyco[3.3.1]nonane hydride; alternatively, cyclopentyl 9-borabicyco[3.3.1]nonane hydride; alternatively, 2-methylcyclopentyl 9-borabicyco[3.3.1]nonane hydride; alternatively, cyclohexyl 9-borabicyco[3.3.1]nonane hydride; alternatively, 2-methylcyclohexyl 9-borabicyco[3.3.1]nonane hydride; alternatively, 2-norbornyl 9-borabicyco[3.3.1]nonane hydride; alternatively, phenyl 9-borabicyco[3.3.1]nonane hydride; or alternatively, benzyl 9-borabicyco[3.3.1]nonane hydride. Other borohydride compound portions of the borohydride compound salts can be readily envisioned and contemplated from the present disclosure. Additionally, any borohydride compound portion of the borohydride compound salt disclosed herein can be combined with any cation, A$'''$, of the borohydride compound salts described herein to describe hydrogen-boron bond containing compound (e.g., borohydride compound salts) which can be utilized in processes described herein.

In an embodiment, the hydroborohalide, which can be utilized in the processes described herein, or can be the hydroborohalide portion of a hydroborohalide-neutral ligand complex, which can be utilized in the processes described herein, can be chloroborane, bromoborane, dichloroborane, dibromoborane, or bromochloroborane; alternatively, chloroborane, or bromoborane; alternatively, dichloroborane, dibromoborane, or bromochloroborane; alternatively, chloroborane; alternatively, bromoborane; alternatively, dichloroborane; alternatively, dibromoborane; or alternatively, bromochloroborane. Other hydroborohalides can be readily envisioned and contemplated from the present disclosure. Additionally, any hydroborohalide disclosed herein can be combined with any neutral ligand described herein to describe hydroborohalide-neutral ligand complexes which can be utilized in processes described herein.

In an embodiment, the hydrogen-boron bond containing compound, which can be utilized in the processes described herein, or can be the hydrogen-boron bond containing compound portion of a hydrogen-boron bond containing compound-neutral ligand complex, which can be utilized in the processes described herein, can be borane, diborane, methylborane, ethylborane, n-propylborane, isopropylborane, n-butylborane, tert-butylborane, n-pentylborane, 2-methylbut-1-ylborane, n-hexylborane, 2-methylpent-2-ylborane, 2,3-dimethylbut-2-ylborane, cyclopentylborane, 2-methylcyclopentylborane, cyclohexylborane, 2-methylcyclohexylborane, norboran-2-ylborane, 2,6,6-trimethylbicyclo(3.1.1)heptan-3-ylborane, phenylborane, dimethylborane, diethylborane, di-n-propylborane, diisopropylborane, di-n-butylborane, di-tert-butylborane, di-n-pentylborane, di-2-methylbut-1-ylborane, di-n-hexylborane, di-2-methylpent-2-ylborane, di-2,3-dimethylbut-2-ylborane, dicyclopentylborane, di-2-methylcyclopentylborane, dicyclohexylborane, di-2-methylcyclohexylborane, di-2,6,6-trimethylbicyclo(3.1.1)heptan-3-ylborane, diphenylborane, tert-butyl(2-methyl-but-2-yl)borane, tert-butyl(cyclopentyl)borane, tert-butyl(2-methylcyclopentyl)borane, tert-butyl(cyclohexyl)borane, tert-butyl(2-methylcyclohexyl)borane, 2,3-dimethylbut-2-yl(2-methyl-but-2-yl)borane, 2,3-dimethylbut-2-yl(cyclopentyl)borane, 2,3-dimethylbut-2-yl(2-methylcyclopentyl)borane, 2,3-dimethylbut-2-yl(cyclohexyl)borane, 2,3-dimethylbut-2-yl(2-methylcyclohexyl)borane, or 9-borabicyco[3.3.1]nonane; alternatively, methylborane, ethylborane, n-propylborane, isopropylborane, n-butylborane, tert-butylborane, n-pentylborane, 2-methylbut-1-ylborane, n-hexylborane, 2-methylpent-2-ylborane, or 2,3-dimethylbut-2-ylborane, cyclopentylborane, 2-methylcyclopentylborane, cyclohexylborane, 2-methylcyclohexylborane, norboran-2-ylborane, 2,6,6-trimethylbicyclo(3.1.1)heptan-3-ylborane, or phenylborane; alternatively, dimethylborane, diethylborane, di-n-propylborane, diisopropylborane, di-n-butylborane, di-tert-butylborane, di-n-pentylborane, di-2-methylbut-1-ylborane, di-n-hexylborane, di-2-methylpent-2-ylborane, di-2,3-dimethylbut-2-ylborane, dicyclopentylborane, di-2-methylcyclopentylborane, dicyclohexylborane, di-2-methylcyclohexylborane, di-2,6,6-trimethylbicyclo(3.1.1)heptan-3-ylborane, or diphenylborane; or alternatively, tert-butyl(2-methyl-but-2-yl)borane, tert-butyl(cyclopentyl)borane, tert-butyl(2-methylcyclopentyl)borane, tert-butyl(cyclohexyl)borane, tert-butyl(2-methylcyclohexyl)borane, 2,3-dimethylbut-2-yl(2-methyl-but-2-yl)borane, 2,3-dimethylbut-2-yl(cyclopentyl)borane, 2,3-dimethylbut-2-yl(2-methylcyclopentyl)borane, 2,3-dimethylbut-2-yl(cyclohexyl)borane, or 2,3-dimethylbut-2-yl(2-methylcyclohexyl)borane, or 9-borabicyco[3.3.1]nonane.

In some embodiments, the hydrogen-boron bond containing compound, which can be utilized in the processes described herein, or can be the hydrogen-boron bond containing compound portion of a hydrogen-boron bond containing compound-neutral ligand complex, which can be utilized in the processes described herein, can be methylborane, ethylborane, n-propylborane, isopropylborane, n-butylborane, tert-butylborane, n-pentylborane, 2-methylbut-1-ylborane, n-hexylborane, 2-methylpent-2-ylborane, or 2,3-dimethylbut-2-ylborane; alternatively, cyclopentylborane, 2-methylcyclopentylborane, cyclohexylborane, 2-methylcyclohexylborane, norboran-2-ylborane, 2,6,6-trimethylbicyclo(3.1.1)heptan-3-ylborane, or phenylborane; alternatively, dimethylborane, diethylborane, di-n-propylborane, diisopropylborane, di-n-butylborane, di-tert-butylborane, di-n-pentylborane, di-2-methylbut-1-ylborane, di-n-hexylborane, di-2-methylpent-2-ylborane, or di-2,3-dimethylbut-2-ylborane; alternatively, dicyclopentylborane, di-2-methylcyclopentylborane, dicyclohexylborane, di-2-methylcyclohexylborane, di-2,6,6-trimethylbicyclo(3.1.1)heptan-3-ylborane, or diphenylborane; alternatively, tert-butyl(2-methyl-but-2-yl)borane, tert-butyl(cyclopentyl)borane, tert-butyl(2-methylcyclopentyl)borane, tert-butyl(cyclohexyl)borane, or tert-butyl(2-methylcyclohexyl)borane; alternatively, 2,3-dimethylbut-2-yl(2-methyl-but-2-yl)borane, 2,3-dimethylbut-2-yl(cyclopentyl)borane, 2,3-dimethylbut-2-yl(2-methylcyclopentyl)borane, 2,3-dimethylbut-2-yl(cyclohexyl)borane, or 2,3-dimethylbut-2-yl(2-methylcyclohexyl)borane; alternatively, borane; alternatively, diborane; alternatively, methylborane, alternatively, ethylborane; alternatively, n-propylborane; alternatively, isopropylborane; alternatively, n-butylborane; alternatively, tert-butylborane; alternatively, n-pentylborane;

alternatively, 2-methylbut-1-ylborane; alternatively, n-hexylborane; alternatively, 2-methylpent-2-ylborane; alternatively, 2,3-dimethylbut-2-ylborane; alternatively, cyclopentylborane; alternatively, 2-methylcyclopentylborane; alternatively, cyclohexylborane; alternatively, 2-methylcyclohexylborane; alternatively, norboran-2-ylborane; alternatively, 2,6,6-trimethylbicyclo(3.1.1)heptan-3-ylborane; alternatively, phenylborane; alternatively, dimethylborane; alternatively, diethylborane; alternatively, di-n-propylborane; alternatively, diisopropylborane; alternatively, di-n-butylborane; alternatively, di-tert-butylborane; alternatively, di-n-pentylborane; alternatively, di-2-methylbut-1-ylborane; alternatively, di-n-hexylborane; alternatively, di-2-methylpent-2-ylborane; alternatively, di-2,3-dimethylbut-2-ylborane; alternatively, dicyclopentylborane, di-2-methylcyclopentylborane; alternatively, dicyclohexylborane; alternatively, di-2-methylcyclohexylborane; alternatively, di-2,6,6-trimethylbicyclo(3.1.1)heptan-3-ylborane; alternatively, diphenylborane; alternatively, tert-butyl(2-methylbut-2-yl)borane; alternatively, tert-butyl(cyclopentyl)borane; alternatively, tert-butyl(2-methylcyclopentyl)borane; alternatively, tert-butyl(cyclohexyl)borane; alternatively, tert-butyl(2-methylcyclohexyl)borane; alternatively, 2,3-dimethylbut-2-yl(2-methyl-but-2-yl)borane; alternatively, 2,3-dimethylbut-2-yl(cyclopentyl)borane; alternatively, 2,3-dimethylbut-2-yl(2-methylcyclopentyl)borane; alternatively, 2,3-dimethylbut-2-yl(cyclohexyl)borane; alternatively, 2,3-dimethylbut-2-yl(2-methylcyclohexyl)borane; or alternatively, 9-borabicyco[3.3.1]nonane. Other hydrocarbyllboranes can be readily envisioned and contemplated from the present disclosure. Additionally, any hydrocarbylborane disclosed herein can be combined with any neutral ligand described herein to describe neutral ligand complexes which can be utilized in processes described herein.

In an embodiment, the hydrogen-boron bond containing compound, which can be utilized in the processes described herein, or can be the hydrogen-boron bond containing compound portion of a hydrogen-boron bond containing compound-neutral ligand complex, which can be utilized in the processes described herein, can be methylchlororborane, ethylchloroborane, n-propylchloroborane, isopropylchloroborane, n-butylchloroborane, tert-butylchloroborane, n-pentylchloroborane, 2-methylbut-1-ylchloroborane, n-hexylchloroborane, 2-methylchloropent-2-ylborane, 2,3-dimethylchlorobut-2-ylborane, cyclopentychlorolborane, cyclohexylchloroborane, 2,6,6-trimethylbicyclo(3.1.1)heptan-3-ylchloroborane, or phenylchloroborane; alternatively, methylchlororborane, ethylchloroborane, n-propylchloroboranechloride, isopropylchloroborane, n-butylchloroborane, tert-butylchloroborane, n-pentylchloroborane, 2-methylbut-1-ylchloroborane, n-hexylchloroborane, 2-methylchloropent-2-ylborane, or 2,3-dimethylchlorobut-2-ylborane; alternatively, cyclopentychlorolborane, cyclohexylchloroborane, 2,6,6-trimethylbicyclo(3.1.1)heptan-3-ylchloroborane, or phenylchloroborane. In some embodiments, the hydrogen-boron bond containing compound, which can be utilized in the processes described herein, or can be the hydrogen-boron bond containing compound portion of a hydrogen-boron bond containing compound-neutral ligand complex, which can be utilized in the processes described herein, can be methylchlororborane; alternatively, ethylchloroborane; alternatively, n-propylchloroborane; alternatively, isopropylchloroborane; alternatively, n-butylchloroborane; alternatively, tert-butylchloroborane; alternatively, n-pentylchloroborane; alternatively, 2-methylbut-1-ylchloroborane; alternatively, n-hexylchloroborane; alternatively, 2-methylchloropent-2-ylborane; alternatively, 2,3-dimethylchlorobut-2-ylborane; alternatively, cyclopentychlorolborane; alternatively, cyclohexylchloroborane; alternatively, 2,6,6-trimethylbicyclo(3.1.1)heptan-3-ylchloroborane; or alternatively, phenylchloroborane. Other alkylhaloborane can be readily envisioned and contemplated from the present disclosure. Additionally, any alkylhaloborane disclosed herein can be combined with any neutral ligand described herein to describe alkylhaloborane-neutral ligand complexes which can be utilized in processes described herein.

In an embodiment, the amine which can be complexed with any hydrogen-boron bond containing compound described herein to form the hydrogen-boron bond containing compound-amine complex which can be utilized in the processes described herein can be ammonia, methylamine, ethylamine, isopropylamine, n-butylamine, tert-butylamine, cyclopentylamine, cyclohexylamine, phenylamine, dimethylamine, diethylamine, diisopropylamine, di-n-butylamine, di-tert-butylamine, dicyclopentylamine, dicyclohexylamine, diphenylamine, pyrrolidine, piperdine, pyrrole, trimethylamine, triethylamine, triisopropylamine, tri-n-butylamine, tri-tert-butylamine, tricyclopentylamine, tricyclohexylamine, triphenylamine, tetramethylamineethylenediamine, pyridine, or any combinations thereof; alternatively, methylamine, ethylamine, isopropylamine, n-butylamine, tert-butylamine, cyclopentylamine, cyclohexylamine, phenylamine, or any combination thereof; alternatively, dimethylamine, diethylamine, diisopropylamine, di-n-butylamine, di-tert-butylamine, dicyclopentylamine, dicyclohexylamine, diphenylamine, pyrrolidine, piperdine, pyrrole, or any combination thereof; alternatively, trimethylamine, triethylamine, triisopropylamine, tri-n-butylamine, tri-tert-butylamine, tricyclopentylamine, tricyclohexylamine, triphenylamine, tetramethylamineethylenediamine, pyridine, or any combinations thereof. In some embodiments, the amine which can be complexed with any hydrogen-boron bond containing compound described herein to form the hydrogen-boron bond containing compound-amine complex which can be utilized in the processes described herein can be methylamine, ethylamine, isopropylamine, n-butylamine, tert-butylamine, cyclopentylamine, cyclohexylamine, or any combinations thereof; alternatively, dimethylamine, diethylamine, diisopropylamine, di-n-butylamine, di-tert-butylamine, dicyclopentylamine, dicyclohexylamine, diphenylamine, pyrrolidine, piperdine, or any combinations thereof; alternatively, trimethylamine, triethylamine, triisopropylamine, tri-n-butylamine, tri-tert-butylamine, tricyclopentylamine, tricyclohexylamine, tetramethylamineethylenediamine, or any combinations thereof; alternatively, ammonia; alternatively; methylamine; alternatively, ethylamine; alternatively, isopropylamine; alternatively, n-butylamine; alternatively, tert-butylamine; alternatively, cyclopentylamine; alternatively, cyclohexylamine; alternatively, phenylamine; alternatively, dimethylamine; alternatively, diethylamine; alternatively, diisopropylamine; alternatively, di-n-butylamine; alternatively, di-tert-butylamine; alternatively, dicyclopentylamine; alternatively, dicyclohexylamine; alternatively, diphenylamine; alternatively, pyrrolidine; alternatively, piperdine; alternatively, pyrrole; alternatively, trimethylamine; alternatively, triethylamine; alternatively, triisopropylamine; alternatively, tri-n-butylamine; alternatively, tri-tert-butylamine; alternatively, tricyclopentylamine; alternatively, tricyclohexylamine; alternatively, triphenylamine; alternatively, tetramethylamineethylenediamine; or alternatively, pyridine.

In an embodiment, the phosphine which can be complexed with any hydrogen-boron bond containing compound described herein to form the hydrogen-boron bond containing compound-phosphine complex which can be utilized in the processes described herein can be phosphine, methylphosphine, ethylphosphine, isopropylphosphine, tert-butylphosphine, phenylphosphine, dimethylphosphine, diethylphosphine, diisopropylphosphine, di-tert-butylphosphine, diphenylphosphine, trimethylphosphine, triethylphosphine, triisopropylphosphine, tri-tert-butylphosphine, triphenylphosphine, or any combination thereof; alternatively, methylphosphine, ethylphosphine, isopropylphosphine, tert-butylphosphine, phenylphosphine, or any combination thereof; alternatively, dimethylphosphine, diethylphosphine, diisopropylphosphine, di-tert-butylphosphine, diphenylphosphine, or any combination thereof; alternatively, trimethylphosphine, triethylphosphine, triisopropylphosphine, tri-tert-butylphosphine, triphenylphosphine, or any combination thereof; alternatively, phosphine; alternatively, methylphosphine; alternatively, ethylphosphine; alternatively, isopropylphosphine; alternatively, tert-butylphosphine; alternatively, phenylphosphine; alternatively, dimethylphosphine; alternatively, diethylphosphine; alternatively, diisopropylphosphine; alternatively, di-tert-butylphosphine; alternatively, diphenylphosphine; alternatively, trimethylphosphine; alternatively, triethylphosphine; alternatively, triisopropylphosphine; alternatively, tri-tert-butylphosphine; or alternatively, triphenylphosphine. In other embodiments, the phosphine which can be complexed with any hydrogen-boron bond containing compound described herein to form the hydrogen-boron bond containing compound-phosphine complex which can be utilized in the processes described herein can be trifluorophosphine. In an embodiment, the phosphite which can be complexed with any hydrogen-boron bond containing compound described herein to form the hydrogen-boron bond containing compound-phosphite complex which can be utilized in the processes described herein can be trimethylphosphite, triethylphosphite, triisopropyl phosphite, or triphenylphosphite; alternatively, trimethylphosphite; alternatively, triethylphosphite; alternatively, triisopropylphosphite; or alternatively, triphenylphosphite.

In an embodiment, the ether which can be complexed with any hydrogen-boron bond containing compound described herein to form the hydrogen-boron bond containing compound-ether complex which can be utilized in the processes described herein can be dimethylether, diethylether, diisopropylether, diphenylether, furan, tetrahydrofuran, pyran, dihydropyran, tetrahydropyran, 1,3-dioxane, 1,4-dioxane, or any combination thereof; alternatively, dimethylether, diethylether, diisopropylether, tetrahydrofuran, tetrahydropyran, or any combination thereof; alternatively, dimethylether; alternatively, diethylether; alternatively, diisopropylether; alternatively, diphenylether; alternatively, furan; alternatively, tetrahydrofuran; alternatively, pyran; alternatively, dihydropyran; alternatively, tetrahydropyran; alternatively, 1,3-dioxane; or alternatively, 1,4-dioxane. In an embodiment, the sulfide which can be complexed with any hydrogen-boron bond containing compound described herein to form the hydrogen-boron bond containing compound-sulfide complex which can be utilized in the processes described herein can be dimethylsulfide, diethylsulfide, diisopropylsulfide, diphenylsulfide, thiophene, thiophane, thiane, or any combination thereof; alternatively, dimethylsulfide, diethylsulfide, diphenylsulfide, thiolane, thiane, or any combination thereof; alternatively, dimethylsulfide; alternatively, diethylsulfide; alternatively, diisopropylsulfide; alternatively, diphenylsulfide; alternatively, thiophene; alternatively, thiophane; or alternatively, thiane.

In an embodiment, the hydrogen borinic acid ester, which can be utilized in the processes described herein, or can be the hydrogen borinic acid ester of a hydrogen borinic acid ester-neutral ligand complex, which can be utilized in the processes described herein, can be methyl borinate, ethyl borinate, n-propyl borinate, isopropyl borinate, n-butyl borinate, tert-butyl borinate, phenyl borinate, or any combination thereof; alternatively, methyl borinate; alternatively, ethyl borinate; alternatively, n-propyl borinate; alternatively, isopropyl borinate; alternatively, n-butyl borinate; alternatively, tert-butyl borinate; or alternatively, phenyl borinate. Other hydrogen borinic acid esters can be readily envisioned and contemplated from the present disclosure. Additionally, any hydrogen borinic acid ester disclosed herein can be combined with any neutral ligand described herein to describe hydrogen borinic acid ester-neutral ligand complex which can be utilized in processes described herein.

In an embodiment, the hydrogen borinic thio acid ester, which can be utilized in the processes described herein, or can be the hydrogen borinic thio acid ester of a hydrogen borinic thio acid ester-neutral ligand complex, which can be utilized in the processes described herein, can be methyl thioborinate, ethyl thioborinate, n-propyl thioborinate, isopropyl thioborinate, n-butyl thioborinate, tert-butyl thioborinate, phenyl thioborinate, or any combination thereof; alternatively, methyl thioborinate; alternatively, ethyl thioborinate; alternatively, n-propyl thioborinate; alternatively, isopropyl thioborinate; alternatively, n-butyl thioborinate; alternatively, tert-butyl thioborinate; phenyl thioborinate. Other hydrogen borinic thio acid esters can be readily envisioned and contemplated from the present disclosure. Additionally, any hydrogen borinic thio acid ester disclosed herein can be combined with any neutral ligand described herein to describe hydrogen borinic thio acid ester-neutral ligand complex which can be utilized in processes described herein.

In an embodiment, the hydrogen monoaminoborane, which can be utilized in the processes described herein, or can be the hydrogen monoaminoborane of a hydrogen monoaminoborane-neutral ligand complex, which can be utilized in the processes described herein, can be dimethylaminylborane, diethylaminylborane, di-n-propyaminylborane, diisopropylaminylborane, di-n-butylaminylborane, di-tert-butylaminylborane, dicyclopentylaminylborane, dicyclohexylaminylborane, pyrrolidinylborane, or piperdinylborane; alternatively, dimethylaminylborane; alternatively, diethylaminylborane; alternatively, di-n-propyaminylborane; alternatively, diisopropylaminylborane; alternatively, di-n-butylaminylborane; alternatively, di-tert-butylaminylborane; alternatively, dicyclopentylaminylborane; alternatively, dicyclohexylaminylborane; alternatively, pyrrolidinylborane; or alternatively, piperdinylborane. In some embodiments, the hydrogen monoaminoborane, which can be utilized in the processes described herein, or can be the hydrogen monoaminoborane of a hydrogen monoaminoborane-neutral ligand complex, which can be utilized in the processes described herein, can be methyl(dimethylaminyl)borane, methyl(diethylaminyl)borane, methyl(di-n-propyaminyl)borane, methyl(diisopropylaminyl)borane, methyl(di-n-butylaminyl)borane, methyl(dicyclopentylaminyl)borane, methyl(dicyclohexylaminyl)borane, methyl(pyrrolidinyl)borane, methyl(piperidinyl)borane, tert-butyl(dimethylaminyl)borane, tert-butyl(diethylaminyl)borane, tert-butyl(di-n-propyaminyl)borane, tert-butyl(diisopropylaminyl)borane, tert-butyl(di-n-butylaminyl)borane, tert-butyl(dicyclopentylaminyl)borane, tert-butyl(dicyclohexylaminyl)borane, tert-butyl(pyrrolidinyl)borane, tert-butyl(piperidinyl)borane, 2,3-dimethylbut-2-yl(dimethylaminyl)borane, 2,3-dimethylbut-2-yl(diethylaminyl)borane, 2,3-dimethylbut-2-yl(di-n-propyaminyl)borane, 2,3-dimethylbut-2-yl(diisopropylaminyl)borane, 2,3-dimethylbut-2-yl(di-n-butylaminyl)borane, 2,3-dimethylbut-2-yl(dicyclopentylaminyl)borane, 2,3-dimethylbut-2-yl(dicyclohexylaminyl)borane, 2,3-dimethylbut-2-yl(pyrrolidinyl)borane, or 2,3-dimethylbut-2-yl(piperidinyl)borane; alternatively, methyl(dimethylaminyl)borane, methyl(diethylaminyl)borane, methyl(di-n-propyaminyl)borane, methyl(diisopropylaminyl)borane, methyl(di-n-butylaminyl)borane, methyl(dicyclopentylaminyl)borane, methyl(dicyclohexylaminyl)borane, methyl(pyrrolidinyl)borane, or methyl(piperidinyl)borane; alternatively, tert-butyl(dimethylaminyl)borane, tert-butyl(diethylaminyl)borane, tert-butyl(di-n-propyaminyl)borane, tert-butyl(diisopropylaminyl)borane, tert-butyl(di-n-butylaminyl)borane, tert-butyl(dicyclopentylaminyl)borane, tert-butyl(dicyclohexylaminyl)borane, tert-butyl(pyrrolidinyl)borane, or tert-butyl(piperidinyl)borane; alternatively, 2,3-dimethylbut-2-yl(dimethylaminyl)borane, 2,3-dimethylbut-2-yl(diethylaminyl)borane, 2,3-dimethylbut-2-yl(di-n-propyaminyl)borane, 2,3-dimethylbut-2-yl(diisopropylaminyl)borane, 2,3-dimethylbut-2-yl(di-n-butylaminyl)borane, 2,3-dimethylbut-2-yl(dicyclopentylaminyl)borane, 2,3-dimethylbut-2-yl(dicyclohexylaminyl)borane, 2,3-dimethylbut-2-yl(pyrrolidinyl)borane, or 2,3-dimethylbut-2-yl(piperidinyl)borane; alternatively, methyl(dimethylaminyl)borane; alternatively, methyl(diethylaminyl)borane; alternatively, methyl(di-n-propyaminyl)borane; alternatively, methyl(diisopropylaminyl)borane; alternatively, methyl(di-n-butylaminyl)borane; alternatively, methyl(dicyclopentylaminyl)borane; alternatively, methyl(dicyclohexylaminyl)borane; alternatively, methyl(pyrrolidinyl)borane; alternatively, methyl(piperidinyl)borane; alternatively, tert-butyl(dimethylaminyl)borane; alternatively, tert-butyl(diethylaminyl)borane; alternatively, tert-butyl(di-n-propyaminyl)borane; alternatively, tert-butyl(diisopropylaminyl)borane; alternatively, tert-butyl(di-n-butylaminyl)borane; alternatively, tert-butyl(dicyclopentylaminyl)borane; alternatively, tert-butyl(dicyclohexylaminyl)borane; alternatively, tert-butyl(pyrrolidinyl)borane; alternatively, tert-butyl(piperidinyl)borane; alternatively, 2,3-dimethylbut-2-yl(dimethylaminyl)borane; alternatively, 2,3-dimethylbut-2-yl(diethylaminyl)borane; alternatively, 2,3-dimethylbut-2-yl(di-n-propyaminyl)borane; alternatively, 2,3-dimethylbut-2-yl(diisopropylaminyl)borane; alternatively, 2,3-dimethylbut-2-yl(di-n-butylaminyl)borane; alternatively, 2,3-dimethylbut-2-yl(dicyclopentylaminyl)borane; alternatively, 2,3-dimethylbut-2-yl(dicyclohexylaminyl)borane; alternatively, 2,3-dimethylbut-2-yl(pyrrolidinyl)borane; or alternatively, 2,3-dimethylbut-2-yl(piperidinyl)borane. Other hydrogen monoaminoborane can be readily envisioned and contemplated from the present disclosure. Additionally, any hydrogen monoaminoborane disclosed herein can be combined with any neutral ligand described herein to describe hydrogen monoaminoborane-neutral ligand complex which can be utilized in processes described herein.

In an embodiment, the hydrogen boronic acid ester, which can be utilized in the processes described herein, or can be the hydrogen boronic acid ester of a hydrogen boronic acid ester-neutral ligand complex, which can be utilized in the processes described herein, can be dimethyl boronate, diethyl boronate, di-n-propyl boronate, diisopropyl boronate, di-n-butyl boronate, di-tert-butyl boronate, diphenyl boronate, 1,3,2-dioxaborolane, 4,4,5,5-tetramethyl-1,3,2-dioxaborolane (pinacolborane), 1,3,2-benzodioxaborole (catecholborane), or any combination thereof; alternatively, dimethyl boronate; alternatively, diethyl boronate; alternatively, di-n-propyl boronate; alternatively, diisopropyl boronate; alternatively, di-n-butyl boronate; alternatively, di-tert-butyl boronate; alternatively, diphenyl boronate, alternatively, 1,3,2-dioxaborolane; alternatively, 4,4,5,5-tetramethyl-1,3,2-dioxaborolane (pinacolborane); or alternatively, 1,3,2-benzodioxaborole (catecholborane). Other hydrogen boronic acid esters can be readily envisioned and contemplated from the present disclosure. Additionally, any hydrogen boronic acid ester disclosed herein can be combined with any neutral ligand described herein to describe hydrogen boronic acid ester-neutral ligand complex which can be utilized in processes described herein.

In an embodiment, the hydrogen boronic dithio acid ester, which can be utilized in the processes described herein, or can be the hydrogen boronic thio acid ester of a hydrogen boronic dithio acid ester-neutral ligand complex, which can be utilized in the processes described herein, can be dimethyl dithioboronate, diethyl dithioboronate, di-n-propyl dithioboronate, diisopropyl dithioboronate, di-n-butyl dithioboronate, di-tert-butyl dithioboronate, diphenyl dithioboronate, or any combination thereof; alternatively, dimethyl dithioboronate; alternatively, diethyl dithioboronate; alternatively, di-n-propyl dithioboronate; alternatively, diisopropyl dithioboronate; alternatively, di-n-butyl dithioboronate; alternatively, di-tert-butyl dithioboronate; or diphenyl dithioboronate. Other hydrogen boronic dithio acid esters can be readily envisioned and contemplated from the present disclosure. Additionally, any hydrogen boronic dithio acid ester disclosed herein can be combined with any neutral ligand described herein to describe hydrogen boronic dithio acid ester-neutral ligand complex which can be utilized in processes described herein.

In an embodiment, the hydrogen diaminoborane, which can be utilized in the processes described herein, or can be the hydrogen diaminoborane of a hydrogen diaminoborane-neutral ligand complex, which can be utilized in the processes described herein, can be bis(dimethylaminyl)borane, bis(diethylaminyl)borane, bis(di-n-propyaminyl)borane, bis(diisopropylaminyl)borane, bis(di-n-butylaminyl)borane, bis(di-tert-butylaminyl)borane, bis(dicyclopentylaminyl)borane, or bis(dicyclohexylaminyl)borane; alternatively, bis(dimethylaminyl)borane; alternatively, bis(diethylaminyl)borane; alternatively, bis(di-n-propyaminyl)borane; alternatively, bis(diisopropylaminyl)borane; alternatively, bis(di-n-butylaminyl)borane; alternatively, bis(di-tert-butylaminyl)borane; alternatively, bis(dicyclopentylaminyl)borane; or alternatively, bis(dicyclohexylaminyl)borane. Other hydrogen monoaminoborane can be readily envisioned and contemplated from the present disclosure. Additionally, any hydrogen monoaminoborane disclosed herein can be combined with any neutral ligand described herein to describe hydrogen monoaminoborane-neutral ligand complex which can be utilized in processes described herein.

In a non-limiting embodiment, the hydrogen-boron bond containing compound can be a hydrogen azaborolidine, a hydrogen diazaborlidine; alternatively, a hydrogen azaborolidine or alternatively, a hydrogen diazaborolidine. In an embodiment, the hydrogen-boron bond containing compound can be a hydrogen azaborolidine represented by the formula

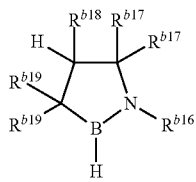

where $R^{b16}$, each $R^{b17}$, $R^{b18}$, each $R^{b19}$ independently can be hydrogen, a halogen, or an organyl group; alternatively, hydrogen, a halogen, or a hydrocarbyl group; alternatively, hydrogen; or alternatively, a halogen. In an embodiment, each $R^{b17}$, $R^{b18}$, each $R^{b19}$ can be the same; or alternatively, one or more of $R^{17}$, $R^{18}$, each $R^{19}$ can be different. In some embodiments, the organyl group which can be utilized as $R^{b16}$, each $R^{b17}$, $R^{b18}$, each $R^{b19}$ (when $R^{b16}$, $R^{b17}$, $R^{b18}$, $R^{b19}$ are not hydrogen or a halogen) independently can be a $C_1$ to $C_{15}$ organyl group; alternatively, a $C_1$ to $C_{10}$ organyl group; or alternatively, a $C_1$ to $C_6$ organyl group; alternatively, $C_1$ to $C_{15}$ hydrocarbyl group; alternatively, a $C_1$ to $C_{10}$ hydrocarbyl group; or alternatively, a $C_1$ to $C_6$ hydrocarbyl group. In an embodiment, the hydrocarbyl group which can be utilized as a $R^{16}$, each $R^{17}$, $R^{18}$, each $R^{19}$ (when $R^{b16}$, $R^{b17}$, $R^{b18}$, $R^{b19}$ are not hydrogen or a halogen) independently can be $C_1$ to $C_{15}$ alkyl group, a $C_4$ to $C_{15}$ cycloalkyl group, a $C_4$ to $C_{15}$ substituted cycloalkyl group, a $C_6$ to $C_{15}$ aryl group, or a $C_7$ to $C_{15}$ substituted aryl group; alternatively, a $C_4$ to $C_{15}$ cycloalkyl group or a $C_4$ to $C_{15}$ substituted cycloalkyl group; alternatively, a $C_6$ to $C_{15}$ aryl group or a $C_7$ to $C_{15}$ substituted aryl group; alternatively, a $C_1$ to $C_{15}$ alkyl group; alternatively, a $C_4$ to $C_{15}$ cycloalkyl group; alternatively, a $C_4$ to $C_{15}$ substituted cycloalkyl group; alternatively, a $C_6$ to $C_{15}$ aryl group; or alternatively, a $C_7$ to $C_{15}$ substituted aryl group. In an embodiment, $R^{16}$, each $R^{17}$, $R^{18}$, each $R^{19}$ alkyl group (when $R^{b16}$, $R^{b17}$, $R^{b18}$, $R^{b19}$ are not hydrogen or a halogen) independently can be a methyl group, an ethyl group, a propyl group, a butyl group; or alternatively, a methyl group, an ethyl group, a propyl group, a butyl group, or a pentyl group; alternatively, a methyl group, an ethyl group, an n-propyl group, an isopropyl group, an n-butyl group, a tert-butyl group, or a neopentyl group; alternatively, a methyl group; alternatively, an ethyl group; independently, a propyl group; alternatively, an n-propyl group; independently, an isopropyl group; alternatively, a butyl group; alternatively, an n-butyl group; alternatively, a tert-butyl group; alternatively, a pentyl group; or alternatively, a neopentyl group. In an embodiment, $R^{16}$, each $R^{17}$, $R^{18}$, each $R^{19}$ alkyl group (when $R^{b16}$, $R^{b17}$, $R^{b18}$, $R^{b19}$ are not hydrogen or a halogen) independently can be a cyclobutyl group, a cyclopentyl group, a cyclohexyl group, a cycloheptyl group, or cyclooctyl group; alternatively, a cyclopentyl group, or a cyclohexyl group; alternatively, a cyclopentyl group; or alternatively, a cyclohexyl group. In an embodiment, $R^{16}$, each $R^{17}$, $R^{18}$, each $R^{19}$ alkyl group (when $R^{b16}$, $R^{b17}$, $R^{b18}$, $R^{b19}$ are not hydrogen or a halogen) independently can be a phenyl group, or a substituted phenyl group; alternatively, a phenyl group or a methylphenyl group; alternatively, a phenyl group, a 2-methylphenyl group, or a 4-methylphenyl group; alternatively, a phenyl group; alternatively, a substituted phenyl group; alternatively, a methylphenyl group; alternatively, a 2-methylphenyl group; or alternatively, a 4-methylphenyl group. In some embodiments, $R^{b16}$ can be any hydrocarbyl group disclosed herein (e.g. alkyl group, a cycloalkyl group, or a substituted cycloalkyl group, aryl group, or substituted aryl group) while each $R^{17}$, $R^{18}$, each $R^{19}$ can be any group disclosed herein. In an embodiment, the hydrogen-boron bond containing compound can be 4S,5R-4-methyl-5-phenyl-oxazaborolidine, 1-cyclohexyl-2-ethyl-1,2,azaborolidine, or 9,10-azaborabicyclo[3.3.2]decane; alternatively, 4S,5R-4-methyl-5-phenyl-oxazaborolidine alternatively, 1-cyclohexyl-2-ethyl-1,2, azaborolidine; or alternatively, 9,10-azaborabicyclo[3.3.2] decane.

In an aspect, the hydrogen-boron bond containing compound can be any one or more of the compounds represented by Formulas I through CXXXVII of Table 3.

TABLE 3

| | |
|---|---|
| $HBCl_2 \cdot OEt_2$ | (I) |
| $HBCl_2 \cdot NMe_3$ | (II) |
| $HBCl_2 \cdot SMe_2$ | (III) |
| $HBBr_2 \cdot SMe_2$ | (IV) |
| $HBI_2 \cdot SMe_2$ | (V) |
| $H_2BCl$ | (VI) |
| $H_2BCl \cdot TMEDA$ | (VII) |
| $H_2BCl \cdot NEt_3$ | (VIII) |
| $H_2BCl \cdot SMe_2$ | (IX) |
| $H_2BBr \cdot NEt_3$ | (X) |
| $H_2BBr \cdot SMe_2$ | (XI) |
| $BH_3$ | (XII) |
| $BH_3 \cdot OMe_2$ | (XIII) |
| $BH_3 \cdot THF$ | (XIV) |
| $BH_3 \cdot NH_3$ | (XV) |
| $BH_3 \cdot HN_2Me$ | (XVI) |
| $BH_3 \cdot NH2tBu$ | (XVII) |
| $BH_3 \cdot NHMe_2$ | (XVIII) |
| $BH_3 \cdot NMe_3$ | (XIX) |
| $BH_3 \cdot NEt_3$ | (XX) |
| $BH_3 \cdot Py$ | (XXI) |
| $BH_3 \cdot TMEDA$ | (XXII) |
| $BH_3 \cdot SMe_2$ | (XXIII) |
| $BH_3 \cdot Thiolane$ | (XXIV) |
| $BH_3 \cdot PF_3$ | (XXV) |
| $BH_3 \cdot PH_3$ | (XXVI) |
| $BH_3 \cdot PPh_3$ | (XXVII) |
| $BH_3 \cdot P(OMe)_3$ | (XXVIII) |
| $BH_3 \cdot P(Oi-Pr)_3$ | (XXIX) |
| $Al(BH_4)_3$ | (XXX) |
| $LiBH_4$ | (XXXI) |
| $NaBH_4$ | (XXXII) |
| $Hf(BH_4)_4$ | (XXXIII) |
| $NaCNBH_3$ | (XXXIV) |
| $K(Oi-Pr)_3BH$ | (XXXV) |
| $K(s-BuO)_3BH)$ | (XXXVI) |

TABLE 3-continued
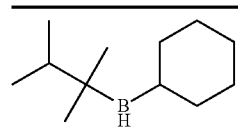 (XLI)
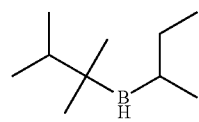 (XLII)
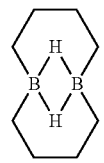 (XLIII)
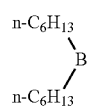 (XLIV)
n-C$_6$H$_{13}$\BH
n-C$_6$H$_{13}$
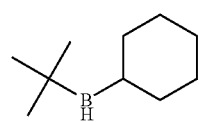 (XLV)
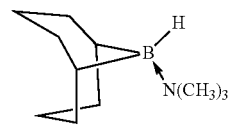 (XLVI)
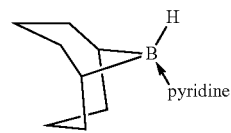 (XLVII)
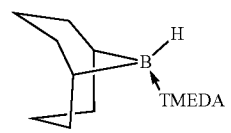 (XLVIII)
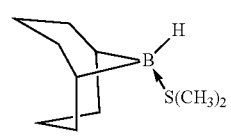 (XLIX)
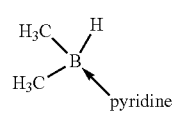 (L)
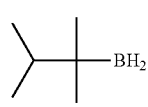 (LI)
H$_3$C—BH$_2$ (LII)
n-C$_6$H$_{13}$—BH$_2$ (LIII)
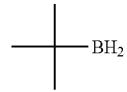 (LIV)
TABLE 3-continued
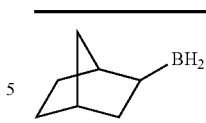 (LV)
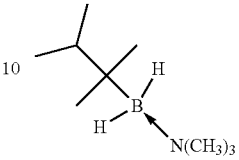 (LVI)
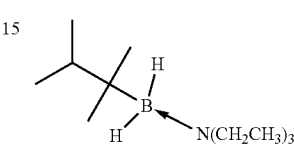 (LVII)
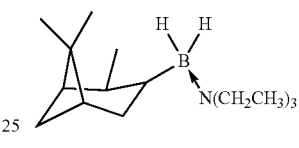 (LVIII)
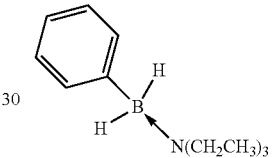 (LIX)
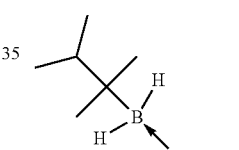 (LX)
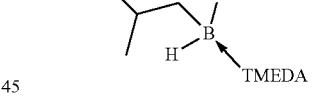 (LXI)
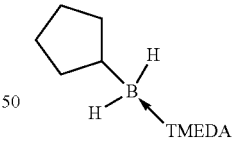 (LXII)
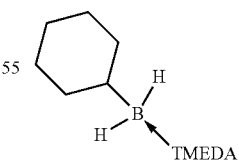 (LXIII)
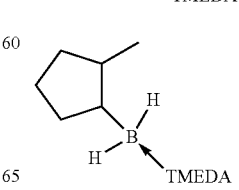 (LXIV)

TABLE 3-continued
| | |
|---|---|
| 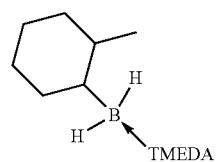 | (LXV) |
| 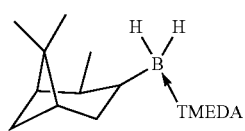 | (LXVI) |
| 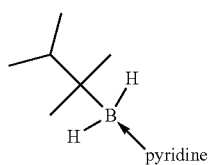 | (LXVII) |
| 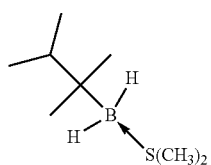 | (LXVIII) |
| 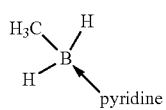 | (LXIX) |
| 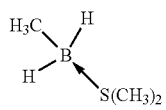 | (LXX) |
| 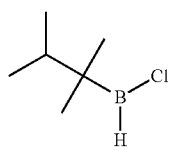 | (LXXI) |
| 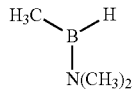 | (LXXII) |
| 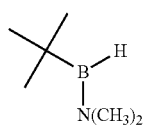 | (LXXIII) |
| 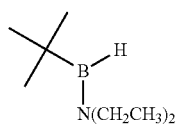 | (LXXIV) |
| 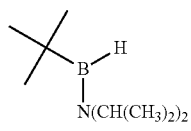 | (LXXV) |
TABLE 3-continued
| | |
|---|---|
| 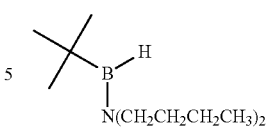 | (LXXVI) |
| 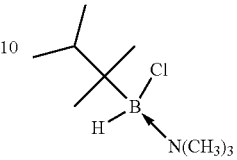 | (LXXVII) |
| 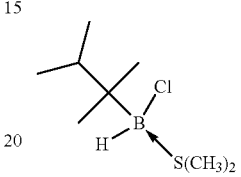 | (LXXIX) |
| 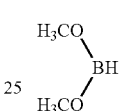 | (LXXX) |
| 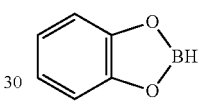 | (LXXXI) |
| 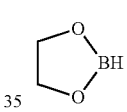 | (LXXXII) |
| 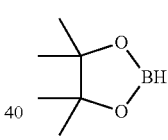 | (LXXXIII) |
| 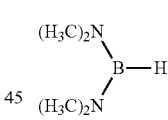 | (LXXXIV) |
| 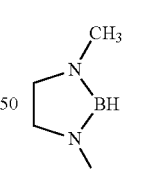 | (LXXXV) |
| 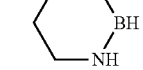 | (LXXXVI) |
| 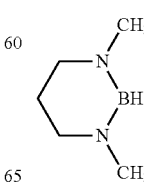 | (LXXXVII) |

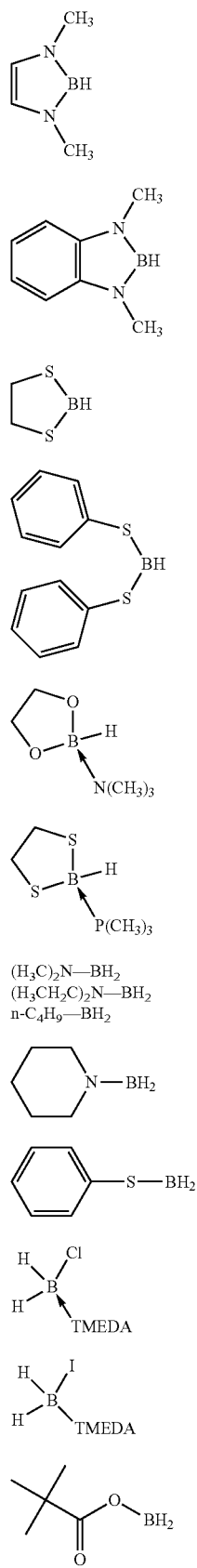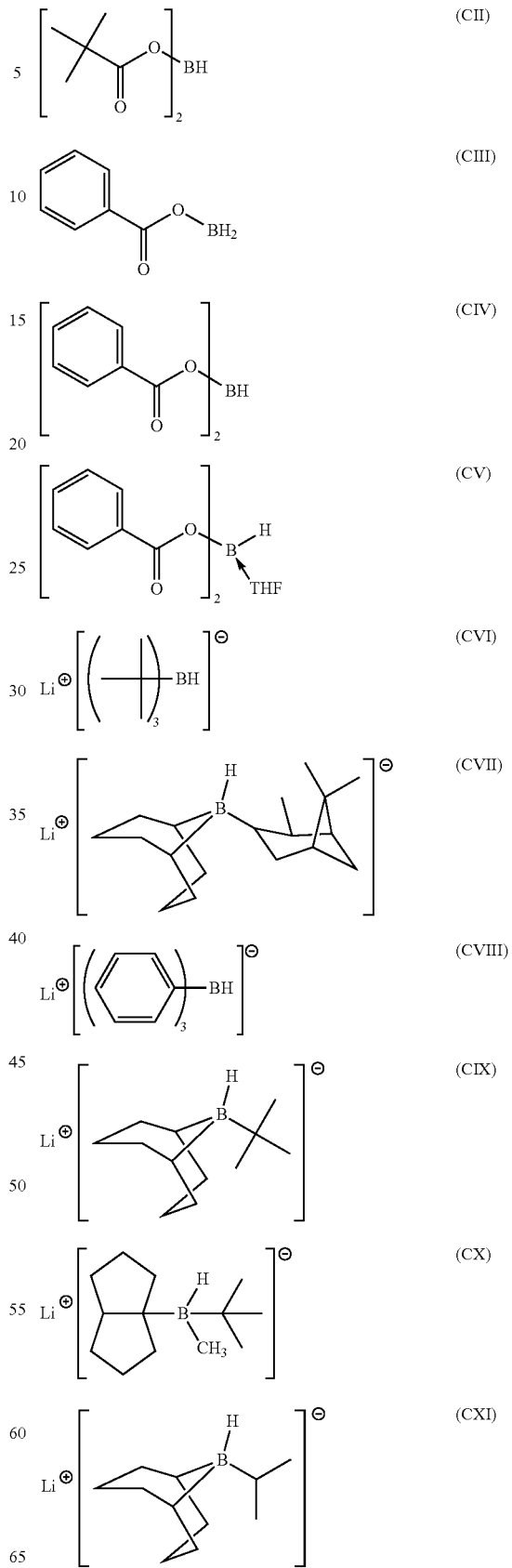

TABLE 3-continued
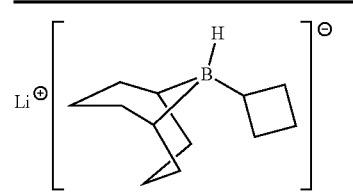 (CXII)
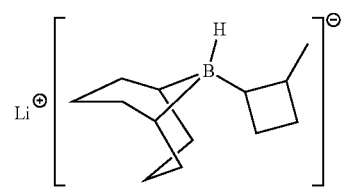 (CXIII)
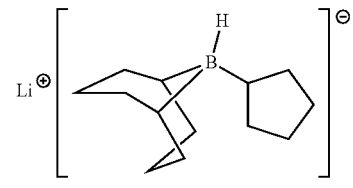 (CXIV)
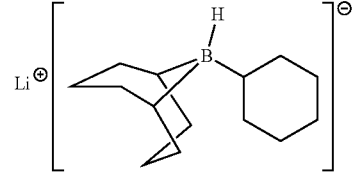 (CXV)
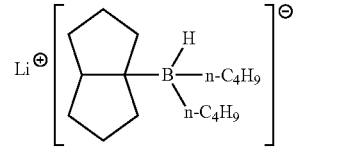 (CXVI)
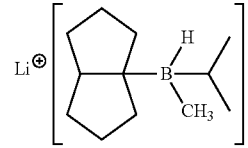 (CXVII)
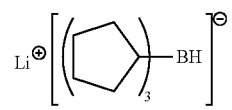 (CXVIII)
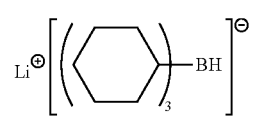 (CXIX)
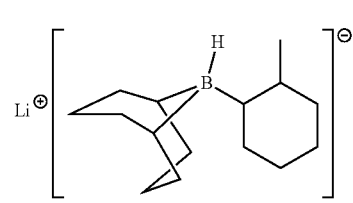 (CXX)
TABLE 3-continued
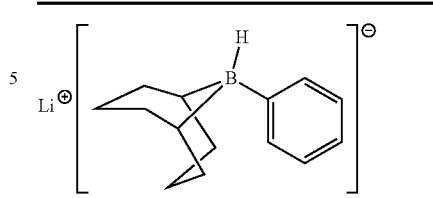 (CXXI)
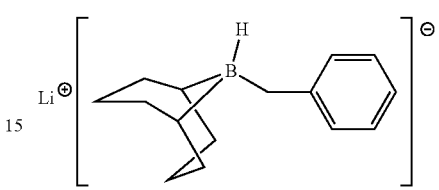 (CXXII)
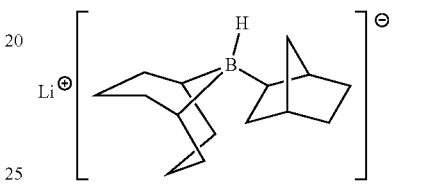 (CXXIII)
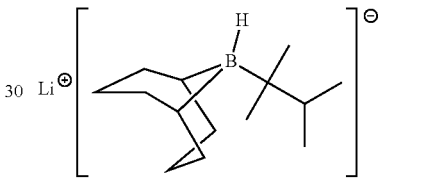 (CXXIV)
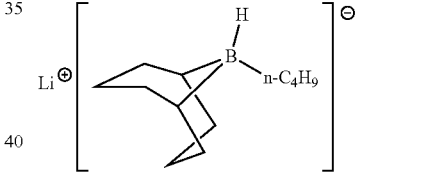 (CXXV)
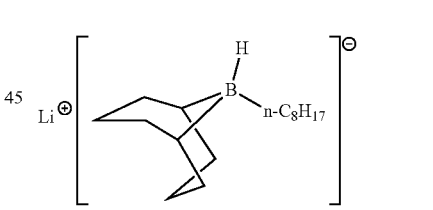 (CXXVI)
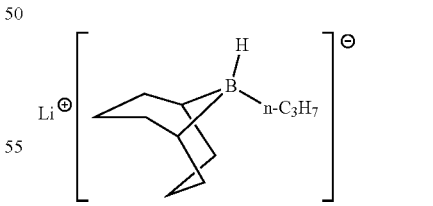 (CXXVII)
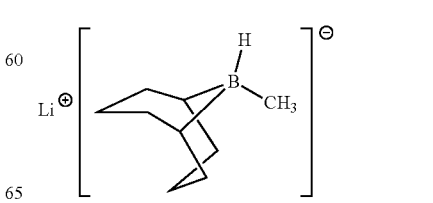 (CXXVIII)

TABLE 3-continued (CXXIX) Li⊕ [cyclopentane-fused-cyclopentane-B(H)(C₂H₅)(CH₃)]⊖

(CXXX) Li⊕ [cyclopentane-fused-cyclopentane-B(H)(n-C₄H₉)(CH₃)]⊖

(CXXXI) Li⊕ [decalin-fused bicyclic B–H]⊖

(CXXXII) Li⊕ [9-BBN-H(p-tolyl)]⊖

(CXXXIII) Li⊕ [(methylcyclopentyl)₃BH]⊖

(CXXXIV) Li⁺[CH₃CH₂)₃BH]⁺
(CXXXV) Li⁺[n-C₄H₉)₃BH]⁻

(CXXXVI) Na⊕ [(cyclopentyl)₃BH]⊖

(CXXXVII) K⊕ [9-BBN-H(n-C₄H₉)]⊖

Process for Formation of Alkylboron Compound

In an aspect, the present disclosure relates to processes for hydroborating olefins (e.g., alkenes). In an embodiment, the processes described herein can comprise contacting an alkene, a hydrogen-boron bond containing compound, and a metal complex to form an alkyl-boron compound under conditions suitable to form an alkylboron compound. In some embodiment, the processes described herein can comprise contacting an alkene, a hydrogen-boron bond containing compound, and a metal complex to form an alkyl-boron compound under conditions suitable to form an alkylboron compound. In an embodiment, the process can further comprise recovering the alkyl-boron compound. In an embodiment, when the olefin (alkene) is an internal (or linear internal) olefin (or alkene) the processes can further comprise forming a terminal (or linear internal) olefin (or alkene) under conditions suitable to form a terminal boron (terminal alkylboron or terminal linear alkylboron) compound. In an embodiment, the processes can further comprise recovering the terminal boron (terminal alkylboron or terminal linear alkylboron) compound.

In an alternative aspect, the processes described herein can comprise contacting an internal alkene, a hydrogen-boron bond containing compound, and a metal complex to form a terminal alkylboron compound; alternatively, the processes described herein can comprise contacting a linear internal alkene, a hydrogen-boron bond containing compound, and a metal complex to form a terminal alkylboron compound. In an embodiment, the processes can further comprise recovering the terminal boron (terminal alkylboron or terminal linear alkylboron) compound.

For the processes described herein, the olefins and/or alkenes, the hydrogen-boron bond containing compounds, the metal complexes, the alkyl-boron compounds (terminal alkyl-boron compounds or linear terminal alkyl-boron compounds), the conditions capable of forming alkylboron compounds, the conditions capable of forming terminal alkylboron compounds, and other process features of these processes are independently described herein. These independently described features can be utilized, in any combination and without limitation to further describe the processes described herein. It should be noted that while these features can be disclosed under headings within this application, a heading does not limit the disclosure found therein. Additionally the various aspects and embodiments disclosed herein can be combined in any manner.

The metal complexes which can be utilized in the processes described herein can be selected from the group consisting of an $N^2$-phosphinyl amidine metal complex, an $N^2$-phosphinyl formamidine complex, and an $N^2$-phosphinyl guanidine metal complex. These metal complexes are further described herein and these metal complex descriptions can be utilized without limitation to further describe the processes described herein.

In an aspect, the contacting of the metal complex, hydrogen-boron bond containing compound, and alkene can occur in a solvent or diluent. Alternatively, the contacting of the metal complex, hydrogen-boron bond containing compound, and alkene can occur in the substantial absence of a solvent or diluent. Within the present disclosure, the substantial absence of a solvent or diluent can be less than 5 wt. %, 3, wt. %, 2 wt. %, or 1 wt. % components which are not olefins (or alternatively, alkenes) based upon the amount of olefins charged to the process.

In an aspect, conditions suitable to form the alkylboron compound can include a temperature to form the alkylboron compound. In some embodiments, the temperature to form the alkylboron compound can range from −50° C. to 200° C. In some embodiments, the temperature to form the alkylboron compound can range from −20° C. to 150° C.; alternatively, range from 0° C. to 120° C.; alternatively, range from 10° C. to 100° C.; alternatively, range from 15° C. to 80° C.; alternatively, range from 15° C. to 50° C.; or alternatively, range from 15° C. to 30° C. In an aspect, conditions suitable to form a terminal alkylboron compound (or a linear terminal alkylboron compound) can include a temperature to form the alkylboron compound. In some embodiments, the temperature to form the terminal alkylboron compound (or the linear terminal alkylboron compound) can range from −50° C. to 200° C. In some embodiments, the temperature to form the terminal alkylboron compound (or the linear terminal alkylboron compound) can range from −20° C. to 150° C.; alternatively, range from 0° C. to 120° C.; alternatively, range from 10° C. to 100° C.; alternatively, range from 15° C. to 80°

C.; alternatively, alternatively, range from 15° C. to 50° C.; or alternatively, range from 15° C. to 30° C. In an embodiment, the temperature suitable to form the alkylboron compound can b the same as the temperature suitable to form the terminal alkylboron compound (or the linear terminal alkylboron compound); or alternatively, the temperature to form the alkylboron compound can be different form the temperature suitable to form the terminal alkylboron compound (or the linear terminal alkylboron compound).

In an aspect, conditions suitable to form the alkylboron compound and/or the conditions suitable to form a terminal alkylboron compound (or a linear terminal alkylboron compound) can include a molar ratio of the metal complex to the hydrogen-boron bond containing compound. The molar ratio of the metal complex to hydrogen-boron bond containing compound can be any molar ratio which can catalyze hydroboration of the olefin (e.g., alkene, among others). In an embodiment, molar ratio of the metal complex to the hydrogen-boron bond containing compound can range from 10:1 to $10^6$:1; alternatively, range from $10^2$:1 to $10^6$:1; or alternatively, range from $10^3$:1 to $10^6$:1. In an embodiment, the molar ratio of the metal complex to the hydrogen-boron bond containing compound suitable to form an alkylboron compound can be the same as the molar ratio of the metal complex to the hydrogen-boron bond containing compound to form a terminal alkylboron compound (or the linear terminal alkylboron compound); or alternatively, the molar ratio of the metal complex to the hydrogen-boron bond containing compound suitable to form an alkylboron compound can be the different from the molar ratio of the metal complex to the hydrogen-boron bond containing compound to form a terminal alkylboron compound (or the linear terminal alkylboron compound).

In an aspect, conditions suitable to form the alkylboron compound can include a contact time to form the desired quantity of alkylboron compound, a contact time to obtain a desired catalyst productivity, and/or a contact time to obtain a desired yield of alkylboron compound. In an embodiment, the contact time contact time to form the desired quantity of alkylboron compound, a contact time to obtain a desired catalyst productivity, and/or a contact time to obtain a desired yield of alkylboron compound can be any contact time necessary to form the desired quantity of alkylboron compound, to obtain a desired catalyst productivity, and/or to obtain a desired yield of alkylboron compound. In some embodiments, the contact time to form the desired quantity of alkylboron compound, to obtain a desired catalyst productivity, and/or to obtain a desired yield of alkylboron compound can range from 1 minute to 48 hours; alternatively, from 30 minutes to 36 hours; alternatively, from 1 hour to 12 hours; or alternatively, from 1 hour to 8 hours. In an aspect, conditions suitable to form the terminal alkylboron compound (or linear terminal alkylboron compound) can include a contact time to form the desired quantity of terminal alkylboron compound (or linear terminal alkylboron compound), a contact time to obtain a desired catalyst productivity, and/or a contact time to obtain a desired yield of terminal alkylboron compound (or linear terminal alkylboron compound). In an embodiment, the contact time contact time to form the desired quantity of terminal alkylboron compound (or linear terminal alkylboron compound), a contact time to obtain a desired catalyst productivity, and/or a contact time to obtain a desired yield of terminal alkylboron compound (or linear terminal alkylboron compound) can be any contact time necessary to form the desired quantity of terminal alkylboron compound (or linear terminal alkylboron compound), to obtain a desired catalyst productivity, and/or to obtain a desired yield of terminal alkylboron compound (or linear terminal alkylboron compound). In some embodiments, the contact time to form the desired quantity of terminal alkylboron compound (or linear terminal alkylboron compound), to obtain a desired catalyst productivity, and/or to obtain a desired yield terminal alkylboron compound (or linear terminal alkylboron compound) can range from 1 minute to 48 hours; alternatively, from 30 minutes to 36 hours; alternatively, from 1 hour to 12 hours; or alternatively, from 1 hour to 8 hours. In an embodiment the contact time to form the alkylboron compound can include a contact time to form the desired quantity of alkylboron compound, a contact time to obtain a desired catalyst productivity, and/or a contact time to obtain a desired yield of alkylboron compound can be the same contact time to the terminal alkylboron compound (or linear terminal alkylboron compound) can include a contact time to form the desired quantity of terminal alkylboron compound (or linear terminal alkylboron compound), a contact time to obtain a desired catalyst productivity, and/or a contact time to obtain a desired yield of terminal alkylboron compound (or linear terminal alkylboron compound); or alternatively, the contact time to form the alkylboron compound can include a contact time to form the desired quantity of alkylboron compound, a contact time to obtain a desired catalyst productivity, and/or a contact time to obtain a desired yield of alkylboron compound can be different from the contact time to the terminal alkylboron compound (or linear terminal alkylboron compound) can include a contact time to form the desired quantity of terminal alkylboron compound (or linear terminal alkylboron compound), a contact time to obtain a desired catalyst productivity, and/or a contact time to obtain a desired yield of terminal alkylboron compound (or linear terminal alkylboron compound).

In an embodiment, the molar yield of alkylboron compound can be greater than or equal to 70 wt. %; alternatively, greater than or equal to 75 wt. %; alternatively, greater than or equal to 80 wt. %; alternatively, greater than or equal to 85 wt. %; or alternatively, greater than or equal to 90 wt. %. In other embodiments, the molar yield of alkylboron compound can be from 60 to 99.5 wt. % of the alkene is converted to the alkylboron compound; alternatively, from 70 to 99 wt. %; alternatively, from 75 to 97.5 wt. %; or alternatively, from 80 to 95 wt. %. In an embodiment, the molar yield of terminal alkylboron compound (or linear terminal alkylboron compound) can be greater than about 70 wt. %; alternatively, greater than or equal to 75 wt. %; alternatively, greater than or equal to 80 wt. %; alternatively, greater than or equal to 85 wt. %; or alternatively, greater than or equal to 90 wt. %. In other embodiments, the molar yield of terminal alkylboron compound (or linear terminal alkylboron compound) from 60 to 99.5 wt. % of the internal alkene is converted to the alkylboron compound; alternatively, from 70 to 99 wt. %; alternatively, from 75 to 97.5 wt. %; or alternatively, from 80 to 95 wt. %. As one having ordinary skill in the art would recognize, the molar yield of alkylboron compound or terminal alkylboron compound (or linear terminal alkylboron compound is based upon the limiting reagent (the hydrogen-boron bond containing compound or the olefin or alkene (linear alkene, terminal alkene, linear terminal alkene, internal alkene, or linear internal alkene, among others)) of the process.

In an embodiment, the alkylboron compound (linear or branched, or terminal or otherwise) can be utilized in further process without isolating the alkylboron compound. In an embodiment, one or more alkylboron compounds (linear or branched, or terminal or otherwise) can be recovered from the mixture formed by contacting the alkene, hydrogen-boron bond containing compound, and the metal complex, to form the alkylboron compound. The alkylboron compound can be recovered from the mixture using any suitable procedure such as filtration, distillation, washing, or any combination thereof. In an embodiment the recovered alkylboron compound can be utilized without any further processing. Alternatively, the recovered alkylboron compound can be subjected to additional processing steps (e.g., crystallization) as consistent with a user and/or process goal.

Dehydroboration

In an embodiment of the processes disclosed herein, the alkene can be an internal alkene (or linear internal alkene) and alkylboron compound can be a terminal alkylboron compound (or linear terminal alkylboron compound) In an embodiment, the alkylboron compound (or terminal alkylboron compound, or linear terminal alkylboron compound) can be subjected to thermal dehydroboration to form an alkene (terminal alkene or linear internal alkene). Thermal dehydroboration of the alkylboron (or terminal alkylboron compound, or linear terminal alkylboron compound) can be carried out using any suitable thermal conditions to effect cleavage of the boron-carbon bond to form the alkene. In an embodiment, the thermal dehydroboration of the alkylboron compound (or terminal alkylboron compound, or linear terminal alkylboron compound) can be carried out at a temperature ranging from 100° C. to 250° C.; alternatively, 120° C. to 230° C.; or alternatively, 140° C. to 220° C.

Substituent Groups

Various aspects and embodiments described herein refer to general substituents and/or non-hydrogen substituents such as halogen (or halo, halide), hydrocarbyl, hydrocarboxy, alkyl, and/or alkoxy substituents. In an embodiment, each general substituent and/or non-hydrogen substituent of any aspect or embodiment calling for a substituent can be a halogen, a hydrocarbyl group, or a hydrocarboxy group; alternatively, a halogen or a hydrocarbyl group; alternatively, a halogen or a hydrocarboxy group; alternatively, a hydrocarbyl group or a hydrocarboxy group; alternatively, a halogen; alternatively, a hydrocarbyl group; or alternatively, a hydrocarboxy group. In an embodiment, each hydrocarbyl substituent can be a $C_1$ to $C_{10}$ hydrocarbyl group; or alternatively, a $C_1$ to $C_5$ hydrocarbyl group. In an embodiment, each hydrocarboxy substituent of any aspect or embodiment calling for a substituent can be a $C_1$ to $C_{10}$ hydrocarboxy group; or alternatively, a $C_1$ to $C_5$ hydrocarboxy group. In an embodiment, any halide substituent of any aspect or embodiment calling for a substituent can be a fluoride, chloride, bromide, or iodide; alternatively, a fluoride or chloride. In some embodiments, any halide substituent of any aspect or embodiment calling for a substituent can be a fluoride; alternatively, a chloride; alternatively, a bromide; or alternatively, an iodide.

In an embodiment, any hydrocarbyl substituent of any aspect or embodiment calling for a substituent can be an alkyl group, an aryl group, or an aralkyl group; alternatively, an alkyl group; alternatively, an aryl group; or alternatively, an aralkyl group. In an embodiment, any alkyl substituent of any aspect or embodiment calling for a substituent can be a methyl group, an ethyl group, an n-propyl group, an isopropyl group, an n-butyl group, a sec-butyl group, an isobutyl group, a tert-butyl group, an n-pentyl group, a 2-pentyl group, a 3-pentyl group, a 2-methyl-1-butyl group, a tert-pentyl group, a 3-methyl-1-butyl group, a 3-methyl-2-butyl group, or a neo-pentyl group; alternatively, a methyl group, an ethyl group, an isopropyl group, a tert-butyl group, or a neo-pentyl group; alternatively, a methyl group; alternatively, an ethyl group; alternatively, an isopropyl group; alternatively, a tert-butyl group; or alternatively, a neo-pentyl group. In an embodiment, any aryl substituent of any aspect or embodiment calling for a substituent can be phenyl group, a tolyl group, a xylyl group, or a 2,4,6-trimethylphenyl group; alternatively, a phenyl group; alternatively, a tolyl group, alternatively, a xylyl group; or alternatively, a 2,4,6-trimethylphenyl group. In an embodiment, any aralkyl substituent of any aspect or embodiment calling for a substituent can be benzyl group or an ethylphenyl group (2-phenyleth-1-yl or 1-phenyleth-1-yl); alternatively, a benzyl group; alternatively, an ethylphenyl group; alternatively a 2-phenyleth-1-yl group; or alternatively, a 1-phenyleth-1-yl group.

In an embodiment, any hydrocarboxy substituent of any aspect or embodiment calling for a substituent can be an alkoxy group, an aryloxy group, or an aralkoxy group; alternatively, an alkoxy group; alternatively, an aryloxy group, or an aralkoxy group. In an embodiment, any alkoxy substituent of any aspect or embodiment calling for a substituent can be a methoxy group, an ethoxy group, an n-propoxy group, an isopropoxy group, an n-butoxy group, a sec-butoxy group, an isobutoxy group, a tert-butoxy group, an n-pentoxy group, a 2-pentoxy group, a 3-pentoxy group, a 2-methyl-1-butoxy group, a tert-pentoxy group, a 3-methyl-1-butoxy group, a 3-methyl-2-butoxy group, or a neo-pentoxy group; alternatively, a methoxy group, an ethoxy group, an isopropoxy group, a tert-butoxy group, or a neo-pentoxy group; alternatively, a methoxy group; alternatively, an ethoxy group; alternatively, an isopropoxy group; alternatively, a tert-butoxy group; or alternatively, a neo-pentoxy group. In an embodiment, any aryloxy substituent of any aspect or embodiment calling for a substituent can be phenoxy group, a toloxy group, a xyloxy group, or a 2,4,6-trimethylphenoxy group; alternatively, a phenoxy group; alternatively, a toloxy group, alternatively, a xyloxy group; or alternatively, a 2,4,6-trimethylphenoxy group. In an embodiment, any aralkoxy substituent of any aspect or embodiment calling for a substituent can be benzoxy group.

Solvents

The methods described herein can utilize one or more solvents. Solvents which can be utilized in aspects of the present disclosure include without limitation water, hydrocarbons, halogenated hydrocarbons, ethers, carbonates, esters, ketones, aldehydes, alcohols, nitriles and combinations thereof. In some embodiments, an aspect of the present disclosure can call for a polar solvent. Polar solvents which can be utilized include without limitation water, ethers, carbonates, esters, ketones, aldehydes, alcohols, nitriles, and mixtures thereof; alternatively, ethers, carbonates, esters, ketones, aldehydes, alcohols, nitriles, and mixtures thereof; alternatively, ethers, esters, ketones, alcohols, nitriles, and mixtures thereof; alternatively, ethers; alternatively, carbonates; alternatively, esters; alternatively, ketones; alternatively, aldehydes; alternatively, alcohols; or alternatively, nitriles. In some embodiments, an aspect of the present disclosure can call for an aprotic polar solvent. Aprotic polar solvents which can be utilized include without limitation ethers, esters, ketones, aldehydes, nitriles, and mixtures thereof; alternatively, ethers, nitriles and mixtures thereof; alternatively, esters, ketones, aldehydes and mixtures thereof; alternatively, ethers; alternatively, esters; alternatively, ketones; alternatively, aldehydes; or alternatively, nitriles. In other embodiments, an aspect of the disclosure can call for a non-polar solvent. Non-polar solvents include without limitation hydrocarbons, halogenated hydrocarbons, or mixtures thereof; alternatively, a hydrocarbon; or alternatively, a halogenated hydrocarbon. In another embodiment, an aspect of the present disclosure can call for a solvent that is substantially unreactive with a metal alkyl. Solvents which are unreactive with a metal alkyl include without limitation ethers, hydrocarbons, and mixtures thereof; alternatively, ethers; or alternatively, hydrocarbons.

Hydrocarbons and halogenated hydrocarbon can include, for example, aliphatic hydrocarbons, aromatic hydrocarbons, petroleum distillates, halogenated aliphatic hydrocarbons, halogenated aromatic hydrocarbons, or combinations thereof; alternatively aliphatic hydrocarbons, aromatic hydrocarbons, halogenated aliphatic hydrocarbons, halogenated aromatic hydrocarbons, and combinations thereof; alternatively, aliphatic hydrocarbons; alternatively, aromatic hydrocarbons; alternatively, halogenated aliphatic hydrocarbons; or alternatively, halogenated aromatic hydrocarbons. Aliphatic hydrocarbons which can be useful as a solvent include $C_3$ to $C_{20}$ aliphatic hydrocarbons; alternatively $C_4$ to $C_{15}$ aliphatic hydrocarbons; or alternatively, $C_5$ to $C_{10}$ aliphatic hydrocarbons. The aliphatic hydrocarbons can be cyclic or acyclic and/or can be linear or branched, unless otherwise specified. Non-limiting examples of suitable acyclic aliphatic hydrocarbon solvents that can be utilized singly or in any combination include propane, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, iso-butane, n-butane, butane (n-butane or a mixture of linear and branched $C_4$ acyclic aliphatic hydrocarbons), pentane (n-pentane or a mixture of linear and branched $C_5$ acyclic aliphatic hydrocarbons), hexane (n-hexane or mixture of linear and branched $C_6$ acyclic aliphatic hydrocarbons), heptane (n-heptane or mixture of linear and branched $C_7$ acyclic aliphatic hydrocarbons), octane (n-octane or a mixture of linear and branched $C_8$ acyclic aliphatic hydrocarbons), and combinations thereof; alternatively, propane; alternatively, iso-butane; alternatively, n-butane; alternatively, butane (n-butane or a mixture of linear and branched $C_4$ acyclic aliphatic hydrocarbons); alternatively, pentane (n-pentane or a mixture of linear and branched $C_5$ acyclic aliphatic hydrocarbons); alternatively, hexane (n-hexane or mixture of linear and branched $C_6$ acyclic aliphatic hydrocarbons); alternatively, heptane (n-heptane or mixture of linear and branched $C_7$ acyclic aliphatic hydrocarbons); or alternatively, octane (n-octane or a mixture of linear and branched $C_8$ acyclic aliphatic hydrocarbons). Non-limiting examples of suitable cyclic aliphatic hydrocarbon solvents include cyclohexane, methyl cyclohexane; alternatively cyclohexane; or alternatively, methylcyclohexane. Aromatic hydrocarbons which can be useful as a solvent include $C_6$ to $C_{20}$ aromatic hydrocarbons; or alternatively, $C_6$ to $C_{10}$ aromatic hydrocarbons. Non-limiting examples of suitable aromatic hydrocarbons that can be utilized singly or in any combination include benzene, toluene, xylene (including ortho-xylene, meta-xylene, para-xylene, or mixtures thereof), and ethylbenzene, or combinations thereof; alternatively, benzene; alternatively, toluene; alternatively, xylene (including ortho-xylene, meta-xylene, para-xylene or mixtures thereof); or alternatively, ethylbenzene.

Halogenated aliphatic hydrocarbons which can be useful as a solvent include $C_1$ to $C_{15}$ halogenated aliphatic hydrocarbons; alternatively, $C_1$ to $C_{10}$ halogenated aliphatic hydrocarbons; or alternatively, $C_1$ to $C_5$ halogenated aliphatic hydrocarbons. The halogenated aliphatic hydrocarbons can be cyclic or acyclic and/or can be linear or branched, unless otherwise specified. Non-limiting examples of suitable halogenated aliphatic hydrocarbons which can be utilized include methylene chloride, chloroform, carbon tetrachloride, dichloroethane, trichloroethane, and combinations thereof; alternatively, methylene chloride, chloroform, dichloroethane, trichloroethane, and combinations thereof; alternatively, methylene chloride; alternatively, chloroform; alternatively, carbon tetrachloride; alternatively, dichloroethane; or alternatively, trichloroethane. Halogenated aromatic hydrocarbons which can be useful as a solvent include $C_6$ to $C_{20}$ halogenated aromatic hydrocarbons; or alternatively, $C_6$ to $C_{10}$ halogenated aromatic hydrocarbons. Non-limiting examples of suitable halogenated aromatic hydrocarbons include chlorobenzene, dichlorobenzene, and combinations thereof; alternatively chlorobenzene and dichlorobenzene.

Ethers, carbonates, esters, ketones, aldehydes, or alcohols which can be useful as a solvent include $C_2$ to $C_{20}$ ethers, carbonates, esters, ketones, aldehydes, or alcohols; alternatively, $C_2$ to $C_{10}$ ethers, carbonates, esters, ketones, aldehydes, or alcohols; or alternatively, $C_2$ to $C_5$ ethers, carbonates, esters, ketones, aldehydes, or alcohols. Suitable ether solvents can be cyclic or acyclic. Non-limiting examples of suitable ethers which can be useful as a solvent include dimethyl ether, diethyl ether, methyl ethyl ether, monoethers or diethers of glycols (e.g., dimethyl glycol ether), furans, substituted furans, dihydrofuran, substituted dihydrofurans, tetrahydrofuran (THF), substituted tetrahydrofurans, tetrahydropyrans, substituted tetrahydropyrans, 1,3-dioxanes, substituted 1,3-dioxanes, 1,4-dioxanes, substituted 1,4-dioxanes, or mixtures thereof. In an embodiment, each substituent of a substituted furan, substituted dihydrofuran, substituted tetrahydrofuran, substituted tetrahydropyran, substituted 1,3-dioxane, or substituted 1,4-dioxane, can be a $C_1$ to $C_5$ alkyl group. $C_1$ to $C_5$ alkyl substituent group are disclosed herein and can be utilized without limitation of further describe the substituted tetrahydrofuran, dihydrofuran, furan, 1,3-dioxane, or 1,4 dioxane solvents. Non-limiting examples of suitable carbonates which can be utilized as a solvent include ethylene carbonate, propylene carbonate, diethyl carbonate, diethyl carbonate, glycerol carbonate, and combinations thereof. Non-limiting examples of suitable esters which can be utilized as a solvent include ethyl acetate, propyl acetate, butyl acetate, isobutyl isobutyrate, methyl lactate, ethyl lactate, and combinations thereof. Non-limiting examples of suitable ketones which can be utilized as a solvent include acetone, ethyl methyl ketone, methyl isobutyl ketone, and combinations thereof. Non-limiting examples of suitable alcohols which can be utilized as a solvent include methanol, ethanol, propanol, isopropanol, n-butanol, isobutanol, pentanol, hexanol, heptanol, octanol, benzyl alcohol, phenol, cyclohexanol, and the like, or combinations thereof.

General Disclosure Information

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can suggest themselves to one of ordinary skill in the art without departing from the spirit of the present invention or the scope of the appended claims.

The data and descriptions provided in the following examples are given to show particular aspects and embodiments of the compounds, catalyst systems, and oligomerization and/or polymerization methods disclosed, and to demonstrate a number of the practices and advantages thereof. The examples are given as a more detailed demonstration of some of the aspects and embodiments described herein and are not intended to limit the disclosure or claims in any manner.

Examples

General Procedures

The following general procedures were followed for the experimental investigations of this disclosure. Unless otherwise noted, all experiments were conducted under nitrogen in an MBraun glovebox or using standard Schlenk techniques. Dry, deoxygenated solvents were used unless otherwise indicated. Pentane was deoxygenated and dried by sparging with nitrogen and subsequent passage through a double-column solvent purification system purchased from MBraun Inc. with one column packed with activated alumina and one column packed with activated Q5. Diethyl ether ($Et_2O$) and tetrahydrofuran (THF) were dried over Na/benzophenone and distilled under nitrogen. $CDCl_3$ (Cambridge Isotopes) was used as received. All alkenes were degassed via three repeated freeze-pump-thaw cycles and were stored over activated 4 Å molecular sieves for a minimum of 12 hours prior to use. Pinacolborane (HBPin, Alfa) was used as received and stored under nitrogen. $^1H$ and $^{13}C$ NMR characterization data were collected at 300K on a Bruker AV-300 spectrometer operating at 300.1 and 75.5 MHz (respectively) with chemical shifts reported in parts per million downfield of $SiMe_4$. For boron-containing products, a $^{13}C$ NMR resonance for the carbon attached to the quadrupolar boron center was not observed. $^{11}B$ NMR characterization data were collected at 300K on a Bruker AV-300 spectrometer operating at 96.3 MHz with chemical shifts reported in parts per million downfield of $BF_3.OEt_2$. The $N^2$-phosphinoamidine ligands were generally prepared as described in U.S. Pat. No. 8,680,003.

Hydroborations were performed utilizing an $N^2$-phosphinoamidine metal complex having Structure PAMC1, or an $N^2$-phosphinoamidine metal complex having Structure PAMC2.

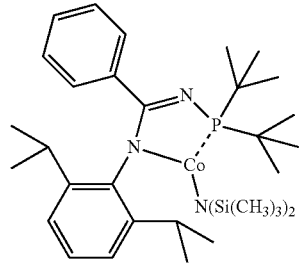

PAMC1

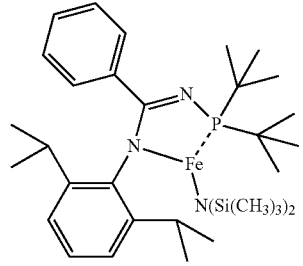

PAMC2

The cobalt $N^2$-phosphinoamidine metal complex having Structure PAMC1 was prepared as follows: A solution of $LiN(SiMe_3)_2$ (0.788 g, 4.71 mmol) in $Et_2O$ (10 mL) was added via pipette over 2 minutes to a magnetically stirred slurry of $CoCl_2$ (0.306 g, 2.36 mmol) in $Et_2O$ (5 mL). A color change from pale blue to deep blue green was observed over the course of 5 minutes. The reaction mixture was magnetically stirred for a total of 3 hours, over which time the formation of a white precipitate was observed. Subsequently, the ligand

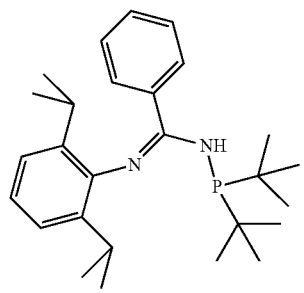 [SMILES: CC(C)c1cccc(C(C)C)c1/N=C(/NP(C(C)(C)C)C(C)(C)C)c1ccccc1]

(1.00 g, 2.36 mmol) was added to the reaction mixture as a solid and a color change from deep blue green to deep red was observed over the course of 2 minutes. After stirring for an additional 2 hours the reaction mixture was filtered through Celite, the eluent was collected, and the $Et_2O$ was removed under reduced pressure. The deep red residue was then extracted with pentane (10 mL) and filtered through Celite.

The filtrate was then concentrated under reduced pressure to a volume of ca. 3 mL, and the solution was placed in the freezer at −35° C. for 18 hours. After 18 hours the brown supernatant solution was decanted and the red solid crystalline precipitate was washed with cold (−35° C.) pentane (2×0.5 mL). The remaining red solid crystalline material (cobalt catalyst) was dried under reduced pressure (0.786 g, 52%). Spectral data for the cobalt catalyst were in close agreement to those described in A Ruddy et. al, *Organometallics* 2013, 32, 5581-5588. The iron $N^2$-phosphinoamidine metal complex having Structure PAMC2 was prepared similarly.

General Procedure for Determination of Conversion of Catalytic Alkene Hydroboration (GP1).

In a nitrogen atmosphere glovebox, an oven-dried screw-capped vial containing a stirbar was charged with the desired quantity of pinacolborane and the desired quantity of the desired alkene. The desired quantity of the desired catalyst was then added as a solid and the vial was sealed with a cap containing a PTFE septum and stirred in the glovebox for 1 hour. After 1 hour the vial was removed from the glovebox and the catalyst mixture was deactivated by exposure to air. The contents of the vial were extracted with $CDCl_3$ and filtered through silica into a NMR tube. The $^1H$ and/or $^{11}B$ NMR spectra were analyzed to monitor the progress of the reaction. If no pinacolborane or alkene/carbonyl compound was found to be present in the sample, the reaction was determined to have achieved full conversion. For 4-octene isomers, the $^{13}C$ DEPT-Q NMR spectrum was also analyzed to aid in determining if an isomerization process involving the starting alkene had occurred.

General Procedure for Isolation of Alkene Hydroboration Products (Solvent Free) (GP2)

In a nitrogen atmosphere glovebox, an oven-dried screw-capped vial containing a stirbar was charged with the desired quantity of pinacolborane and the desired quantity of the desired alkene. The desired quantity of the desired catalyst was then added as a solid and the vial was sealed with a cap containing a PTFE septum and stirred in the glovebox for 1 hour. After 1 hour the vial was removed from the glovebox and the catalyst mixture was deactivated by exposure to air. The contents were extracted with $Et_2O$ (3×2 mL) and the ether extracts were subsequently filtered through silica. The eluent was collected and concentrated under reduced pressure to furnish the hydroboration product. The $^1H$ and $^{13}C$ NMR spectra of the isolated material were analyzed to determine the purity of the sample.

General Procedure for Isolation of Alkene Hydroboration Products (with Solvent) (GP3).

In a nitrogen atmosphere glovebox, an oven-dried screw-capped vial containing a stirbar was charged with the desired quantity of pinacolborane (145 µL, 1 mmol) and the desired quantity of the desired alkene. The desired quantity of the desired catalyst was then added as a stock solution in $Et_2O$ (typically 2 mM in 250 µL) and the vial was sealed with a cap containing a PTFE septum and stirred in the glovebox for 1 hour. After 1 hour the vial was removed from the glovebox and the catalyst mixture was deactivated by exposure to air. The contents were extracted with $Et_2O$ (3×2 mL) and filtered through silica. The eluent was collected and concentrated under reduced pressure to furnish the hydroboration product. The $^1H$ and $^{13}C$ NMR spectra were analyzed to determine the purity of the sample.

1-Hexene Hydroboration

The hydroboration of 1-hexene using the compositions and methods disclosed herein in the absence of solvent was investigated. Specifically 1-hexene was contacted with pinacolborane and 0.1 to 1.0 mol % of the $N^2$-phosphinyl amidine metal complex having Structure PAMC1 or Structure PAMC2. The conversion of 1-hexene was determined according to GP1 and after drying in vacuo the alkylboron product, 2-hex-1-yl-4,4,5,5-tetramethyl-1,3,2-dioxaborolane, depicted as Structure ABP1, was isolated as a colorless oil.

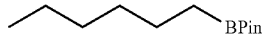

ABP1

NMR characterization of the alkylboron product resulted in the following: $^1H$ NMR (300.1 MHz, $CDCl_3$): δ 1.33 (m, 2H), 1.18-1.24 (overlapping peaks, 18H), 0.81 (m, 3H), 0.70 (t, 2H, J=8 Hz). $^{13}C\{^1H\}$NMR (75.5 MHz, $CDCl_3$): δ 83.0, 32.3, 31.8, 25.0, 24.1, 22.7, 14.2. $^{11}B$ NMR (96.3 MHz, $CDCl_3$): δ 34.2. Spectral data obtained were in close agreement with previously reported $^1H$ and $^{13}C$ NMR characterization data for 2-hex-1-yl-4,4,5,5-tetramethyl-1,3,2-dioxaborolane. The percentage conversion of the 1-hexene as a function of time and the mol. % catalyst is presented in Table 4.

TABLE 4

| No. | Substrate | Mol % Fe/Co | Time (h) | % Conversion |
|---|---|---|---|---|
| 1 | 1-hexene | 1 (Fe) | 1 | >95 |
| 2 | 1-hexene | 0.25 (Fe) | 1 | >95 |
| 3 | 1-hexene | 0.1 (Fe) | 1 | ~50 |
| 4 | 1-hexene | 0.1 (Fe) | 24 | ~50 |
| 5 | 1-hexene | 1 (Co) | 1 | >95 |
| 6 | 1-hexene | 0.25 (Co) | 1 | >95 |
| 7 | 1-hexene | 0.1 (Co) | 1 | >95 |
| 8 | 1-hexene | 0.05 (Co) | 1 | <5 |

The hydroboration of 1-hexene using the compositions and methods disclosed herein in the presence of solvent was also investigated. Specifically, 2-hex-1-yl-4,4,5,5-tetramethyl-1,3,2-dioxaborolane was synthesized according to GP3 using the following amounts of alkene substrate and catalyst: 1-hexene (128 µL, 1 mmol), PAMC1 (0.0032 g, 0.5 mol %). After removal of solvent 2-hex-1-yl-4,4,5,5-tetramethyl-1,3,2-dioxaborolane was isolated in 92% yield (0.196 g, 0.92 mmol) as a colorless oil. The results demonstrated that a higher yield of the alkylboron compound was afforded at lower mol % catalyst usage when using the PMAC1 catalyst. In another experiment using procedure GP1, $^{11}B$ NMR analysis indicated full conversion of the pinacolborane starting material using pinacolborane (1 mmol), 1-hexene (128 µL, 1 mmol), and PMAC1 (0.0064 g, 1 mol %).

Octene Hydroboration

The hydroboration of 1-octene using the compositions and methods disclosed herein was also investigated. Specifically 1-octene was contacted with pinacolborane and 0.1 to 1.0 mol % of the $N^2$-phosphinyl amidine complex of Structure PAMC1 or Structure PAMC2. The reaction was carried out in the absence of solvent. Specifically, 2-oct-1-yl-4,4,5,5-tetramethyl-1,3,2-dioxaborolane, depicted as Structure ABP2, was synthesized according to GP2 and after drying in vacuo the product was isolated as a colorless oil.

ABP2

The reaction progress was followed by the use of NMR and the results of the hydroboration reaction are presented in Table 5. NMR characterization of the alkylboron product resulted in the following: $^1$H NMR (300.1 MHz, CDCl$_3$): δ 1.35 (m, 2H), 1.18-1.22 (overlapping peaks, 22H), 0.83 (m, 3H), 0.72 (t, 2H, J=8 Hz). $^{13}$C{$^1$H}NMR (75.5 MHz, CDCl$_3$): δ 83.0, 32.6, 32.1, 29.5-29.6 (overlapping peaks), 25.0, 24.2, 22.9, 14.3. $^{11}$B NMR (96.3 MHz, CDCl$_3$): δ 34.1. Spectral data are in close agreement with previously reported $^1$H and $^{13}$C NMR characterization data for of 2-oct-1-yl-4,4,5,5-tetramethyl-1,3,2-dioxaborolane.

TABLE 5

| No. | Substrate | Mol % Fe/Co | Time (h) | % Conversion |
|---|---|---|---|---|
| 8 | 1-octene | 1 (Fe) | 1 | >95 |
| 9 | 1-octene | 1 (Fe) | 24 | >95 |
| 10 | 1-octene | 5 (Fe) | 1 | >95 |
| 11 | 1-octene | 5 (Fe) | 24 | >95 |
| 12 | 1-octene | 1 (Co) | 1 | >95 |
| 13 | 1-octene | 5 (Co) | 1 | >95 |

The data demonstate that both PAMC1 and PMAC2 efficiently catalyzed the conversion of 1-octene. For example, when the conversion of 1-octene was determined according to GP1 using the following amounts of alkene substrate and catalyst: 1-octene (160 μL, 1 mmol) and either PMAC1 (0.0064 g, 1 mol %) or PMAC2 (0.0064 g, 1 mol %), the $^1$H and $^{11}$B NMR spectra obtained indicated full conversion of the starting materials.

Cis-Octene and Trans-Octene Hydroboration

The hydroboration of cis-4-octene or trans-4-octene using the compositions and methods disclosed herein was also investigated. Specifically cis-4-octene or trans-4-octene was contacted with pinacolborane and 0.1 to 1.0 mol % of the N$^2$-phosphinyl amidine complex of Structure PAMC1 or Structure PAMC2. The reaction was carried out in the absence of solvent and 2-oct-1-yl-4,4,5,5-tetramethyl-1,3,2-dioxaborolane, depicted as Structure ABP2, was synthesized according to GP2. After drying in vacuo the alkyl product was isolated as a colorless oil. Data obtained from $^{13}$C DEPT-Q NMR experiments confirmed the formation of the terminal hydroboration product. The reaction progress was followed by the use of NMR and the results of the hydroboration reaction are presented in Table 6.

TABLE 6

| No. | Substrate | Mol % Fe/Co | Time (h) | % Conversion |
|---|---|---|---|---|
| 14 | Cis-4-octene | 1 (Fe) | 1 | <5 |
| 15 | Cis-4-octene | 1 (Fe) | 24 | <5 |
| 16 | Cis-4-octene | 1 (Co) | 1 | >95 |
| 17 | Cis-4-octene | 1 (Co) | 24 | >95 |
| 18 | Trans-4-octene | 1 (Fe) | 24 | <5 |
| 19 | Trans-4-octene | 5 (Fe) | 24 | <5 |
| 20 | Trans-4-octene | 5 (Co) | 1 | >95 |
| 21 | Trans-4-octene | 5 (Co) | 24 | >95 |
| 22 | Trans-4-octene | 5 (Co) | 1 | >95 |
| 23 | Trans-4-octene | 2.5 (Co) | 1 | >95 |
| 24 | Trans-4-octene | 2.5 (Co) | 1 | ~90 |

The results demonstrate that less than 5% of the cis-4-octene was observed to convert to 2-oct-1-yl-4,4,5,5-tetramethyl-1,3,2-dioxaborolane when using up to 1.0 mol. % of the N$^2$-phosphinyl amidine complex of Structure PAMC2 as the reaction catalyst in contrast to a conversion of greater than 95% observed when using 1.0 mol. % of the N$^2$-phosphinyl amidine complex of Structure PAMC1. However, when using the following amounts of alkene substrate and catalyst: cis-4-octene (160 μL, 1 mmol), PMAC2 (0.0016 g, 2.5 mol %), the $^1$H and $^{11}$B NMR spectra obtained indicated full conversion of the starting materials.

The results were similar when using trans-4-octene as the substrate. For example, when using trans-4-octene (160 μL, 1 mmol) and PMAC1 (0.016 g, 2.5 mol %) according to GP1, the $^1$H and $^{11}$B NMR spectra obtained indicated full conversion of the starting materials. In contrast, when using trans-4-octene (160 μL, 1 mmol) and PMAC2 (0.032 g, 5 mol %) according to GP1, the $^1$H and $^{11}$B NMR spectra obtained indicated a small amount of the starting materials were converted.

Octene Mixture Hydroboration

The hydroboration of 1:1:1 mixture of 1-octene, cis-4-octene and trans-4-octene using the compositions and methods disclosed herein was also investigated. Specifically, a 1:1:1 mixture of 1-octene, cis-4-octene and trans-4-octene was contacted with pinacolborane and 0.1 to 1.0 mol % of the N$^2$-phosphinyl amidine complex of Structure PAMC1 or Structure PAMC2. The reaction was carried out in the absence of solvent. For example, using the following amounts of alkene substrates and catalyst: 1-octene (53 μL, 0.33 mmol), cis-4-octene (53 μL, 0.33 mmol), trans-4-octene (54 μL, 0.34 mmol), PAMC1 (0.016 g, 2.5 mol %) the alkylboron product was obtained according to GP2. The reaction progress was followed by the use of NMR and the results of the hydroboration reaction are presented in Table 7.

TABLE 7

| No. | Substrate | Mol % Fe/Co | Time (h) | % Conversion |
|---|---|---|---|---|
| 25 | All octenes | 5 (Fe) | 1 | <5 (trans) |
| 26 | 1-octene | 5 (Fe) | 24 | <5 (trans) |
| 27 | 1-octene | 5 (Co) | 3.5 | >95 |
| 28 | 1-octene | 5 (Co) | 24 | >95 |

4-Methyl-1-Pentene Hydroboration

The hydroboration of 4-methyl-1-pentene using the compositions and methods disclosed herein was also investigated. Specifically, 2-(4-methylpent-1-yl)-4,4,5,5-tetramethyl-1,3,2-dioxaborolane, depicted as Structure ABP3, was synthesized according to GP3 by contacting 4-methyl-1-pentene (130 μL, 1 mmol), and PAMC1 (0.0064 g, 1 mol %). In the presence of solvent, 2-(4-methylpent-1-yl)-4,4,5,5-tetramethyl-1,3,2-dioxaborolane was isolated in 92% yield (0.193 g, 0.92 mmol) as a colorless oil after the removal of solvent. In the absence of solvent 2-(4-methylpent-1-yl)-4,4,5,5-tetramethyl-1,3,2-dioxaborolane was synthesized according to GP2 using the following amounts of alkene substrate and catalyst: 4-methyl-1-pentene (130 μL, 1 mmol), PAMC1 (0.0064 g, 1 mol) and isolated in 98% yield (0.208 g, 0.98 mmol) as a colorless oil. NMR characterization of the alkylboron product resulted in the following: 1H NMR (300.1 MHz, CDCl$_3$): δ 1.49 (m, 1H), 1.35 (m, 2H), 1.20 (s, 12H), 1.13 (m, 2H), 0.82 (d, 6H, J=7 Hz), 0.73 (t, 2H, J=7 Hz). $^{13}$C{$^1$H}NMR (75.5 MHz, CDCl$_3$): δ 83.0, 42.2, 28.0, 25.0, 22.8, 22.0. $^{11}$B NMR (96.3 MHz, CDCl$_3$): δ 34.2. The $^{11}$B NMR spectrum obtained in both experiments indicated full conversion of the pinacolborane starting material. Spectral data are in close agreement with previously reported $^1$H and $^{13}$C NMR characterization data for 2-(4-methylpent-1-yl)-4,4,5,5-tetramethyl-1,3,2-dioxaborolane.

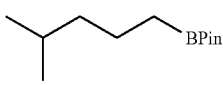

ABP3

Allyltrimethylsilane Hydroboration

The hydroboration of allyltrimethylsilane using the compositions and methods disclosed herein was also investigated. Specifically, the borane having Structure ABP4, was synthesized according to GP3 using the following amounts of alkene substrate and catalyst: allyltrimethylsilane (164 μL, 1 mmol), PAMC1 (0.0032 g, 0.5 mol %).

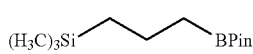

ABP4

After removal of solvent the borane having Structure ABP4 was isolated in 97% yield. In the absence of solvent, the borane having Structure ABP4 was synthesized according to GP2 using the following amounts of alkene substrate and catalyst: allyltrimethysilane (164 μL, 1 mmol), PAMC1 (0.0064 g, 1 mol %). After drying in vacuo, the borane was isolated in 98% yield (0.238 g, 0.98 mmol) as a colorless oil. NMR characterization of the product resulted in the following: $^1$H NMR (300.1 MHz, CDCl$_3$): δ 1.39 (m, 2H), 1.20 (s, 12H), 0.78 (t, 2H, J=8 Hz), 0.48 (m, 2H), −0.08 (s, 9H). $^{13}$C{$^1$H}NMR (75.5 MHz, CDCl$_3$): δ 83.2, 25.0, 20.3, 18.8, −1.4. $^{11}$B NMR (96.3 MHz, CDCl$_3$): δ 34.0. The $^{11}$B NMR spectrum obtained in both experiments indicated full conversion of the pinacolborane starting material. Spectral data are in close agreement with previously reported $^1$H and $^{13}$C NMR characterization data for the borane having Structure ABP4.

Tert-Butylethylene Hydroboration

The hydroboration of tert-butylethylene using the compositions and methods disclosed herein was also investigated. Specifically, 2-(3,3-dimethylbut-1-yl)-4,4,5,5-tetramethyl-1,3,2-dioxaborolane, depicted as Structure ABP5, was synthesized in the absence of solvent according to GP2 using the following amounts of alkene substrate and catalyst: tert-butylethylene (129 μL, 1 mmol), PAMC1 (0.0096 g, 1.5 mol %). After drying in vacuo the alkyl boron product was isolated in 98% yield (0.208 g, 0.98 mmol) as a colorless oil.

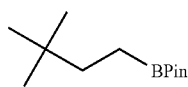

ABP5

NMR characterization of the product resulted in the following: $^1$H NMR (300.1 MHz, CDCl$_3$): δ 1.20-1.29 (overlapping peaks, 14H), 0.81 (s, 9H), 0.67 (t, 2H, J=9 Hz). $^{13}$C{$^1$H}NMR (75.5 MHz, CDCl$_3$): δ 83.0, 37.9, 31.0, 29.0, 25.0. $^{11}$B NMR (96.3 MHz, CDCl$_3$): δ 34.4. The $^{11}$B NMR spectrum obtained in both experiments indicated full conversion of the pinacolborane starting material. Spectral data are in close agreement with previously reported $^1$H and $^{13}$C NMR characterization data for -(3,3-dimethylbut-1-yl)-4,4,5,5-tetramethyl-1,3,2-dioxaborolane.

2-Methyl-1-Pentene Hydroboration

The hydroboration of 2-methyl-1-pentene using the compositions and methods disclosed herein was also investigated. Specifically, 2-(2-methylpent-1-yl)-4,4,5,5-tetramethyl-1,3,2-dioxaborolane, depicted as Structure ABP6, was synthesized in the absence of solvent according to GP2 using the following amounts of alkene substrate and catalyst: 2-methyl-1-pentene (150 μL, 1.2 mmol), PAMC1(0.013 g, 2 mol %). After drying in vacuo the alkylboron product was isolated in 90% yield (0.191 g, 0.90 mmol) as a colorless oil.

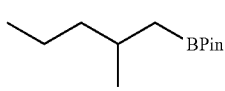

ABP6

NMR characterization of the product resulted in the following: $^1$H NMR (300.1 MHz, CDCl$_3$): δ 1.66 (m, 1H), 1.13-1.32 (overlapping peaks, 16H), 0.76-0.88 (overlapping peaks, 7H), 0.64 (m, 1H). $^{13}$C{$^1$H}NMR (75.5 MHz, CDCl$_3$): δ 83.1, 42.2, 29.4, 25.1, 25.0, 22.8, 20.1, 14.5. $^{11}$B NMR (96.3 MHz, CDCl$_3$): δ 34.0. The $^{11}$B NMR spectrum obtained in both experiments indicated full conversion of the pinacolborane starting material. Spectral data are in close agreement with previously reported $^1$H and $^{13}$C NMR characterization data for 2-(2-methylpent-1-yl)-4,4,5,5-tetramethyl-1,3,2-dioxaborolane.

Cyclohexene Hydroboration

The hydroboration of cyclohexene using the compositions and methods disclosed herein was also investigated. Specifically, 2-cyclohexyl-4,4,5,5-tetramethyl-1,3,2-dioxaborolane, depicted as Structure ABP7, was synthesized in the absence of solvent according to GP2 using the following amounts of alkene substrate and catalyst: cyclohexene (121 μL, 1.2 mmol), PAMC1 (0.032 g, 5 mol %). After drying in vacuo the alkylboron compound was isolated in 92% yield (0.194 g, 0.92 mmol) as a pale yellow oil.

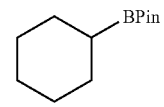

ABP7

NMR characterization of the product resulted in the following: $^1$H NMR (300.1 MHz, CDCl$_3$): δ 1.49-1.66 (overlapping peaks, 4H), 1.25-1.37 (overlapping peaks, 18H), 0.95 (m, 1H). $^{13}$C{$^1$H}NMR (75.5 MHz, CDCl$_3$): δ 82.7, 28.1, 27.3, 27.0, 24.9. $^{11}$B NMR (96.3 MHz, CDCl$_3$): δ 33.2. The $^{11}$B NMR spectrum obtained in both experiments indicated full conversion of the pinacolborane starting material. Spectral data are in close agreement with previously reported $^1$H and $^{13}$C NMR characterization data for 2-cyclohexyl-4,4,5,5-tetramethyl-1,3,2-dioxaborolane.

Cyclooctene Hydroboration

The hydroboration of cyclooctene using the compositions and methods disclosed herein was also investigated. Specifically, cyclooctyl-4,4,5,5-tetramethyl-1,3,2-dioxaborolane, depicted as Structure ABP8 was synthesized in the absence of solvent according to GP2 using the following amounts of alkene substrate and catalyst: cyclooctene (164 μL, 1.2 mmol), PAMC1(0.0064 g, 1 mol %). After drying in vacuo the alkylboron compound was isolated in 96% yield (0.230 g, 0.96 mmol) as a colorless oil.

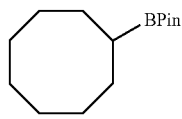

ABP8

NMR characterization of the product resulted in the following: $^1$H NMR (300.1 MHz, CDCl$_3$): δ 1.49-1.74 (overlapping peaks, 14H), 1.20 (s, 12H), 1.08 (m, 1H). $^{13}$C{$^1$H}NMR (75.5 MHz, CDCl$_3$): δ 82.9, 27.8, 27.2, 27.1, 26.9, 24.9. $^{11}$B NMR (96.3 MHz, CDCl$_3$): δ 33.2. The $^{11}$B NMR spectrum obtained in both experiments indicated full conversion of the pinacolborane starting material. Spectral data are in close agreement with previously reported $^1$H and $^{13}$C NMR characterization data for cyclooctyl-4,4,5,5-tetramethyl-1,3,2-dioxaborolane.

While preferred embodiments of the invention have been shown and described, modifications thereof can be made by one skilled in the art without departing from the spirit and teachings of the disclosure. The embodiments described herein are exemplary only, and are not intended to be limiting. Many variations and modifications of the disclosure are possible and are within the scope of the invention. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The discussion of a reference in the Background is not an admission that it is prior art to the present invention, especially any reference that can have a publication date after the priority date of this application. The disclosures of all patents, patent applications, and publications cited herein are hereby incorporated by reference, to the extent that they provide exemplary, procedural or other details supplementary to those set forth herein.

The following are enumerated embodiments are provided as non-limiting examples.

A first embodiment which is a process comprising contacting an alkene, a hydrogen-boron bond containing compound, and a metal complex selected from the group consisting of an N$^2$-phosphinyl amidine metal complex, an N$^2$-phosphinyl formamidine complex, and an N$^2$-phosphinyl guanidine metal complex to form an alkyl-boron compound under conditions suitable to form an alkylboron compound.

A second embodiment which is the process of the first embodiment, wherein the hydrogen-boron bond containing compound comprises borane, diborane, a borane-amine complex, a borane-phosphine complex, borane-phosphite complex, a borane-ether complex, a borane-sulfide complex, a hydrogen borinic acid ester, a hydrogen boronic acid ester, a hydrogen monoaminoborane, a hydrogen diaminoborane, a hydrogen azaborolidine, a hydrogen diazaborlidine, or any combination thereof.

A third embodiment which is the process of any of the first through second embodiments, wherein the hydrogen-boron bond containing compound comprise a hydrogen borinic acid ester, a hydrogen boronic acid ester, or combinations thereof.

A fourth embodiment which is the process of any of the first through third embodiments, wherein the alkylborane compound is formed at a temperature of from 15° C. to 30° C.

A fifth embodiment which is the process of any of the first through fourth embodiments, wherein the metal complex is a transition metal complex The sixth embodiment which is the process of any of the first through fifth embodiments, wherein the metal complex is a Group 8 or Group 9 metal complex.

The seventh embodiment which is the process of the sixth embodiment, wherein the Group 8 or Group 9 metal complex is a Fe complex or a Co complex.

An eighth embodiment which is the process of any of the first through seventh embodiments, wherein the alkene comprises a linear terminal alkene or a linear internal alkene.

A ninth embodiment which is the process of the eighth embodiment, wherein the linear internal alkene comprises a trans linear internal alkene.

A tenth embodiment which is the process of any of the first through ninth embodiments, wherein the N$^2$-phosphinyl amidine metal complex has the structure:

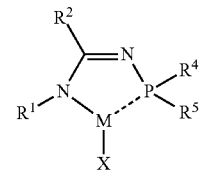

wherein R$^1$ is a C$_1$ to C$_{30}$ organyl group, R$^2$ is a C$_1$ to C$_{30}$ organyl group consisting essentially of inert functional groups, R$^4$ and R$^5$ are each independently a C$_1$ to C$_{30}$ organyl group consisting essentially of inert functional groups, M is Fe or Co, and X is a hydrocarboxide, a dihydrocarbylazanide, a bis(trihydrocarbylsilyl)azanide, or a dihydrocarbylphosphinide.

An eleventh embodiment which is the process of any of the first through tenth embodiments, wherein the N$^2$-phosphinyl guanadine metal complex has the structure:

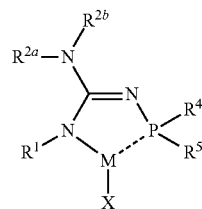

wherein R$^1$ is a C$_1$ to C$_{30}$ organyl group, R$^{2a}$ and R$^{2b}$ independently are C$_1$ to C$_{30}$ organyl groups consisting essentially of inert functional groups, R$^4$ and R$^5$ each independently are C$_1$ to C$_{30}$ organyl groups consisting essentially of inert functional groups, M is Fe or Co, and X is a hydrocarboxide, a dihydrocarbylazanide, a bis (trihydrocarbylsilyl)azanide, or a dihydrocarbylphosphinide.

A twelfth embodiment which is the process of any of the first through eleventh embodiments, wherein the N$^2$-phosphinyl formamidine metal complex has the structure:

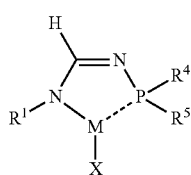

wherein $R^1$ is a $C_1$ to $C_{30}$ organyl group, $R^4$ and $R^5$ are each independently a $C_1$ to $C_{30}$ organyl group consisting essentially of inert functional groups, M is Fe or Co, and X is a hydrocarboxide, a dihydrocarbylazanide, a bis(trihydrocarbylsilyl)azanide, or a dihydrocarbylphosphinide.

A thirteenth embodiment which is the process of any of the first through twelfth embodiments, wherein greater than 95% of the alkene is converted to the alkylboron compound A fourteenth embodiment which is the process of any of the first through thirteenth embodiments, wherein the contacting occurs in the absence of solvent A fifteenth embodiment which is the process of any of the first through fourteenth embodiments, wherein the alkene comprises a $C_2$ to $C_{60}$ alkene.

A sixteenth embodiment which is the process of any of the first through fifteenth embodiments, wherein the molar ratio of hydrogen boron-bond containing compound to metal amidine complex ranges from 10:1 to $1 \times 10^6:1$.

A seventeenth embodiment which is the process of any of the first through sixteenth embodiments, wherein the alkene is a linear internal alkene and the process further comprises forming a terminal alkylboron compound.

An eighteenth embodiment which is the process of the seventeenth embodiment, wherein the terminal alkylboron compound is formed at a temperature from 15° C. to 30° C.

A nineteenth embodiment which is the process of any of the first through eighteenth embodiments, further comprising dehydroboration of the alkylboron compound to form a terminal olefin.

A twentieth embodiment which is a process comprising contacting a linear internal alkene, a metal complex selected from the group consisting of an $N^2$-phosphinyl amidine metal complex, an $N^2$-phosphinyl formamidine complex, and an $N^2$-phosphinyl guanidine metal complex to form a terminal alkylboron compound under conditions suitable to form a terminal alkylboron compound.

A twenty-first embodiment which is the process of the twentieth embodiment, wherein conditions suitable for formation of a terminal alkylboron compound comprises a temperature of from 15° C. to 30° C.

A twenty-second embodiment which is the process of any of the twentieth through twenty-first embodiments, wherein the hydrogen-boron bond containing compound comprises borane, diborane, a borane-amine complex, a borane-phosphine complex, a borane-phosphite complex, a borane-ether complex, a borane-sulfide complex, a hydrogen borinic acid ester, a hydrogen boronic acid ester, a hydrogen monoaminoborane, a hydrogen diaminoborane, a hydrogen azaborolidine, hydrogen diazaborlidine, or any combination thereof.

A twenty-third embodiment which is the process of any of the twentieth through twenty-second embodiments, wherein the hydrogen-boron bond containing compound comprise a hydrogen borinic acid ester, a hydrogen boronic acid ester, or combinations thereof.

A twenty-fourth embodiment which is the process of any of the twentieth through twenty-third embodiments, further comprising dehydroboration of the terminal alkylboron compound to give a linear terminal alkene.

What is claimed:

1. A process comprising:

contacting (i) an alkene, (ii) a hydrogen-boron bond containing compound, and (iii) a metal complex selected from the group consisting of an $N^2$-phosphinyl amidine metal complex, an $N^2$-phosphinyl formamidine complex, and an $N^2$-phosphinyl guanidine metal complex to form an alkyl-boron compound wherein the alkylboron compound is formed at a temperature of from 15° C. to 30° C.

2. The process of claim 1, wherein the hydrogen-boron bond containing compound comprises borane, diborane, a borane-amine complex, a borane-phosphine complex, a borane-phosphite complex, a borane-ether complex, a borane-sulfide complex, a hydrogen borinic acid ester, a hydrogen boronic acid ester, a hydrogen monoaminoborane, a hydrogen diaminoborane, a hydrogen azaborolidine, a hydrogen diazaborlidine, or any combination thereof.

3. The process of claim 1, wherein the hydrogen-boron bond containing compound comprises a hydrogen borinic acid ester, a hydrogen boronic acid ester, or combinations thereof.

4. The process of claim 1 wherein the metal complex is a transition metal complex.

5. The process of claim 1, wherein the metal complex is a Group 8 or Group 9 metal complex.

6. The process of claim 5, wherein the Group 8 or Group 9 metal complex is a Fe complex or a Co complex.

7. The process of claim 1, wherein the alkene comprises a linear terminal alkene or a linear internal alkene.

8. The process of claim 7, wherein the linear internal alkene comprises a trans linear internal alkene.

9. The process of claim 1, wherein the $N^2$-phosphinyl amidine metal complex has the structure:

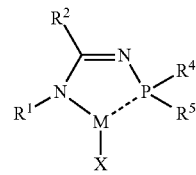

wherein:

$R^1$ is a $C_1$ to $C_{30}$ organyl group, $R^2$ is a $C_1$ to $C_{30}$ organyl group consisting essentially of inert functional groups, $R^4$ and $R^5$ are each independently a $C_1$ to $C_{30}$ organyl group consisting essentially of inert functional groups, M is Fe or Co, and X is a hydrocarboxide, a dihydrocarbylazanide, a bis(trihydrocarbylsilyl)azanide, or a dihydrocarbylphosphinide.

10. The process of claim 1, wherein the $N^2$-phosphinyl guanadine metal complex has the structure:

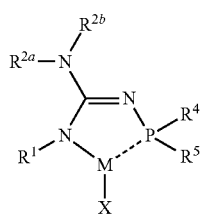

wherein:
$R^1$ is a $C_1$ to $C_{30}$ organyl group,
$R^{2a}$ and $R^{2b}$ independently are $C_1$ to $C_{30}$ organyl groups consisting essentially of inert functional groups,
$R^4$ and $R^5$ each independently are $C_1$ to $C_{30}$ organyl groups consisting essentially of inert functional groups,
M is Fe or Co, and
X is a hydrocarboxide, a dihydrocarbylazanide, a bis(trihydrocarbylsilyl)azanide, or a dihydrocarbylphosphinide.

11. The process of claim 1, wherein the $N^2$-phosphinyl formamidine metal complex has the structure:

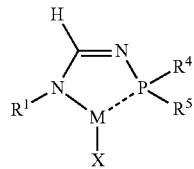

wherein:
$R^1$ is a $C_1$ to $C_{30}$ organyl group,
$R^4$ and $R^5$ are each independently a $C_1$ to $C_{30}$ organyl group consisting essentially of inert functional groups,
M is Fe or Co, and
X is a hydrocarboxide, a dihydrocarbylazanide, a bis(trihydrocarbylsilyl)azanide, or a dihydrocarbylphosphinide.

12. The process of claim 1, wherein greater than 95% of the alkene is converted to the alkylboron compound.

13. The process of claim 1, wherein the contacting occurs in the absence of solvent.

14. The process of claim 1, wherein the alkene comprises a $C_2$ to $C_{60}$ alkene.

15. The process of claim 1, wherein the molar ratio of hydrogen-boron bond containing compound to metal amidine complex ranges from 10:1 to $1\times10^6:1$.

16. The process of claim 1, wherein the alkene is a linear internal alkene and the process further comprises forming a terminal alkylboron compound.

17. The process of claim 16, wherein the terminal alkylboron compound is formed at a temperature from 15° C. to 30° C.

18. The process of claim 1, further comprising dehydroboration of the alkylboron compound to form a terminal olefin.

19. A process comprising: contacting (i) a linear internal alkene, (ii) a hydrogen-boron bond containing compound, and (iii) a metal complex selected from the group consisting of an $N^2$-phosphinyl amidine metal complex, an $N^2$-phosphinyl formamidine complex, and an $N^2$-phosphinyl guanidine metal complex to form a terminal alkylboron compound wherein the terminal alkylboron compound is formed at a temperature of from 15° C. to 30° C.

20. The process of claim 19, wherein the hydrogen-boron bond containing compound comprises borane, diborane, a borane-amine complex, a borane-phosphine complex, a borane-phosphite complex, a borane-ether complex, a borane-sulfide complex, a hydrogen borinic acid ester, a hydrogen boronic acid ester, a hydrogen monoaminoborane, a hydrogen diaminoborane, a hydrogen azaborolidine, a hydrogen diazaborlidines, or any combination thereof.

21. The process of claim 19, wherein the hydrogen-boron bond containing compound comprises a hydrogen borinic acid ester, a hydrogen boronic acid ester, or combinations thereof.

22. The process of claim 19, further comprising dehydroboration of the terminal alkylboron compound to give a linear terminal alkene.

\* \* \* \* \*